US010106805B2

(12) United States Patent
Spangenberg et al.

(10) Patent No.: US 10,106,805 B2
(45) **Date of Patent: *Oct. 23, 2018**

(54) MANIPULATING FRUCTAN BIOSYNTHESIS AND ENHANCING PLANT BIOMASS

(75) Inventors: German Spangenberg, Bundoora (AU); Aidyn Mouradov, Mill Park (AU); Timothy Ivor Sawbridge, Collingwood (AU)

(73) Assignee: Agriculture Victoria Services Pty Ltd., Attwood (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/283,813

(22) Filed: Oct. 28, 2011

(65) Prior Publication Data

US 2012/0144526 A1 Jun. 7, 2012

Related U.S. Application Data

(63) Continuation-in-part of application No. 12/722,878, filed on Mar. 12, 2010, now Pat. No. 9,840,695, and a continuation of application No. PCT/AU2010/000481, filed on Apr. 27, 2010.

(60) Provisional application No. 61/173,272, filed on Apr. 28, 2009.

(51) Int. Cl.
*C12N 15/82* (2006.01)
*C12N 9/10* (2006.01)

(52) U.S. Cl.
CPC ....... *C12N 15/8246* (2013.01); *C12N 9/1051* (2013.01); *C12N 9/1055* (2013.01); *C12N 15/8245* (2013.01); *C12N 15/8261* (2013.01); *Y02A 40/146* (2018.01)

(58) Field of Classification Search
CPC . C12N 9/1055; C12N 9/1051; C12N 15/8246
See application file for complete search history.

(56) References Cited

U.S. PATENT DOCUMENTS 5,908,975 A * 6/1999 Caimi .................. C12N 9/1051 435/320.1
5,986,173 A 11/1999 Smeekens et al.
7,227,055 B2 * 6/2007 Spangenberg ..... C12N 15/8271 435/320.1
2003/0237108 A1 * 12/2003 Demmer et al. .............. 800/284
2004/0168215 A1 * 8/2004 Jiang .................. C12N 15/8216 800/287

FOREIGN PATENT DOCUMENTS

WO 94/14970 A1 7/1994
WO 2008/128293 A1 10/2008
WO 2010028456 A1 3/2010

OTHER PUBLICATIONS

Caimi et el (Plant Physio. (1996) 110: 355-363).*
Cairns (Journal of Experimental Botany,2003, vol. 54 No. 382).*
Vijn et al (Plant Physiology, Jun. 1999, vol. 120 pp. 351-359).*
Chalmers et al (J. Plant Physiology (2003) vol. 160, p. 1385-1391.*
GenBank Accession No: AAO86693.1) 2003.*
GenBank Accession EFH30007.1 (2013).*
GenBank Accession , GAN03469.1 (2015).*
GenBank Accession WP_043962714.1 (2015).*
Pilon-Smits et al (Plant Physiol. Biochem., 1995, 107: 125-130)—cited in IDS filed on Nov. 17, 2011.*
Ji et al (New Phytologist (2007) 173: 50-62).*
Randhir Singh, Sarla P. Malhotra, Carbon fixation, sucrose synthesis and its transport to storage tissues, In: Anil Kumar Gupta and Narinder Kaur, Editor(s), Developments in Crop Science, Elsevier, 2000, vol. 26, pp. 1-34, ISSN 0378-519X, ISBN 9780444502698, http://dx.doi.org/10.1016/S0378-519X(00)80002-1. (http://www.sciencedirect.com/science/.*
Pilon-Smits et al (Plant Physiol. Biochem., 1999, 37 (4), 313-317).*
Perlak, F. J. et al., Modification of the Coding Sequence Enhances Plant Expression of Insect Control Protein Genes, Proceedings of the National Academy of Sciences, US, 1991, pp. 3324-3328, vol. 88.
Caimi, P.G. et al. "Cytosolic expression of the Bacillus amyloliquefaciens SacB protein inhibits tissue development in transgenic tobacco and potato." New Phytol., 1997, pp. 1928, vol. 136.
Caimi, P.G. et al. "Fructan Accumulation and Sucrose Metabolism in Transgenic Maize Endosperm Expressing a Bacillus amyloliquefaciens SacB Gene." Plant Physiol., 1996, pp. 355-363, vol. 110.
Cairns, A. "Fructan biosynthesis in transgenic plants." Journal of Experimental Botany, Jan. 2003, pp. 549-567, vol. 54, No. 382.
Chalmers, J. et al. "Molecular genetics of fructan metabolism in perennial ryegrass" Plant Biochemistry Journal, 2005, pp. 459-474, vol. 3.
Ebskamp, M. et al. "Accumulation of Fructose Polymers in Transgenic Tobacco." Nature Publishing Group, Mar. 1994, pp. 272-275, vol. 12.
Gerrits, N. et al. "Sucrose Metabolism in Plastids" Plant Physiology, Feb. 2001, pp. 926-934, vol. 125.

(Continued)

*Primary Examiner* — Lee A Visone
(74) *Attorney, Agent, or Firm* — Larson & Anderson, LLC

(57) ABSTRACT

Genetic constructs capable of manipulating fructan biosynthesis in photosynthetic cells of a plant include a promoter, or functionally active fragment or variant thereof, operatively linked to a nucleic acid encoding a bacterial FT enzyme, or a functionally active fragment or variant thereof. Such constructs can be used in the modification of fructan biosynthesis in plants and, more particularly, to methods of manipulating fructan biosynthesis in photosynthetic cells, for increasing plant biomass and, more particularly, to methods of enhancing biomass yield and/or yield stability, including shoot and/or root growth in a plant, and for enhancing the productivity of biochemical pathways.

27 Claims, 66 Drawing Sheets

(56) References Cited

OTHER PUBLICATIONS

Figure 1:
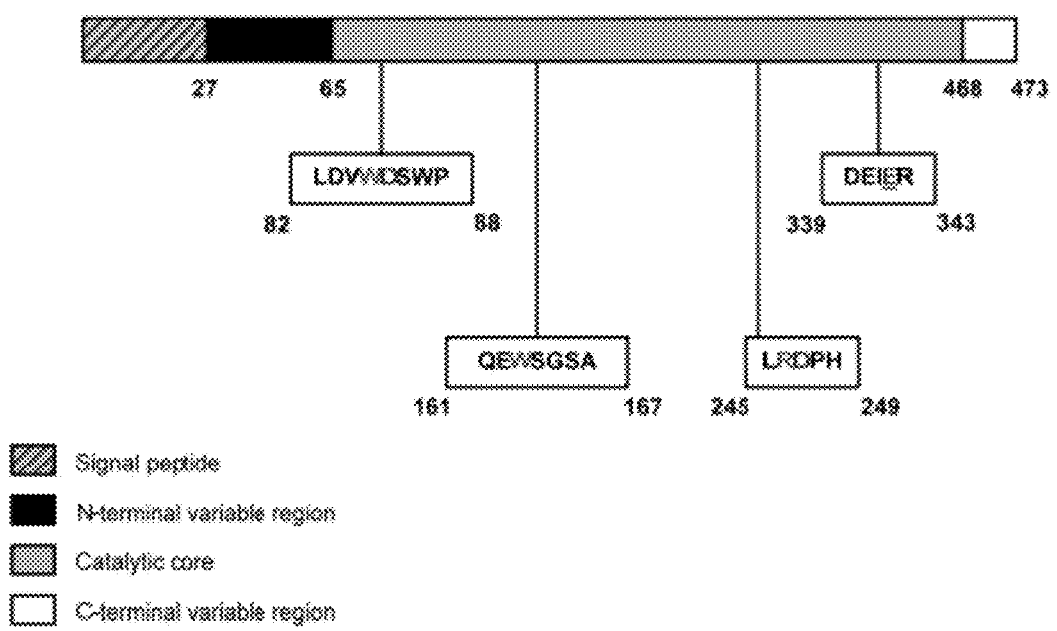

Hattori, T. et al. "Molecular cloning and nucleotide sequence of cDNA for sporamin, the major soluble protein of sweet potato tuberous roots." Plant Molecular Biology, 1985, pp. 313-320, vol. 5.
Li, S. et al. "Cloning of Three MYB-like Genes from *Arabidopsis thaliana* (Accession No. U26933, AF048841, and U26934)." Plant Gene Register PGR99-138, Plant Physiol, 1999, p. 313, vol. 121.
Pilon-Smits, E. et al. "Improved Performance of Transgenic Fructan-Accumulating Tobacco under Drought Stress" Plant Physiol., 1995, pp. 125-130, vol. 107.
Pilon-Smits, E. et al. "Enhanced drought resistance in fructan-producing sugar beet" Plant Physiol. Biochem., 1999, pp. 313-317, vol. 37, No. 4.
Sasanuma, T. et al. "Characterization of the rbcS multigene family in wheat: subfamily classification, determination of chromosomal location and evolutionary analysis." Mol Genet Genomics, 2001, pp. 161-171, vol. 265.
Schardi, C.L. et al. "Design and construction of a versatile system for the expression of foreign genes in plants" Gene, 1987, pp. 1-11, vol. 61.
Wei-Ke, Z. et al. "PCR Amplification and Sequencing of a Wheat rbc S Gene Promotor." Acta Botanica Sinica, 1995, pp. 496-500, vol. 37, No. 6.
Ye, X.D. et al. "Altered fructan accumulation in transgenic Lolium multiflorum plants expressing a Bacillus subtilis sacB gene." Plant Cell Reports, 2001, pp. 205-212, vol. 20.

* cited by examiner

FIGURE 2

ATGAACATCAAAAAGTTTGCAAAACAAGCAACAGTATTAACCTTTACTACCGCACTGCTGGCAGGAGGCGCAACTCA
AGCGTTTGCGAAAGAAACGAACCAAAAGCCATATAAGGAAACATACGGCATTTCCCATATTACACGCCATGATATGC
TGCAAATCCCTGAACAGCAAAAAAATGAAAAATATCAAGTTCCTGAATTCGATTCGTCCACAATTAAAAATATCTCT
TCTGCAAAAGGCCTGGACGTTTGGGACAGCTGGCCATTACAAAACGCTGACGGCACTGTCGCAAACTATCACGGCTA
CCACATCGTCTTTGCATTAGCCGGAGATCCTAAAAATGCGGATGACACATCGATTTACATGTTCTATCAAAAAGTCG
GCGAAACTTCTATTGACAGCTGGAAAAACGCTGGCCGCGTCTTTAAAGACAGCGACAAATTCGATGCAAATGATTCT
ATCCTAAAAGACCAAACACAAGAATGGTCAGGTTCAGCCACATTTACATCTGACGGAAAAATCCGTTTATTCTACAC
TGATTTCTCCGGTAAACATTACGGCAAACAAACACTGACAACTGCACAAGTTAACGTATCAGCATCAGACAGCTCTT
TGAACATCAACGGTGTAGAGGATTATAAATCAATCTTTGACGGTGACGGAAAAACGTATCAAAATGTACAGCAGTTC
ATCGATGAAGGCAACTACAGCTCAGGCGACAACCATACGCTGAGAGATCCTCACTACGTAGAAGATAAAGGCCACAA
ATACTTAGTATTTGAAGCAAACACTGGAACTGAAGATGGCTACCAAGGCGAAGAATCTTTATTTAACAAAGCATACT
ATGGCAAAAGCACATCATTCTTCCGTCAAGAAAGTCAAAAACTTCTGCAAAGCGATAAAAAACGCACGGCTGAGTTA
GCAAACGGCGCTCTCGGTATGATTGAGCTAAACGATGATTACACACTGAAAAAAGTGATGAAACCGCTGATTGCATC
TAACACAGTAACAGATGAAATTGAACGCGCGAACGTCTTTAAAATGAACGGCAAATGGTACCTGTTCACTGACTCCC
GCGGATCAAAAATGACGATTGACGGCATTACGTCTAACGATATTTACATGCTTGGTTATGTTTCTAATTCTTTAACT
GGCCCATACAAGCCGCTGAACAAAACTGGCCTTGTGTTAAAAATGGATCTTGATCCTAACGATGTAACCTTTACTTA
CTCACACTTCGCTGTACCTCAAGCGAAAGGAAACAATGTCGTGATTACAAGCTATATGACAAACAGAGGATTCTACG
CAGACAAACAATCAACGTTTGCGCCAAGCTTCCTGCTGAACATCAAAGGCAAGAAAACATCTGTTGTCAAAGACAGC
ATCCTTGAACAAGGACAATTAACAGTTAACAAATAA

FIGURE 3

MNIKKFAKQATVLTFTTALLAGGATQAFAKETNQKPYKETYGISHITRHDMLQIPEQQKNEKYQVPEFDSSTIKNIS
SAKGLDVWDSWPLQNADGTVANYHGYHIVFALAGDPKNADDTSIYMFYQKVGETSIDSWKNAGRVFKDSDKFDANDS
ILKDQTQEWSGSATFTSDGKIRLFYTDFSGKHYGKQTLTTAQVNVSASDSSLNINGVEDYKSIFDGDGKTYQNVQQF
IDEGNYSSGDNHTLRDPHYVEDKGHKYLVFEANTGTEDGYQGEESLFNKAYYGKSTSFFRQESQKLLQSDKKRTAEL
ANGALGMIELNDDYTLKKVMKPLIASNTVTDEIERANVFKMNGKWYLFTDSRGSKMTIDGITSNDIYMLGYVSNSLT
GPYKPLNKTGLVLKMDLDPNDVTFTYSHFAVPQAKGNNVVITSYMTNRGFYADKQSTFAPSFLLNIKGKKTSVVKDS
ILEQGQLTVNK

FIGURE 4

ATGTTGGAAAATAAAAATCATAAAAAGATATCTTTAAGCGGAAAATCTTTGTTAATGGGAACCTTGTCAACAGCAGC
AATTGTATTAAGTGCATCAACTGCAAATGCTGCGACTATTAATGCAGACAATGTTAATGAAAATCAAACTGTAGAAG
TAACTGCTAGTTCAGTAAACAATGAAAATAATAAGCAAGTAACTGAAAAAGATAGTGCAGATAAAAGTACTAGTGAT
GTGGCTGAAGATGCTAACACCAAGAAATCAAACGAAAATACAGAAACTACAGAAAAGAATACTCAAACAGTTGTTAC
TAATGCGCCAGTAAGTGATGTGAAAAATACAAACACAGTTACCGCTGAAACACCTGTTGATAAAGTAGTAAATAATA
GTGATCAAAAGACAACTAATGCTGCAACTACTGATACTAAAAAAGATGATGTAAAACAAGTTGAAAAGAAAGACTCA
GTAGATAAAACAAATGCTGAGGAAAATAAAGATAGTTCAGTAAAGCCAGCTGAAAATGCTACTAAGGCTGAATTAAA
GGGCCAAGTTAAAGATATCGTTGAAGAATCTGGTGTTGATACTAGCAAGTTAACTAATGATCAAATTAATGAATTAA
ATAAAATTAATTTCTCCAAAGAAGCAAAAAGTGGTACTCAGTTAACTTACAACGACTTTAAAAAAATTGCTAAAACT
TTAATTGAACAAGATGCTCGTTATGCTATTCCATTCTTCAATGCAAGTAAAATTAAAAATATGCCTGCTGCTAAAAC
ACTTGATGCTCAAAGTGGAAAAGTAGAAGATTTGGAAATTTGGGATTCATGGCCTGTTCAAGATGCAAAAACTGGTT
ACGTATCTAACTGGAATGGCTACCAATTAGTGATTGGTATGATGGGAGTTCCAAACGTCAATGATAACCACATTTAT
CTTCTTTACAACAAGTATGGTGATAATAATGACTTTAATCATTGGAAGAATGCCGGTCCTATTTTCGGTCTAGGTACTCC
AGTTATTCAACAATGGTCTGGATCAGCAACTTTAAATAAAGATGGCTCAATTCAACTTTACTACACTAAGGTTGATA
CTAGTGATAATAATACTAACCACCAAAAACTCGCTAGTGCAACTGTTTACTTAAATCTTGAAAAAGATCAAGATAAG
ATTTCTATTGCTCATGTTGACAACGACCATATTGTCTTTGAAGGTGATGGTTACCACTACCAAACTTATGACCAATG
GAAAGAAACTAACAAGGGTGCTGACAATATCGCAATGCGTGATGCACACGTGATTGATGATGATAATGGTAATCGTT
ACCTTGTGTTTGAAGCAAGTACTGGAACCGAAAATTATCAAGGTGATGATCAAATTTATCAATGGTTAAATTACGGC
GGTACTAACAAGGATAATTTAGGTGATTTCTTCCAAATTTTATCTAACTCCGATATTAAAGATAGAGCTAAATGGTC
AAACGCTGCAATTGGTATCATTAAATTAAATGATGATGTTAAGAATCCAAGTGTTGCAAAGGTCTACAGCCCACTTA
TTAGTGCACCAATGGTAAGTGATGAAATTGAACGCCCTGATGTTGTTAAATTAGGTAATAAGTATTACTTATTTGCT
GCTACTAGATTAAACCGTGGTAGTAACGATGATGCTTGGATGGCAACTAACAAAGCAGTTGGTGATAACGTAGCTAT
GATTGGTTATGTTTCTGATAACTTAACTCATGGTTATGTTCCATTGAATGAATCTGGCGTTGTTTTAACTGCATCTG
TACCGGCTAACTGGCGTACTGCAACTTATTCATACTATGCAGTTCCAGTAGAAGGAAGAGATGATCAACTTTTAATT
ACTTCATACATCACTAATCGTGGTGAGGTTGCTGGAAAGGGTATGCATGCAACTTGGGCACCAAGTTTCTTGTTACA
AATTAATCCAGATAACACTACTACTGTTTTAGCTAAAATGACTAACCAAGGGGATTGGATTTGGGATGATAGTAGTG
AAAATCCAGATATGATGGGTGTACTTGAAAAAGATGCTCCAAATAGTGCTGCCCTTCCTGGAGAATGGGGAAAACCA
GTTGATTGGGATTTAATTGGTGGATACAACTTGAAGCCACACCAACCTGTAACTCCTATTCCAAATGTACCAACTAC
TCCTGAAACCCCAACCACACCAGATAAGCCAGAGGTACCAACTACCCCTGAAGTTCCAACCACTCCAGAAACTCCAA
CTCCAGAAGCTCCAAAGAATCCAGTTAAGAAAACTAGTCAGTCTAAACTTCCAAAGGCTGGAGATAAAAATAGCTTT
GCAGCAGTTGTTTTAGGTGCTGTAAGTTCAATATTAGGTGCTGTTGGTTTAACAGGTGTTTCAAAACGTAAACGTAA
TAATTAA

FIGURE 5

MLENKNHKKISLSGKSLLMGTLSTAAIVLSASTANAATINADNVNENQTVEVTASSVNNENNKQVTEKDSADKSTSD
VAEDANTKKSNENTETTEKNTQTVVTNAPVSDVKNTNTVTAETPVDKVVNNSDQKTTNAATTDTKKDDVKQVEKKDS
VDKTNAEENKDSSVKPAENATKAELKGQVKDIVEESGVDTSKLTNDQINELNKINFSKEAKSGTQLTYNDFKKIAKT
LIEQDARYAIPFFNASKIKNMPAAKTLDAQSGKVEDLEIWDSWPVQDAKTGYVSNWNGYQLVIGMMGVPNVNDNHIY
LLYNKYGDNDFNHWKNAGPIFGLGTPVIQQWSGSATLNKDGSIQLYYTKVDTSDNNTNHQKLASATVYLNLEKDQDK
ISIAHVDNDHIVFEGDGYHYQTYDQWKETNKGADNIAMRDAHVIDDDNGNRYLVFEASTGTENYQGDDQIYQWLNYG
GTNKDNLGDFFQILSNSDIKDRAKWSNAAIGIIKLNDDVKNPSVAKVYSPLISAPMVSDEIERPDVVKLGNKYYLFA
ATRLNRGSNDDAWMATNKAVGDNVAMIGYVSDNLTHGYVPLNESGVVLTASVPANWRTATYSYYAVPVEGRDDQLLI
TSYITNRGEVAGKGMHATWAPSFLLQINPDNTTTVLAKMTNQGDWIWDDSSENPDMMGVLEKDAPNSAALPGEWGKP
VDWDLIGGYNLKPHQPVTPIPNVPTTPETPTTPDKPEVPTTPEVPTTPETPTPEAPKNPVKKTSQSKLPKAGDKNSF
AAVVLGAVSSILGAVGLTGVSKRKRNN

FIGURE 6

ATGAAAGCCTTCACACTCGCTCTCTTCTTAGCTCTTTTCCTCTATCTCCTGCCCAATCCAGCCCATTCCAGGTTCAA
TCCCATCCGGCCTCCCCACCACACACGAACCCGCCTCCTCTGAAACTCCAGTACTCGACATCAACGGCGACGAGGTCC
GCGCCGGCGGGAACTACTACATGGTCTCCGGCCATATGGGGAGCCGGCGGGGGAGGGCTAAGACTCGCCCACTTGGAC
ACGATGTCCAAATGCGCCAGCGACGTCATCGTATCCCCCAACGACTTAGACAACGGCGACCCCATCACCATCACGCC
GGCGACGGCCGACCGGAATCCACCGTGGTCATGGGGTCGACCTACCAGACTTTCCGGTTCAATATCGCCAACAACA
AACTGTGCGTGAAGAACGTGAACTGGGGAATCCAGCACGACAGCGCGTCCGGGCAGTATTTCCTGAAAGACGGCGAG
TTTGTCTCCGACAATAGCAACCAGTTCAAGATTGAGGTGGTGGATGCCAACCTTAACTTCTACAAACTCACTTACTG
TCAGTTCGGCTCCGACAAATGCTACAACTGCGGCAGATTCCACGACCCCATGTTGAGGACCACGCGCTTGGCTCTCT
CCAATTCTCCCTTCGTTTTTGTCATCAAACCTACCGATGTG

FIGURE 7

MKAFTLALFLALFLYLLPNPAHSRFNPIRLPTTHEPASSETPVLDINGDEVRAGGNYYMVSAIWGAGGGGLRLAHLD
TMSKCASDVIVSPNDLDNGDPITITPATADPESTVVMASTYQTFRFNIANNKLCVKNVNWGIQHDSASGQYFLKDGE
FVSDNSNQFKIEVVDANLNFYKLTYCQFGSDKCYNVGRFHDPMLRTTRLALSNSPFVFVIKPTDV

FIGURE 8

<u>ATGAAAGCCTTCACACTCGCTCTCTTCTTAGCTCTTTTCCTCTATCTCCTGCCCAATCCAGCCCATTCC</u>ACGAACCA
AAAGCCATATAAGGAAACATACGGCATTTCCCATATTACAGGCCATGATATGCTGCAAATCCCTGAACAGCAAAAAA
ATGAAAAATATCAAGTTCCTGAATTCGATTCGTCCACAATTAAAAATATCTCTTCTGCAAAAGGCCTGGACGTTTGG
GACAGCTGGCCATTACAAAACGCTGACGGCACTGTCGCAAACTATCACGGCTACCACATCGTCTTTGCATTAGCCGG
AGATCCTAAAAATGCGGATGACACATCGATTTACATGTTCTATCAAAAAGTCGGCGAAACTTCTATTGACAGCTGGA
AAAACGCTGGCCGCGTCTTTAAAGACAGCGACAAATTCGATGCAAATGATTCTATCCTAAAAGACCAAACACAAGAA
TGGTCAGGTTCAGCCACATTTACATCTGACGGAAAAATCCGTTTATTCTACACTGATTTCTCCGGTAAACATTACGG
CAAACAAACACTGACAACTGCACAAGTTAACGTATCAGCATCAGACAGCTCTTTGAACATCAACGGTGTAGAGGATT
ATAAATCAATCTTTGACGGTGACGGAAAAACGTATCAAAATGTACAGCAGTTCATCGATGAAGGCAACTACAGCTCA
GGCGACAACCATACGCTGAGAGATCCTCACTACGTAGAAGATAAAGGCCACAAATACTTAGTATTTGAAGCAAACAC
TGGAACTGAAGATGGCTACCAAGGCGAAGAATCTTTATTTAACAAAGCATACTATGGCAAAAGCACATCATTCTTCC
GTCAAGAAAGTCAAAAACTTCTGCAAAGCGATAAAAAACGCACGGCTGAGTTAGCAAACGGCGCTCTCGGTATGATT
GAGCTAAACGATGATTACACACTGAAAAAAGTGATGAAACCGCTGATTGCATCTAACACAGTAACAGATGAAATTGA
ACGCGCGAACGTCTTTAAAATGAACGGCAAATGGTACCTGTTCACTGACTCCCGCGGATCAAAAATGACGATTGACG
GCATTACGTCTAACGATATTTACATGCTTGGTTATGTTTCTAATTCTTTAACTGGCCCATACAAGCCGCTGAACAAA
ACTGGCCTTGTGTTAAAAATGGATCTTGATCCTAACGATGTAACCTTTACTTACTCACACTTCGCTGTACCTCAAGC
GAAAGGAAACAATGTCGTGATTACAAGCTATATGACAAACAGAGGATTCTACGCAGACAAACAATCAACGTTTGCGC
CAAGCTTCCTGCTGAACATCAAAGGCAAGAAAACATCTGTTGTCAAAGACAGCATCCTTGAACAAGGACAATTAACA
GTTAACAAATAA

FIGURE 9

MKAFTLALFLALFLYLLPNPAHSTNQKPYKETYGISHITRHDMLQIPEQQKNEKYQVPEFDSSTIKNISSAKGLDVW
DSWPLQNADGTVANYHGYHIVFALAGDPKNADDTSIYMFYQKVGETSIDSWKNAGRVFKDSDKFDANDSILKDQTQE
WSGSATFTSDGKIRLFYTDFSGKHYGKQTLTTAQVNVSASDSSLNINGVEDYKSIFDGDGKTYQNVQQFIDEGNYSS
GDNHTLRDPHYVEDKGHKYLVFEANTGTEDGYQGEESLFNKAYYGKSTSFFRQESQKLLQSDKKRTAELANGALGMI
ELNDDYTLKKVMKPLIASNTVTDEIERANVFKMNGKWYLFTDSRGSKMTIDGITSNDIYMLGYVSNSLTGPYKPLNK
TGLVLKMDLDPNDVTFTYSHFAVPQAKGNNVVITSYMTNRGFYADKQSTFAPSFLLNIKGKKTSVVKDSILEQGQLT
VNK

FIGURE 11

ATGAAAGCCTTCACACTCGCTCTCTTCTTAGCTCTTTTCCTCTATCTCCTGCCCAATCCAGCCCATTCCACTATTAA
TGCAGACAATGTTAATGAAAATCAAACTGTAGAAGTAACTGCTAGTTCAGTAAACAATGAAAATAATAAGCAAGTAA
CTGAAAAAGATAGTGCAGATAAAAGTACTAGTGATGTGGCTGAAGATGCTAACACCAAGAAATCAAACGAAAATACA
GAAACTACAGAAAAGAATACTCAAACAGTTGTTACTAATGCGCCAGTAAGTGATGTGAAAAATACAAACACAGTTAC
CGCTGAAACACCTGTTGATAAAGTAGTAAATAATAGTGATCAAAAGACAACTAATGCTGCAACTACTGATACTAAAA
AAGATGATGTAAAACAAGTTGAAAAGAAAGACTCAGTAGATAAAACAAATGCTGACGAAAATAAAGATAGTTCAGTA
AAGCCAGCTGAAAATGCTACTAAGGCTGAATTAAAGGGCCAAGTTAAAGATATCGTTGAAGAATCTGGTGTTGATAC
TAGCAAGTTAACTAATGATCAAATTAATGAATTAAATAAAATTAATTTCTCCAAAGAAGCAAAAAGTGGTACTCAGT
TAACTTACAACGACTTTAAAAAAATTGCTAAAACTTTAATTGAACAAGATGCTGGTTATGCTATTCCATTCTTCAAT
GCAAGTAAAATTAAAAATATGCCTGCTGCTAAAACACTTGATGCTCAAAGTGGAAAAGTAGAAGATTTGGAAATTTG
GGATTCATGGCCTGTTCAAGATGCAAAAACTGGTTACGTATCTAACTGGAATGGCTACCAATTAGTGATTGGTATGA
TGGGAGTTCCAAACGTCAATGATAACCACATTTATCTTCTTTACAACAAGTATGGTGATAATGACTTTAATCATTGG
AAGAATGCCGGTCCTATTTTCGGTCTAGGTACTCCAGTTATTCAACAATGGTCTGGATCAGCAACTTTAAATAAAGA
TGGCTCAATTCAACTTTACTACACTAAGGTTGATACTAGTGATAATAATACTAACCACCAAAAACTCGCTAGTGCAA
CTGTTTACTTAAATCTTGAAAAAGATCAAGATAAGATTTCTATTGCTCATGTTGACAACGACCATATTGTCTTTGAA
GGTGATGGTTACCACTACCAAACTTATGACCAATGGAAAGAAACTAACAAGGGTGCTGACAATATCGCAATGCGTGA
TGCACACGTGATTGATGATGATAATGGTAATCGTTACCTTGTGTTTGAAGCAAGTACTGGAACCGAAAATTATCAAG
GTGATGATCAAATTTATCAATGGTTAAATTACGGCGGTACTAACAAGGATAATTTAGGTGATTTCTTCCAAATTTTA
TCTAACTCCGATATTAAAGATAGAGCTAAATGGTCAAACGCTGCAATTGGTATCATTAAATTAAATGATGATGTTAA
GAATCCAAGTGTTGCAAAGGTCTACAGCCCACTTATTAGTGCACCAATGGTAAGTGATGAAATTGAACGCCCTGATG
TGGTTAAATTAGGTAATAAGTATTACTTATTTGCTGCTACTAGATTAAACCGTGGTAGTAACGATGATGCTTGGATG
GCAACTAACAAAGCAGTTGGTGATAACGTAGCTATGATTGGTTATGTTTCTGATAACTTAACTCATGGTTATGTTCC
ATTGAATGAATCTGGCGTTGTTTTAACTGCATCTGTACCGGCTAACTGGCGTACTGCAACTTATTCATACTATGCAG
TTCCAGTAGAAGGAAGAGATGATCAACTTTTAATTACTTCATACATCACTAATCGTGGTGAGGTTGCTGGAAAGGGT
ATGCATGCAACTTGGGCACCAAGTTTCTTGTTACAAATTAATCCAGATAACACTACTACTGTTTTAGCTAAAATGAC
TAACCAAGGGGATTGGATTTGGGATGATAGTAGTGAAAATCCAGATATGATGGGTGTACTTGAAAAAGATGCTCCAA
ATAGTGCTGCCCTTCCTGGAGAATGGGGAAAACCAGTTGATTGGGATTTAATTGGTGGATACAACTTGAAGCCACAC
CAACCTGTAACTCCTATTCCAAATGTACCAACTACTCCTGAAACCCCAACCACACCAGATAAGCCAGAGGTACCAAC
TACCCCTGAAGTTCCAACCACTCCAGAAACTCCAACTCCAGAAGCTCCAAAGAATCCAGTTAAGAAAACTAGTCAGT
CTAAACTTCCAAAGGCTGGAGATAAAAATAGCTTTGCAGCAGTTGTTTTAGGTGCTGTAAGTTCAATATTAGGTGCT
GTTGGTTTAACAGGTGTTTCAAAACGTAAACGTAATAATTAA

FIGURE 12

MKAFTIALALFLALFLYLLPNPAHSYINADNVNENQTVSVTASSVNNENNKQVTEKDSADKSTSDVAEDANTKKSNENT
ETTEKNTQTVVTNAPVSDVKNTNTVTAETPVDKVVNNSDQKTTNAATTDTKKDDVKQVEKKDSVDKTNAEENKDSSV
KPAENATKAELKGQVKDIVEESGVDTSKLTNDQINELNKINFSEEAKSGTQLTYNDFKKIAKTLIEQDARYAIPFFN
ASKIKNMPAAKTLDAQSGKVEDLEIWDSWPVQDAKTGYVSNWNGYQLVIGMMGVPNVNDNHIYLLYNKYGDNDFNHW
KNAGPIFGLGTPVIQQWSGSATLNKDGSIQLYYTKVDTSDNNTNHQKLASATVYLNLEKDQDKISIAHVDNDHIVFE
GDGYHYQTYDQWKETNKGADNIAMRDAHVIDDDNGNRYLVFEASTGTENYQGDDQIYQWLNYGGTNKDNLGDFFQIL
SNSDIKDRAKNGNAAIGIIKLNDDVKNPSVAKVYSPLISAPMVSDEIERPDVVKLGNKYYLFAATRLNRGSNDDAWM
ATNKAVGDNVAMIGYVSDNLTHGYVPLNESGVVLTASVPANWRTATYSYYAVPVEGRDDQLLITSYITNRGEVAGKG
MHATWAPSFLLQINPDNTTTVLAKMTNQGDWIWDDSSENPDMMGVLEKDAPNSAALPGEMGKPVDWDLIGGYNLKPH
QPVTPIPNVPTTPETPTTPDKPEVPTTPEVPTTPETPTPEAPKNPVKKTSQSKLPKAGDKNSFAAVVLGAVSSILGA
VGLTGVSKRKRNN

1-SST

FIGURE 15

ATGCAACCAGGGAACGTCGTCCACCCCTTCCACATCCTGTATCAAATTAAGGAACGGGCGCTGAGCCTATGCCGAGA
CATATATAATGCGGCGACTCGGACATGGAGGGGCCTCAGGCATAGCCCAGCTAGTTATCTCATTCTCTCCTTAGCAA
TAATACTTAGCACCATGGCCCCGCGGTGGAATTCATGGAGTCCCCAAGCGCCGTCGTCCCCGGCACCACGGCGCCG
CTGCTTCCTTATGCGTACGCGCCGCTGCCGTCGTCCGCCGACGACGCCCGTCAAAACCGGAGTGGCGGGAGGTGGCG
CGCGTGCGCCGCCGTGCTGGCCGCATCGGCGTTGGCGGTGGTCGTCGTGGTCGGGCTCCTCGCGGCGGCAGGTGG
ATCGGGTCCCGGCCGGCGGAGACGTGGCGTCGGCCACGGTGCCGGCCGTGCCGATGGAGTTCCCGAGGAGGCCGGGC
AAGGACTTCGGCGTGTCGGAGAAGTCCTCCGGTGCCTACTCCACCGACGGCGGGTTCCCGTGGAGCAACGCCATGCT
GCAGTGGCAGCGCACCGGGTTCCATTTCCAGCCGGAGCAGCACTACATGAACGATCCCAACGGCCCCGTGTACTACG
GCGGATGGTACCACCTCTTCTACCAGCACAACCCCAAGGGCGACAGCTGGGGCAACATCGCGTGGGCCCACGCCGTC
TCCAAGGACATGGTCAACTGGCGCCACCTCCCTCTCGCCATGGTTCCCGACCAGTGGTACGACAGCAACGGCGTCCT
CACCGGCTCCATCACCGTGCTCCCCGACGGCCAGGTCATCCTGCTCTACACCGGCAACACCGACACCCTAGCCCAGG
TCCAGTGCCTCGCCACGCCCGCCGACCCGTCCGACCCGCTCCTCCGCGAGTGGGTCAAGCACCCCGCCAACCCCATC
CTCTACCCTCCCCCCGGCATCGGCCTCAAGGACTTCCGCGACCCCCTCACCGCCTGGTTCGACCACTCCGACCACAC
CTGGCGCACCGTCATCGGCTCCAAGGACGACGACGGCCACGCCGGCATCATCCTCAGCTACAAGACCAAGGACTTCG
TCAACTACGAGCTCATGCCGGGGAACATGCACCGCGGGCCCGACGGCACCGGAATGTACGAGTGCATCGACCTCTAC
CCCGTCGGCGGCAACTCGTCCGAGATGCTCGGCGGCGACGACTCGCCCGGCGTGCTCTTCGTGCTCAAGGAGAGCAG
CGACGACGAGCGCCACGACTACTACGCGCTCGGAAGGTTCGACGCCGTCGCCAACGTTTGGACGCCCATCGACCGGG
AGCTGGACCTTGGGATCGGGCTCAGATACGACTGGGGAAAGTACTACGCCTCCAAGTCCTTCTACGACCAGAAGAAG
AACCGCCGCATCGTATGGGCATACATCGGCGAGACCGACTCCGAGCAGGCCGACATCACCAAGGGATGGGCCAATCT
CATGACGATTCCAAGAACGGTGGAGCTTGACAGGAAGACCCGCACAAACCTCATCCAATGGCCAGTGGAGGAGGTCG
ACACCCTCCGCAGGAACTCCACGGACCTCGGTCGCATCACCGTCAACGCCGGCTCCGTCATTCGCCTCCCCCTCCAC
CAGGGCGCTCAACTCGACATCGAGGCCTCCTTCCAACTCAACTCTTCCGACGTGGATGCTATCAACGAGGCCGACGT
CGGCTACAACTGCAGCACCAGTGGTGCCGCCGTACGGGGCGCGCTCGGCCCCTTTGGCCTCCTCGTCCTTGCCAACG
GCCGCACCGAACAGACGGCTGTGTACTTCTACGTGTCCAAGGGCGTCGACGGTGCCCTCCAGACCCACTTCTGCCAC
GACGAGTCACGGTCAACGCGGGCAAAGGATGTCGTGAATAGGATGATTGGCAGCATCGTGCCGGTGCTTGACGGTGA
GACCTTTTCGGTGAGGGTGCTAGTGGACCACTCCATCGTGCAGAGCTTCGCGATGGGCGGGAGGATCACGGCGACGT
CGCGGGCGTACCCGACGGAGGCCATCTACGCGGCCGCGGGGGTCTACCTCTTCAACAACGCCACGGGCGCCACCGTC
ACCGCCGAGAGGCTCGTCGTGCACGAGATGGCCTCAGCTGACAACCATATCTTCACGAACGACGACTTG

FIGURE 16

*MESPSAVVPGTTAPLLPYAYAPLPSSADDARQNRSGGRWRACAAVLAASALAVVVVVGLLAGGRVDRVPAGG*DVASA
TVPAVPMEPPRSRGKDFGVSEKSSGAYSTDGGFPWSNAMLQWQRTGFHFQPEQHYMNDPNGPVYYGGWYHLFYQHNP
KGDSWGNIAWAHAVSKDMVNWKHLPLAMVPDQWYDSNGVLTGSITVLPDGQVILLYTGNTDTLAQVQCLATPADPSD
PLLREWVKHPANPILYPPPGIGLKDFRDPLTAWFDHSDNTWRTVIGSKDDDGHAGIILSYKTKDFVNYELMPGNMHR
GPDGTGMYECIDLYPVGGNSSEMLGGDDSPGVLFVLKESSDDERHDYYALGRFDAVANVWTPIDRELDLGIGLRYDW
GKYYASKSFYDQKKNRRIVWAYIGETDSEQADITKGWANLMTIPRTVELDRKTRTNLIQWPVEEVDTLRRNSTDLGR
ITVNAGSVIRLPLHQGAQLDIEASFQLNSSDVDAINEADVGYNCSTSGAAVRGALGPFGLLVLANGRTEQTAVYFYV
SKGVDGALQTHFCHDESRSTRANDVVNRMIGSIVPVLDGETFSVRVLVDHSIVQSFAMGGRITATSRAIPTEAIYAA
AGVYLFNNATGATVTAERLVVHEMASADNHIFTNDDL

FIGURE 17

ATGGAGTCCCCAAGGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGAGGTGGCGCGCGTGCGCGCCGTGCTGGCCGCATCGGCG
TTGGCGGTGGTCGTCGTGGTCGGGCTCCTCGCGGCGGCAGGGTGGATCGGGTCCCCGGCCGCGGCGGAACGAACCAA
AAGCCATATAAGGAAACATACGGCATTTCCCATATTACACGCCATGATATGCTGCAAATCCCTGAACAGCAAAAA
AATGAAAAATATCAAGTTCCTGAATTCGATTCGTCCACAATTAAAAATATCTCTTCTGCAAAAGGCCTGGACGTT
TGGGACAGCTGGCCATTACAAAACGCTGACGGCACTGTCGCAAACTATCACGGCTACCACATCGTCTTTGCATTA
GCCGGAGATCCTAAAAATGCGGATGACACATCGATTTACATGTTCTATCAAAAAGTCGGCGAAACTTCTATTGAC
AGCTGGAAAAACGCTGGCCGCGTCTTTAAAGACAGCGACAAATTCGATGCAAATGATTCTATCCTAAAAGACCAA
ACACAAGAATGGTCAGGTTCAGCCACATTTACATCTGACGGAAAAATCCGTTTATTCTACACTGATTTCTCCGGT
AAACATTACGGCAAACAAACACTGACAACTGCACAAGTTAACGTATCAGCATCAGACAGCTCTTTGAACATCAAC
GGTGTAGAGGATTATAAATCAATCTTTGACGGTGACGGAAAAACGTATCAAAATGTACAGCAGTTCATCGATGAA
GGCAACTACAGCTCAGGCGACAACCATACGCTGAGAGATCCTCACTACGTAGAAGATAAAGGCCACAAATACTTA
GTATTTGAAGCAAACACTGGAACTGAAGATGGCTACCAAGGCGAAGAATCTTTATTTAACAAAGCATACTATGGC
AAAAGCACATCATTCTTCCGTCAAGAAAGTCAAAAACTTCTGCAAAGCGATAAAAAACGCACGGCTGAGTTAGCA
AACGGCGCTCTCGGTATGATTGAGCTAAACGATGATTACACACTGAAAAAAGTGATGAAACCGCTGATTGCATCT
AACACAGTAACAGATGAAATTGAACGCGCGAACGTCTTTAAAATGAACGGCAAATGGTACCTGTTCACTGACTCC
CGCGGATCAAAAATGACGATTGACGGCATTACGTCTAACGATATTTACATGCTTGGTTATGTTTCTAATTCTTTA
ACTGGCCCATACAAGCCGCTGAACAAAACTGGCCTTGTGTTAAAAATGGATCTTGATCCTAACGATGTAACCTTT
ACTTACTCACACTTCGCTGTACCTCAAGCGAAAGGAAACAATGTCGTGATTACAAGCTATATGACAAACAGAGGA
TTCTACGCAGACAAACAATCAACGTTTGCGCCAAGCTTCCTGCTGAACATCAAAGGCAAGAAAACATCTGTTGTC
AAAGACAGCATCCTTGAACAAGGACAATTAACAGTTAACAAATAA

FIGURE 18

*MESPSAVVPGTTAPLLPYAYAPLPSSADDARQNRSGGRWRACAAVLAASALAVVVVVGLLAGGRVDRVPAGG*TNQ
KPYKETYGISHITRHDMLQIPEQQKNEKYQVPEFDSSTIKNISSAKGLDVWDSWPLQNADGTVANYHGYHIVFAL
AGDPKNADDTSIYMFYQKVGETSIDSWKNAGRVFKDSDKFDANDSILKDQTQEWSGSATFTSDGKIRLFYTDFSG
KHYGKQTLTTAQVNVSASDSSLNINGVEDYKSIFDGDGKTYQNVQQFIDEGNYSSGDNHTLRDPHYVEDKGHKYL
VFEANTGTEDGYQGEESLFNKAYYGKSTSFFRQESQKLLQSDKKRTAELANGALGMIELNDDYTLKKVMKPLIAS
NTVTDEIERANVFKMNGKWYLFTDSRGSKMTIDGITSNDIYMLGYVSNSLTGPYKPLNKTGLVLKMDLDPNDVTF
TYSHFAVPQAKGNNVVITSYMTNRGFYADKQSTFAPSFLLNIKGKKTSVVKDSILEQGQLTVNK

FIGURE 20

ATGGAGTCCCCAAGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGAGGTGGCGCGCGTGCGCCGCCGTGCTGGCCGCATCGGCG
TTGGCGGTGGTCGTCGTGGTCGGGCTCCTCGCGGGCGGCAGGGTGGATCGGGTCCCGGCCGGCGGAACTATTAAT
GCAGACAATGTTAATGAAAATCAAACTGTAGAAGTAACTGCTAGTTCAGTAAACAATGAAAATAATAAGCAAGTA
ACTGAAAAAGATAGTGCAGATAAAAGTACTAGTGATGTGGCTGAAGATGCTAACACCAAGAAATCAAACGAAAAT
ACAGAAACTACAGAAAAGAATACTCAAACAGTTGTTACTAATGCGCCAGTAAGTGATGTGAAAAATACAAACACA
GTTACCGCTGAAACACCTGTTGATAAAGTAGTAAATAATAGTGATCAAAAGACAACTAATGCTGCAACTACTGAT
ACTAAAAAAGATGATGTAAAACAAGTTGAAAAGAAAGACTCAGTAGATAAAACAAATGCTGAGGAAAATAAAGAT
AGTTCAGTAAAGCCAGCTGAAAATGCTACTAAGGCTGAATTAAAGGGCCAAGTTAAAGATATCGTTGAAGAATCT
GGTGTTGATACTAGCAAGTTAACTAATGATCAAATTAATGAATTAAATAAAATTAATTTCTCCAAAGAAGCAAAA
AGTGGTACTCAGTTAACTTACAACGACTTTAAAAAAATTGCTAAAACTTTAATTGAACAAGATGCTCGTTATGCT
ATTCCATTCTTCAATGCAAGTAAAATTAAAAATATGCCTGCTGCTAAAACACTTGATGCTCAAAGTGGAAAAGTA
GAAGATTTGGAAATTTGGGATTCATGGCCTGTTCAAGATGCAAAAACTGGTTACGTATCTAACTGGAATGGCTAC
CAATTAGTGATTGGTATGATGGGAGTTCCAAACGTCAATGATAACCACATTTATCTTCTTTACAACAAGTATGGT
GATAATGACTTTAATCATTGGAAGAATGCCGGTCCTATTTTCGGTCTAGGTACTCCAGTTATTCAACAATGGTCT
GGATCAGCAACTTTAAATAAAGATGGCTCAATTCAACTTTACTACACTAAGGTTGATACTAGTGATAATAATACT
AACCACCAAAAACTCGCTAGTGCAACTGTTTACTTAAATCTTGAAAAAGATCAAGATAAGATTTCTATTGCTCAT
GTTGACAACGACCATATTGTCTTTGAAGGTGATGGTTACCACTACCAAACTTATGACCAATGGAAAGAAACTAAC
AAGGGTGCTGACAATATCGCAATGCGTGATGCACACGTGATTGATGATGATAATGGTAATCGTTACCTTGTGTTT
GAAGCAAGTACTGGAACCGAAAATTATCAAGGTGATGATCAAATTTATCAATGGTTAAATTACGGCGGTACTAAC
AAGGATAATTTAGGTGATTTCTTCCAAATTTTATCTAACTCCGATATTAAAGATAGAGCTAAATGGTCAAACGCT
GCAATTGGTATCATTAAATTAAATGATGATGTTAAGAATCCAAGTGTTGCAAAGGTCTACAGCCCACTTATTAGT
GCACCAATGGTAAGTGATGAAATTGAACGCCCTGATGTTGTTAAATTAGGTAATAAGTATTACTTATTTGCTGCT
ACTAGATTAAACCGTGGTAGTAACGATGATGCTTGGATGGCAACTAACAAAGCAGTTGGTGATAACGTAGCTATG
ATTGGTTATGTTTCTGATAACTTAACTCATGGTTATGTTCCATTGAATGAATCTGGCGTTGTTTTAACTGCATCT
GTACCGGCTAACTGGCGTACTGCAACTTATTCATACTATGCAGTTCCAGTAGAAGGAAGAGATGATCAACTTTTA
ATTACTTCATACATCACTAATCGTGGTGAGGTTGCTGGAAAGGGTATGCATGCAACTTGGGCACCAAGTTTCTTG
TTACAAATTAATCCAGATAACACTACTACTGTTTTAGCTAAAATGACTAACCAAGGGGATTGGATTTGGGATGAT
AGTAGTGAAAATCCAGATATGATGGGTGTACTTGAAAAAGATGCTCCAAATAGTGCTGCCCTTCCTGGAGAATGG
GGAAAACCAGTTGATTGGGATTTAATTGGTGGATACAACTTGAAGCCACACCAACCTGTAACTCCTATTCCAAAT
GTACCAACTACTCCTGAAACCCCAACCACACCAGATAAGCCAGAGGTACCAACTACCCCTGAAGTTCCAACCACT
CCAGAAACTCCAACTCCAGAAGCTCCAAAGAATCCAGTTAAGAAAACTAGTCAGTCTAAACTTCCAAAGGCTGGA
GATAAAAATAGCTTTGCAGCAGTTGTTTTAGGTGCTGTAAGTTCAATATTAGGTGCTGTTGGTTTAACAGGTGTT
TCAAAACGTAAACGTAATAATTAA

FIGURE 21

*MESPSAVVPGTTAPLLPYAYAPLPSSADDARQNRSGGRWRACAAVLAASALAVVVVVGLLAGGRVDRVPAGG*TINAD
NVNENQTVEVTASSVNNENNKQVTEKDSADKSTSDVAEDANTKKSNENTETTEKNTQTVVTNAPVSDVKNTNTVTAE
TPVDKVVNNSDQKTTNAATTDTKKDDVKQVEKKDSVDKTNAEENKDSSVKPAENATKAELKGQVKDIVEESGVDTSK
LTNDQINELNKINFSKEAKSGTQLTYNDFKKIAKTLIEQDARYAIPFFNASKIKNMPAAKTLDAQSGKVEDLEINDS
WPVQDAKTGYVSNWKGYQLVIGNNGVPNVNDNHIYLLYNKYGDNDFNHWKNAGPIFGLGTPVIQQNSGSATLNKDGS
IQLYVTKVDTSDNWTNHQKLASATVYLNLEKDQDKISIAHVDNDHIVFEGDGYHYQTYDQWKETNKGADNIAMRDAH
VIDDDNGNRYLVFEASTGTENYQGDDQIYQWLNYGGTNKDNLGDFFQILSNSDIKDRAKWSNAAIGIIKLNDDVKNP
SVAKVYSPLISAPMVSDEIERPDVVKLGNKYYLFAATRLNRGSNDDAWMATNKAVGDNVAMIGYVSDNLTHGYVPLN
ESGVVLTASVPANWRTATYSYYAVPVEGRDDQLLITSYITNRGEVAGKGMHATWAPSFLLQINPDNTTTVLAKMTNQ
GDWIWDDSSENPDMMGVLEKDAPNSAALPGEWGKPVDWDLIGGYNLKPHQPVTPIPNVPTTPETPTTPDKPEVPTTP
EVPTTPETPTPEAPKNPVKKTSQSKLPKAGDKNSFAAVVLGAVSSILGAVGLTGVSKRKRNN

FIGURE 23 cgtggtcgagattgtgtattattctttagttattacaagactttagctaaaatttgaaagaatttactttaagaaa
atcttaacatctgagataatttcagcaatagattatatttttcattactctagcagtattttgcagatcaatcgca
acatatatggttgttagaaaaaatgcactatatatatatatattattttttcaattaaaagtgcatgatatataata
tatatatatatatatatatgtgtgtgtgtatatggtcaaagaaattcttatacaaatatacacgaacacatatattt
gacaaaatcaaagtattacactaaacaatgagttggtgcatggccaaaacaaatatgtagattaaaaattccagcct
ccaaaaaaaaatccaagtgttgtaaagcattatatatatatagtagatcccaaatttttgtacaattccacactgat
cgaatttttaaagttgaatatctgacgtaggatttttttaatgtcttacctgaccatttactaataacattcatacg
ttttcatttgaaatatccctctataattatattgaatttggcacataataagaaacctaattggtgatttattttact
agtaaatttctggtgatgggctttctactagaaagctctcggaaaatcttggaccaaatccatattccatgacttcg
attgttaaccctattagtttttcacaaacatactatcaatatcattgcaacggaaaaggtacaagtaaaacattcaat
ccgatagggaagtgatgtaggaggttgggaagacaggcccagaaagagatttatctgacttgttttgtgtatagttt
tcaatgttcataaaggaagatggagacttgagaagtttttttggactttgtttagctttgttgggcgtttttttt
tttgatcaataactttgttgggcttatgatttgtaatatttcgtggactctttagtttatttagacgtgctaactt
tgttgggcttatgacttgttgtaacatattgtaacagatgacttgatgtgcgactaatctttacacattaaacatag
ttctgtttttgaaagttcttattttcatttttatttgaatgttatatatttttctatatttataattctagtaaaa
ggcaaatttgctttaaatgaaaaaaatatatattccacagtttcacctaatcttatgcatttagcagtacaaatt
caaaaatttcccatttttattcatgaatcataccattatatattaactaaatccaaggtaaaaaaaaggtatgaaag
ctctatagtaagtaaaatataaattccccataaggaaagggccaagtccaccaggcaagtaaaatgagcaagcacca
ctccaccatcacacaatttcactcatagataacgataagattcatggaattatcttccacgtggcattattccagcg
gttcaagccgataagggtctcaacacctctccttaggcctttgtggccgttaccaagtaaaattaacctcacacata
tccacactcaaaatccaacggtgtagatcctagtccacttgaatctcatgtatcctagaccctccgatcactccaaa
gcttgttctcattgttgttatcattatatatagatgacccaaagcactagaccaaacctcagtcacacaaagagtaaa
gaagaacaATGAAAGCCTTCACACTCGCTCTCTTCTTAGCTCTTTTCCTCTATCTCCTGCCCAATCCAGCCCATTCC
ACGAACCAAAAGCCATATAAGGAAACATACGGCATTTCCCATATTACACGCCATGATATATGCTGCAAATCCCTGAACA
GCAAAAAAATGAAAAATATCAAGTTCCTGAATTCGATTCGTCCACAATTAAAAATATCTCTTCTGCAAAAGCCTGG
ACGTTTGGGACAGCTGGCCATTACAAAACGCTGACGGCACTGTCGCAAACTATCACGGCTACCACATCGTCTTTGCA
TTAGCCGGAGATCCTAAAAATGCGGATGACACATCGATTTACATGTTCTATCAAAAAGTCGGCGAAACTTCTATTGA
CAGCTGGAAAAACGCTGGCCCGGTCTTTAAAGACAGCGACAAATTCGATGCAAATGATTCTATCCTAAAAGACCAAA
CACAAGAATGGTCAGGTTCAGCCACATTTACATCTGACGGAAAAATCCGTTTATTCTACACTGATTTCTCCGGTAAA
CATTACGGCAAACAAACACTGACAACTGCACAAGTTAACGTATCAGCATCAGACAGCTCTTTGAACATCAACGGTGT
AGAGGATTATAAATCAATCTTTGACGGTGACGGAAAAACGTATCAAAATGTACAGCAGTTCATCGATGAAGGCAACT
ACAGCTCAGGCGACAACCATACGCTGAGAGATCCTCACTACGTAGAAGATAAAGGCCACAAATACTTAGTATTTGAA
GCAAACACTGGAACTGAAGATGGCTACCAAGGCGAAGAATCTTTATTTAACAAAGCATACTATGGCAAAAGCACATC
ATTCTTCCGTCAAGAAAGTCAAAAACTTCTGCAAAGCGATAAAAAACGCACGGCTGAGTTAGCAAACGGCGCTCTCG
GTATGATTGAGCTAAACGATGATTACACACTGAAAAAAGTGATGAAACCGCTGATTGCATCTAACACAGTAACAGAT

FIGURE 23 (CONT'D)

GAAATTGAACGCGCGAACGTCTTTAAAATGAACGGCAAATGGTACCTGTTCACTGACTCCCGCGGATCAAAAATGAC
GATTGACGGCATTACGTCTAACGATATTTACATGCTTGGTTATGTTTCTAATTCTTTAACTGGCCCATACAAGCCGC
TGAACAAAACTGGCCTTGTGTTAAAAATGGATCTTGATCCTAACGATGTAACCTTTACTTACTCACACTTCGCTGTA
CCTCAAGCGAAAGGAAACAATGTCGTGATTACAAGCTATATGACAAACAGAGGATTCTACGCAGACAAACAATCAAC
GTTTGCGCCAAGCTTCCTGCTGAACATCAAAGGCAAGAAAACATCTGTTGTCAAAGACAGCATCCTTGAACAAGGAC
AATTAACAGTTAACAAATAAGatcgttcaaacatttggcaataaagtttcttaagaatgaatcctgttgccggtctt
gcgatgattatcatataatttctgttgaattacgttaagcatgaaataattaacatgtaatgcatgacgttatttat
gagatgggtttttatgattagagtcccgcaattatacatttaatacgcgatagaaaacaaaatatagcgcgcaaact
aggataaattatcgcgcgcggtgtcatcaatgttactagatc

FIGURE 24

*cgtggtcgagattgtgtattattctttagttattacaagactttagctaaaatttgaaagaatttactttaagaaa*
*atctttaacatctgagataatttcagcaatagattatattttcattactctagcagtatttttgcagatcaatcgca*
*acatatatggttgttagaaaaaatgcactatatatatatatattatttttcaattaaaagtgcatgatatataata*
*tatatatatatatatatgtgtgtgtgtatatggtcaaagaaatctttatacaaatatacacgaacacatatattt*
*gacaaaatcaaagtattacactaaacaatgagttggtgcatggccaaaacaaatacgtagattaaaaattccagcct*
*ccaaaaaaaatccaagtgttgtaaagcattatatatatatagtagatcccaaatttttgtacaattccacactgat*
*cgaatttttaaagttgaatatctgacgtaggatttttttaatgtcttacctgaccatttactaataacattcatacg*
*tttccatttgaaatatccctataattatattgaatttggcacataataagaaacctaattggtgatttattttact*
*agtaaatttctggtgatgggctttctactagaaagctctcggaaaatcttggaccaaatcccatattccatgacttcg*
*attgttaaccctattagttttcacaaacatactatcaatatcattgcaacggaaaaggtacaagtaaaacattcaat*
*ccgatagggaagtgatgtaggaggttgggaagacaggcccagaaagagatttatctgacttgttttgtgtatagttt*
*tcaatgttcataaaggaagatggagacttgagaagtttttttggactttgtttagctttgttgggcgttttttttt*
*tttgatcaataacttgttgggcccatgatttgtaatatttccgtggactctttagtttatttcagacgtgctaactt*
*tgttgggcttatgacttgtttgtaacatattgtaacagatgacttgatgtgcgactaatctttacacattaaacatag*
*ttctgtttttttgaaagttcctatttttcatttttatttgaatgttatatatttttctatatttataatttctagtaaaa*
*ggcaaattttgctttttaaatgaaaaaatatatattccacagtttcacctaatctttatgcatttagcagtacaaatt*
*caaaaatttcccatttttcattcatgaatcataccattatatattaactaaatccaaggtaaaaaaaggtatgaaag*
*ctctatagtaagtaaaatataaactccccataaggaaagggccaagtccaccaggcaagtaaaatgagcaagcacca*
*ctccaccatcacacaatttcactcatagataacgataagattcatggaattatctttccacgtggcattattccagcg*
*gttcaagccgataagggtctcaacacctctccttaggcctttgtggccgttaccaagtaaaattaacctcacacata*
*tccacactcaaaatccaacggtgtagatcctagtccacttgaatctcatgtatcctagaccctccgatcactccaaa*
*gcttgttctcattgttgttatcaccatatatagatgaccaaagcactagaccaaacctcagtcacacaaagagtaaa*
*gaagaaca*<u>ATGAAAGCCTTCACACTCGCTCTCTTCTTAGCTCTTTTCCTCTATCTCCTGCCCAATCCAGCCCATTCC</u>
ACTATTAATGCAGACAATGTTAATGAAAATCAAACTGTAGAAGTAACTGCTAGTTCAGTAAACAATGAAAATAATAA
GCAAGTAACTGAAAAAGATAGTGCAGATAAAAGTACTAGTGATGTGGCTGAAGATGCTAACACCAAGAAATCAAACG
AAAATACAGAAACTACAGAAAAGAATACTCAAACAGTTGTTACTAATGCGCCAGTAAGTGATGTGAAAAATACAAAC
ACAGTTACCGCTGAAACACCTGTTGATAAAGTAGTAAATAATAGTGATCAAAAGACAACTAATGCTGCAACTACTGA
TACTAAAAAAGATGATGTAAAACAAGTTGAAAAGAAAGACTCAGTAGATAAAACAAATGCTGAGGAAAATAAAGATA
GTTCAGTAAAGCCAGCTGAAAATGCTACTAAGGCTGAATTAAAGGGCCAAGTTAAAGATATCGTTGAAGAATCTGGT
GTTGATACTAGCAAGTTAACTAATGATCAAATTAATGAATTAAATAAAATTAATTTCTCCAAAGAAGCAAAAAGTGG
TACTCAGTTAACTTACAACGACTTTAAAAAAATTGCTAAAACTTTAATTGAACAAGATGCTCGTTATGCTATTCCAT
TCTTCAATGCAAGTAAAATTAAAAATATGCCTGCTGCTAAAACACTTGATGCTCAAAGTGGAAAAGTAGAAGATTTG
GAAATTTGGGATTCATGGCCTGTTCAAGATGCAAAAACTGGTTACGTATCTAACTGGAATGGCTACCAATTAGTGAT
TGGTATGATGGGAGTTCCAAACGTCAATGATAACCACATTTATCTTCTTTACAACAAGTATGGTGATAATGACTTTA
ATCATTGGAAGAATGCCGGTCCTATTTTCGGTCTAGGTACTCCAGTTATTCAACAATGGTCTGGATCAGCAACTTTA
AATAAAGATGGCTCAATTCAACTTTACTACACTAAGGTTGATACTAGTGATAATAATACTAACCACCAAAAACTCGC

FIGURE 24 (CONT'D)

TAGTGCAACTGTTTACTTAAATCTTGAAAAAGATCAAGATAAGATTTCTATTGCTCATGTTGACAACGACCATATTG
TCTTTGAAGGTGATGGTTACCACTACCAAACTTATGACCAATGGAAAGAAACTAACAAGGGTGCTGACAATATCGCA
ATGCGTGATGCACACGTGATTGATGATGATAATGGTAATCGTTACCTTGTGTTTGAAGCAAGTACTGGAACCGAAAA
TTATCAAGGTGATGATCAAATTTATCAATGGTTAAATTACGGCGGTACTAACAAGGATAATTTAGGTGATTTCTTCC
AAATTTTATCTAACTCCGATATTAAAGATAGAGCTAAATGGTCAAACGCTGCAATTGGTATCATTAAATTAAATGAT
GATGTTAAGAATCCAAGTGTTGCAAAGGTCTACAGCCCACTTATTAGTGCACCAATGGTAAGTGATGAAATTGAACG
CCCTGATGTTGTTAAATTAGGTAATAAGTATTACTTATTTGCTGCTACTAGATTAAACCGTGGTAGTAACGATGATG
CTTGGATGGCAACTAACAAAGCAGTTGGTGATAACGTAGCTATGATTGGTTATGTTTCTGATAACTTAACTCATGGT
TATGTTCCATTGAATGAATCTGGCGTTGTTTTAACTGCATCTGTACCGGCTAACTGGCGTACTGCAACTTATTCATA
CTATGCAGTTCCAGTAGAAGGAAGAGATGATCAACTTTTAATTACTTCATACATCACTAATCGTGGTGAGGTTGCTG
GAAAGGGTATGCATGCAACTTGGGCACCAAGTTTCTTGTTACAAATTAATCCAGATAACACTACTACTGTTTTAGCT
AAAATGACTAACCAAGGGGATTGGATTTGGGATGATAGTAGTGAAAATCCAGATATGATGGGTGTACTTGAAAAAGA
TGCTCCAAATAGTGCTGCCCTTCCTGGAGAATGGGGAAAACCAGTTGATTGGGATTTAATTGGTGGATACAACTTGA
AGCCACACCAACCTGTAACTCCTATTCCAAATGTACCAACTACTCCTGAAACCCCAACCACACCAGATAAGCCAGAG
GTACCAACTACCCCTGAAGTTCCAACCACTCCAGAAACTCCAACTCCAGAAGCTCCAAAGAATCCAGTTAAGAAAAC
TAGTCAGTCTAAACTTCCAAAGGCTGGAGATAAAAATAGCTTTGCAGCAGTTGTTTTAGGTGCTGTAAGTTCAATAT
TAGGTGCTGTTGGTTTAACAGGTGTTTCAAAACGTAAACGTAATAATTAAgatcgttcaaacatttggcaataaagt
ttcttaagaatgaatcctgttgccggtcttgcgatgattatcatataatttctgttgaattacgttaagcatgaaat
aattaacatgtaatgcatgacgtaatttatgagatgggtttttatgattagagtcccgcaattatacatttaatacg
cgatagaaaacaaaatatagcgcgcaaactaggataaattatcgcgcgcggtgtcatcaatgttactagatc

FIGURE 25

*cgcggtcgagacttgtgtattatttctttcagttattacaagactttagctaaaatttgaaagactttactttaagaaa*
*atctttaacatctgagataatttcagcaatagattatatttcttcattactctagcagtatttcttgcagatcaatcgca*
*acatatatggtttgttagaaaaaatgcactatatatatatatattatttttcaatcaaaagcgcatgatatataata*
*tatatatatatatatatatgtgtgtgtgtatatggtcaaagaaatttcttatacaaatatacagaacacatatattt*
*gacaaaatcaaagtattacactaaacaatgagttggtgcatggccaaaacaaatatgtagattaaaaattccagcct*
*ccaaaaaaaatccaagtgttgtaaagcattatatatatatagtagacccaaatttttgtacaattccacactgat*
*cgaatttttaaagttgaatatctgacgtaggatttttttaatgtctttacctgaccatttactaataacattcatacg*
*tttcaatttgaaatacccctatacttatattgaatttggcacataataagaaacctaatcggtgatttatttcact*
*agtaaatttctggtgatgggctttctactagaaagctctggaaaactttggaccaaatccatattccatgacttcg*
*atttgttaaccctattagtttttcacaaacatactatcaatatcattgcaacggaaaggtacaagtaaaacattcaat*
*ccgatagggaagtgatgcaggaggtttggaagacaggcccagaaagagatttatctgactttgttttgtgtatagttt*
*tcaatgcttcataaaggaagatggagacttgagaagttttttttcggactttgtttagctttgtttggcgttttttttt*
*tttgatcaataactttgttcggcttatgatttgtaacatcttcgtggacttttagtttatttagacgtgctaactt*
*tgttgggcttatgacttgttgtaacatattgtaacagatgacttgatgtgcgactaatctttacacattaaacatag*
*tttcgtttttttgaaagtttttatttccatttttatttgaacgttatatattttttccatattcataattctagtaaaa*
*ggcaaatttttgctttttaaatgaaaaaaatatatactccacagtttcacctaatcttatgcatttagcagtacaaatt*
*caaaaatttcccatttttattcatgaatcatacccattatatattaactaaatccaaggtaaaaaaaaggtatgaaag*
*ctctatagtaagtaaaatataaattccccataaggaaagggccaagtccacccaggcaagtaaaatgagcaagcacca*
*ctccaccatcacacaatttcactcatagataacgataagattcatggaatttactttccacgtggcatttattccagcg*
*gttcaagccgataagggtctcaacacctctcctcaggcctttgtggccgttaccaagtaaaattaacctcacacata*
*tcccacactcaaaatccaacggtgtagatcctagtccacttgaatctcatgtatcctagaccctccgaccactccaaa*
*gcttgttctcacttgttgctatcacttatatatagatgaccaaagcactagaccaaacctcagtcacacaaagagtaaa*
*gaagaaca*ATGGAGTCCCCAAGCGCCGTCGTCCCCGGCACCACGGCGCCGCTGCTTCCTTATGCGTACGCGCCGCTG
CCGTCGTCCCGCCGACGACGCCCGTCAAAACCGGAGTGGCGGGAGGTGGCGCGCGTGCGCCGCCGTGCTGGCCGCATC
GGCGTTGGCGGTGGTCGTCGTGGTCGGGCTCCTCGGCGGCGGCAGGGTGGATCGGGTCCCGGCCGGCGGAACGAACC
AAAAGCCATATAAGGAAACATACGGCATTTCCCATATTACACGCCATGATATGCTGCAAATGCCTGAACAGCAAAAA
AATGAAAAATATCAAGTTCCTGAATTCGATTCCTCCACAATTAAAAATATCTCTTCTGCAAAAGGCCTGGACGTTTG
GGACAGCTGGCCATTACAAAACGCTGACGGCACTGTCCGAAACTATCACGGCTACCACATCGTCTTTGCATTAGCCG
GAGATCCTAAAAATGCGGATGACACATCGATTTACATGTTCTATCAAAAAGTCGGCGAAACTTCTATTGACAGCTGG
AAAAACGCTGGCCGGTCTTTAAAGACAGCGACAAATTCGATGCAAATGATTCTATCCTAAAAGACCAAACACAAGA
ATGGTCAGGTTCAGCCACATTTACATCTGACGGAAAAATCCGTTTATTCTACACTGATTTCTCCGGTAAACATTACG
GCAAACAAACACTGACAACTGCACAAGTTAACGTATCAGCATCAGACAGCTCTTTGAACATCAACGGTGTAGAGGAT
TATAAATCAATCTTTGACGGTGACGGAAAAACGTATCAAAATGTACAGCAGTTCATCGATGAAGGCAACTACAGCTC
AGGCGACAACCATACGCTGAGAGATCCTCACTACGTAGAAGATAAAGGCCACAAATACTTAGTATTTGAAGCAAACA
CTGGAACTGAAGATGGCTACCAAGGCGAAGAATCTTTATTTAACAAAGCATACTATGGCAAAAGCACATCATTCTTC
CGTCAAGAAAGTCAAAAACTTCTGCAAAGCGATAAAAAACGCACGGCTGAGTTAGCAAACGGCGCTCTCGGTATGAT

FIGURE 25 (CONT'D)

TGAGCTAAACGATGATTACACACTGAAAAAAGTGATGAAACCGCTGATTGCATCTAACACAGTAACAGATGAAATTG
AACGCGCGAACGTCTTTAAAATGAACGGCAAATGGTACCTGTTCACTGACTCCCGCGGATCAAAAATGACGATTGAC
GGCATTACGTCTAACGATATTTACATGCTTGGTTATGTTTCTAATTCTTTAACTGGCCCATACAAGCCGCTGAACAA
AACTGGCCTTGTGTTAAAAATGGATCTTGATCCTAACGATGTAACCTTTACTTACTCACACTTCGCTGTACCTCAAG
CGAAAGGAAACAATGTCGTGATTACAAGCTATATGACAAACAGAGGATTCTACGCAGACAAACAATCAACGTTTGCG
CCAAGCTTCCTGCTGAACATCAAAGGCAAGAAAACATCTGTTGTCAAAGACAGCATCCTTGAACAAGGACAATTAAC
AGTTAACAAATAAgatcgttcaaacatttggcaataaagtttcttaagaatgaatcctgttgccggtcttgcgatga
ttatcatataatttctgttgaattacgttaagcatgaaataattaacatgtaatgcatgacgtaatttatgagatgg
gtttttatgattagagtcccgcaattatacatttaatacgcgatagaaaacaaaatatagcgcgcaaactaggataa
attatcgcgcgcggtgtcatcaatgttactagatc

FIGURE 26 cgtggtcgagattgtgtacttattccttagttattacaagacttttagctaaaatttgaaagaattcacttcaagaaa
atcttaacatctgagataatttcagcaatagattatactttttcattactctagcagtattcttgcagatcaatcgca
acatatatggttgttagaaaaaatgcactatatatatatatattattcttttcaattaaaagtgcatgatatataata
tatatatatatatatatacgtgtgtgtgtatatggtcaaagaaattcttatacaaatatacacgaacacatatattt
gacaaaatcaaagtattacactaaacaatgagttggtgcatggccaaaacaaatatgtagattaaaaattccagcct
ccaaaaaaaaatccaagtgttgtaaagcattatatatatatagtagatccccaaattttgtacaattccacactgat
cgaattttcaaagttgaatatctgacgtaggatttttcaatgtccttacctgaccatttactaataacattcatacg
ttttcatttgaaatatcctctataattatattgaatttggcacataataagaaacctaattggtgatttcattttact
agtaaattttctggtgatgggctttctactagaaagctctcggaaaatcttggaccaaatccatattccatgacttcg
attgttaacccctattagttttcacaaacatactatcaatatcattgcaacggaaaggtacaagtaaaacattcaat
ccgatagggaagtgatgtaggaggttgggaagacaggcccagaaagagatttatctgacttgttttgtgtatagttt
tcaatgttcataaaggaagatggagacttgagaagtttttttggactttgtttagctttgttgggcgttttttttt
tttgatcaatactttgttgggcttatgatttgtaatatttcgtggactcttagtttatttagacgcgctaactt
tgttgggcttatgacttgttgtaacatattgtaacagatgacttgatgtgcgactaatctttacacattaaacatag
ttctgtttttgaaagttcttatttttcatttttatttgaatgttatatatttttctatatttatatttctagtaaaa
ggcaaatttgctttaaatgaaaaaatatatattccacagtttcacctaatcttatgcatttagcagtacaaatt
caaaaattcccatttttattcatgaatcatacccattatatattaactaaatccaggtaaaaaaaaggtatgaaag
ctctatagtaagtaaaatataaattccccataaggaaagggccaagtccaccaggcaagtaaaatgagcaagcacca
ctccacccatcacacaatttcactcatagataacgataagattcatggaattatcttccacgtggcattattccgcg
gttcaagccgataagggtctcaacacctctccttaggcctttgtggccgttaccaagtaaaattaacctcacacata
tccacactcaaatccaacggtgtagatcctagtccacttgaatctcatgtatcctagaccctccgatcactccaaa
gcttgttcctcattgttgttatcattatatatagatgacccaaagcactagaccaaaccctcagtcacacaaagagtaaa
gaagaaca*ATGGAGTCCCCAAGCGCCGTCGTCCCCGGCACCACGGCGCCGCTGCTTCCTTATGCGTACGCGCCGCTG*
*CCGTCGTCCGCCGACGACGCCCGTCAAAACCGGAGTGGCGGGAGGTGGCGCGCGTGCGCCGCCGTGCTGGCCGCATC*
*GGCGTTGGCGGTGGTCGTCGTGGTCGGGCTCCTCGCGGCGGCAGGGTGGATCGGGTCCCGGCCGGCGGA*ACTATTA
ATGCAGACAATGTTAATGAAAATCAAACTGTAGAAGTAACTGCTAGTTCAGTAAACAATGAAAATAATAAGCAAGTA
ACTGAAAAAGATAGTGCAGATAAAAGTACTAGTGATGTGGCTGAAGATGCTAACACCAAGAAATCAAACGAAAATAC
AGAAACTACAGAAAAGAATACTCAAACAGTTGTTACTAATGCGCCAGTAAGTGATGTGAAAAATACAAACACAGTTA
CCGCTGAAACACCTGTTGATAAAGTAGTAAATAATAGTGATCAAAAGACAACTAATGCTGCAACTACTGATACTAAA
AAAGATGATGTAAAACAAGTTGAAAAAGAAAGACTCAGTAGATAAAACAAATGCTGAGGAAAATAAAGATAGTTCAGT
AAAGCCAGCTGAAAATGCTACTAAGGCTGAATTAAAGGGCCAAGTTAAAGATATCGTTGAAGAATCTGGTGTTGATA
CTAGCAAGTTAACTAATGATCAAATTAATGAATTAAATAAAATTAATTTCTCCAAAGAAGCAAAAAGTGGTACTCAG
TTAACTTACAACGACTTTAAAAAAATTGCTAAAACTTTAATTGAACAAGATGCTCGTTATGCTATTCCATTCTTCAA
TGCAAGTAAAATTAAAAATATGCCTGCTGCTAAAACACTTGATGCTCAAAGTGGAAAAGTAGAAGATTTGGAAATTT
GGGATTCATGGCCTGTTCAAGATGCAAAAACTGGTTACGTATCTAACTGGAATGGCTACCAATTAGTGATTGGTATG
ATGGGAGTTCCAAACGTCAATGATAACCACATTTATCTTCTTTACAACAAGTATGGTGATAATGACTTTAATCATTG

FIGURE 26 (CONT'D)

GAAGAATGCCGGTCCTATTTTCGGTCTAGGTACTCCAGTTATTCAACAATGGTCTGGATCAGCAACTTTAAATAAAG
ATGGCTCAATTCAACTTTACTACACTAAGGTTGATACTAGTGATAATAATACTAACCACCAAAAACTCGCTAGTGCA
ACTGTTTACTTAAATCTTGAAAAAGATCAAGATAAGATTTCTATTGCTCATGTTGACAACGACCATATTGTCTTTGA
AGGTGATGGTTACCACTACCAAACTTATGACCAATGGAAAGAAACTAACAAGGGTGCTGACAATATCGCAATGCGTG
ATGCACACGTGATTGATGATGATAATGGTAATCGTTACCTTGTGTTTGAAGCAAGTACTGGAACCGAAAATTATCAA
GGTGATGATCAAATTTATCAATGGTTAAATTACGGCGGTACTAACAAGGATAATTTAGGTGATTTCTTCCAAATTTT
ATCTAACTCCGATATTAAAGATAGAGCTAAATGGTCAAACGCTGCAATTGGTATCATTAAATTAAATGATGATGTTA
AGAATCCAAGTGTTGCAAAGGTCTACAGCCCACTTATTAGTGCACCAATGGTAAGTGATGAAATTGAACGCCCTGAT
GTTGTTAAATTAGGTAATAAGTATTACTTATTTGCTGCTACTAGATTAAACCGTGGTAGTAACGATGATGCTTGGAT
GGCAACTAACAAAGCAGTTGGTGATAACGTAGCTATGATTGGTTATGTTTCTGATAACTTAACTCATGGTTATGTTC
CATTGAATGAATCTGGCGTTGTTTTAACTGCATCTGTACCGGCTAACTGGCGTACTGCAACTTATTCATACTATGCA
GTTCCAGTAGAAGGAAGAGATGATCAACTTTTAATTACTTCATACATCACTAATCGTGGTGAGGTTGCTGGAAAGGG
TATGCATGCAACTTGGGCACCAAGTTTCTTGTTACAAATTAATCCAGATAACACTACTACTGTTTTAGCTAAAATGA
CTAACCAAGGGGATTGGATTTGGGATGATAGTAGTGAAAATCCAGATATGATGGGTGTACTTGAAAAAGATGCTCCA
AATAGTGCTGCCCTTCCTGGAGAATGGGGAAAACCAGTTGATTGGGATTTAATTGGTGGATACAACTTGAAGCCACA
CCAACCTGTAACTCCTATTCCAAATGTACCAACTACTCCTGAAACCCCAACCACACCAGATAAGCCAGAGGTACCAA
CTACCCCTGAAGTTCCAACCACTCCAGAAACTCCAACTCCAGAAGCTCCAAAGAATCCAGTTAAGAAAACTAGTCAG
TCTAAACTTCCAAAGGCTGGAGATAAAAATAGCTTTGCAGCAGTTGTTTTAGGTGCTGTAAGTTCAATATTAGGTGC
TGTTGGTTTAACAGGTGTTTCAAAACGTAAACGTAATAATTAAgatcgttcaaacatttggcaataaagtttcttaa
gaatgaatcctgttgccggtcttgcgatgattatcatataatttctgttgaattacgttaagcatgaaataattaac
atgtaatgcatgacgtaatttatgagatgggtttttatgattagagtcccgcaattatacatttaatacgcgataga
aaacaaaatatagcgcgcaaactaggataaattatcgcgcgcggtgtcatctatgttactagatc

A

B

C

D

FIGURE 29 gatccggtgactcaaaaagaagagccgccatctgtccaagcgccactcctacgagaactaaaatccctattccctcc
gtaaataaatataagagtgtttagatcactactctttacagagaatttccttccctccaaggggaggcgaatccat
aggcacatcgacggatatggaggggggaaacatatatttactatgctagttcagttaattctaccagaaaacata
tatttattttgacaaacattgtataaatgtagacattcacatacacgtatgtacaccaccccctatgattgcacac
ccgcacactatatgcctatgagcatactttcaagagtgagccagcaaatttcatgataaaatgaaatatttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACGAAC
CAAAAGCCATATAAGGAAACATACGGCATTTCCCATATTACACGCCATGATATGCTGCAAATCCCTGAACAGCAAAA
AAATGAAAAAATATCAAGTTCCTGAATTCGATTCGTCCACAATTAAAAATATCTCTTCTGCAAAAGGCCTGGACGTTT
GGGACAGCTGGCCATTACAAAACGCTGACGGCACTGTCGCAAACTATCACGGCTACCACATCGTCTTTGCATTAGCC
GGAGATCCTAAAAATGCGGATGACACATCGATTTACATGTTCTATCAAAAAGTCGGCGAAACTTCTATTGACAGCTG
GAAAAACGCTGGCCGCGTCTTTAAAGACAGCGACAAATTCGATGCAAATGATTCTATCCTAAAAGACCAAACACAAG
AATGGTCAGGTTCAGCCACATTTACATCTGACGGAAAAATCCGTTTATTCTACACTGATTTCTCCGGTAAACATTAC
GGCAAACAAACACTGACAACTGCACAAGTTAACGTATCAGCATCAGACAGCTCTTTGAACATCAACGGTGTAGAGGA
TTATAAATCAATCTTTGACGGTGACGGAAAAACGTATCAAAATGTACAGCAGTTCATCGATGAAGGCAACTACAGCT
CAGGCGACAACCATACGCTGAGAGATCCTCACTACGTAGAAGATAAAGGCCACAAATACTTAGTATTTGAAGCAAAC
ACTGGAACTGAAGATGGCTACCAAGGCGAAGAATCTTTATTTAACAAAGCATACTATGGCAAAAGCACATCATTCTT
CCGTCAAGAAAGTCAAAAACTTCTGCAAAGCGATAAAAAACGCACGGCTGAGTTAGCAAACGGCGCTCTCGGTATGA
TTGAGCTAAACGATGATTACACACTGAAAAAAGTGATGAAACCGCTGATTGCATCTAACACAGTAACAGATGAAATT
GAACGCGCGAACGTCTTTAAAATGAACGGCAAATGGTACCTGTTCACTGACTCCCGCGGATCAAAAATGACGATTGA
CGGCATTACGTCTAACGATATTTACATGCTTGGTTATGTTTCTAATTCTTTAACTGGCCCATACAAGCCGCTGAACA
AAACTGGCCTTGTGTTAAAAATGGATCTTGATCCTAACGATGTAACCTTTACTTACTCACACTTCGCTGTACCTCAA
GCGAAAGGAAACAATGTCGTGATTACAAGCTATATGACAAACAGAGGATTCTACGCAGACAAACAATCAACGTTTGC
GCCAAGCTTCCTGCTGAACATCAAAGGCAAGAAAACATCTGTTGTCAAAGACAGCATCCTTGAACAAGGACAATTAA
CAGTTAACAAATAAactatgagttgaaacaatggcctatctcatatgaagatcttttgtgaatttcacttttgtcca
cgacctctgttgcacgactctgctttccgacccggagcatacctttgttctatatgatttgtgtatgtatgtaggaa
cctatgttctcgagcatgcatacataattccctcataggtctatatacacggctatccatatgcaaaacctgtgtaa
tatttgttatatacaacacgcggaccattgtcttgctgttattaattcttttttcccgcaaaaaaggaaaagtttct
ttatttggcactgcaatggatatgcctcacagctagtgggtggagaattcagtatttgacattaagattccctgatt
tgcaattgcaaatttcagtttctttacttatatcactacaaaagtcttattgcttctttttccacgtcattaccatct
gctccattggtttttgctagtagaataggatgaagcatggacacagattaactgagctcgagctcatatgagctcgg
gtgaacaataaaatctgaaaatacttagaaagaattcaaaatttttctgtttttgtggcaaaatttgacaaatgtta
taaatgcttgcaaagtttcatcatagaacgacattcgtggatgtcatggcaaaaaacaaattcagcactctgaaaat
aactttttttgaagtatcg

FIGURE 30 gatccggtgactcaaaaagaagagcgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggaggggggaaacatatatttactatgctagttcagttaattctaccaagaaaacata
tattttatttgacaaacattgtataaatgtagacattcacatacacgtatgtacaccaccctctatgattgcacac
ccgcacactatatgcctatgagcatactttcaagagtgagccagcaaatttttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttctccact
gatccggagaagataaggaaacgaggcaaccagcgaacgtgagccatcccaaccacatctgtaccaaagaaacgggg
ctatatatacgtggtgacccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACGAAC
CAAAAGCCATATAAGGAAACATACGGCATTTCCCATATTACACGCCATGATATGCTGCAAATCCCTGAACAGCAAAA
AAATGAAAAATATCAAGTTCCTGAATTCGATTCGTCCACAATTAAAAATATCTCTTCTGCAAAAGGCCTGGACGTTT
GGGACAGCTGGCCATTACAAAACGCTGACGGCACTGTCGCAAACTATCACGGCTACCACATCGTCTTTGCATTAGCC
GGAGATCCTAAAAATGCGGATGACACATCGATTTACATGTTCTATCAAAAAGTCGGCGAAACTTCTATTGACAGCTG
GAAAAACGCTGGCCGCGTCTTTAAAGACAGCGACAAATTCGATGCAAATGATTCTATCCTAAAAGACCAAACACAAG
AATGGTCAGGTTCAGCCACATTTACATCTGACGGAAAAATCCGTTTATTCTACACTGATTTCTCCGGTAAACATTAC
GGCAAACAAACACTGACAACTGCACAAGTTAACGTATCAGCATCAGACAGCTCTTTGAACATCAACGGTGTAGAGGA
TTATAAATCAATCTTTGACGGTGACGGAAAAACGTATCAAAATGTACAGCAGTTCATCGATGAAGGCAACTACAGCT
CAGGCGACAACCATACGCTGAGAGATCCTCACTACGTAGAAGATAAAGGCCACAAATACTTAGTATTTGAAGCAAAC
ACTGGAACTGAAGATGGCTACCAAGGCGAAGAATCTTTATTTAACAAAGCATACTATGGCAAAAGCACATCATTCTT
CCGTCAAGAAAGTCAAAAACTTCTGCAAAGCGATAAAAAACGCACGGCTGAGTTAGCAAACGGCGCTCTCGGTATGA
TTGAGCTAAACGATGATTACACACTGAAAAAAGTGATGAAACCGCTGATTGCATCTAACACAGTAACAGATGAAATT
GAACGCGCGAACGTCTTTAAAATGAACGGCAAATGGTACCTGTTCACTGACTCCCGCGGATCAAAAATGACGATTGA
CGGCATTACGTCTAACGATATTTACATGCTTGGTTATGTTTCTAATTCTTTAACTGGCCCATACAAGCCGCTGAACA
AAACTGGCCTTGTGTTAAAAATGGATCTTGATCCTAACGATGTAACCTTTACTTACTCACACTTCGCTGTACCTCAA
GCGAAAGGAAACAATGTCGTGATTACAAGCTATATGACAAACAGAGGATTCTACGCAGACAAACAATCAACGTTTGC
GCCAAGCTTCCTGCTGAACATCAAAGGCAAGAAAACATCTGTTGTCAAAGACAGCATCCTTGAACAAGGACAATTAA
CAGTTAACAAATAAactatgagttgaaacaatggcctatctcatatgaagatctttttgtgaatttcactttttgtcca
cgacctctgttgcacgactctgctttccgaccggagcataccttttgtttctatatgatttgtgtatgtatgtaggaa
cctatgttctcgagcatgcatacataatttcctcataggtctatatacaccggctatccatatgcaaaaacctgtgtaa
tatttgttatatacaacacgcggaccattgtcttgctgttatttaattctttttttcccgcaaaaaaggaaaagtttct
ttatttggcactgcaatggatatgcctcacagctagtgggtggagaattcagcatttgacattaagattccctgatt
tgcaattgcaaatttcagtttctttacttatatcactacaaaagtcttattgtttctttccacgtcattaccatct
gctccattggtttttgctagtagaataggatgaagcatggacacagattaactgagctcgagctcatatgagctcgg
gtgaacaataaaatctgaaaatacttagaaagaattcaaaatttttctgttttttgtggcaaaatttgacaaatgtta

FIGURE 30 (CONT'D)

taaatgcttgcaaagtttcatcatagaacgacattcgtggatgtcatggcaaaaaacaaattcagcactctgaaaat
aactttttttgaagcatcggttttgtgttcttctagattaatcctccaaactttttgattaaccaaaaaaatttatcaaact
aacatgtttctccttttttcttttagaaattctaacgaatttatctttatactgatttgaatatactttaatttggtcat
ttggatgcccttttacaacctccttaccaaactcactatggcaaatatatactattttccattgtaacataaatgtcc
ataatttgaattaaattggttgcagtacgaaaccatccaactttgtccaaaaacaaaatccttataactatttactt
taatgtaaatatatcctctactttcgtttttacaaccctagctcaaacaaatttattatttgcgataaaaaatcata
tcgaacaaactcgatgatttttttttttcttacgttattaatgaaactaaaatatagaaaaaaaacaagatgaaccaaa
ttttcacctatctaactacttaaatataatatgattaaatttggtaaagtttgaaaagttttctttagaaatatgaa
atattgatcacagtttctattgctaaaatcaccaacaaaacgcatgtcgccattcataattatggtttcacactac
aactagcctaataagtaaataagtagacaactagactcagtttgaaaaaaccataaagccatatagcgttttctc
atttaaactacgaacacgatcatgtgaatgttgcagtttctagttttgatacaaacaaacaaaacacaatttaatc
ttagattaaaagaaaaaagagaacaggagcccactagccactcctcaaacgtgtcttaccaactctcttctagaaa
caaattaggcttcaccttccctttccaaccctctctctctctctctctctcttttctcaaaccatctctccataaag
ccctaattctttcatcacaagaatcagaagaatactgcaaaaaactATGGACCTGCATCTAATTTTCGGTCCAACT
TGCACAGGAAAGACGACGACCGCGATAGCTCTTGCCCAGCAGACAGGCTTCCAGTCCTTTCGCTTGATCGGTCCA
ATGCTGTCCTCAACTATCAACCGGAACGGACGACCAACAGTGGAAGAACTGAAAGGAACGACGCGTCTCTACCTTG
ATGATCGGCCTCTGGTGGAGGTATCATCGCAGCCAAGCAAGCTCATCATAGGCTGATCGAGGAGGTGTATAATCAT
GAGGCCAACGGCGGGCTTATTCTTGAGGGAGGATCCACTTCGTTGCTCAACTGCATGGCGCGAAACAGCTATTGGAG
TGCAGATTTTCGTTGGCATATTATTCGCCACAAGTTACCCGACCAAGAGACCTTCATGAAAGCGGCCAAGGCCAGAG
TTAAGCAGATGTTGCACCCCGCTGCAGGCCATTCTATTATTCAAGAGTTGGTTTATCTTTGGAATGAACCTCGGCTG
AGGCCCATTCTGAAAGAGATCGATGGATATCGATATGCCATGTTGTTTGCTAGCCAGAACCAGATCACGGCAGATAT
GCTATTGCAGCTTGACGCAAATATGGAAGGTAAGTTGATTAATGGGATCGCTCAGGAGTATTTCATCCATGCGCGCC
AACAGGAACAGAAATTCCCCCAAGTTAACGCAGCCGCTTTCGACGGATTCGAAGGTCATCCGTTCGGAATGTATTAG
GTAAgtccgcaaaaaatcaccagtctctctctacaaatctatctctctctatttttctccagaataatgtgtgagtag
ttcccagataagggaatttagggttcttatagggtttcgctcatgtgttgagcatataagaaacccttagtatgtatt
tgtatttgtaaaatacttctatcaataaaatttctaattcctaaaaccaaaatccagtgacct

FIGURE 31

*gatccggtgactcaaaaagaagagccgccatctgtccaagcgccactcctacgagaactaaatcctattccctcc*
*gtaaacaaatataagagtgttagatcactacttcttacagagaattccttccctccaggggaggcgaatccat*
*aggcacatcgacggatatggaggggggaaacatatattttactatgctagttcagttaattctaccaagaaaacata*
*tattttcattttgacaaacattgtataaatgtagacattcacatacacgtatgtacacccaccctctatgattgcacac*
*ccgcacactatatgcctatgagcatactttcaagagtgagccagcaaatttatgataaaatgaaatattttgccca*
*gccaactcagtcgcatcctcggacaatttgttatccaaggaactcacccaaaaacaagcaaagctagaaaaaggttgt*
*gtggcagcccacctaatgacatgaaggactgaaatttccagcacacacaatgtatcccgacggcaatgcttcttccact*
*gatccggagaagataaggaaacgaggcaaccagcgaacgtgagccatcccaacccacatctgtacccaagaaacgggg*
*ctatatataccgtggtgacccggcaatggggtccttcaactgtagcggcatcctcctctcctccgataatacaaata*
*cc*<u>ATGAAAGCCTTCACACTCGCTCTCTTCTTAGCTCTTTTCCTCTATCTCCTGCCCAATCCAGCCCATTCC</u>ACTATT
AATGCAGACAATGTTAATGAAAATCAAACTGTTAGAAGTAACTGCTAGTTCAGTAAACAATGAAAATAATAAGCAAGT
AACTGAAAAAGATAGTGCAGATAAAAGTACTAGTGATGTGGCTGAAGATGCTAACACCAAGAAATCAAACGAAAATA
CAGAAACTACAGAAAAAGAATACTCAAACAGTTGTTACTAATGCGCCAGTAAGTGATGTGAAAAATACAAACACAGTT
ACCGCTGAAACACCTGTTGATAAAGTAGTAAATAATAGTGATCAAAAGACAACTAATGCTGCAACTACTGATACTAA
AAAAGATGATGTAAAACAAGTTGAAAAGAAAGACTCAGTAGATAAAACAAATGCTGAGGAAAATAAAGATAGTTCAG
TAAAGCCAGCTGAAAAATGCTACTAAGCTGAATTAAAGGGCCAAGTTAAAGATATCGTTGAAGAATCTGGTGTTGAT
ACTAGCAAGTTAACTAATGATCAAATTAATGAATTAAATAAAATTAATTTCTCCAAAGAAGCAAAAAGTGGTACTCA
GTTAACTTACAACGACTTTAAAAAAATTGCTAAAACTTTAATTGAACAAGATGCTCGTTATGCTATTCCATTCTTCA
ATGCAAGTAAAATTAAAAATATGCCTGCTGCTAAAACACTTGATGCTCAAAGTGGAAAAGTAGAAGATTTGGAAATT
TGGGATTCATGGCCTGTTCAAGATGCAAAAACTGGTTACGTATCTAACTGGAATGGCTACCAATTAGTGATTGGTAT
GATGGGAGTTCCAAACGTCAATGATAACCACATTTATCTTCTTTACAACAAGTATGGTGATAATGACTTTAATCATT
GGAAGAATGCCGGTCCTATTTTCGGTCTAGGTACTCCAGTTATTCAACAATGGTCTGGATCAGCAACTTTAAATAAA
GATGGCTCAATTCAACTTTACTACACTAAGGTTGATACTAGTGATAATAATACTAACCACCAAAAACTCGCTAGTGC
AACTGTTTACTTAAATCTTGAAAAAGATCAAGATAAGATTTCTATTGCTCATGTTGACAACGACCATATTGTCTTTG
AAGGTGATGGTTACCACTACCAAACTTATGACCAATGGAAAGAAACTAACAAGGTGCTGACAATATCGCAATGCGT
GATGCACACGTGATTGATGATGATAATGGTAATCGTTACCTTGTGTTTGAAGCAAGTACTGGAACCGAAAATTATCA
AGGTGATGATCAAATTTATCAATGGTTAAATTACGGCGGTACTAACAAGGATAATTTAGGTGATTTCTTCCAAATTT
TATCTAACTCCGATATTAAAGATAGAGCTAAATGGTCAAACGCTGCAATTGGTATCATTAAATTAAATGATGATGTT
AAGAATCCAAGTGTTGCAAAGGTCTACAGCCCACTTATTAGTGCACCAATGGTAAGTGATGAAATTGAACGCCCTGA
TGTTGTTAAATTAGGTAATAAGTATTACTTATTTGCTGCTACTAGATTAAACCGTGGTAGTAACGATGATGCTTGGA
TGGCAACTAACAAAGCAGTTGGTGATAACGTAGCTATGATTGGTTATGTTTCTGATAACTTAACTCATGGTTATGTT
CCATTGAATGAATCTGGCGTTGTTTTAACTGCATCTGTACCGGCTAACTGGGGTACTGCAACTTATTCATACTATGC
AGTTCCAGTAGAAGGAAGAGATGATCAACTTTTAATTACTTCATACATCACTAATCGTGGTGAGGTTGCTGGAAAGG
GTATGCATGCAACTTGGGCACCAAGTTTCTTGTTACAAATTAATCCAGATAACACTACTACTGTTTTAGCTAAAATG
ACTAACCAAGGGGATTGGATTTGGGATGATAGTAGTGAAAATCCAGATATGATGGGTGTACTTGAAAAAGATGCTCC
AAATAGTGCTGCCCTTCCTGGAGAATGGGGAAAACCAGTTGATTGGGATTTAATTGGTGGATACAACTTGAAGCCAC
ACCAACCTGTAACTCCTATTCCAAATGTACCAACTACTCCTGAAACCCCAACCACACCAGATAAGCCAGAGGTACCA

FIGURE 31 (CONT'D)

ACTACCCCTGAAGTTCCAACCACTCCAGAAACTCCAACTCCAGAAGCTCCAAAGAATCCAGTTAAGAAAACTAGTCA
GTCTAAACTTCCAAAGCCTGGAGATAAAAATAGCTTTGCAGCAGTTGTTTTAGGTGCTGTAAGTTCAATATTAGGTG
CTGTTGGTTTAACAGGTGTTTCAAAACGTAAACGTAATAATTAAactatgagttgaaacaatggcctatctcatatg
aagatcttttgtgaatttcacttttgtcccacgacctctgttgcacgactctgctttccgaccggagcataccttttg
ttctatatgatttgtgtatgtatgtaggaacctatgttctcgagcatgcatacataattcctcataggtctatatac
accggctatccatatgcaaaacctgtgtaatatttgttatatacaacacgcggaccattgtcttgctgttattaatt
ctttttttcccgcaaaaaaggaaaagttctttatttggcactgcaatggatatgcctcacagctagtgggtggagaa
ttcagtatttgacattaagattccctgatttgcaattgcaaatttcagtttctttacttatatcactacaaaagtct
tattgtttctttcccacgtcattaccatctgctccattggtttttgctagtagaataggatgaagcatggacacaga
ttaactgagctcgagctcatatgagctcgggtgaacaataaaatctgaaaatacttagaaagaattcaaaattttct
gtttttttgtggcaaaatttgacaaatgttataaatgcttgcaaagtttcatcatagaacgacattcgtggatgtcat
ggcaaaaaacaaattcagcactctgaaaataacttttttgaagtatcg

FIGURE 32 gatccggtgactcaaaaagaagagccgccatctgtccaagcgccactcctacgagaactaaatcctattccctcc
gtaaataaatataagagtgtttagatcactacttctttacagagaatttcttccctccaaggggaggcgaatccat
aggcacatcgacggatatggaggggggaaacatatatttttactatgctagttcagttaattctaccaagaaaacata
tattttatttgacaaacattgtataaatgtagacattcacatacacgtatgtacaccaccctctatgattgcacac
ccgcacactatatgcctatgagcatactttcaagagtgagccagcaaatttatgataaaatgaaatatttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACTATT
AATGCAGACAATGTTAATGAAAATCAAACTGTAGAAGTAACTGCTAGTTCAGTAAACAATGAAAATAATAAGCAAGT
AACTGAAAAAGATAGTGCAGATAAAAGTACTAGTGATGTGGCTGAAGATGCTAACACCAAGAAATCAAACGAAAATA
CAGAAACTACAGAAAAGAATACTCAAACAGTTGTTACTAATGCGCCAGTAAGTGATGTGAAAAATACAAACACAGTT
ACCGCTGAAACACCTGTTGATAAAGTAGTAAATAATAGTGATCAAAAGACAACTAATGCTGCAACTACTGATACTAA
AAAAGATGATGTAAAACAAGTTGAAAAGAAAGACTCAGTAGATAAAACAAATGCTGAGGAAAATAAAGATAGTTCAG
TAAAGCCAGCTGAAAATGCTACTAAGGCTGAATTAAAGGGCCAAGTTAAAGATATCGTTGAAGAATCTGGTGTTGAT
ACTAGCAAGTTAACTAATGATCAAATTAATGAATTAAATAAAATTAATTTCTCCAAAGAAGCAAAAAGTGGTACTCA
GTTAACTTACAACGACTTTAAAAAAATTGCTAAAACTTTAATTGAACAAGATGCTCGTTATGCTATTCCATTCTTCA
ATGCAAGTAAAATTAAAAATATGCCTGCTGCTAAAACACTTGATGCTCAAAGTGGAAAAGTAGAAGATTTGGAAATT
TGGGATTCATGGCCTGTTCAAGATGCAAAAACTGGTTACGTATCTAACTGGAATGGCTACCAATTAGTGATTGGTAT
GATGGGAGTTCCAAACGTCAATGATAACCCACATTTATCTTCTTTACAACAAGTATGGTGATAATGACTTTAATCATT
GGAAGAATGCCGGTCCTATTTTCGGTCTAGGTACTCCAGTTATTCAACAATGGTCTGGATCAGCAACTTTAAATAAA
GATGGCTCAATTCAACTTTACTACACTAAGGTTGATACTAGTGATAATAATACTAACCACCAAAAACTCGCTAGTGC
AACTGTTTACTTAAATCTTGAAAAAGATCAAGATAAGATTTCTATTGCTCATGTTGACAACGACCATATTGTCTTTG
AAGGTGATGGTTACCACTACCAAACTTATGACCAATGGAAAGAAACTAACAAGGGTGCTGACAATATCGCAATGCGT
GATGCACACGTGATTGATGATGATAATGGTAATCGTTACCTTGTGTTTGAAGCAAGTACTGGAACCGAAAATTATCA
AGGTGATGATCAAATTTATCAATGGTTAAATTACGGCGGTACTAACAAGGATAATTTAGGTGATTTCTTCCAAATTT
TATCTAACTCCGATATTAAAGATAGAGCTAAATGGTCAAACGCTGCAATTGGTATCATTAAATTAAATGATGATGTT
AAGAATCCAAGTGTTGCAAAGGTCTACAGCCCACTTATTAGTGCACCAATGGTAAGTGATGAAATTGAACGCCCTGA
TGTTGTTAAATTAGGTAATAAGTATTACTTATTTGCTGCTACTAGATTAAACCGTGGTAGTAACGATGATGCTTGGA
TGGCAACTAACAAAGCAGTTGGTGATAACGTAGCTATGATTGGTTATGTTTCTGATAACTTAACTCATGGTTATGTT
CCATTGAATGAATCTGGCGTTGTTTTAACTGCATCTGTACCGGCTAACTGGCGTACTGCAACTTATTCATACTATGC
AGTTCCAGTAGAAGGAAGAGATGATCAACTTTTAATTACTTCATACATCACTAATCGTGGTGAGGTTGCTGGAAAGG
GTATGCATGCAACTTGGGCACCAAGTTTCTTGTTACAAATTAATCCAGATAACACTACTACTGTTTTAGCTAAAATG
ACTAACCAAGGGGATTGGATTTGGGATGATAGTAGTGAAAATCCAGATATGATGGGTGTACTTGAAAAAGATGCTCC
AAATAGTGCTGCCCTTCCTGGAGAATGGGGAAAACCAGTTGATTGGGATTTAATTGGTGGATACAACTTGAAGCCAC
ACCAACCTGTAACTCCTATTCCAAATGTACCAACTACTCCTGAAACCCCAACCACACCAGATAAGCCAGAGGTACCA

FIGURE 32 (CONT'D)

ACTACCCCTGAAGTTCCAACCACTCCAGAAACTCCAACTCCAGAAGCTCCAAAGAATCCAGTTAAGAAAACTAGTCA
GTCTAAACTTCCAAAGGCTGGAGATAAAAATAGCTTTGCAGCAGTTGTTTTAGGTGCTGTAAGTTCAATATTAGGTG
CTGTTGGTTTAACAGGTGTTTCAAAACGTAAACGTAATAATTAAactatgagttgaaacaatggcctatctcatatg
aagatcttttgtgaatttcactttgtccacgacctctgttgcacgactctgctttccgacggagcatacctttttg
ttctatatgatttgtgtatgtatgtaggaacctatgttctcgagcatgcatacataattcctcataggtctatatac
accggctatccatatgcaaaacctgtgtaatatttgttatatacaacacgcggaccattgtcttgctgttattaatt
ctttttcccgcaaaaaaggaaaagtttctttatttggcactgcaatggatatgcctcacagctagtgggtggagaa
ttcagtatttgacattaagattccctgatttgcaattgcaaatttcagtttctttacttatatcactacaaagtct
tattgtttctttccacgtcattaccatctgctccattggtttttgctagtagaataggatgaagcatggacacaga
ttaactgagctcgagctcatatgagctcgggtgaacaataaaatctgaaaatacttagaaagaattcaaatttttct
gtttttgtggcaaaatttgacaaatgttataaatgcttgcaaagtttcatcatagaacgacattcgtggatgtcat
ggcaaaaaacaaattcagcactctgaaaataactttttgaagtatcggtttgtgtcttctagattaatcctccaaa
ctttgattaaccaaaaaaattatcaaactaacatgttctcctttttctttagaaactctaacgaatttatcttta
tactgatttgaatatacttaatttggtcatttggatgccctttacaacctccttaccaaactcactatggcaaatat
atactattttccattgtaacataaatgtccataatttgaactaaattcgtttgcagtacgaaaccatccaactttgtc
caaaaacaaaatccttataactatttactttaatgtaaatatatcctctactttttgtttttacaaccctagctcaaa
caaatttatttatttgcgataaaaaatcatatcgaacaaactcgatgatttttttttcttacgttattaatgaaact
aaaatatagaaaaaaacaagatgaaccaaatttttcacctatctaactacttaaatataatatgattaaatttggtaa
agtttgaaaagtttctttaggaaatgtgaaatatttgatcacagtttctatttgctaaaatcaccaacaaaacgcatgt
cgccatttcataattatggtttcacacctacaactaggctaataagtaaataagtagacaactagactcaggtttgaa
aaaaccataaaagcccatatagcgtttttctccattgaaactgcgaacacgatcgtgtgaatgttgcagtttctagtttt
gatacaaacaaacaaaaacacaatttaatcttagttaaaaagaaaaaagagaacggagcccactagccactccttc
aaacgtgtcttaccaactctcttctagaaacaaattaggcttcaccttcctcttccaaactctctctctctctctct
ctctctttctcaaaccatctctccataaagccctaatttcttcatcacaagaatcagaagaatactgcaaaaaactt
ATGGACCTGCATCTAATTTTCGGTCCAACTTGCACAGGAAAGACGACGACCGCGATAGCTCTTGCCCAGCAGACAGG
GCTTCCAGTCCTTTCGCTTAATCGGGTCCAATGCTGTCCTCAACTATCAACCGGAAGCGGACGACCAACAGTGGAAG
AACTGAAAGGAACGACGCGTCTCTACCTTGATGATCGGCCTCTGGTGGAGGGTATCATCGCAGCCAAGCAAGCTCAT
CATAGGCTGATCGAGGAGGTGTATAATCATGAGGCCAACGGCGGGCTTATTCTTGAGGGAGGATCCACCTCGTTGCT
CAACTGCATGGCGCGAAACAGCTATTGGAGTGCAGATTTTCGTTGGCATATTATTCGCCACAAGTTACCCGACCAAG
AGACCTTCATGAAAGCGGCCAAGGCCAGAGTTAAGCAGATGTTGCACCCCGCTGCAGGCCATTCTATTATTCAAGAG
TTGGTTTATCTTTGGAATGAACCTCGGCTGAGGCCCATTCTGAAAGAGATCGATGGATATCGATATGCCATGTTGTT
TGCTAGCCAGAACCAGATCACGGCAGATATGCTATTGCAGCTTGACGCAAATATGGAAGGTAAGTTGATTAATGGGA
TCGCTCAGGAGTATTTCATCCATGCGCGCCAACAGGAACAGAAATTCCCCCAAGTTAACGCAGCCGCTTTCGACGGA
TTCGAAGGTCATCCGTTCGGAATGTATTAGGTAAgtcggcaaaaatcaccagtctctctctacaaatctatctctct
ctatttttctccagaataatgtgtgagtagttcccagataaggaattagggttcttataggggtttcgctcatgtgt
tgagcatataagaaacccttagtatgtatttgtatttgtaaaatacttctatcaataaaatttctaattcctaaaac
caaaatccagtgacct

FIGURE 33

GATCCGGTGACTCAAAAAAGAAGAGCCGCCATCTGTCCAAGCGCCACTCCTACGAGAACTAAAATCCTATTCCCTCC
GTAAATAAATATAAGAGTGTTTAGATCACTACTTCTTTACAGAGAATTTCCTTCCCTCCAAGGGGAGGCGAATCCAT
AGGCACATCGACGGATATGGAGGGGGGAAACATATATTTTACTATGCTAGTTCAGTTAATTCTACCAAGAAAACATA
TATTTTATTTTGACAAACATTGTATAAATGTAGACATTCACATACACGTATGTACACCACCCTCTATGATTGCACAC
CGGCACACTATATGCCTATGAGCATACTTTCAAGAGTGAGCGAGCAAATTTTATGATAAAATGAAATATTTTGCCCA
GCCAACTCAGTCGCATCCTCGGACAATTTGTTATCAAGGAACTCACCCAAAAACAAGCAAAGCTAGAAAAAGGTGGT
GTGGCAGCCACCTAATGACATGAAGGACTGAAATTTCCAGCACACACAATGTATCCGACGGCAATGCTTCTTCCACT
GATCCGGAGAAGATAAGGAAACGAGGCAACCAGCGAACGTGAGGCATCCCAACCACATCTGTACCAAAGAAACGGGG
CTATATATACCGTGGTGACCCGGCAATGGGGTCCTCAACTGTAGCCGGCATCCTCCTCTCCTCCGATAATACAAATA
CC*ATGGAGTCCCCAAGCGCCGTCGTCCCCGGCACCACGGCGCCGCTGCTTCCTTATGCGTACGCGCCGCTGCCGTCG*
*TCCGCCGACGACGCCCGTCAAAACCGGAGTGGCGGGAGGTGGCGCGCGTGCGCCGCCGTGCTGGCCGCATCGGCGTT*
*GGCGGTGGTCGTCGTGGTCGGGCTCCTCGCGGGCGGCAGGGTGGATCGGGTCCCGGCCGGCGGA*ACGAACCAAAAGC
CATATAAGGAAACATACGGCATTTCCCATATTACACGCCATGATATGCTGCAAATCCCTGAACAGCAAAAAAATGAA
AAATATCAAGTTCCTGAATTCGATTCGTCCACAATTAAAAATATCTCTTCTGCAAAAGGCCTGGACGTTGGGACAG
CTGGCCATTACAAAACGCTGACGGCACTGTCGCAAACTATCACGGCTACCACATCGTCTTTGCATTAGCCGGAGATC
CTAAAAATGCGGATGACACATCGATTTACATGTTCTATCAAAAAGTCGGCGAAACTTCTATTGACAGCTGGAAAAAC
GCTGGCCGCGTCTTTAAAGACAGCGACAAATTCGATGCAAATGATTCTATCCTAAAAGACCAAACACAAGAATGGTC
AGGTTCAGCCACATTTACATCTGACGGAAAAATCCGTTTATTCTACACTGATTTCTCCGGTAAACATTACGGCAAAC
AAACACTGACAACTGCACAAGTTAACGTATCAGCATCAGACAGCTCTTTGAACATCAACGGTGTAGAGGATTATAAA
TCAATCTTTGACGGTGACGGAAAAACGTATCAAAATGTACAGCAGTTCATCGATGAAGGCAACTACAGCTCAGGCGA
CAACCATACGCTGAGAGATCCTCACTACGTAGAAGATAAAGGCCACAAATACTTAGTATTTGAAGCAAACACTGGAA
CTGAAGATGGCTACCAAGGCGAAGAATCTTTATTTAACAAAGCATACTATGGCAAAAGCACATCATTCTTCCGTCAA
GAAAGTCAAAAACTTCTGCAAAGCGATAAAAAACGCACGGCTGAGTTAGCAAACGGCGCTCTCGGTATGATTGAGCT
AAACGATGATTACACACTGAAAAAAGTGATGAAACCGCTGATTGCATCTAACACAGTAACAGATGAAATTGAACGCG
CGAACGTCTTTAAAATGAACGGCAAATGGTACCTGTTCACTGACTCCCGCGGATCAAAAATGACGATTGACGGCATT
ACGTCTAACGATATTTACATGCTTGGTTATGTTTCTAATTCTTTAACTGGCCCATACAAGCCGCTGAACAAAACTGG
CCTTGTGTTAAAAATGGATCTTGATCCTAACGATGTAACCTTTACTTACTCACACTTCGCTGTACCTCAAGCGAAAG
GAAACAATGTCGTGATTACAAGCTATATGACAAACAGAGGATTCTACGCAGACAAACAATCAACGTTTGCGCCAAGC
TTCCTGCTGAACATCAAAGGCAAGAAAACATCTGTTGTCAAAGACAGCATCCTTGAACAAGGACAATTAACAGTTAA
CAAATAAAactatgagttgaaacaatggcctatctcatatgaagatctttgtgaatttcactttgtccacgacctc
tgttgcacgactctgctttccgacggagcataccttttgttctatatgatttgtgtatgtatgtaggaacctatgt
tctcgagcatgcatacataattcctcatggtctatatacaccggctatccatatgcaaaacctgtgtaatatttgt
tatatacaacacgcggaccattgtcttgctgttattaattcttttttcccgcaaaaaaggaaaagtttctttatttg
gcactgcaatggatatgcctcacagctagtgggtggagaacttcagtatttgacattaagattccctgatttgcaatt
gcaaatttcagtttctttacttatatcactacaaaagtcttattgtttctttttcacgtcattaccatctgctccat
tggtttttgctagtagaatagggatgaagcatggacacagattaactgagctcgagctcatatgagctcgggtgaaca
ataaaatctgaaaatacttagaaagaattcaaaactttctgtttttttgtggcaaaacttgacaaatgttataaatgc

FIGURE 33 (CONT'D)

ttgcaaagtttcatcatagaacgacattcgtggatgtcatggcaaaaaacaaattcagcactctgaaaataacttttt
ttgaagtatcg

FIGURE 34

*gatccggtgactcaaaaagaagagccgccatctgtccaagcgccactcctacgagaactaaatcctattccctcc*
*gtaaataaatataagagtgtttagatcactactttctttacagagaatttccttccctccaaggggaggcgaatccat*
*aggcacatcgacggatatggaggggggaaacatatattttactatgctagttcagttaatttctaccaagaaaacata*
*tatttcattttgacaaacattgtataaatgtagacattcacatacacgtatgtacaccaccctctatgattgcacac*
*ccgcacactatatgcctatgagcatactttcaagagtgagccagcaaatttttatgataaaatgaaatattttgccca*
*gccaactcagtcgcatccccggacaatttgtttatcaaggaactcacccaaaaacaagcaaagctagaaaaaggttgt*
*gtggcagccacctaatgacatgaaggactgaaatttccagcacacacaatgtatccgacggcaatgctttcttccact*
*gatcccggagaagataaggaaacgaggcaaccagcgaacgtgagccatcccaaccacatctgtaccaaagaaacgggg*
*ctatatataccgtggtgacccggcaatggggtcctcaactgtagccggcatccctcctctcctccgataatacaaata*
*cc*__*ATGGAGTCCCCAAGCGCCGTCGTCCCCGGCACCACGGCGCCGCTGCTTCCTTATGCGTACGCGCCGCTGCCGTCG*__
__*TCCGCCGACGACGCCCGTCAAAACCGGAGTGGCGGGAGGTGGCGCGCGTGCGCCGCCGTGCTGGCCGCATCGGCGTT*__
__*GGCGGTGGTCGTCGTGGTCGGGCTCCTCGCGGGCGGCAGGGTGGATCGGGTCCCGGCCGGCGGA*__ACGAACCAAAAGC
CATATAAGGAAACATACGGCATTTCCCATATTACACGCCATGATATGCTGCAAATCCCTGAACAGCAAAAAAATGAA
AAATATCAAGTTCCTGAATTCGATTCGTCCACAATTAAAAATATCTCTTCTGCAAAAGGCCTGGACGTTTGGGACAG
CTGGCCATTACAAAACGCTGACGGCACTGTCGCAAACTATCACGGCTACCACATCGTCTTTGCATTAGCCGGAGATC
CTAAAAATGCGGATGACACATCGATTTACATGTTCTATCAAAAAGTCGGCGAAACTTCTATTGACAGCTGGAAAAAC
GCTGGCCGCGTCTTTAAAGACAGCGACAAATTCGATGCAAATGATTCTATCCTAAAAGACCAAACACAAGAATGGTC
AGGTTCAGCCACATTTACATCTGACGGAAAAATCCGTTTATTCTACACTGATTTCTCCGGTAAACATTACGGCAAAC
AAACACTGACAACTGCACAAGTTAACGTATCAGCATCAGACAGCTCTTTGAACATCAACGGTGTAGAGGATTATAAA
TCAATCTTTGACGGTGACGGAAAAACGTATCAAAATGTACAGCAGTTCATCGATGAAGGCAACTACAGCTCAGGCGA
CAACCATACGCTGAGAGATCCTCACTACGTAGAAGATAAAGGCCACAAATACTTAGTATTTGAAGCAAACACTGGAA
CTGAAGATGGCTACCAAGGCGAAGAATCTTTATTTAACAAAGCATACTATGGCAAAAGCACATCATTCTTCCGTCAA
GAAAGTCAAAAACTTCTGCAAAGCGATAAAAAACGCACGGCTGAGTTAGCAAACGGCGCTCTCGGTATGATTGAGCT
AAACGATGATTACACACTGAAAAAAGTGATGAAACCGCTGATTGCATCTAACACAGTAACAGATGAAATTGAACGCG
CGAACGTCTTTAAAATGAACGGCAAATGGTACCTGTTCACTGACTCCCGCGGATCAAAAATGACGATTGACGGCATT
ACGTCTAACGGATATTTACATGCTTGGTTATGTTTCTAATTCTTTAACTGGCCCATACAAGCCGCTGAACAAAACTGG
CCTTGTGTTAAAAATGGATCTTGATCCTAACGATGTAACCTTTACTTACTCACACTTCGCTGTACCTCAAGCGAAAG
GAAACAATGTCGTGATTACAAGCTATATGACAAACAGAGGATTCTACGCAGACAAACAATCAACGTTTGCGCCAAGC
TTCCTGCTGAACATCAAAGGCAAGAAAACATCTGTTGTCAAAGACAGCATCCTTGAACAAGGACAATTAACAGTTAA
CAAATAAactatgagttgaaacaatggcctatctcatatgaagatcttttgtgaatttcacttttgtcccacgacctc
tgttgcacgactctgctttccgacccggagcataccttttgttctatatgatttgtgtatgtatgtaggaacctatgt
tctcgagcatgcatacataatttcctcataggtctatatacaccggctatccatatgcaaaacctgtgtaatattttgt
tatatacaacacgcggacccattgtcttgctgttattaatttcttttttcccgcaaaaaaggaaaagtttcttttatttg
gcactgcaatggatatgcctcacagctagtgggtggagaattcagtatttgacattaagattccctgatttgcaatt
gcaaatttcagtttctttacttatatcactacaaaagtcttattgtttctttttcccacgtcattaccatctgctccat
tggttttttgctagtagaatggatgaagcatggacacagattaactgagctcgagctcatatgagctcgggtgaaca
ataaaatctgaaaatacttagaaagaatttcaaaattttctgtttttttgtggcaaaatttgacaaatgttataaatgc

FIGURE 34 (CONT'D)

ttgcaaagtttcatcatagaacgacattcgtggatgtcatggcaaaaaacaaattcagcactctgaaaataactttt
ttgaagtatcgg[illegible]

[illegible]

FIGURE 35 gatccggtgactcaaaaaagaagagccgccatctgtccaagcgccactcctacgagaactaaatcctattccctcc
gtaaataaatataagagcgtttagatcactacttctttacagagaatttccttccctccaaggggaggcgaatccat
aggcacatcgacggatatggagggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaatttatgataaaatgaaatatttgccca
gccaactcagtcgcatcctcggacaatttgtttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctccctcctccgataatacaaata
cc*ATGGAGTCCCCAAGCGCCGTCGTCCCCGGCACCACGGCGCCGCTGCTTCCTTATGCGTACGCGCCGCTGCCGTCG*
*TCCGCCGACGACGCCCGTCAAAACCGGAGTGGCGGAGGTGGCGCGCGTGCGCCGCCGTGCTGGCCGCATCGGCGTT*
*GGCGGTGGTCGTCGTGGTCGGGCTCCTCGCGGCGGCAGGGTGGATCGGGTCCCGGCCGGCGGA*ACTATTAATGCAG
ACAATGTTAATGAAAATCAAACTGTAGAAGTAACTGCTAGTTCAGTAAACAATGAAAATAATAAGCAAGTAACTGAA
AAAGATAGTGCAGATAAAAGTACTAGTGATGTGGCTGAAGATGCTAACACCAAGAAATCAAACGAAAATACAGAAAC
TACAGAAAAAGAATACTCAAACAGTTGTTACTAATGCGCCAGTAAGTGATGTGAAAAAATACAAACACAGTTACCGCTG
AAACACCTGTTGATAAAGTAGTAAATAATAGTGATCAAAAGACAACTAATGCTGCAACTACTGATACTAAAAAAGAT
GATGTAAAACAAGTTGAAAAGAAAGACTCAGTAGATAAAACAAATGCTGAGGAAAATAAAGATAGTTCAGTAAAGCC
AGCTGAAAATGCTACTAAGGCTGAATTAAAGGGCCAAGTTAAAGATATCGTTGAAGAATCTGGTGTTGATACTAGCA
AGTTAACTAATGATCAAATTAATGAATTAAATAAAATTAATTTCTCCAAAGAAGCAAAAAAGTGGTACTCAGTTAACT
TACAACGACTTTAAAAAAATTGCTAAAACTTTAATTGAACAAGATGCTCGTTATGCTATTCCATTCTTCAATGCAAG
TAAAATTAAAAATATGCCTGCTGCTAAAACACTTGATGCTCAAAGTGGAAAAGTAGAAGATTTGGAAATTTGGGATT
CATGGCCTGTTCAAGATGCAAAAACTGGTTACGTATCTAACTGGAATGGCTACCAATTAGTGATTGGTATGATGGGA
GTTCCAAACGTCAATGATAACCACATTTATCTTCTTTACAACAAGTATGGTGATAATGACTTTAATCATTGGAAGAA
TGCCGGTCCTATTTTCGGTCTAGGTACTCCAGTTATTCAACAATGGTCTGGATCAGCAACTTTAAATAAAGATGGCT
CAATTCAACTTTACTACACTAAGGTTGATACTAGTGATAATAATACTAACCACCAAAAACTCGCTAGTGCAACTGTT
TACTTAAATCTTGAAAAAGATCAAGATAAGATTTCTATTGCTCATGTTGACAACGACCATATTGTCTTTGAAGGTGA
TGGTTACCACTACCAAACTTATGACCAATGGAAAGAAACTAACAAGGGTGCTGACAATATCGCAATGCGTGATGCAC
ACGTGATTGATGATGATAATGGTAATGGTTACCTTGTGTTTGAAGCAAGTACTGGAACCGAAAATTATCAAGGTGAT
GATCAAATTTATCAATGGTTAAATTACGGCGGTACTAACAAGGATAATTTAGGTGATTTCTTCCAAATTTTATCTAA
CTCCGATATTAAAGATAGAGCTAAATGGTCAAACGCTGCAATTGGTATCATTAAATTAAATGATGATGTTAAGAATC
GAAGTGTTGCAAAGGTCTACAGCCCACTTATTAGTGCACCAATGGTAAGTGATGAAATTGAACGCCCTGATGTTGTT
AAATTAGGTAATAAGTATTACTTATTTGCTGCTACTAGATTAAACCGTGGTAGTAACGATGATGCTTGGATGGCAAC
TAACAAAGCAGTTGGTGATAACGTAGCTATGATTGGTTATGTTTCTGATAACTTAACTCATGGTTATGTTCCATTGA
ATGAATCTGGCGTTGTTTTAACTGCATCTGTACCGGCTAACTGGCGTACTGCAACTTATTCATACTATGCAGTTCCA
GTAGAAGGAAGAGATGATCAACTTTTAATTACTTCATACATCACTAATCGTGGTGAGGTTGCTGGAAAGGGTATGCA
TGCAACTTGGGCACCAAGTTTCTTGTTACAAATTAATCCAGATAACACTACTACTGTTTTAGCTAAAATGACTAACC
AAGGGGATTGGATTTGGGATGATAGTAGTGAAAATCCAGATATGATGGGTGTACTTGAAAAAGATGCTCCAAATAGT

FIGURE 35 (CONT'D)

GCTGCCCTTCCTGGAGAATGGGGAAAACCAGTTGATTGGGATTTAATTGGTGGATACAACTTGAAGCCACACCAACC
TGTAACTCCTATTCCAAATGTACCAACTACTCCTGAAACCCCAACCACACCAGATAAGCCAGAGGTACCAACTACCC
CTGAAGTTCCAACCACTCCAGAAACTCCAACTCCAGAAGCTCCAAAGAATCCAGTTAAGAAAACTAGTCAGTCTAAA
CTTCCAAAGGCTGGAGATAAAAATAGCTTTGCAGCAGTTGTTTTAGGTGCTGTAAGTTCAATATTAGGTGCTGTTGG
TTTAACAGGTGTTTCAAAACGTAAACGTAATAATTAAactatgagttgaaacaatggcctatctcatatgaagatct
tttgtgaatttcacttttgtccacgacctctgttgcacgactctgctttccgaccggagcatacctttgttctata
tgatttgtgtatgtatgtaggaacctatgttctcgagcatgcatacataattcctcataggtctatatacacggct
atccatatgcaaaacctgtgtaatatttgttatatacaacacgcggaccattgtcttgctgttattaattcttttt
cccgcaaaaaaggaaaagtttctttatttggcactgcaatggatatgcctcacagctagtgggtggagaattcagta
tttgacattaagattccctgatttgcaattgcaaatttcagtttctttacttatatcactacaaaagtcttattgtt
tcttttccacgtcattaccatctgctccattggtttttgctagtagaataggatgaagcatggacacagattaactg
agctcgagctcatatgagctcgggtgaacaataaaatctgaaaatacttagaaagaattcaaaattttctgtttttt
gtggcaaaatttgacaaatgttataaatgcttgcaaagtttcatcatagaacgacattcgtggatgtcatggcaaaa
aacaaattcagcactctgaaaataactttttgaagcatcg

FIGURE 36 gatccggtgactcaaaaaagaagagccgccatctgtccaagcgccactcctacgagaactaaatcctattccctcc
gtaaataaatataagagtgtttagatcactacttctttacagagaatttccttccctccaagggggaggcgaatccat
aggcacatcgacggatacggaggggggaaacatacactttactatgctagttcagttaatttctaccaagaaaacata
tatttttatttttgacaaacattgtataaatgtagacattcacatacacgtatgtacaccaccctctatgattgcacac
ccgcacactatatgcctatgagcatactttcaagagtgagccagcaaatttttatgataaaatgaaatatttttgccca
gccaactcagtcgcatccccggacaatttgttatcaaggaactcacccaaaaacaagcaaagctagaaaaaggctgt
gtggcagcccacctaatgacatgaaggactgaaatttccagcacacacaatgtatccgacggcaatgctttcttccact
gatccggagaagataaggaacgaggcaaccagcgaacgtgagccatccccaaccacatctgtaccaaagaaacgggg
ctatatataccgtggtgacccggcaatggggtcctcaactgtagccggcatcctcctctcctccgataatacaaata
ccATGGAGTCCCCAAGCGCCGTCGTCCCCGGCACCACGGCGCCGCTGCTTCCTTATGCGTACGGCGCCGCTGCCGTCG
TCCGCCGACGACGCCCGTCAAAACCGGAGTGGCGGGAGGTGGCGCGCGTGCCGCCCGTGCTGGCCGCATCGGCGTT
GGCGGTGGTCGTCGTGGTCGGGCTCCTCGCGGGCGGCAGGGTGGATCGGGTCCCGGCCGGCGGAACTATTAATGCAG
ACAATGTTAATGAAAATCAAACTGTAGAAGTAACTGCTAGTTCAGTAAACAATGAAAATAATAAGCAAGTAACTGAA
AAAGATAGTGCAGATAAAAGTACTAGTGATGTGGCTGAAGATGCTAACACCAAGAAATCAAACGAAAATACAGAAAC
TACAGAAAAAGAATACTCAAACAGTTGTTACTAATGCGCCAGTAAGTGATGTGAAAAATACAAACACAGTTACCGCTG
AAACACCTGTTGATAAAGTAGTAAATAATAGTGATCAAAAGACAACTAATGCTGCAACTACTGATACTAAAAAAGAT
GATGTAAAACAAGTTGAAAAGAAAGACTCAGTAGATAAAACAAATGCTGACGAAAATAAAGATAGTTCAGTAAAGCC
AGCTGAAAATGCTACTAAGGCTGAATTAAAGGGCCAAGTTAAAGATATCGTTGAAGAATCTGGTGTTGATACTAGCA
AGTTAACTAATGATCAAATTAATGAATTAAATAAAATTAATTTCTCCAAAGAAGCAAAAAGTGGTACTCAGTTAACT
TACAACGACTTTAAAAAAATTGCTAAAACTTTAATTGAACAAGATGCTCGTTATGCTATTCCATTCTTCAATGCAAG
TAAAATTAAAAATATGCCTGCTGCTAAAACACTTGATGCTCAAAGTGGAAAAGTAGAAGATTTGGAAATTTGGGATT
CATGGCCTGTTCAAGATGCAAAAACTGGTTACGTATCTAACTGGAATGGCTACCAATTAGTGATTGGTATGATGGGA
GTTCCAAACGTCAATGATAACCACATTTATCTTCTTTACAACAAGTATGGTGATAATGACTTTAATCATTGGAAGAA
TGCCGGTCCTATTTTCGGTCTAGGTACTCCAGTTATTCAACAATGGTCTGGATCAGCAACTTTAAATAAAGATGGCT
CAATTCAACTTTACTACACTAAGGTTGATACTAGTGATAATAATACTAACCACCAAAAACTCGCTAGTGCAACTGTT
TACTTAAATCTTGAAAAAGATCAAGATAAGATTTCTATTGCTCATGTTGACAACGACCATATTGTCTTTGAAGGTGA
TGGTTACCACTACCAAACTTATGACCAATGGAAAGAAACTAACAAGGGTGCTGACAATATCGCAATGCGTGATGCAC
ACGTGATTGATGATGATAATGGTAATCGTTACCTTGTGTTTGAAGCAAGTACTGGAACCGAAAATTATCAAGGTGAT
GATCAAATTTATCAATGGTTAAATTACGGCGGTACTAACAAGGATAATTTAGGTGATTTCTTCCAAATTTTATCTAA
CTCCGATATTAAAGATAGAGCTAAATGGTCAAACGCTGCAATTGGTATCATTAAATTAAATGATGATGTTAAGAATC
CAAGTGTTGCAAAGGTCTACAGCCCACTTATTAGTGCACCAATGGTAAGTGATGAAATTGAACGCCCTGATGTTGTT
AAATTAGGTAATAAGTATTACTTATTTGCTGCTACTAGATTAAACCGTGGTAGTAACGATGATGCTTGGATGGCAAC
TAACAAAGCAGTTGGTGATAACGTAGCTATGATTGGTTATGTTTCTGATAACTTAACTCATGGTTATGTTCCATTGA
ATGAATCTGGCGTTGTTTTAACTGCATCTGTACCGGCTAACTGGCGTACTGCAACTTATTCATACTATGCAGTTCCA
GTAGAAGGAAGAGATGATCAACTTTTAATTACTTCATACATCACTAATCGTGGTGAGGTTGCTGGAAAGGGTATGCA
TGCAACTTGGGCACCAAGTTTCTTGTTACAAATTAATCCAGATAACACTACTACTGTTTTAGCTAAAATGACTAACC
AAGGGGATTGGATTTGGGATGATAGTAGTGAAAATCCAGATATGATGGGTGTACTTGAAAAAGATGCTCCAAATAGT

FIGURE 36 (CONT'D)

GCTGCCCTTCCTGGAGAATGGGGAAAACCAGTTGATTGGGATTTAATTGGTGGATACAACTTGAAGCCACACCAACC
TGTAACTCCTATTCCAAATGTACCAACTACTCCTGAAACCCCAACCACACCAGATAAGCCAGAGGTACCAACTACCC
CTGAAGTTCCAACCACTCCAGAAACTCCAACTCCAGAAGCTCCAAAGAATCCAGTTAAGAAAACTAGTCAGTCTAAA
CTTCCAAAGGCTGGAGATAAAAATAGCTTTGCAGCAGTTGTTTTAGGTGCTGTAAGTTCAATATTAGGTGCTGTTGG
TTTAACAGGTGTTTCAAAACGTAAACGTAATAATTAAactatgagttgaaacaatggcctatctcatatgaagatct
ttgtgaatttcactttgtccacgacctctgttgcacgactctgctttccgaccggagcatacctttgttctata
tgatttgtgtatgtatgtaggaacctatgttctcgagcatgcatacataattcctcataggtctatatacaccggct
atccatatgcaaaacctgcgcaatatttgttatatacaacacgcggaccattgtcttgctgttattaattcttttt
cccgcaaaaaaggaaaagtttctttatttggcactgcaatggatatgcctcacagctagtgggtggagaattcagta
tttgacattaagattccctgatttgcaattgcaaatttcagtttctttacttatatcactacaaaagtcttattgtt
tctttccacgtcattaccatctgctccattggttttgctagtagaataggatgaagcatggacacagattaactg
agctcgagctcatatgagctcgggtgaacaataaaatctgaaaatacttagaaagaattcaaaatttttctgtttttt
gtggcaaaatttgacaaatgttataaatgcttgcaaagtttcatcatagaacgacattcgtggatgtcatggcaaaa
aacaaattcagcactctgaaataactttttgaagtatcgatttgtgtcttctaggttaatccttccaaactttgg
ttaaccaaaaaaattatcaaactaacatgttctccttttttctttagaaattctaacgaatttatccttatactgat
ttgaatatacttaatttggtcatttggatgcccttacaacctccttaccaaactcactatggcaaatatatactat
tttccattgtaacataaatgtcccatatttgaattaaattcgttgcagtacgaaacatcaactttgtccaaaaac
aaaatccttataactatttactttaatgtaaatatacctctacttttgttttcaaaccctagctcaaacaaattt
attatttgcgataaaaaatcatatcgaacaaactcgatgatttttttttcttacgttattaatgaaactaaaatac
agaaaaaaacaagatgaaccaaatttcacctatctaactacttaaatataatatgatttaaatttggtaaagtttga
aaagtttctttagaaatgtgaaatattgatcacagtttctattgctaaaatcacaacaaaagcatatgtcgccatt
cataattatggtttcacacctacaactaggctaataagtaaataagtagacaactagactcaggtttgaaaaaacca
taaaagccatatagcgttttctcattgaaactgcgaacacgatcgtgtgaatgttgcagtttctagtttgatacaa
acaaacaaaaacacaatttaatcttagattaaaaagaaaaaagagaacggagcccactagccactcctttcaaacgtg
tcttaccaactctcttctagaaacaaattaggcttcaccttcctcttccaacctctctctctctctctctctctctt
tctcaaaccatctctccataaagccctaatttcttcatcacaagaatcagaagaatactgcaaaaaaccATGGACC
TGGATCTAATTTTCGGTCCAACTTGCACACGGAAAGACGACGACCGCGATAGCTCTTGCCCAGCAGACAGGGCTTCCA
GTCCTTTGGCTGGATGGGTCCAATGCTGTTCTCAACTATCAACCGGAAGCGGACGACCAACAGTGGAAGAACTGGA
AGGAACGACGCGTCTCTACCTTGATGATGCGCCTCTGGTGGAGGGTATCATCGTAGCCAAGCAAGCTCATCATAGGC
TGATCGAGGAGGTGTATAATCATGAGGCCAACGGCGGGCTTATTCTTGAGGGAGGATCCACCTCGGTTGCTCAACTGC
AGGGCGCGAAACAGCTATTGGAGTGCAGATTTTCGTTGGCATATTATTCGCCACAAGTTACCGGACCAAGAGACCTT
CATGAAAGCGGCCAAGGCCAGAGTTAAGCAGATGTTGCACCCCGCTGCAGCCATTCTATTATTCAAGAGTGGGTT
ATCTTTGGAATGAACCTCGGCTGAGGCCATTCTGAAAGAGATCGATGGATATCGATATGCCATGTTGTTTCCTAGC
CAGAACCAGATCACGGCAGATATGCTATTGCAGCTTGACGCAAATATGGAAGGTAAGTTGATTAATGGATCGCTCA
GGAGTATTTCATCCATGGCGCCAACAGGAACAGAAATTCCCCCAAGTTAACGCAGCGGCTTTGGACGGATTCGAAG
GTCATCCGTTCGGAATGTATTAGGTAAgtccgcaaaaatcaccagtctctctctacaaatctatctctctctatttt
tctccagaataatgtgtgagtagttcccagataaggggaattagggttcttatagggtttcgctcatgtgttgagcat

FIGURE 36 (CONT'D)

ataagaaacccttagtatgtatttgtatttgtaaaatacttctatcaataaaatttctaattcctaaaaccaaaatc
cagtgacct

FIGURE 38
A
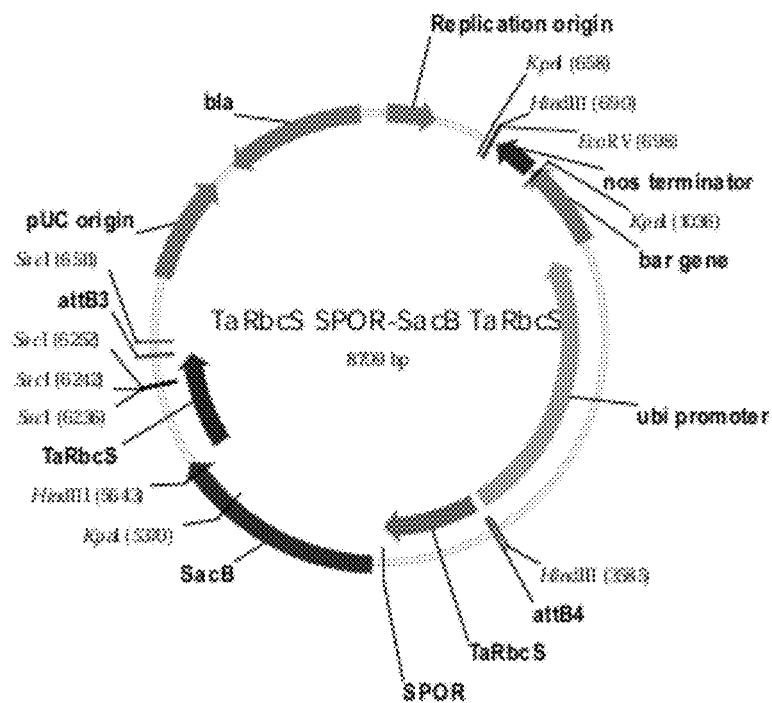
B
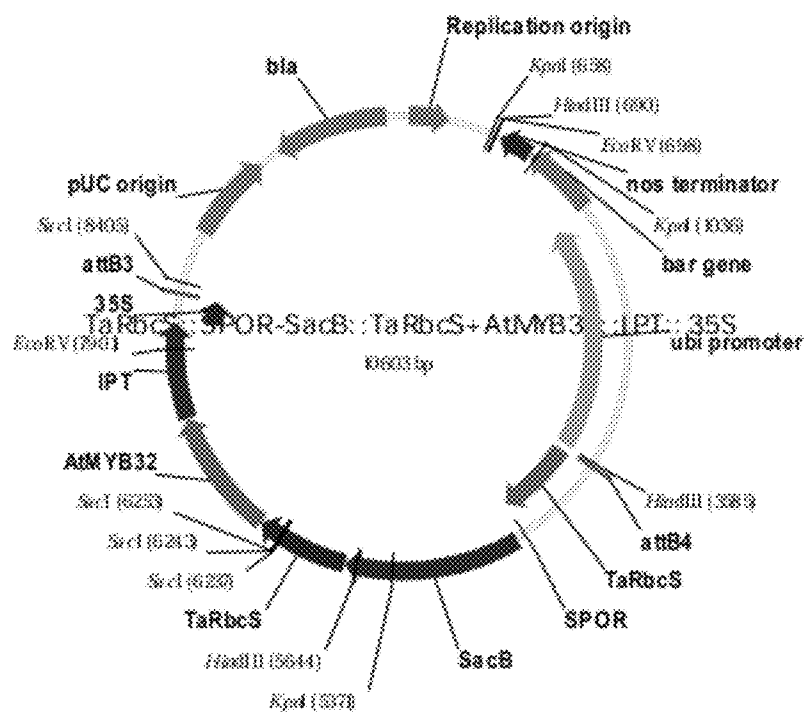

FIGURE 39
A
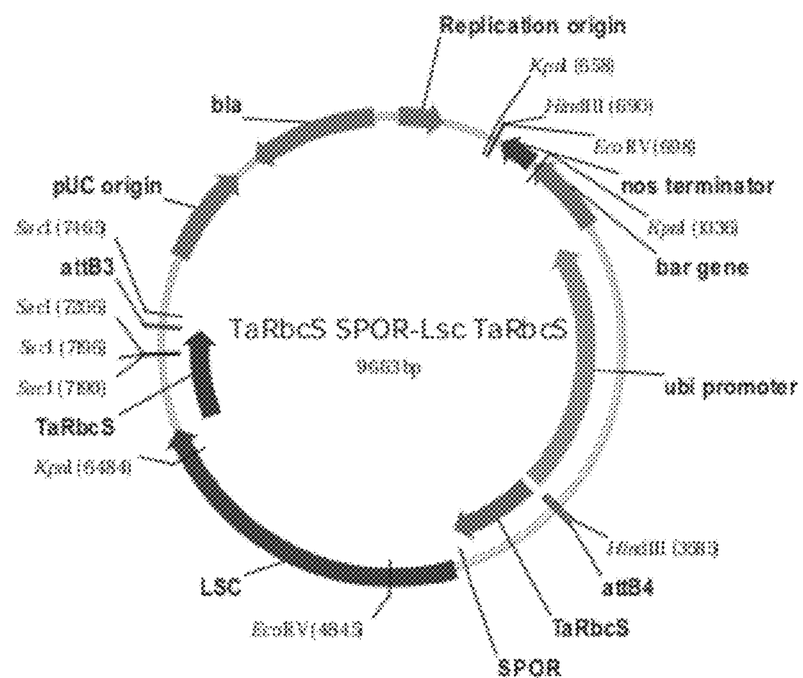
B
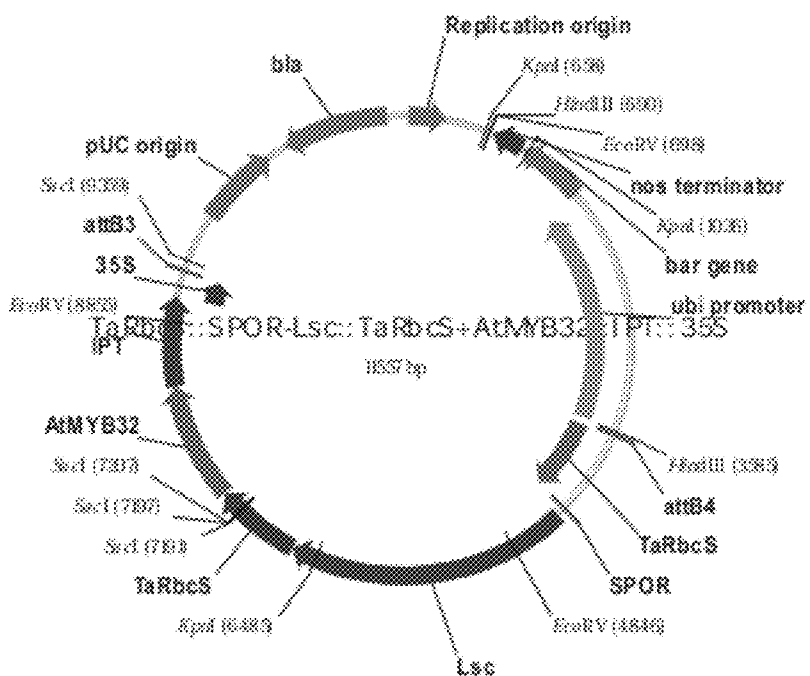

FIGURE 40
A
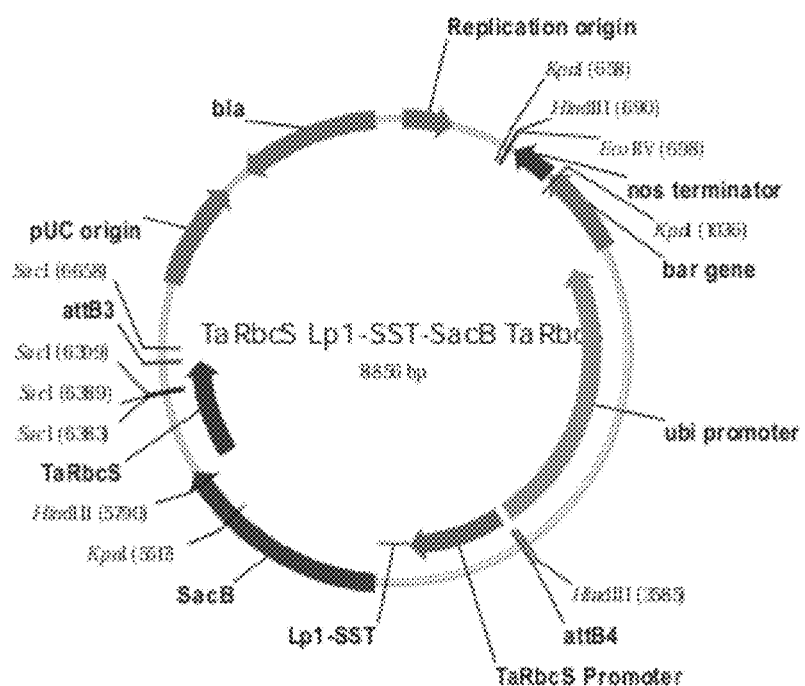
B
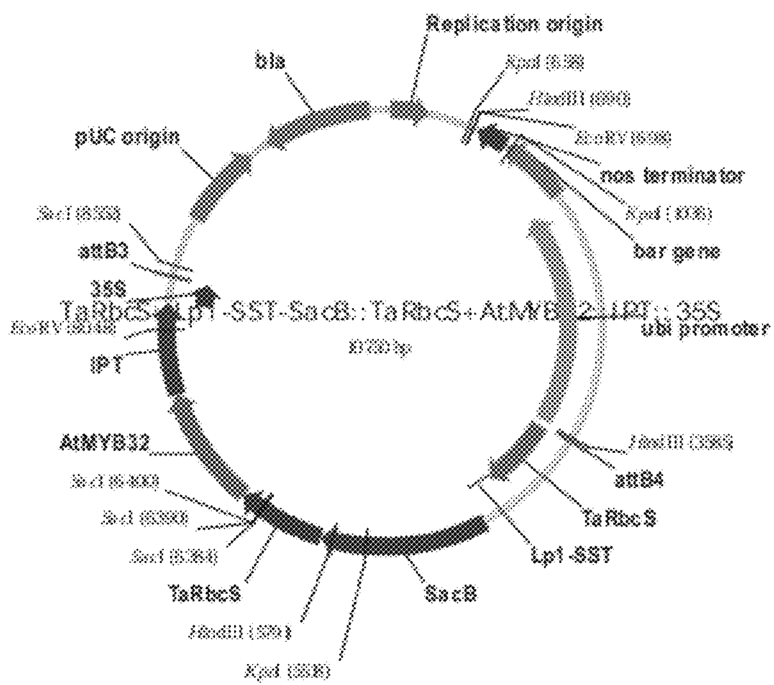

FIGURE 41
A
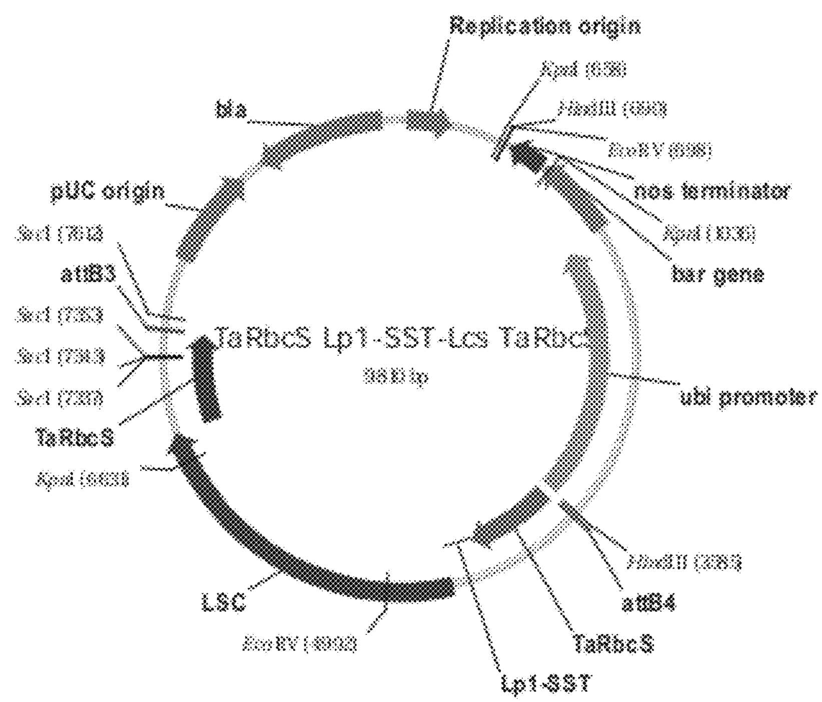
B
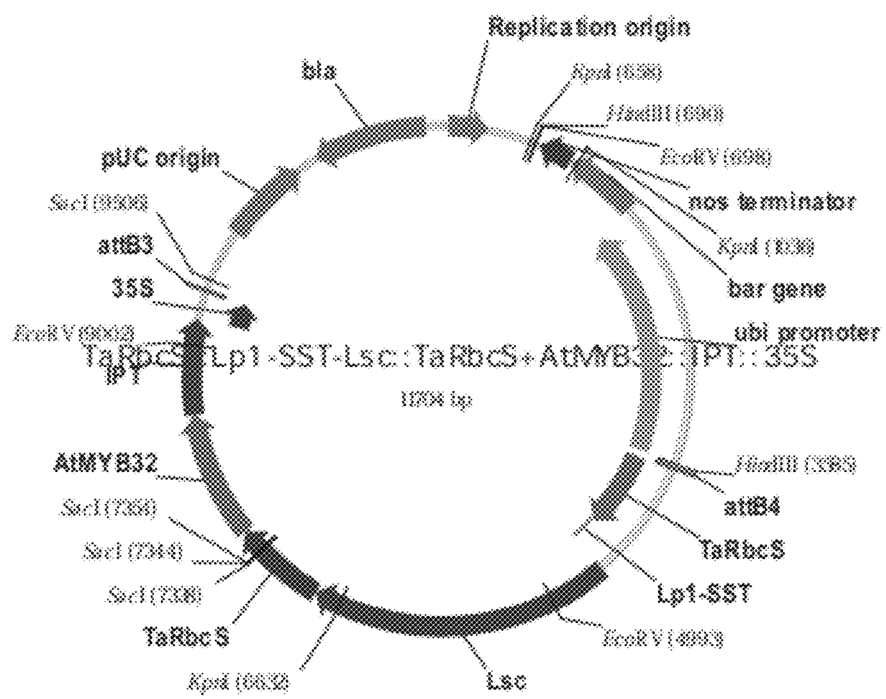

MANIPULATING FRUCTAN BIOSYNTHESIS AND ENHANCING PLANT BIOMASS

FIELD OF THE INVENTION

The present invention relates to the modification of fructan biosynthesis in plants and, more particularly, to methods of manipulating fructan biosynthesis in photosynthetic cells, and to related nucleic acids and constructs.

The present invention also relates to increasing plant biomass and, more particularly, to methods of enhancing biomass yield and/or yield stability, including shoot and/or root growth in a plant, and to related nucleic acids and constructs.

BACKGROUND OF THE INVENTION

Fructans are a type of water-soluble carbohydrate whose primary function is to provide a readily accessible energy reserve for plant growth. Fructans are associated with various advantageous characters in grasses, such as cold and drought tolerance, increased tiller survival, enhanced persistence, good regrowth after cutting or grazing, improved recovery from stress, early spring growth and increased nutritional quality.

Fructan synthesis and metabolism in grasses and cereals is complex. Fructans consist of linear or branched fructose chains attached to sucrose. The chain length of plant fructans ranges from three up to a few hundred fructose units. Different types of fructans can be distinguished based on the linkage types present. In perennial ryegrass three types of fructans have been identified: inulins, inulin neoseries and levan neoseries, with four fructosyltransferse (FT) enzymes involved in this fructan profile.

The enzyme 1-SST (sucrose: sucrose 1-fructosyltransferase) catalyses the first step in fructan biosynthesis while the remaining enzymes elongate the growing fructose chain (1-FFT: fructan: fructan 1-fructosyltransferase, 6G-FFT: 6-glucose fructosyltransferase, and 6-SFT: sucrose: fructose 6-fructosyltransferase). The enzymes 1-FEH or 6-FEH (fructoexohydrolase) reduce fructan chain length by releasing fructose molecules.

Bacteria use only one FT enzyme which contains both 1-SST and 1-FFT activities to synthesize high molecular weight fructan polymers. Most bacterial fructosyltransferases produce levan type fructan (levansucrases), which is characterized by β-2,6 linkages of fructose molecules, although inulosucrases that produce fructans of the inulin type (β-2,1 linkage) have been isolated from a few bacteria.

At least 3 bacterial levansucrases have been expressed in transgenic plants including, the SacB gene from *Bacillus subtilis*, the SacB gene from *Bacillus amyloliquefaciens*, and the FTF gene from *Streptococcus mutans*. Expression of these bacterial levansucrases in plants leads to the synthesis of very high molecular weight fructans of a DP of several thousands (for review see Cairns, 2003).

Fructans represent the major non-structural carbohydrate in 15% of plant species and play a key role in forage quality. Ruminant livestock grazing on high fructan diets show improved animal performance.

In grasses the level and composition of fructans has been increased in stems and leaf sheaths through the engineered expression of FT genes.

However, manipulating biochemical pathways by manipulating the activity of enzymes in the pathways may be difficult because of the ways in which the various enzymes and their substrates may interact.

Thus, it would be desirable to have improved methods of manipulating biochemical pathways, particularly in plants. For example, it would be desirable to have methods of manipulating fructan biosynthesis in plants, including forage grass species such as *Lolium, Festuca*, and *Brachiaria*; sugarcane and other grasses; and sorghum and other cereals such as wheat and maize; thereby facilitating the production of, for example:

- forage grasses with improved herbage quality and/or yield, leading to improved pasture production, improved animal production and/or reduced environmental pollution;
- bioenergy grasses and crops such as switchgrass, *Miscanthus*, sorghum (grain, forage and energy sorghum), sugarcane and energy cane with enhanced biomass yield, such as for bioethanol production; and
- cereals such as wheat, rice, maize, barley with increased grain and/or biomass yield.

Nucleic acid sequences encoding some of the enzymes involved in the fructan biosynthetic pathway have been isolated for certain species of plants. For example, PCT/AU01/00705 to the present applicants, describes fructosyltransferase homologues from *Lolium* and *Festuca*. However, there remains a need for materials useful in the modification of fructan biosynthesis in plants, and also to engineer fructan accumulation in different parts of the plant.

International patent application PCT/AU2009/001211 describes constructs useful for modifying fructan biosynthesis in plants. However, those constructs preferably include a fusion gene encoding a translational fusion of two or more fructan biosynthetic enzymes, the genes making up the fusion preferably corresponding to plant fructan biosynthetic genes.

It is an object of the present invention to overcome, or at least alleviate, one or more of the difficulties or deficiencies associated with the prior art.

SUMMARY OF THE INVENTION

Applicants have found that it is possible to nutritionally enhance plants eg. forage grasses and/or to increase plant biomass by spatial reprogramming of the fructan-biosynthesis pathway in photosynthetic cells using a construct including a promoter or a functionally active fragment or variant thereof, operatively linked to a gene encoding a bacterial FT enzyme, or a functionally active fragment or variant thereof. Using this process it is possible to drive fructan accumulation in leaf blades, the plant organs that are primarily grazed by livestock, and which may not normally accumulate fructans. Thus, accumulation of fructans, especially those exhibiting a high degree of polymerization (high DP fructans'), provides more accessible nutrition for grazing animals. Fructans accumulate in the stems and leaf sheaths, with leaf fructans only forming during periods where $CO_2$ assimilation outperforms growth. Forage grasses may be nutritionally enhanced by expressing fructan genes in photosynthetic cells where sucrose is synthesised, thus driving fructan accumulation preferentially in leaf blades and providing more energy to grazing livestock.

Fructans in forage grasses contribute significantly to the readily available energy in the feed for grazing ruminant animals. The fermentation processes in the rumen require considerable readily available energy. The improvement of the readily available energy in the rumen can increase the efficiency of rumen digestion. An increased efficiency in rumen digestion leads to an improved conversion of the forage protein fed to the ruminant animal into milk or meat, and to a reduction in nitrogenous waste.

Applicants have also found that the methods of the present invention may be facilitated by reprogramming photosynthetic cells for extended life, for example by delaying leaf senescence, to help increase plant biomass.

Applicants have found that a construct including a gene encoding a bacterial FT gene or functionally active fragment or variant thereof, may give superior results to a construct including a fusion gene encoding a translational fusion of two or more fructan biosynthetic enzymes. Use of a bacterial FT gene, for example containing both 1-SST and 1-FFT activities, may be technically less difficult than fusing separate genes, and may result in a construct that is more readily introduced into plants and/or performs better than a construct including fused genes.

For example, by expressing a bacterial FT gene, for example containing both 1-SST and 1-FFT activities, problems associated with differences in the expression patterns of these genes independently integrated into the plant genome may be alleviated, resulting in conversion of the sucrose molecules directly to fructans, those exhibiting a low degree of polymerisation ('low DP fructans') and a high degree of polymerization ('high DP fructans'). Furthermore, the FT protein may form a metabolic channel for the efficient biosynthesis of fructans.

Expression of FT genes in photosynthetic cells leading to the accumulation of low and high DP fructans in photosynthetic cells may lead to a release from inhibition mechanisms of photosynthesis, facilitating solar energy capture and increased $CO_2$ fixation.

Thus, applicants have found that reprogramming photosynthetic cells for extended life and enhanced fructan biosynthesis facilitates solar energy capture and increases plant biomass production including shoot and/or root growth.

Furthermore, since accumulation of low and high DP fructans has been associated with plant's tolerance to abiotic stress such as cold and drought; and since enhanced root growth and delayed leaf senescence has also been implicated in plant's tolerance of drought stress, reprogramming photosynthetic cells for extended life and enhanced fructan biosynthesis may facilitate yield stability and plants' tolerance of abiotic stresses.

Accordingly, in one aspect, the present invention provides a method of manipulating fructan biosynthesis in photosynthetic cells of a plant, said method including introducing into said plant an effective amount of a genetic construct including a promoter, or a functionally active fragment or variant thereof, operatively linked to a nucleic acid encoding a bacterial fructosyltransferase (FT) enzyme, or a functionally active fragment or variant thereof.

By 'manipulating fructan biosynthesis' is generally meant increasing fructan biosynthesis in a transformed plant relative to an untransformed control plant. However, for some applications it may be desirable to reduce or otherwise modify fructan biosynthesis in the transformed plant relative to the untransformed control plant. For example, it may be desirable to increase or decrease the activity of certain enzymes in the fructan biosynthetic pathway, in the transformed plant relative to the untransformed control plant.

By 'photosynthetic cells' is meant those cells of a plant in which photosynthesis takes place. Such cells generally contain the pigment chlorophyll and are otherwise known as green cells. Most photosynthetic cells are contained in the leaves of plants. Preferably, the genetic construct of the present invention is expressed in bundle sheath cells, more preferably in mesophyll and/or parenchymatous bundle sheath cells.

By 'an effective amount' is meant an amount sufficient to result in an identifiable phenotypic trait in said plant, or in a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

By 'genetic construct' is meant a recombinant nucleic acid molecule.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

By 'nucleic acid' is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a bacterial fructosyltransferase (FT) enzyme' or 'bacterial fructosyl transferase gene' is meant a nucleic acid encoding an enzyme normally present in a bacterium which catalyses the synthesis of oligo- and/or polyfructans by transferring fructosyl moieties from sucrose-containing saccharides to acceptor molecules. The bacterial FT enzyme may include levansucrase activity and/or produce levan type fructan. The bacterial FT enzyme may include inulosucrase activity and/or produce inulin type fructan. A preferred bacterial FT includes both sucrose: sucrose 1-fructosyltransferase (1-SST) and fructan:fructan 1-fructosyltransferase (1-FFT) enzymatic activities. A SacB, Lsc or FTF gene may be used. A SacB or Lsc gene is particularly preferred.

By 'functionally active fragment or variant' in relation to a promoter is meant that the fragment or variant (such as an analogue, derivative or mutant) is capable of directing transcription of an operatively linked nucleic acid. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Preferably the fragment has a size of at least 20 nucleotides, more preferably at least 50 nucleotides, more preferably at least 100 nucleotides, more preferably at least 200 nucleotides, more preferably at least 300 nucleotides.

By 'functionally active' in relation to the nucleic acid encoding a bacterial FT enzyme is meant that the fragment or variant (such as an analogue, derivative or mutant) is capable of manipulating fructan biosynthesis in a plant by the method of the present invention, for example by being translated into an enzyme that is able to participate in the fructan biosynthetic pathway. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His Other conservative amino acid substitutions may also be made as follows:

Aromatic: Phe, Tyr, His
Proton Donor: Asn, Gln, Lys, Arg, His, Trp
Proton Acceptor: Glu, Asp, Thr, Ser, Tyr, Asn, Gln Particularly preferred fragments and variants include one or more conserved sucrose binding/hydrolysis domains. Examples of such domains are shown in FIG. 1 and include LDVWDSWP (SEQ ID No.: 1), QEWSGSA (SEQ ID No.: 2), LRDPH (SEQ ID No.: 3) and DEIER (SEQ ID No.: 4).

Particularly preferred fragments and variants include a catalytic core. By a "catalytic core" is meant an internal region of the polypeptide excluding signal peptide and N- and C-terminal variable regions, which contains conserved sucrose binding and/or hydrolysis domains. An example of a catalytic core is shown in FIG. 1 and includes amino acid residues 65-468 of the SacB protein from *Bacillus subtilis*.

Particularly preferred fragments and variants include those lacking a signal peptide. By a "signal peptide" is meant an N-terminal signal sequence. An example of a signal peptide is shown in FIG. 1 and includes amino acids 1-27 of the SacB protein from *Bacillus subtilis*.

Particularly preferred fragments and variants have codon usage adapted for plants, including the start of translation for monocots and dicots.

Particularly preferred fragments and variants have cryptic splice sites and/or RNA destabilizing sequence elements inactivated or removed.

Preferably, the nucleic acid encoding a bacterial FT is isolated from or corresponds to a gene or genes from a bacterial species selected from the group consisting of *Bacillus, Lactobacillus* and *Streptococcus*, including *Bacillus subtilis, Bacillus amyloliquefaciens, Lactobacillus johnsonii* and *Streptococcus mutans*. Even more preferably, the nucleic acid encoding a bacterial FT enzyme is isolated from or corresponds to a SacB gene from *Bacillus subtilis* or *Bacillus amyloliquefaciens*, a Lsc gene from *Lactobacillus johnsonii* or a FTF gene from *Streptococcus mutans*.

In a particularly preferred embodiment the SacB gene includes a sequence selected from the group consisting of the sequence shown in FIG. 2 and the nucleotide sequences encoding the polypeptide sequence shown in FIG. 3; and functionally active fragments and variants thereof.

Ina particularly preferred embodiment the Lsc gene includes a sequence selected from the group consisting of the sequence shown in FIG. 4 and the nucleic acid sequences encoding the polypeptide sequence shown in FIG. 5; and functionally active fragments and variants thereof.

Transgenic plants expressing bacterial levansucrases have been reported, in some instances, to display aberrant developmental phenotypes. While applicants do not wish to be restricted by theory, this may arise from inadequate compartmentalization of the levansucrase enzymes and fructan polymers. Cytosolic expression of a bacterial SacB gene in transgenic tobacco and potato plants was shown to be particularly disruptive to plant development (Caimi et al., 1997). However, plants expressing a bacterial fructosyltransferase fused to vacuole-targeting signals accumulate fructans with no discernible effect on plant development (Ebskamp et al., 1994, Ye et al. 2001).

To reduce the possibility of aberrant developmental phenotypes the bacterial FT gene may be modified to alter its targeting signal sequence to direct the bacterial FT proteins to compartments where high fructan levels exist.

More particularly, a chimeric sequence may be created, whereby the N-signal peptide of the bacterial FT gene may be removed and replaced by a sub-cellular targeting sequence, preferably a vacuolar targeting sequence.

In a preferred embodiment, the vacuolar targeting sequence may be from or correspond to a gene encoding a preprosporamin protein, such as SPOR531 of sweet potato.

In a particularly preferred embodiment, the vacuolar targeting sequence may include a sequence selected from the group consisting of the sequence shown in bold underline in FIG. 6 and the nucleic acid sequences encoding the polypeptide shown in bold underline in FIG. 7; and functionally active fragments and variants thereof.

In a particularly preferred embodiment the nucleic acid encoding the bacterial FT enzyme may be a SPOR:SacB chimeric sequence. Preferably the SPOR:SacB chimeric sequence includes a sequence selected from the group consisting of the sequence shown in FIG. 8 and the nucleic acid sequences encoding the polypeptide sequence shown in FIG. 9; and functionally active fragments and variants thereof.

In a particularly preferred embodiment the nucleic acid encoding the bacterial FT enzyme may be a SPOR:Lsc chimeric sequence. Preferably, the SPOR:Lsc chimeric sequence includes a sequence selected from the group consisting of the sequence shown in FIG. 9 and the nucleic acid sequences encoding the polypeptide sequence shown in FIG. 12; and functionally active fragments and variants thereof.

In a particularly preferred embodiment, the genetic construct includes a sequence selected from the group consisting of the sequences shown in FIGS. 8 and 11 and the nucleic acid sequences encoding the polypeptides shown in FIGS. 9 and 12; and functionally active fragments and variants thereof.

In another preferred embodiment, a chimeric sequence may be is created, whereby the N-signal peptide of the bacterial FT gene may be removed and replaced by a transmembrane domain of a fructosyltransferase enzyme such as 1-SST.

In a particularly preferred embodiment, the transmembrane domain includes a sequence selected from the group consisting of the sequence shown in bold italics in FIG. 15 and the nucleic acid sequences encoding the polypeptide shown in bold italics in FIG. 16; and functionally active fragments and variants thereof.

In a particularly preferred embodiment, the genetic construct includes a sequence selected from the group consisting of the sequences shown in FIGS. 17 and 20 and the nucleic acid sequences encoding the polypeptides shown in FIGS. 18 and 21; and functionally active fragments and variants thereof.

By a 'chimeric sequence' is meant a hybrid produced recombinantly by expressing a fusion gene including two or more linked nucleic acids which originally encoded separate proteins, or functionally active fragments or variants thereof.

By a 'fusion gene' is meant that two or more nucleic acids are linked in such a way as to permit expression of the fusion protein, preferably as a translational fusion. This typically involves removing the stop codon from a nucleic acid sequence coding for a first protein, then appending the nucleic acid sequence of a second protein in frame. The fusion gene is then expressed by a cell as a single protein. The protein may be engineered to include the full sequence of both original proteins, or a functionally active fragment or variant of either or both.

The genetic construct may also include a nucleic acid sequence encoding a linker between the two linked nucleic acids. A 'linker' is any chemical, synthetic, carbohydrate, lipid, polypeptide molecule (or combination thereof) positioned between and joined to two adjacent active fragments in a fusion protein. A preferred linker of the invention is a flexible linker, such as a polypeptide chain consisting of one or more amino acid residues joined by amino acid bonds to the two active fragments. For example, a $(Gly_4\ Ser)_3$ linker may be positioned between the two active fragments in the fusion protein.

The promoter used in the constructs and methods of the present invention may be a constitutive, tissue specific or inducible promoter. In a preferred embodiment, the promoter may be a light-regulated promoter, more preferably a photosynthetic promoter. By a 'light regulated promoter' is meant a promoter capable of mediating gene expression in response to light stimulus. By a 'photosynthetic promoter' is meant a promoter capable of mediating expression of a gene encoding a protein involved in a photosynthetic pathway in plants.

Less fructans accumulate in mature leaf blades than in leaf sheaths and stems. In order to specifically increase the level of fructans in leaf blades, a strategic approach has been devised that co-ordinately expresses fructan biosynthesis genes in photosynthetic cells. While applicants do not wish to be restricted by theory, the use of light-regulated or photosynthetic promoters may provide the following advantages:

Photosynthetic promoters are active in a large group of cells including leaf blades, the upper and outer stem (>55% cells);

They are active in sucrose producing cells (mesophyll and parenchymatous bundle sheath cells);

Their expression pattern temporally and spatially overlaps with sucrose accumulation;

Frutosyltransferase activity will remove sucrose from the source thereby preventing feedback suppression on photosynthesis, and may facilitate increases in $CO_2$ fixation;

Particularly preferred light-regulated promoters include a ribulose-1,5-bisphosphate carboxylase/oxygtenase small subunit (RbcS) promoter and a chlorophyll a/b binding protein (CAB) promoter, and functionally active fragments and variants thereof.

The light-regulated promoter may be from any suitable plant species including monocotyledonous plants [such as maize, rice, wheat, barley, sorghum, sugarcane, energy cane, forage grasses (e.g. *Festuca, Lolium, Brachiaria, Paspalum, Pennisetum*), bioenergy grasses (e.g. switchgrass, *Miscanthus*)], dicotyledonous plants (such as *Arabidopsis*, soybean, canola, cotton, alfalfa and tobacco) and gymnosperms.

For transformation of monocots, preferably the light-regulated promoter is isolated from or corresponds to a promoter from a monocot species, more particularly a *Triticum* or *Lolium* species, even more particularly *Triticum aestivum* or *Lolium perenne.*

For transformation of dicots, preferably the light-regulated promoter is isolated from or corresponds to a promoter from a dicot species, more particularly an *Arabidopsis* species, even more particularly *Arabidopsis thaliana.*

In a particularly preferred embodiment, the RbcS promoter includes a sequence selected from the group consisting of the sequence shown in lower case italics in any one of FIGS. 23 to 26 (SEQ ID No.: 42), and functionally active fragments and variants thereof.

In another particularly preferred embodiment, the RbcS promoter includes a sequence selected from the group consisting of the sequence shown in lower case italics in any one of FIGS. 29 to 36 (SEQ ID No.: 43), and functionally active fragments and variants thereof.

The genetic constructs of the present invention may be introduced into the plants by any suitable technique. Techniques for incorporating the genetic constructs of the present invention into plant cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant to be transformed, and may be readily determined by an appropriately skilled person.

Cells incorporating the genetic constructs of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The methods of the present invention may be applied to a variety of plants, including monocotyledons [such as grasses (e.g. forage and bioenergy grasses including perennial ryegrass, tall fescue, Italian ryegrass, red fescue, reed canarygrass, big bluestem, cordgrass, napiergrass, wildrye, wild sugarcane, *Miscanthus*, switchgrass), corn or maize, rice, wheat, barley, sorghum, sugarcane, rye, oat) and energy crops (e.g. energy cane, energy sorghum)], dicotyledons [such as *Arabidopsis*, tobacco, soybean, canola, alfalfa, potato, cassava, clovers (e.g. white clover, red clover, subterranean clover), vegetable brassicas, lettuce, spinach] and gymnosperms.

In a further aspect of the present invention, there is provided a genetic construct capable of manipulating fructan biosynthesis in photosynthetic cells of a plant, said genetic construct including a light-regulated promoter, or functionally active fragment or variant thereof, operatively linked to a nucleic acid encoding a bacterial FT enzyme, or a functionally active fragment or variant thereof.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

In a preferred embodiment of this aspect of the invention, the genetic construct may further include a terminator; said promoter, gene and terminator being operably linked.

The promoter, gene and terminator may be of any suitable type and may be endogenous to the target plant cell or may be exogenous, provided that they are functional in the target plant cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptll) gene, the hygromycin phosphotransferase (hph) gene, the phosphinothricin acetyltransferase (bar or pat) gene], and reporter genes (such as beta-glucuronidase (GUS) gene (gusA)]. The genetic construct may also contain a ribosome binding site for translation initiation. The genetic construct may also include appropriate sequences for amplifying expression.

In particular, the genetic construct may further include a nucleic acid sequence encoding a linker between the two linked nucleic acids, as hereinbefore described.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated. By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Applicant has also found that the methods of the present invention may result in enhanced biomass in the transformed plant relative to an untransformed control plant. This enhanced biomass may in turn be used as a selection tool for identifying transformed plants. This has the advantage that in some circumstances there may be no need to include an antibiotic resistance or other marker to select for transformants, where subsequent removal of such markers (and for the creation of marker-free plants) may present difficulties.

By 'enhancing biomass' or 'enhanced biomass' is meant enhancement of, increase in, or increased stability of biomass yield, including shoot and/or root growth, in a transformed plant relative to an untransformed control plant. For example, one or more growth characteristics selected from the group consisting of total leaf area, cumulative leaf area, leaf growth dynamics (ie. number of leaves over time), number of shoots, number of tillers, number of roots, root mass or weight, shoot mass or weight, root length, shoot length, stolon length, number of tubers, tuber weight, number of flowers, number of fruits, number of seeds, seed weight, fruit weight, percentage of flowering plants and seed yield per flower or per area sown; may be enhanced, increased or more stable in a transformed plant relative to an untransformed control plant.

This technique is particularly applicable to plants that are substantially genetically uniform or genetically identical or exhibit small phenotype differences in biomass prior to transformation.

Accordingly, in a further aspect of the present invention, there is provided a method of enhancing biomass in a plant, said method including introducing into said plant an effective amount of a genetic construct including a promoter, or a functionally active fragment or variant thereof, operatively liked to a nucleic acid encoding a bacterial FT-enzyme, or a functionally active fragment or variant thereof. Preferably, the promoter is a light regulated promoter.

The methods, nucleic acids and genetic constructs of the present invention may be used in combination with other methods of genetic manipulation, or other transferred nucleic acids or genetic constructs, thereby stacking traits. Thus, transgenic plants, plant cells, plant seeds or other plant parts with stacked genes (or stacked traits) may be produced. For example, the technology of the present invention may be combined with herbicide resistance technology (eg. glufosinate, glyphosate), insect resistance technology (eg. *Bacillus thuringiensis*) or delayed senescence technology. The nucleic acids or genetic constructs may be introduced into the plant by any suitable technique, as hereinbefore described, and may be introduced concurrently, sequentially or separately.

In a still further aspect of the present invention, there is provided a method of enhancing biomass in a plant, said method including introducing into said plant effective amount of (a) a genetic construct capable of manipulating fructan biosynthesis in photosynthetic cells of the plant, said genetic construct including a promoter, or a functionally active fragment or variant thereof, operatively linked to a nucleic acid encoding a bacterial FT enzyme, or a functionally active fragment or variant thereof; and (b) a genetic construct capable of manipulating senescence in the plant.

The genetic constructs may be introduced into the plant by any suitable technique, as hereinbefore described, and may be introduced concurrently, sequentially or separately.

Preferably the genetic construct capable of manipulating fructan biosynthesis is as hereinbefore described.

Preferably the genetic construct capable of manipulating senescence in the plant is capable of manipulating senescence in photosynthetic cells of the plant.

Preferably the genetic construct capable of manipulating senescence includes a myb gene promoter or modified myb gene promoter, or a functionally active fragment or variant thereof, operatively linked to a gene encoding an enzyme involved in biosynthesis of a cytokinin, or a functionally active fragment or variant thereof.

Suitable genetic constructs or vectors are described in International patent application PCT/AU01/01092 and U.S. patent application Ser. No. 11/789,526, the entire disclosures of which are incorporated herein by reference.

"Manipulating senescence" generally relates to delaying senescence in the transformed plant or cells or organs of the transformed plant, eg photosynthetic cells, relative to an untransformed control plant. However, for some applications it may be desirable to promote or otherwise modify senescence in the plant. Senescence may be promoted or otherwise modified for example, by utilizing an antisense gene.

The myb gene promoter may be of any suitable type. Preferably the myb gene promoter is a myb32 gene promoter. Preferably the myb gene promoter is from *Arabidopsis*, more preferably *Arabidopsis thaliana*. Most preferably the myb gene promoter includes a nucleotide sequence selected from the group consisting of the sequence shown in Sequence ID No: 1 of PCT/AU01/01092 (SEQ ID No.: 44) and functionally active fragments and variants thereof.

A suitable promoter is described in Li et al., Cloning of three MYB-like genes from *Arabidopsis* (PGR 99-138) Plant Physiology 121:313 (1999).

By a "modified myb gene promoter" is meant a promoter normally associated with a myb gene, which promoter is modified to delete or inactivate one or more root specific motifs and/or pollen specific motifs in said promoter.

Preferably the modified myb gene promoter is a modified myb32 gene promoter. Preferably the modified myb gene promoter is modified from the myb gene promoter from *Arabidopsis*, or more preferably *Arabidopsis thaliana*.

A suitable promoter which may be modified according to the present invention is described in Li et al., Cloning of three MYB-like genes from *Arabidposis* (PGR 99-138) Plant Physiology 121:313 (1999).

By a "root specific motif" is meant a sequence of 3-7 nucleotides, preferably 4-6 nucleotides, more preferably 5 nucleotides, which directs expression of any associated gene in the roots of a plant.

Preferably the root specific motif includes a consensus sequence ATATT or AATAT.

By a "pollen specific motif" is meant a sequence of 3-7 nucleotides, preferably 4-6 nucleotides, more preferably 4 or 5 nucleotides, which directs expression of an associated gene in the pollen of a plant.

Preferably the pollen specific motif includes a consensus sequence selected from the group consisting of TTTCT, AGAAA, TTCT and AGAA.

A root or pollen specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences show in Sequence ID Nos: 2, 3 and 4 of U.S. Ser. No. 11/789,526 (SEQ ID Nos.: 45-47, respectively) and functionally active fragments and variants thereof.

By a "gene encoding an enzyme involved in biosynthesis of a cytokinin" is meant a gene encoding an enzyme involved in the synthesis of cytokinins such kinetin, zeatin and benzyl adenine, for example a gene encoding isopentyl transferase (ipt), or ipt-like gene such as the sho gene (eg. from *petunia*). Preferably the gene is an isopentenyl transferase (ipt) gene or sho gene. In a preferred embodiment, the gene is from a species selected from the group consisting of *Agrobacterium*, more preferably *Agrobacterium tumefaciens; Lotus*, more preferably *Lotus japonicus*; and *Petunia*, more preferably *Petunia hybrida*.

Most preferably the gene includes a nucleotide sequence selected from the group consisting of the sequences shown in Sequence ID Nos: 5, 7 and 9 of U.S. Ser. No. 11/789,526 (Seq ID No. 48-50, respectively), sequences encoding the polypeptides shown in Sequence ID Nos: 6, 8 and 10 of U.S. Ser. No. 11/789,526, (SEQ ID Nos: 51-53, respectively) and functionally active fragments and variants thereof.

The present invention also provides a method of selecting for transformed plants, said method including introducing into said plants an effective amount of a genetic construct including a promoter, or a functionally active fragment or variant thereof, operatively liked to a nucleic acid encoding a bacterial FT enzyme, or a functionally active fragment or variant thereof and selecting plants with enhanced biomass. Preferably the promoter is a light regulated promoter.

In a further aspect of the present invention there is provided a transgenic plant cell, plant, plant seed or other plant part with modified fructan biosynthetic characteristics or enhanced biomass relative to an untransformed control plant; said plant cell, plant, plant seed or other plant part including a genetic construct or vector according to the present invention.

By “modified fructan biosynthetic characteristics” is meant that the transformed plant exhibits increased fructan biosynthesis and/or contains increased levels of soluble carbohydrate relative to an untransformed control plant.

In a preferred embodiment the a transgenic plant cell, plant, plant seed or other plant part with enhanced biomass has an increase in biomass of at least approximately 15%, more preferably at least approximately 25%, more preferably at least approximately 35%, more preferably at least approximately 50% relative to an untransformed control plant.

For example, biomass may be increased by between approximately 15% and 500%, more preferably between approximately 25% and 300%, more preferably between approximately 35% and 200%, more preferably between approximately 50% and 100% relative to an untransformed control plant.

In a preferred embodiment, the transgenic plant cell, plant, plant seed or other plant part with modified fructan biosynthetic characteristics has an increase in soluble carbohydrate of least approximately 15%, more preferably at least approximately 25%, more preferably at least approximately 35%, more preferably at least approximately 50% relative to an untransformed control plant.

For example, soluble carbohydrates may be increased by between approximately 15% and 500%, more preferably between approximately 25% and 300%, more preferably between approximately 35% and 200%, more preferably between approximately 50% and 100% relative to an untransformed control plant.

Preferably the transgenic plant cell, plant, plant seed or other plant part is produced by a method according to the present invention.

The present invention also provides a transgenic plant, plant seed or other plant part derived from a plant cell of the present invention and including a genetic construct or vector of the present invention.

The present invention also provides a transgenic plant, plant seed or other plant part derived from a plant of the present invention and including a genetic construct or vector of the present invention.

Preferably, the transgenic plant cell, plant, plant seed or other plant part is a *Lolium* species, more preferably *Lolium perenne* or *Lolium arundinaceum*.

Preferably, the transgenic plant cell, plant, plant seed or other plant part is a cereal grain, more preferably a *Triticum* species, more preferably wheat (*Triticum aestivum*).

For example, the present invention enables the production of transgenic perennial ryegrass plants with increased fructans in leaf blades, vigorous growth and greater tolerance to abiotic stress, for improved nutrition for grazing animals.

The present invention also enables the production of transgenic wheat plants with increased fructans, vigorous growth, and tolerance to abiotic stress, for increased mass of usable carbohydrates, eg. for bio-fuel production or animal feed.

By ‘plant cell’ is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

By ‘transgenic’ is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into either the nuclear or plastidic genome.

DETAILED DESCRIPTION OF THE EMBODIMENTS

The present invention will now be more fully described with reference to the accompanying examples and drawings. It should be understood, however, that the description following is illustrative only and should not be taken in any way as a restriction on the generality of the invention described above.

In the figures:

FIG. 1: Schematic representation of SacB protein from *Bacillus subtilis*, member of GH68 family. The four different regions shown are: N-terminal signal sequence; N-terminal variable region; catalytic core; and C-terminal variable region. Amino acid residues, including the catalytic triad (D86, D247 and E342) and sucrose binding (W85, W163 and R246).

FIG. 2. Nucleotide sequence of SacB gene from *Bacillus subtilis* (Levansucrase) (SEQ ID No.: 5). Nucleotide sequence coding for the N-terminal signal peptide is in bold. (SEQ ID No.: 6)

FIG. 3. Amino acid sequence SacB protein from *Bacillus subtilis* (Levansucrase) (SEQ ID No.: 7). The N-terminal signal peptide is in bold. (SEQ ID No.: 8)

FIG. 4. Nucleotide sequence of Lsc gene from *Lactobacillus johnsonii* NCC 533 (Inulosucrase). (SEQ ID No.: 9) Nucleotide sequence coding for the N-terminal signal peptide is in bold. (SEQ ID No.: 10)

FIG. 5. Amino acid sequence of Lsc protein from *Lactobacillus johnsonii* NCC 533 (Inulosucrase). (SEQ ID No.: 11) The N-terminal signal peptide is in bold. (SEQ ID No.: 12)

FIG. 6. Nucleotide sequence of SPOR531, Prepresporamin protein from *I. batatas*. (SEQ ID No.: 13) Vacuolar targeting signal sequence is shown in bold underlined. (SEQ ID No.: 14)

FIG. 7. Amino acid sequence of SPOR531, Prepresporamin protein from *I. batatas*. (SEQ ID No.: 15) Vacuolar targeting signal sequence is shown in bold underlined. (SEQ ID No.: 16)

FIG. 8. SPOR:SacB chimeric nucleotide sequence. (SEQ ID No.: 17) The N-terminal signal sequence of SacB has been replaced by the vacuolar targeting signal of SPOR (indicated by bold underlined).

FIG. 9. SPOR:SacB chimeric protein sequence. (SEQ ID No.: 18) The N-terminal signal sequence of SacB has been replaced by the vacuolar targeting signal of SPOR (indicated by bold underlined).

Figure 10:
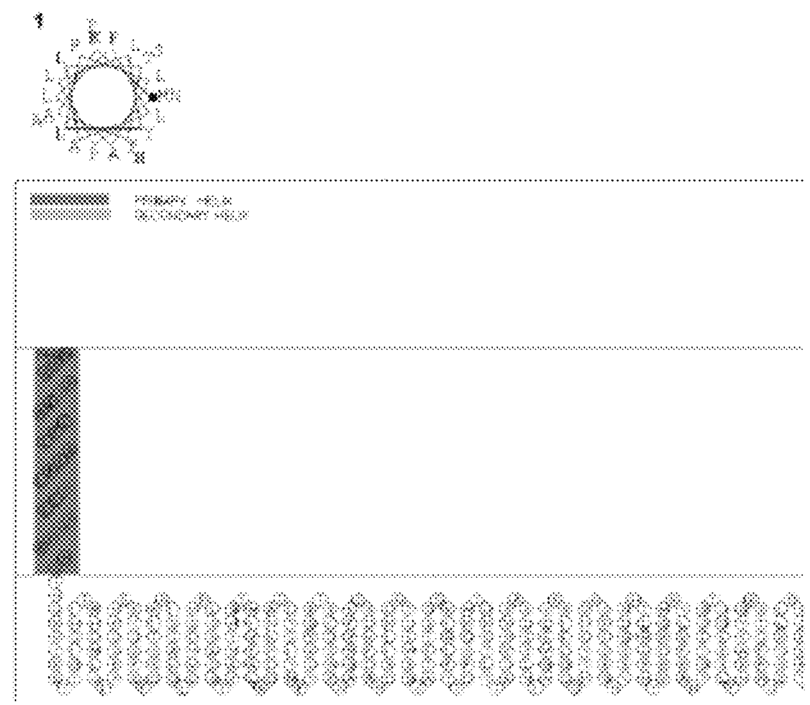

FIG. 10. Secondary Structure Prediction of SPOR-SacB fusion protein using Secondary (Structure Prediction of Membrane Proteins software SOSUI bp.nuap.nagoya-u.ac.jp/sosui.

FIG. 11. SPOR:Lsc chimeric nucleotide sequence. (SEQ ID No.: 19) The N-terminal signal sequence of Lsc has been replaced by the vacuolar targeting signal of SPOR (indicated by bold underlined).

FIG. 12. SPOR:Lsc chimeric protein sequence. (SEQ ID No.: 20) The N-terminal signal sequence of Lsc has been replaced by the vacuolar targeting signal of SPOR (indicated by bold underlined).

Figure 13:
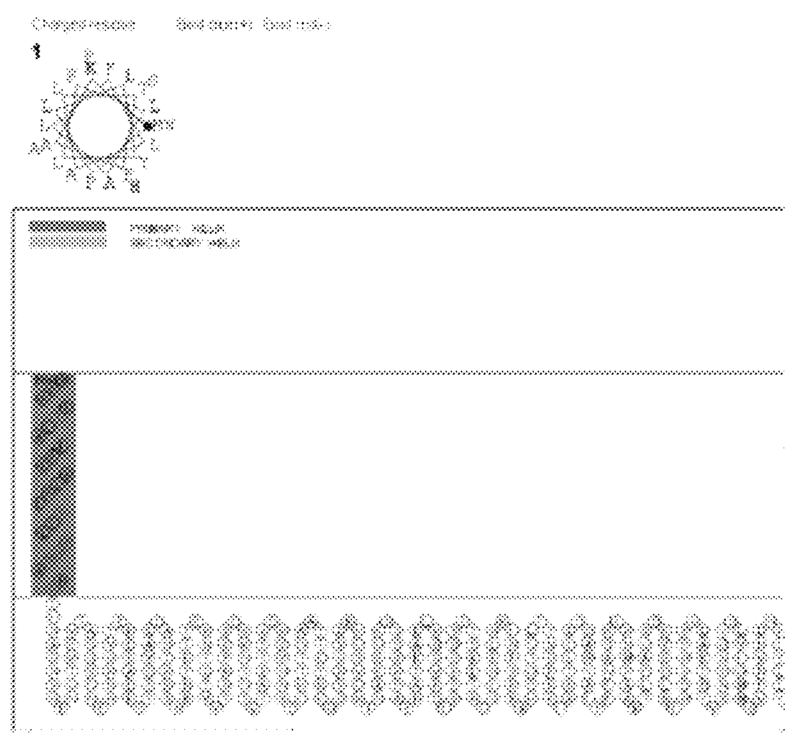

FIG. 13. Secondary Structure Prediction of SPOR-Lsc fusion protein using Secondary Structure Prediction of Membrane Proteins software SOSUI.

Figure 14:
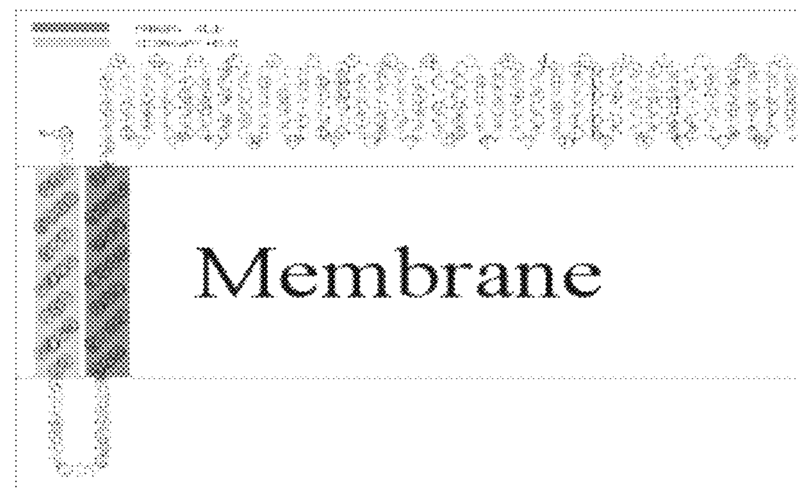

FIG. 14. Secondary Structure Prediction of Lp1-SST using Secondary Structure Prediction of Membrane Proteins software SOSUI.

FIG. 15. Lp1-SST nucleotide sequence from *L. perenne*. (SEQ ID No.: 21) The Lp1-SST transmembrane domain coding sequence is shown in bold italics. (SEQ ID No.: 22)

FIG. 16. Lp1-SST protein sequence from *L. perenne*. (SEQ ID No.: 23) The Lp1-SST transmembrane domain is shown in bold italics. (SEQ ID No.: 24)

FIG. 17. Lp1-SST-SacB chimeric nucleotide sequence. (SEQ ID No.: 25) The N-terminal signal coding sequence of SacB has been replaced by the Lp1-SST transmembrane domain coding sequence (indicated by bold italics). (SEQ ID No.: 26)

FIG. 18. Lp1-SST-SacB chimeric protein sequence. (SEQ ID No.: 27) The N-terminal signal sequence of SacB has been replaced by the Lp1-SST transmembrane domain (indicated by bold italics).

Figure 19:
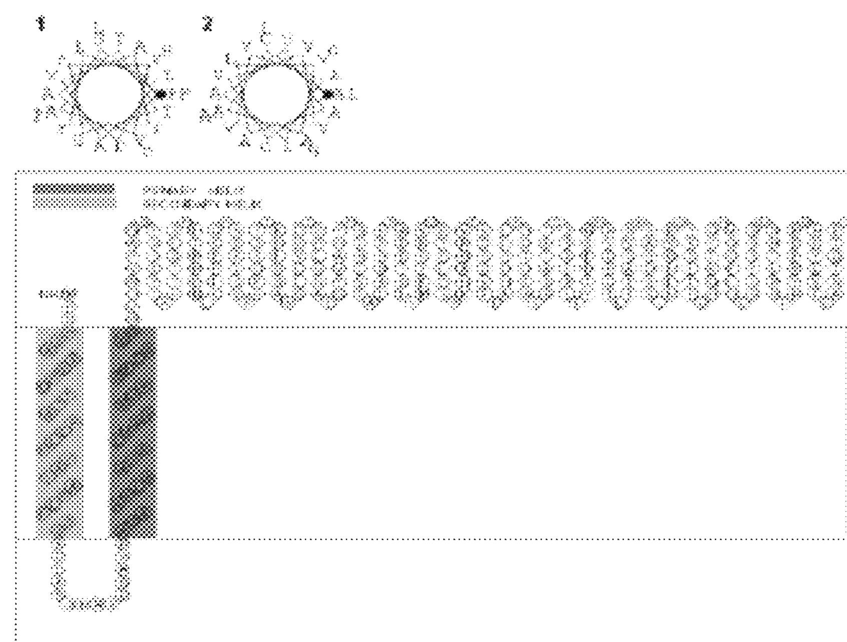

FIG. 19. Secondary Structure Prediction of Lp1-SST-SacB fusion protein using Secondary Structure Prediction of Membrane Proteins software SOSUI.

FIG. 20. Lp1-SST-Lsc chimeric nucleotide sequence. (SEQ ID No.: 28) The N-terminal signal coding sequence of Lsc has been replaced by the Lp1-SST transmembrane domain coding sequence (indicated by bold italics).

FIG. 21. Lp1-SST-Lsc chimeric protein sequence. (SEQ ID No.: 29) The N-terminal signal sequence of Lsc has been replaced by the Lp1-SST transmembrane domain (indicated by bold italics).

Figure 22:
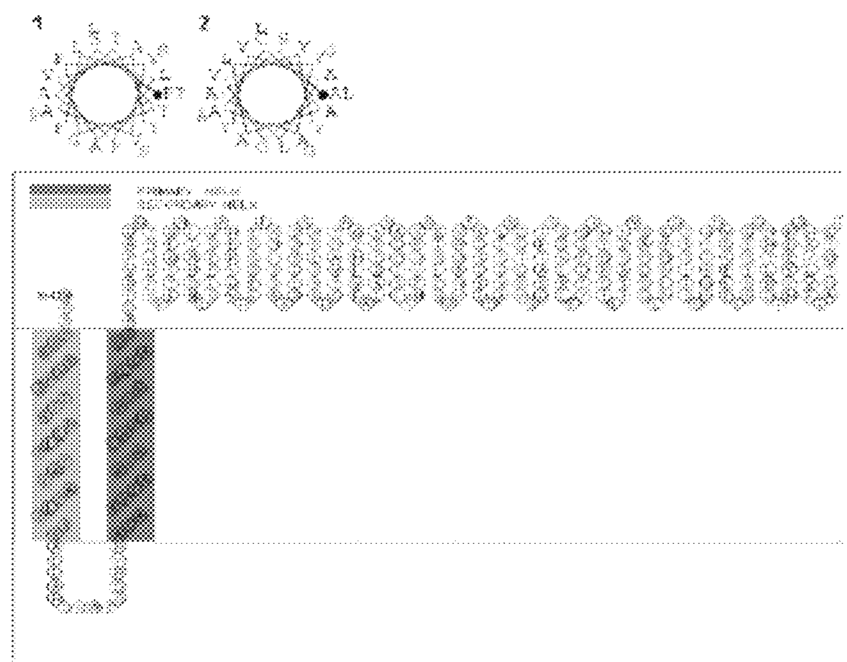

FIG. 22. Secondary Structure Prediction of Lp1-SST-Lsc fusion protein using Secondary Structure Prediction of Membrane Proteins software SOSUI.

FIG. 23. Nucleotide sequences of the AtRbcS::SPOR-SacB::NOS expression cassette (SEQ ID No.: 30).

FIG. 24. Nucleotide sequences of the AtRbcS::SPOR-Lsc::NOS expression cassette (SEQ ID No.: 31).

FIG. 25. Nucleotide sequences of the AtRbcS::Lp1-SST-SacB::NOS expression cassette (SEQ ID No.: 32).

FIG. 26. Nucleotide sequences of the AtRbcS::Lp1-SST-Lsc::NOS expression cassette (SEQ ID No.: 33).

Figure 27:
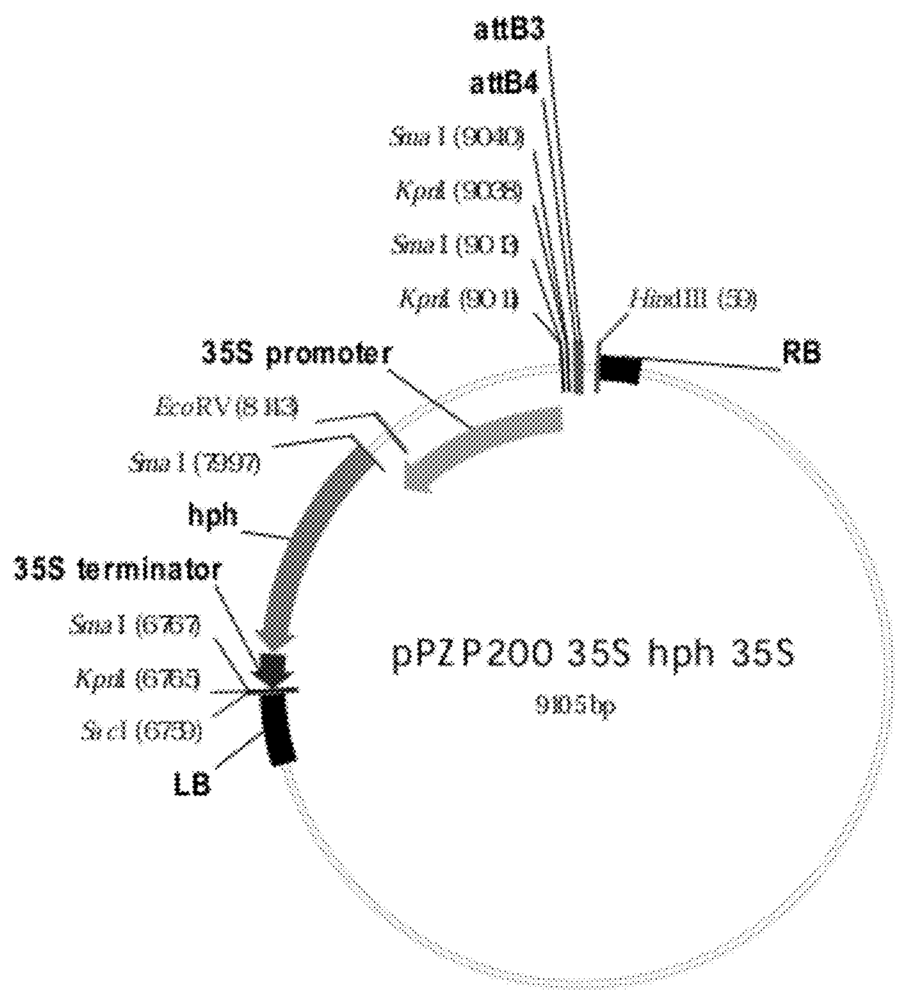

FIG. 27. Gateway pDestination vector

Figure 28:
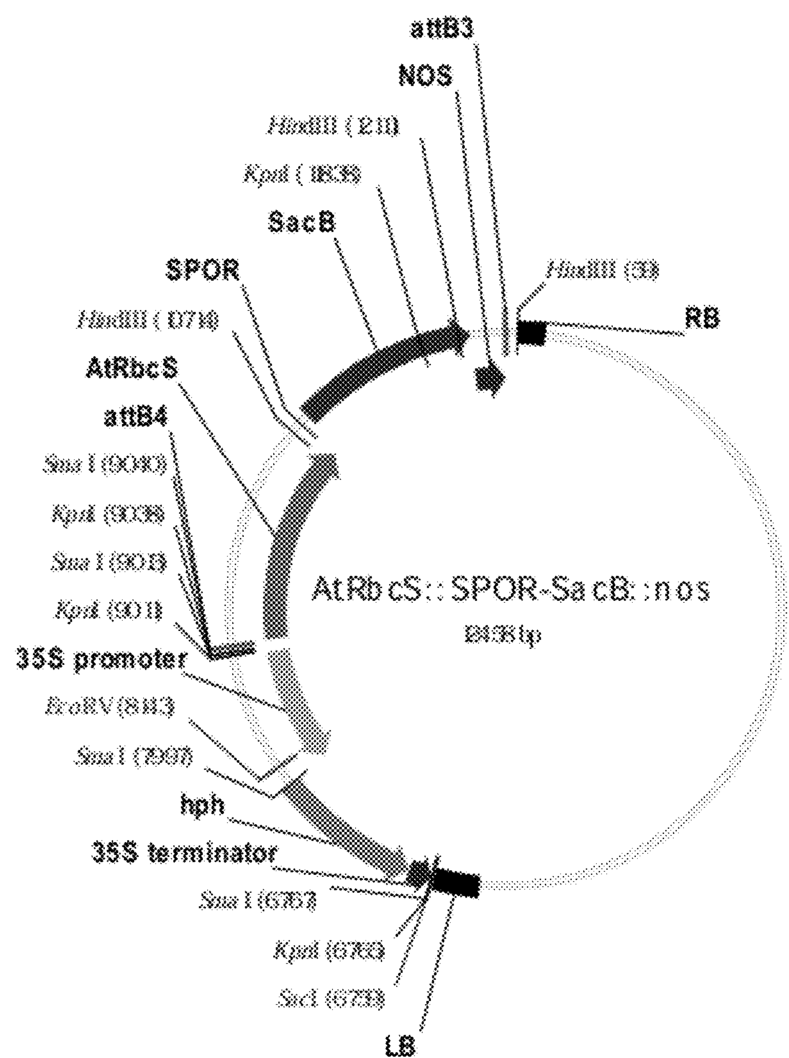
Figure 28:
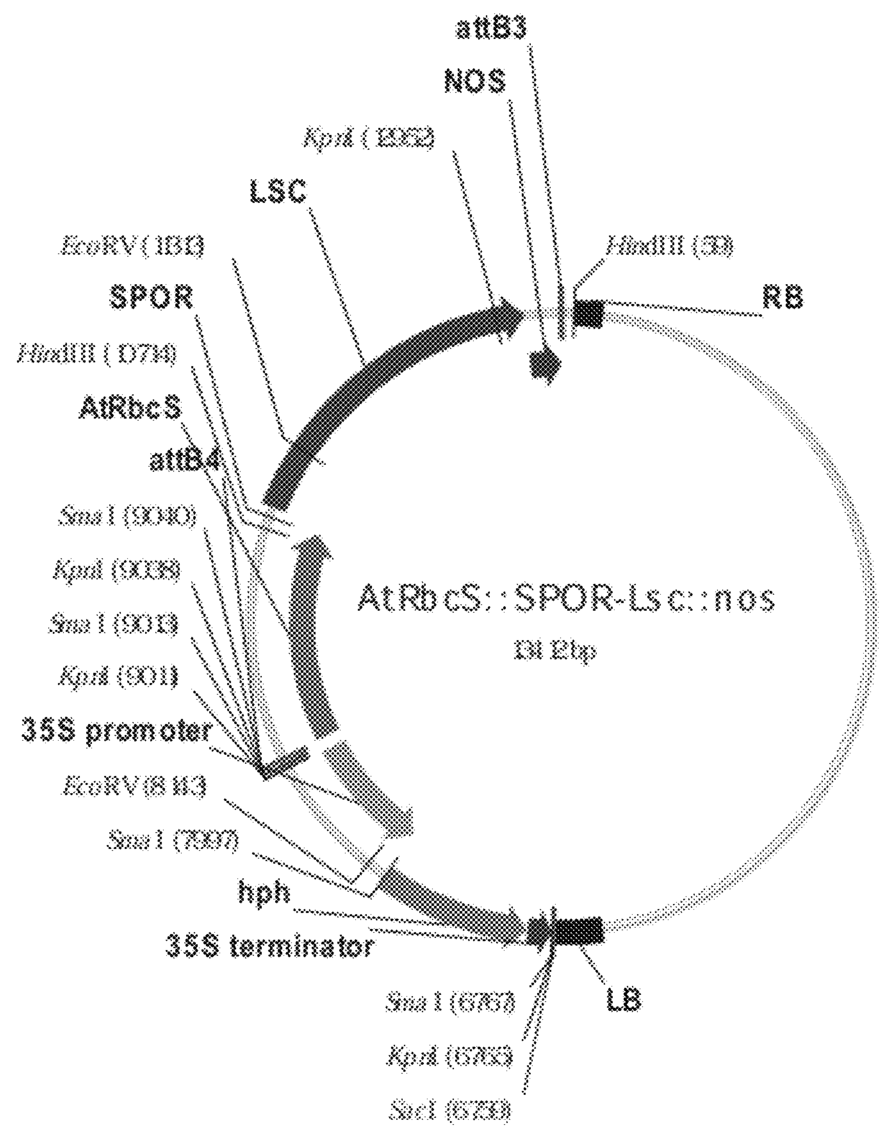
Figure 28:
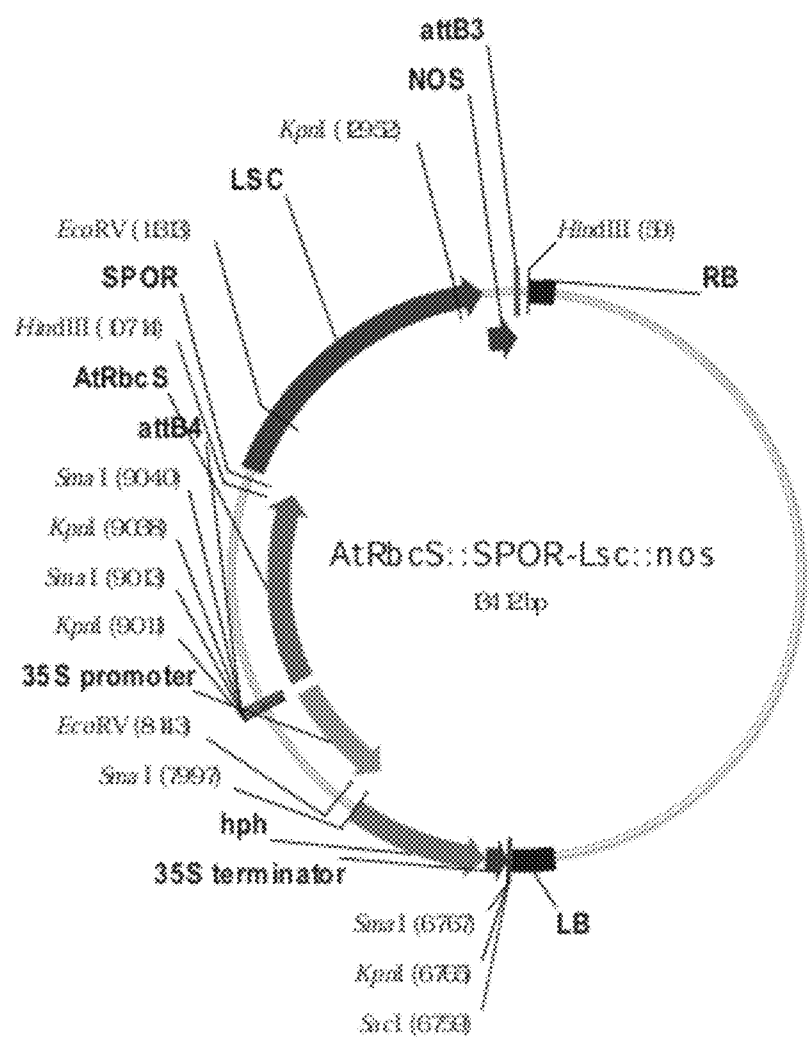
Figure 28:
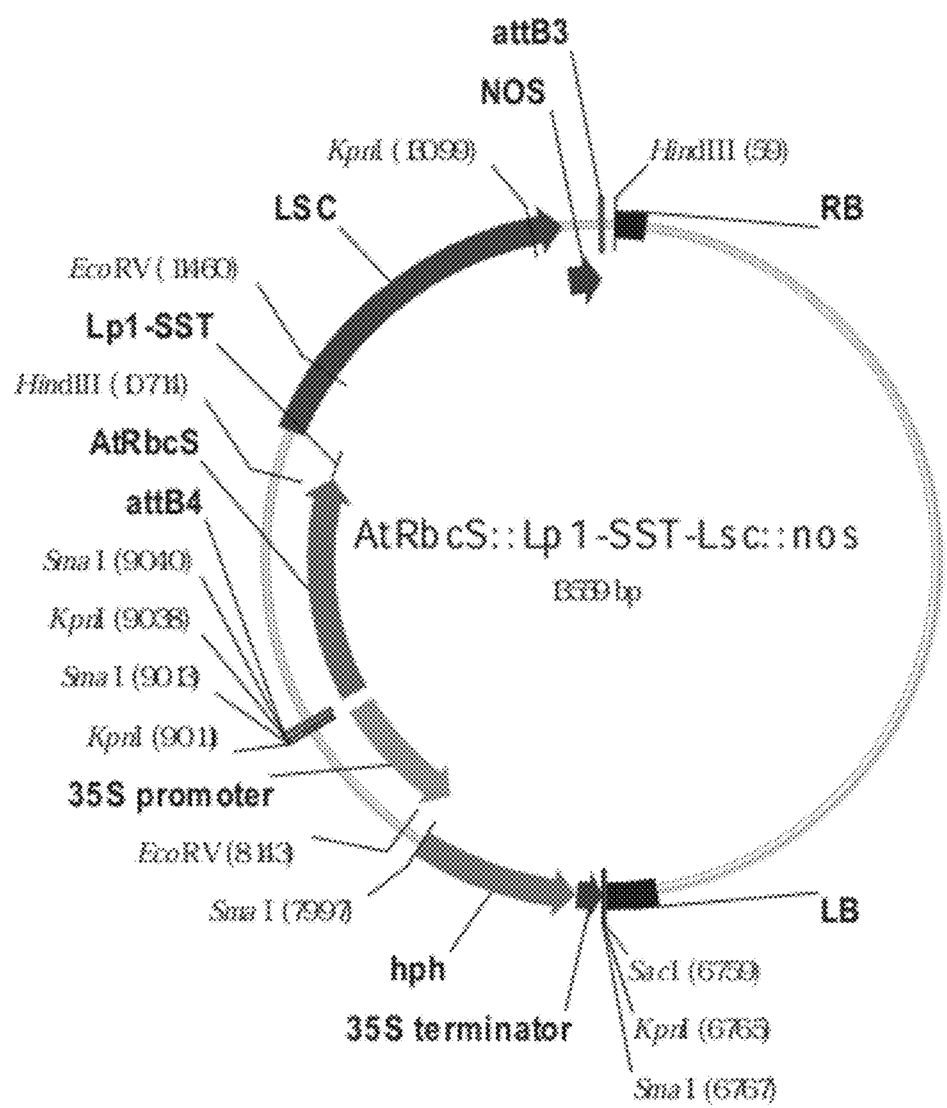

FIG. 28. Gateway pDestination vectors for transformation of dicots:

A. AtRbcS::SPOR-SacB::NOS; B. AtRbcS::SPOR-Lsc::NOS C. AtRbcS::Lp1-SST-SacB::NOS and D. AtRbcS::Lp1-SST-Lsc::NOS.

FIG. 29. Nucleotide sequences of the TaRbcSp::SPOR-SacB::TaRbcst expression cassette (SEQ ID No.: 34).

FIG. 30. Nucleotide sequences of the TaRbcSp::SPOR-SacB::TaRbcst TaRbcst+AtMYB32::IPT::35S expression cassette (SEQ ID No.: 35).

FIG. 31. Nucleotide sequences of the TaRbcSp::SPOR-Lsc::TaRbcst expression cassette (SEQ ID No.: 36).

FIG. 32. Nucleotide sequences of the TaRbcSp::SPOR-Lsc::TaRbcst+AtMYB32::IPT::35S expression cassette (SEQ ID No.: 37).

Figure 33:
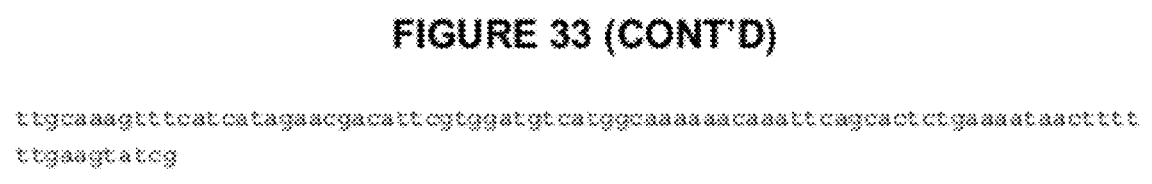

FIG. 33. Nucleotide sequences of the TaRbcSp::Lp1-SST-SacB::TaRbcst expression cassette (SEQ ID No.: 38).

FIG. 34. Nucleotide sequences of the TaRbcSp::Lp1-SST-SacB::TaRbcst TaRbcst+AtMYB32::IPT::35S expression cassette (SEQ ID No.: 39).

FIG. 35. Nucleotide sequences of the TaRbcSp::Lp1-SST-Lsc::TaRbcst expression cassette (SEQ ID No.: 40).

FIG. 36. Nucleotide sequences of the TaRbcSp::SPOR-Lsc::TaRbcst+AtMYB32::IPT::35S expression cassette (SEQ ID No.: 41).

Figure 37:
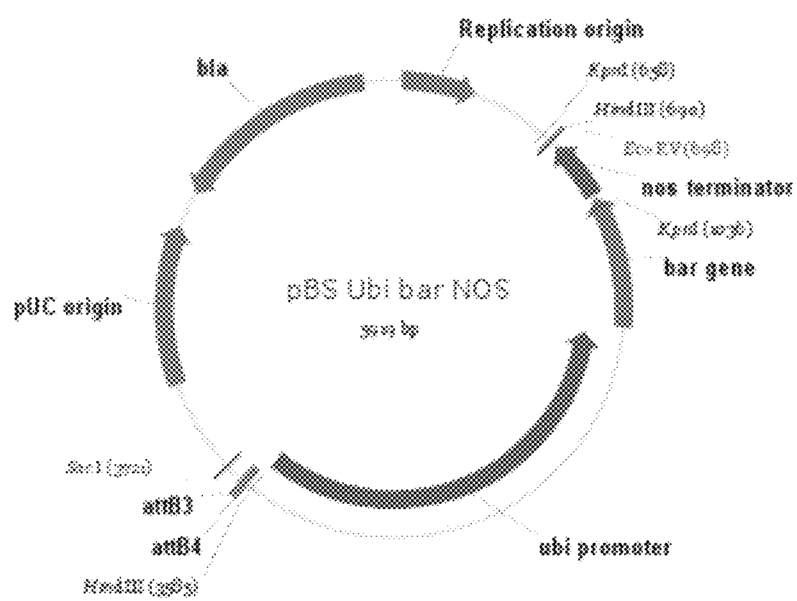

FIG. 37. Gateway pDestination vector pBS:ubi::bar::NOS

FIG. 38. Gateway pDestination vectors for transformation of monocots:

A. TaRbcS::SPOR-SacB::TaRbcS and B. TaRbcS::SPOR-SacB::TaRbcS+AtMYB32::IPT::35S

FIG. 39. Gateway pDestination vectors for transformation of monocots:

A. TaRbcS::SPOR-Lsc::TaRbcS and B. TaRbcS::SPOR-Lsc::TaRbcS+AtMYB32::IPT::35S

Figure 42:
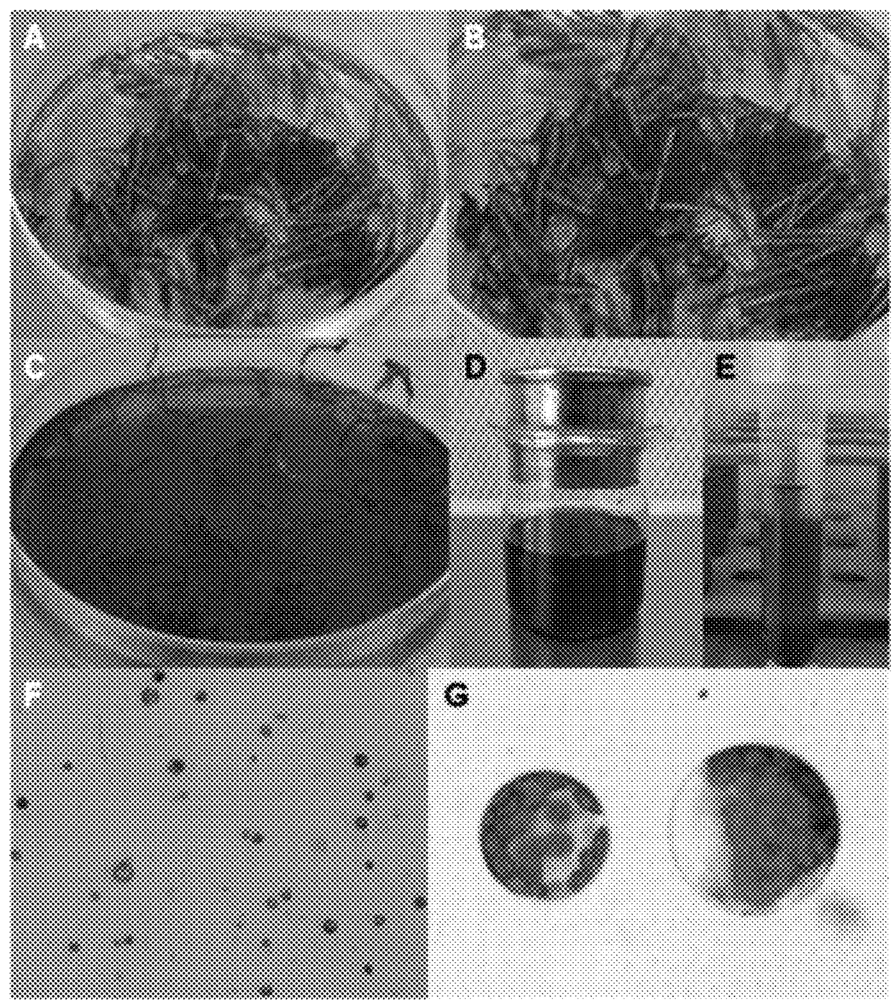

FIG. 40. Gateway pDestination vectors for transformation of monocots:

A. TaRbcS::Lp1-SST-SacB::TaRbcS and B. TaRbcS::Lp1-SST-SacB::TaRbcS+AtMYB32::IPT::35S FIG. 41. Gateway pDestination vectors for transformation of monocots:

A. TaRbcS::Lp1-SST-Lsc::TaRbcS and B. TaRbcS::Lp1-SST-Lsc::TaRbcS+AtMYB32::IPT::35S FIG. 42. Isolation of mesophyll-derived protoplasts of *Nicotiana tabacum*. A)-B) Dissection of 4-6 week-old in vitro leaf material; pre-enzymatic digestion; C) Digestion of 4-6 week-old in vitro leaf material; 16 hours incubation; D) Harvesting of protoplast suspension; E) Separation of protoplast-rich interphase; F)-G) Intact, chloroplast-rich protoplasts.

Figure 43:
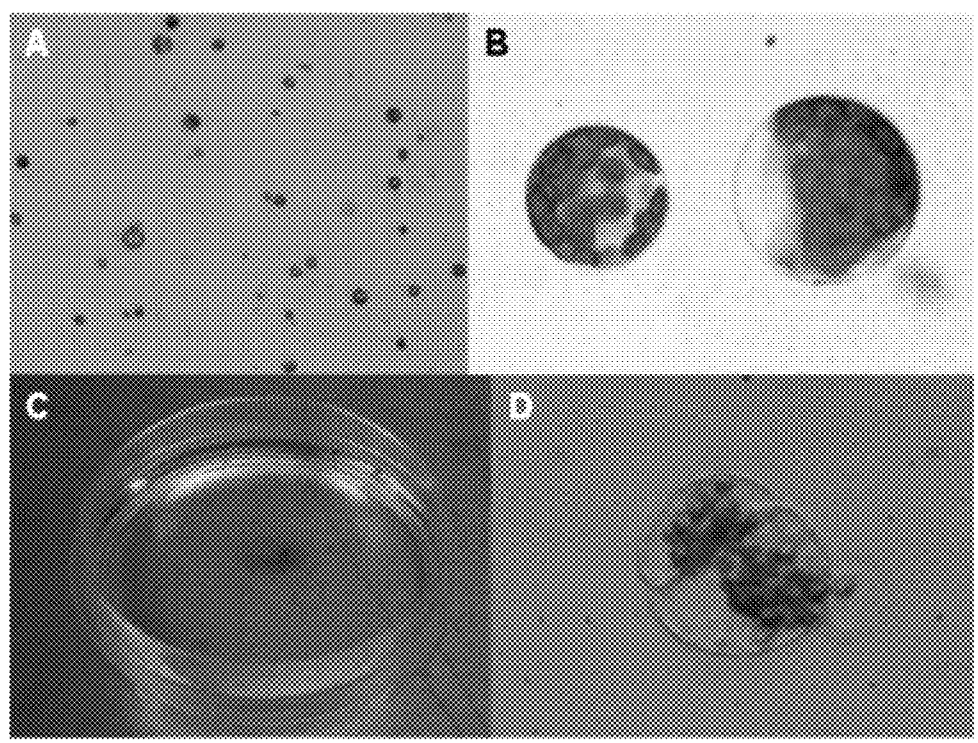

FIG. 43. Isolation of mesophyll-derived protoplasts of *Nicotiana tabacum* for transient expression analysis. A)-B) Intact, chloroplast-rich protoplasts; C) Culturing of protoplasts in liquid enrichment medium; D) Viable protoplast; 48 hours post isolation.

Figure 44:
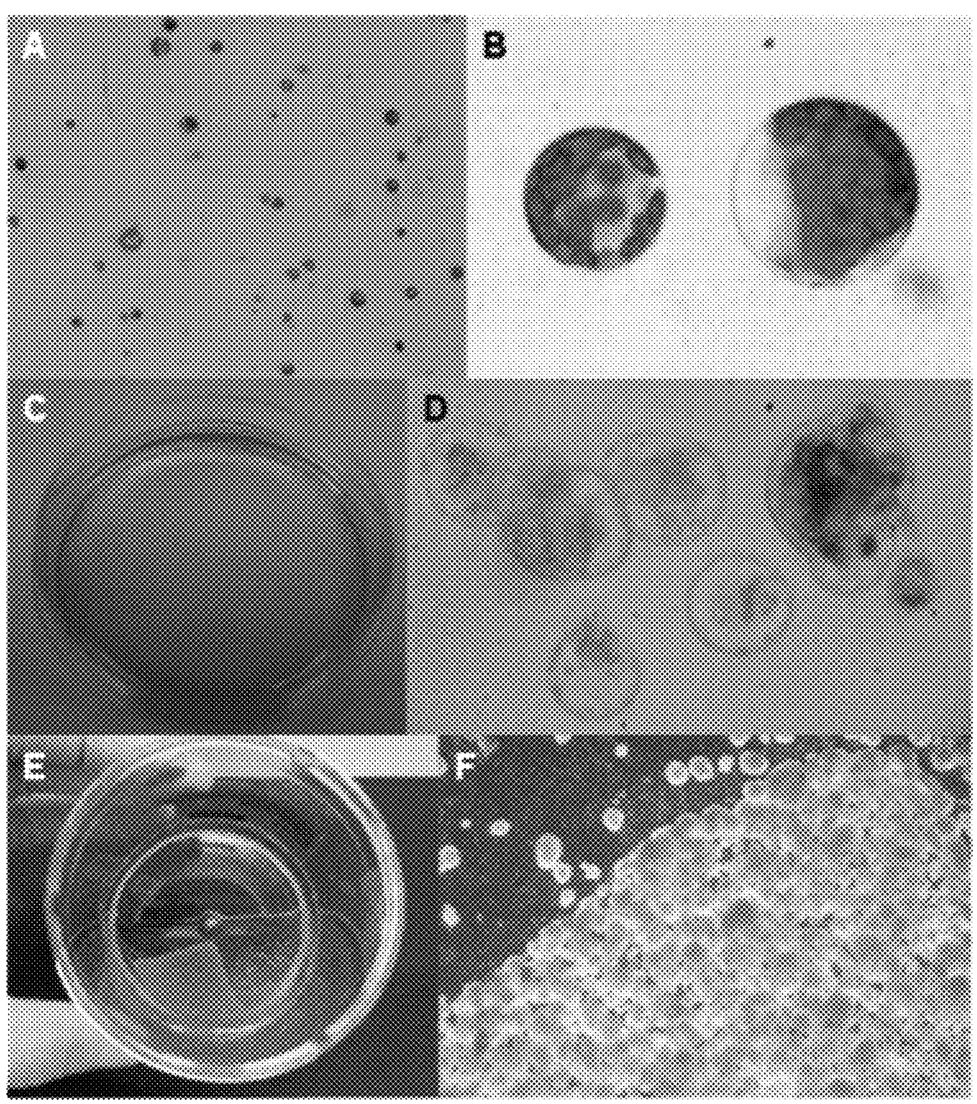

FIG. 44. Isolation of mesophyll-derived protoplasts of *Nicotiana tabacum* for stable transformations. A)-B) Intact, chloroplast-rich protoplasts; C) Protoplast-embedded sea plaque agarose plug, day 0; D) Viable protoplasts; 6 days post isolation and embedding; E)-F) Embedded and liberated protoplast-derived micro-calli; 4 weeks post isolation and embedding.

Figure 45:
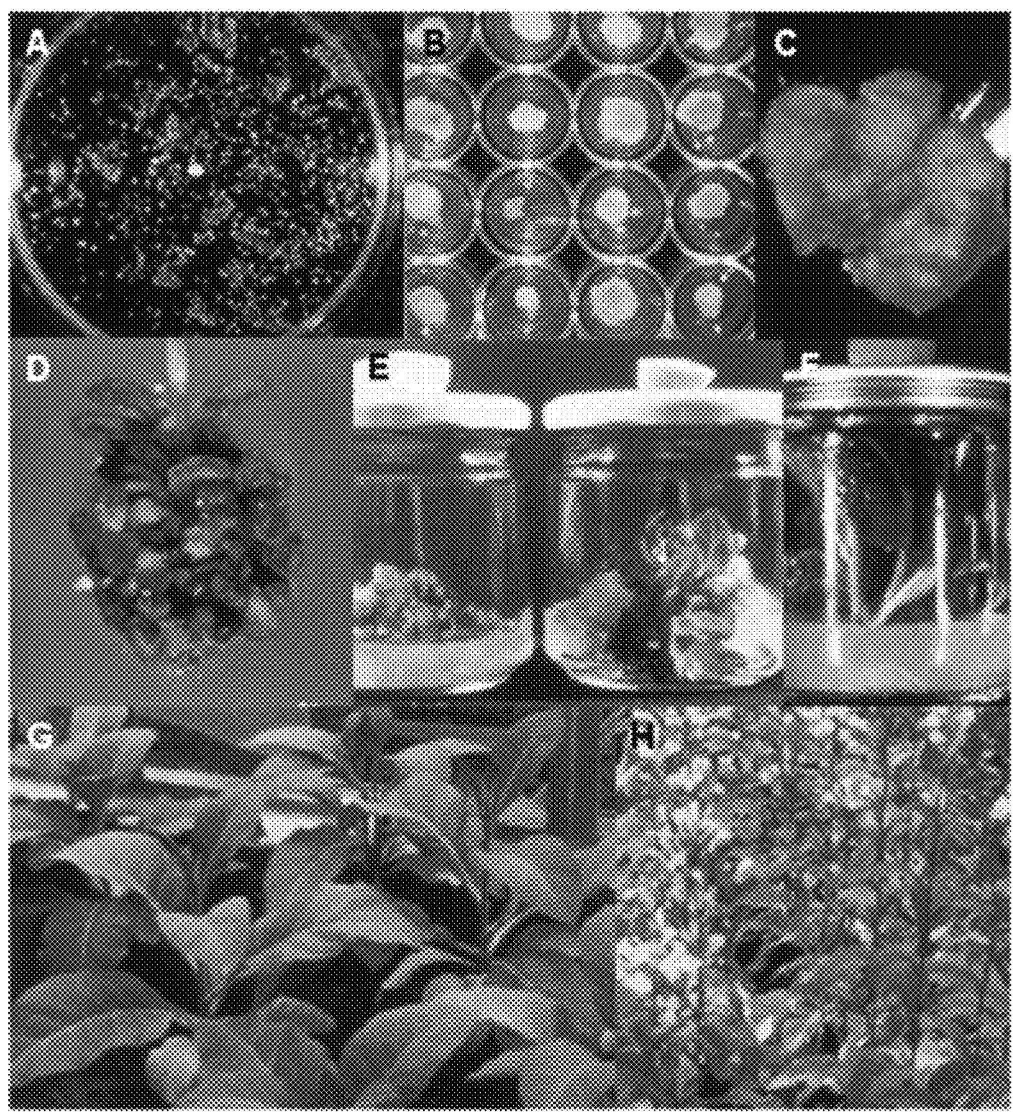

FIG. 45. Regeneration of shoots from mesophyllprotoplast-derived micro-calli of *Nicotiana tabacum*. A) Liberated micro-calli in liquid growth medium A, 6-7 weeks post isolation and embedding; B-C) Proliferation of calli on solidified growth medium; D)-E) Shoot induction and regeneration from mesophyllprotoplast-derived calli; F) Root development from regenerated shoots; G)-H) Growth and development of plants under glasshouse containment.

Figure 46:
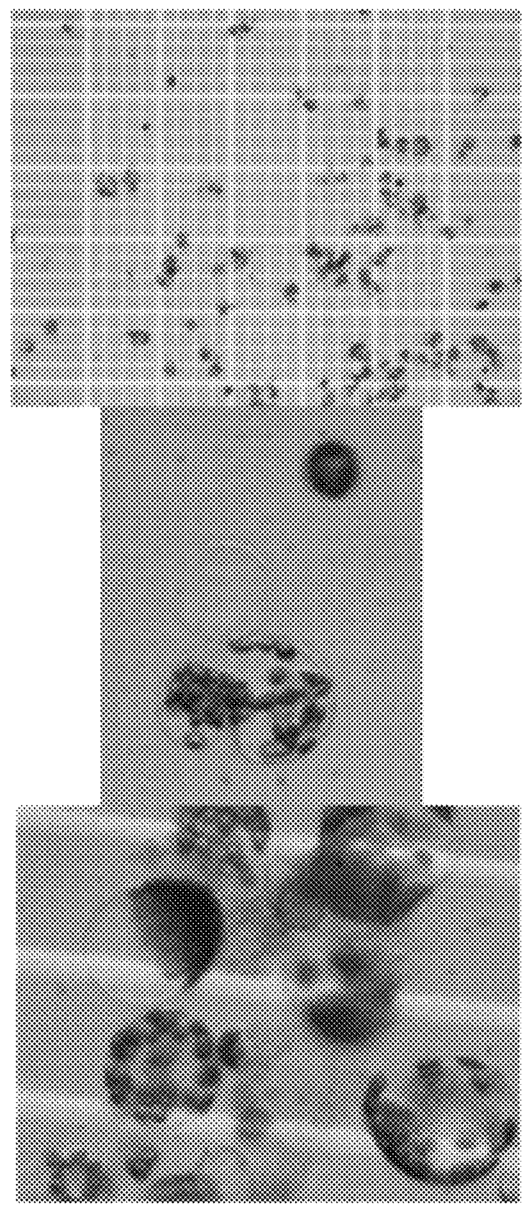

FIG. 46. Evaluation of untransformed protoplast viability; 48 hours post isolation.

Figure 47:
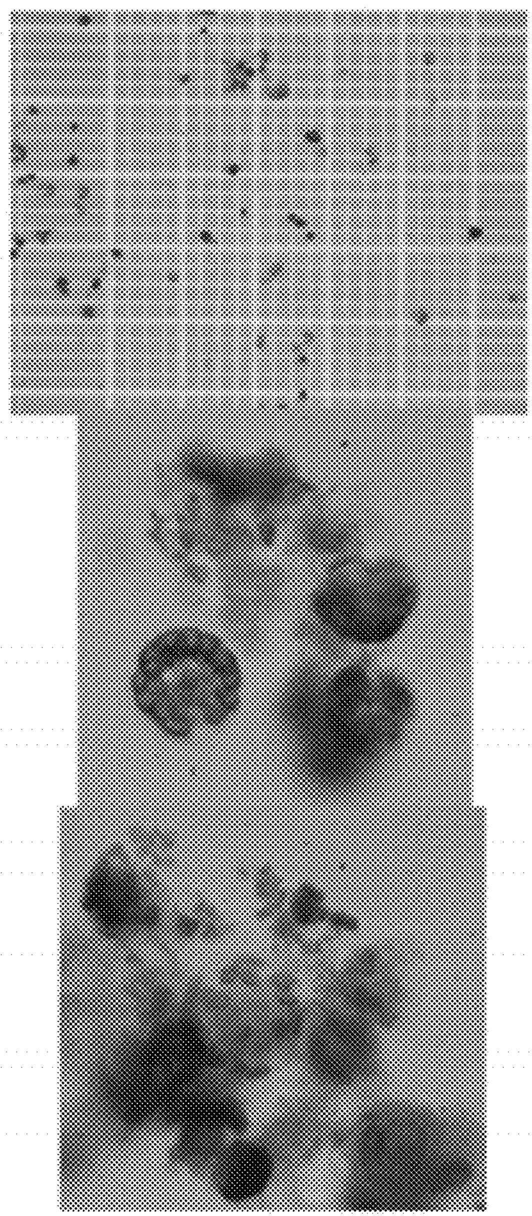

FIG. 47. Evaluation of PEG-transformed protoplast viability; 48 hours post isolation and transfection.

Figure 48:
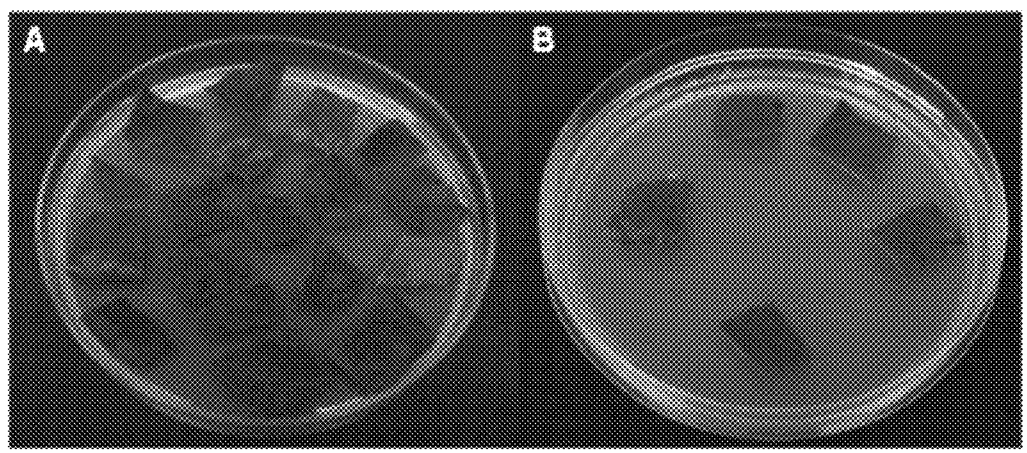

FIG. 48. *Agrobacterium*-mediated transformation of tobacco leaf discs. A) Co-cultivation of transformed leaf discs, day 0; B) Stage 1 initiation of shoots; 3 days post co-cultivation.

Figure 49:
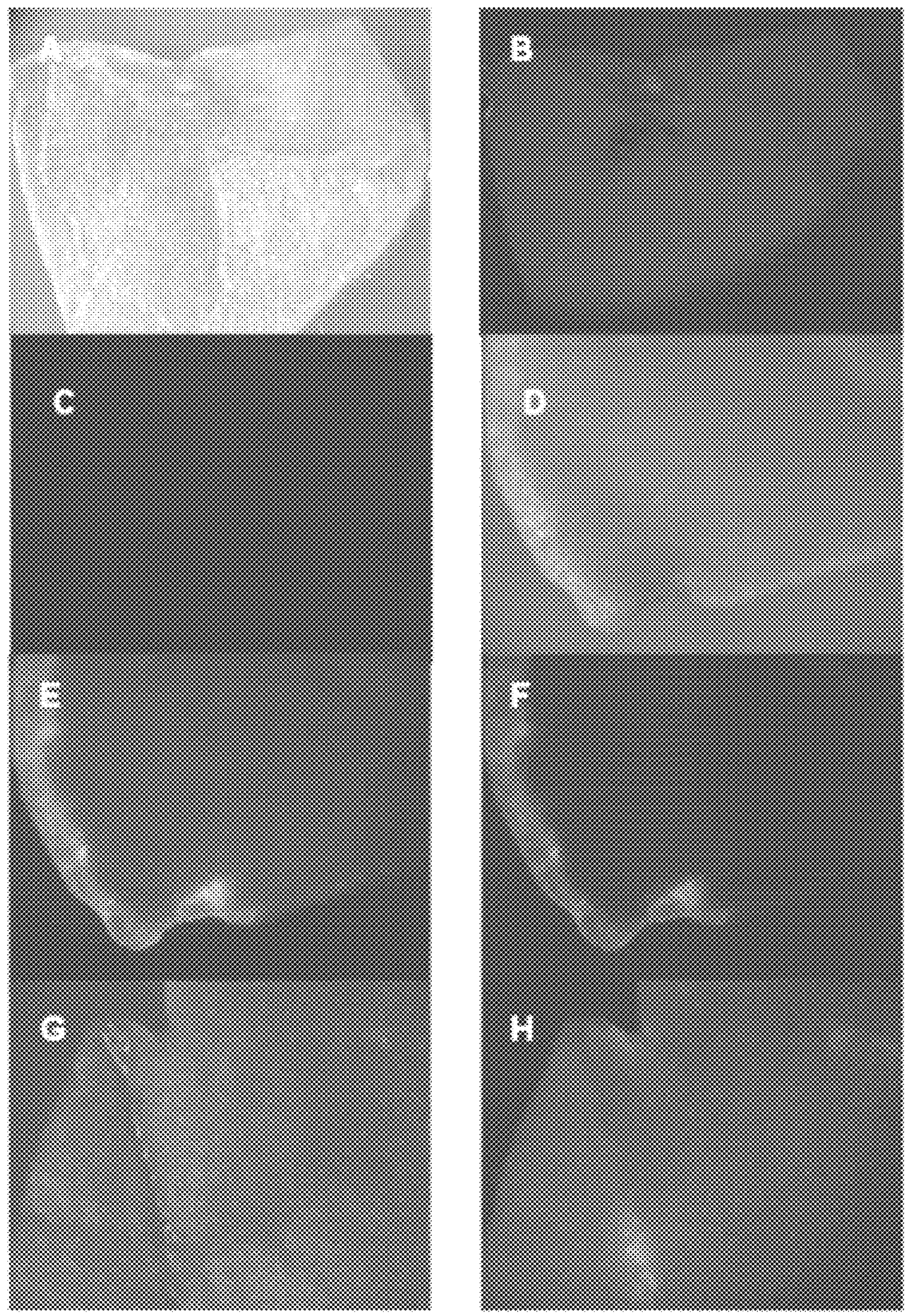
Figure 49:
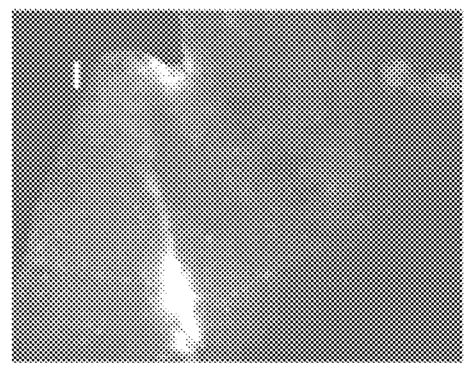

FIG. 49. Detection of gfp expression in transformed leaf discs of Tobacco. A) Untransformed leaf disc, white light; B) Untransformed leaf disc, gfp2 filter; C) Untransformed leaf disc, gfp3 filter; D)&G) Turbo gfp-transformed leaf discs, white light; E)&H) Turbo gfp-transformed leaf discs, gfp2 filter; F)&I) Turbo gfp-transformed leaf discs, gfp3 filter.

Figure 50:
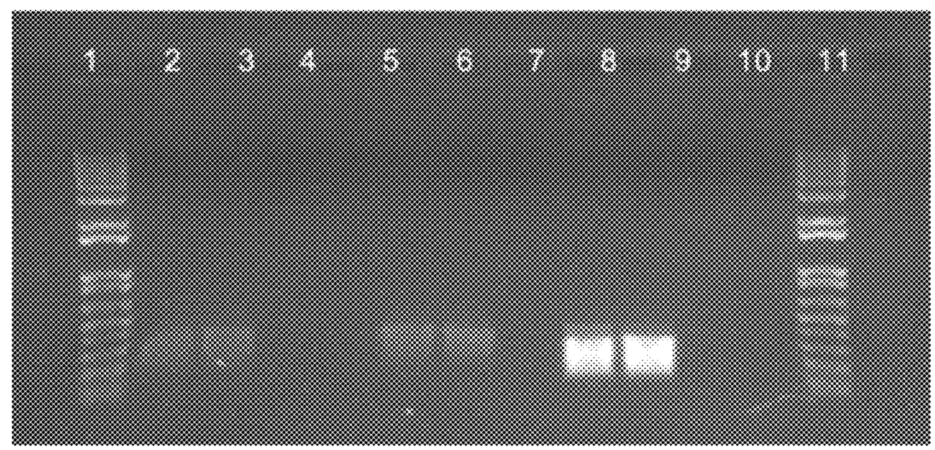

FIG. 50. Electrophoresis of RT-PCR samples and controls.

Lane 1 and 13: 1 kb+DNA Ladder

Lane 2: Amplification of sacB transcript from 2 μL cDNA generated by reverse transcription of mRNA from transfected protoplast 1 (sample 9A) with gene specific primer Lane 3: Amplification of sacB transcript from 1 μL cDNA (sample 9A)

Lane 4: Control reaction performed without reverse transcriptase (sample 9A)

Lane 5: Control reaction performed without template (sacB primers)

Lane 6: Amplification of sacB transcript from 2 μL cDNA generated by reverse transcription of mRNA from transfected protoplast 1 (sample 12A) with gene specific primer Lane 7: Amplification of sacB transcript from 1 μL cDNA (sample 12A)

Lane 8: Control reaction performed without reverse transcriptase (sample 12A)

Lane 9: Amplification of 18S transcript from 2 μL cDNA generated by reverse transcription of mRNA from untransfected protoplast with gene specific primer Lane 10: Amplification of 18S transcript from 1 μL cDNA generated by reverse transcription of mRNA from untransfected protoplast with gene specific primer Lane 11: Control reaction performed without reverse transcriptase (untransfected protoplast)

Lane 12: Control reaction performed without template (18S primers)

EXAMPLES

Example 1

Isolation of Bacterial Fructan Biosynthesis Genes

FIG. 1 presents a schematic representation of SacB protein from *Bacillus subtilis*. The four different regions shown are: N-terminal signal sequence; N-terminal variable region; catalytic core; and C-terminal variable region. Structurally, most of the bacterial inulosucrases and levansucrases share the N-terminal signal peptide, a catalytic triad. This sequence is removed during the sequence modification. The residues involved in sucrose binding are located inside the catalytic core sequences and remain untouched during the modification.

The bacterial levansucrase (SacB) and inulosucrase (Lsc) nucleotide and protein sequences are provided in FIGS. 2-5, respectively. However, for transformation into plants the bacterial levansucrase and inulosucrase sequences are also modified in the following manner:

- Removal of the bacterial N-signal peptide;
- Adaptation of codon usage, including the start of translation for monocots and dicots;
- Removal of cryptic splice sites and RNA destabilizing sequence elements;
- The coding sequence is further modified with putative sub-cellular targeting sequences including vacuolar targeting sequences for monocots and dicots as well as including plant 1-SST-specific transmembrane domains.

Outlines of these changes are indicated in the following example.

Example 2

Modification of Bacterial Fructan Biosynthesis Genes

Targeting of Bacterial FT Genes to Specific Cellular Compartments

To direct the bacterial FT genes away from the cytosol and to compartment where both sucrose and fructan accumulate the coding sequences of SacB and Lsc are modified with a putative vacuolar targeting sequence from the pre-prosporamin protein (SPOR531) of sweet potato (*Ipomoea batatas*). The propeptide of a precursor to sporamin is required for targeting of sporamin to the vacuole (Hattori et al., 1985). The vacuolar targeting information of sporamin is encoded in an amino-terminal propeptide and is indicated in FIGS. 5 and 6.

Sequence modification involves the removal of the N-signal peptide from both the SacB and Lsc bacterial fuctan biosynthesis genes and the addition of SPOR531 vacuolar targeting signal (FIGS. 7-8 and 10-11, respectively).

Prediction of subcellular localisation and topology of the modified proteins using the Secondary Structure Prediction of Membrane Proteins software SOSUI indicates a transmembrane localization triggered by the vacuolar targeting signal (FIGS. 9 and 12).

Addition of Transmembrane Domains from Lp1-SST Protein to Bacterial FT Genes

The SOSUI software was also used to predict the secondary structure of the *Lolium perenne* 1-SST gene. This structure, indicating a transmembrane domain at the N terminus is indicated in FIG. 13. The transmembrane domain coding and protein sequences are indicated in FIGS. 14 and 15, respectively.

Sequence modification involves the removal of the N-signal peptide from both the SacB and Lsc bacterial fuctan biosynthesis genes and the addition of the Lp1-SST transmembrane domain (FIGS. 16-17 and 19-20, respectively). The modified sequences of SacB and Lsc were assessed using the Secondary Structure Prediction of Membrane Proteins software SOSUI for subsellular localization and protein topology and their predicted secondary structures are presented in FIGS. 18 and 21, respectively.

Example 3

Generating Vectors for Stable Transformation in Dicots

Synthesis of Expression Constructs

Expression constructs utlising photosyntheic promoters, the modified bacterial fructan biosynthesis genes indicated in Example 2 and the NOS terminator sequence for transformation into dicot plants is artificially synthesised.

The use of a photosynthetic promoter expresses the genes in tissues that accumulate fructans, while the modified sequences target the protein to specific plant cell compartments.

The Ribulose-1,5-bisphosphate carboxylase/oxygenase Small subunit (RbcS) is a well-characterised light-regulated gene in higher plants. A 1700 bp fragment of the *Arabidopsis thaliana* Ribulose-1,5-bisphosphate carboxylase/oxygenase Small subunit (AtRbcS) promoter sequence has previously been cloned. Primers are designed to amplify a smaller fragment containing the TATA signal from the AtRbcS promoter for use in expression vectors.

The newly predicted sequences for the modified bacterial fructan biosynthetic genes are be artificially synthesised altering codon usage for expression in plants, as well as removing cryptic splice sites and RNA destabilizing sequence elements, to optimise their performance in the plant cell.

FIGS. 23-26 represent the expression cassettes AtRbcS::SPOR-SacB::NOS,

AtRbcS::SPOR-Lsc::NOS, AtRbcS::Lp1-SST-SacB::NOS and AtRbcS::Lp1-SST-Lsc::NOS, respectively, and have not yet had codon optimisation or removal of destabilising elements.

Generation of Constructs Containing Modified Bacterial FT Genes Driven by an *Arabidopsis* Photosynthetic Promoter for Transformation of Dicots Each synthesised expression cassette is placed in a Gateway enabled pDONOR vector for recombination into the final destination vector for transformation into plants.

A Gateway enabled destination vector, containing the 35Sp:hph:35St selectable marker cassette has been generated, pPZP200_35Sp_hph_35St_R4/R3 (FIG. 27).

Gateway LR recombination reactions produce the following destination vectors for transformation into dicots:
AtRbcS::SPOR-SacB::NOS (FIG. 28A);
AtRbcS::SPOR-Lsc::NOS (FIG. 28B);
AtRbcS::Lp1-SST-SacB::NOS (FIG. 28*c*) and
AtRbcS:Ip1-SST-Lsc::NOS (FIG. 28*d*).

Example 4

Generating Vectors for Stable Transformation in Monocots
Synthesis of Expression Constructs Expression constructs utilising the bread wheat photosynthetic promoter (TaRbcsp), the modified bacterial fructan biosynthesis genes, indicated in Example 2, and the TaRbcS terminator sequence for transformation into monocot plants are artificially synthesised. The use of a photosynthetic promoter expresses the genes in tissues that accumulate fructans, while the modified sequences target the protein to specific plant cell compartments.

The bread wheat (*Triticum aestivum*), TaRbcS regulatory sequences (promoter and terminator) have previously been cloned (Zeng, et al., 1995; Sasanuma, 2001). A 695 bp promoter fragment from sequence previously published containing the TATA signal from the TaRbcS gene (NCBI accession number AB042069) is amplified for use in expression vectors.

The newly predicted sequences for the modified bacterial fructan biosynthetic genes are artificially synthesised altering codon usage for expression in plants, as well as removing cryptic splice sites and RNA destabilizing sequence elements, to optimise their performance in the plant cell.

Using the methods outlined above expression cassettes are synthesised to generate transgenic plants that contain both fructan biosynthetic genes and the LXR™ technology. LXR™ technology is based on an expression cassette containing one candidate gene (IPT) for delayed leaf senescence under the control of the AtMYB32 gene promoter. The expression cassette AtMYB3p::IPT::35St is described in International patent application PCT/AU01/01092. The phenotype of transgenic LXR™ plants includes a decrease in leaf yellowing and chlorophyll loss associated with plant age leading to an increased photosynthetic ability resulting in improved tillering and vegetative biomass.

Integration of the two technologies leads to an increased expression of fructans via an extension of activation of the photosynthetic promoters and may have significant impact on the efficacy of a variety of applications by increasing the range of productivity in plants.

FIGS. 29-36 represent the expression cassettes, TaRbcS::SPOR-SacB::TaRbcS, TaRbcS::SPOR-SacB::TaRbcS+AtMYB32::IPT::35S, TaRbcS::SPOR-Lsc::TaRbcS, TaRbcS::SPOR-Lsc::TaRbcS+AtMYB32::IPT::35S, TaRbcS::Lp1-SST-SacB::TaRbcS, TaRbcS::Lp1-SST-SacB::TaRbcS+AtMYB32::IPT::35S, TaRbcS::Lp1-SST-Lsc::TaRbcS and TaRbcS::Lp1-SST-Lsc::TaRbcS+AtMYB32::IPT::35S, respectively, and have not yet had codon optimisation or removal of destabilising elements.

Generation of Constructs Containing Modified Bacterial FT Genes Driven by a *Trificum* Photosynthetic Promoter for Transformation of Monocots Each synthesised expression cassette is placed in a Gateway enabled pDONOR vector for recombination into the final destination vector for transformation into plants.

A Gateway enabled destination vector, containing the Ubi::bar::NOS selectable marker cassette has been generated, pBS::Ubi::bar::NOS_R4/R3 (FIG. 37). Gateway LR recombination reactions produce the following destination vectors for transformation in to monocots:
TaRbcS::SPOR-SacB::TaRbcS (FIG. 38A);
TaRbcS::SPOR-SacB::TaRbcS+AtMYB32::IPT::35S (FigureB);
TaRbcS::SPOR-Lsc::TaRbcS (FIG. 39A);
TaRbcS::SPOR-Lsc::TaRbcS+AtMYB32::IPT::35S (FIG. 39B);
TaRbcS::Lp1-SST-SacB::TaRbcS (FIG. 40A);
TaRbcS::Lp1-SST-SacB::TaRbcS+AtMYB32::IPT::35S (FigureB);
TaRbcS::Lp1-SST-Lsc::TaRbcS (FIG. 41A) and
TaRbcS::Lp1-SST-Lsc::TaRbcS+AtMYB32::IPT::35S (FIG. 41B)

Example 5

Constructs for Dicotolydons—*N. tabacum* Protoplasts and *A. thaliana*

The following constructs were made in versions for direct delivery (transient expression in protoplasts) and versions in binary transformation vectors for stable delivery to *Arabidopsis* (*A. thaliana*) and tobacco (*N. tabacum*)

1. AtRbcS::1-SST-SacB*
2. AtRbcS::SPOR-SacB*
3. AtRbcS::1-SST-Lsc*
4. AtRbcS::SPOR-Lsc*

* The bacterial levansucrase and inulosucrase sequences are modified in the following manner:
Removal of the bacterial N-signal peptide;
Adaptation of codon usage, including the start of translation for monocots and dicots
Removal of cryptic splice sites and RNA destabilizing sequence elements
The coding sequence is further modified with putative sub-cellular targeting sequences including vacuolar targeting sequences for monocots and dicots as well as including plant 1-SST- and FFT-specific transmembrane domains.

Example 6

Polyethylene Glycol-Mediated Transformation of Mesophyll-Derived Protoplasts of Tobacco This example describes delivery of the expression cassettes hereinbefore described to tobacco protoplasts (see FIGS. 42-45).

I. Isolation of Mesophyll-Derived Protoplasts for Direct Gene Transfer

A. Digestion of In Vitro Shoot Cultures to Yield Mesophyll-Derived Protoplasts Enzyme Solution 1.0% (w/v) cellulase "Onozuka" R10 and 1.0% (w/v) Macerozyme® R10 dissolved in K4 medium [medium K3 with 0.4 M sucrose instead of 0.3 M]. Spin down (Sorvall centrifuge, SS 34 rotor; at 7,000 rpm for 10 min.) in order to pellet contaminating starch of the enzyme preparations. Adjust pH 5.6 with KOH and filtersterilize (0.2 μm pore size). Store at 4° C. for no longer than 3-4 weeks.

Materials 400 ml culture vessels containing solidified MS medium with shoot cultures of *Nicotiana tabacum*

90×20 mm sterile Petri dishes

Forceps

Scalpel

Sterile scalpel blades; #11 or #22

Solutions

Enzyme solution; 1% Cellulase and 1% Macerozyme dissolved in K4 medium

Sterile water

Procedure

1. Into sterile 90×20 mm Petri dishes, decant a volume of enzyme solution sufficient to generously cover plate base; 15 ml should suffice.
2. Transfer 2-4 healthy, fully expanded leaves of a 4-6 week-old shoot culture to an empty 90×20 mm Petri dish.
3. With the abaxial-side up, carefully remove the mid-rib of one leaf, ensuring a sharp, sterile blade is used to minimise tearing of surrounding leaf tissue. Repeat for remaining 3 leaves.
   Handle small quantities of leaf material (maximum 4) at any one time to minimise desiccating effect of laminar flow.
4. Gently stack leaf halves and, with a sharp, sterile blade, slice into 1-2 mm strips.
5. Carefully transfer leaf segments into a Petri dish containing enzyme solution (abaxial-side down). Seal dish with Parafilm® and incubate overnight for 16-18 hours at 25° C. in the dark without shaking.

B. Isolation of Mesophyll-Derived Protoplasts

Materials

Sterile 5 ml pipettes

Sterile 10 ml pipettes

Pipette boy

Sterilised protoplast filtration unit: 100 μm stainless steel mesh sieve resting on a 100 ml glass beaker Sterile 14 ml plastic round-bottomed centrifuge tubes Clements Orbital 500 bench centrifuge Waterbath Media 90×20 mm sterile Petri dish/es containing digesting leaves of *Nicotiana tabacum*

Solidified 1:1 mix of K3:H medium containing 0.6% Sea Plaque™ agarose

Solutions

Autoclaved W5 Solution

Autoclaved K3 Solution

Procedure

6. Gently agitate the overnight digest to release protoplasts into the enzyme solution.
   Agitation should be gentle, yet thorough, and performed in a side-to-side (horizontal) motion.
7. Angle plate slightly to aid transfer of digesting suspension (enzyme solution and plant debris). Using a 10 ml sterile pipette, transfer digesting suspension to a sterilised protoplast filtration unit to separate protoplast suspension from plant debris.
8. Tap filtration unit gently to release excess liquid caught in sieve.
9. Mix the protoplast suspension gently and distribute into 14 ml sterile plastic round-bottomed centrifuge tubes, filling to approximately 8 ml (maximum 9 ml).
10. Re-distribute suspension to obtain a uniform distribution of volumes (max. 9 ml).
11. Carefully overlay each suspension with 1.5 ml W5 solution.
    To aid dispensing W5 solution, place suspension-filled tube on an angle and allow pipette tip to touch wall surface near tube opening before slowly lowering to just above the suspension surface. Slowly dispense W5 solution, adding drop-by-drop, ensuring to keep pipette tip as close to the suspension surface as possible. Minimal agitation of protoplast suspension and, thus, mixing with W5 solution will result if correctly performed.
12. Carefully replace lids and centrifuge tubes for 5 minutes at 70 g (Clements Orbital 500 bench centrifuge, swing-out rotor, 400 rpm). Protoplasts will float at the interphase.
13. Keeping protoplast-filled tube upright, carefully lower a sterile 5 ml pipette to a point just above the layer of protoplasts and collect the protoplasts at the interphase, taking as little as possible of the lower phase.
    W5 solution will be collected simultaneously.
14. Collect and transfer protoplasts to one new 14 ml centrifuge tube. Upon completing protoplast collection, gently mix protoplast suspension by gently pipetting up and down.
15. Determine protoplast yield by removing a 100 μl aliquot of the protoplast suspension and transferring to a tube containing 900 μl W5 solution. Count the protoplasts in a haemocytometer and determine the number of protoplasts per ml.
16. Calculate the total volume required to obtain approximately $1\times10^6$ (maximum $1.5\times10^5$) protoplasts per ml. Distribute protoplast suspension in new 14 ml round-bottomed centrifuge tubes, ensuring equal volumes are obtained.
17. Using a 10 ml pipette, fill each protoplast-containing tube with W5 solution up to a total volume of 10 ml. To minimise disruption to the protoplasts, spray W5 solution along the tube wall when filling.
18. Replace lids and resuspend the protoplasts by gently inverting the capped tube once.
19. Pellet the protoplasts [spin 70 g (Clements Orbital 500 bench centrifuge, 400 rpm) for 5 min.] before removing all W5 solution, leaving pure protoplast suspension.
20. Resuspend protoplast suspensions by gently shaking.
21. Fill each protoplast-containing tube to a total volume of 5 ml with W5 solution and incubate at room temperature for a minimum of 1 hour and a maximum of 4.
22. During 1-4 hour incubation time, organise the following components in preparation for direct gene transfer into isolated protoplasts:
    Remove 40% PEG solution from −20° C. storage and store at room temperature. 30 minutes prior to proceeding with the direct gene transfer, incubate PEG solution in a beaker of hot water.
    Melt solidified K3:H medium in microwave. Once completely melted, place in a 40° C. water-bath until ready to use.

II. Direct Gene Transfer to Protoplasts Using Polyethylene Glycol

Transforming DNA

Plasmid DNA is sterilized by precipitation and washing in 100% (v/v) ethanol and dried in a laminar flow hood [precipitation of plasmid DNA in 70% ethanol is also possible, but DNA pellet will take longer to dry]. DNA pellet is resuspended in 30 μl sterile double distilled water at a final concentration of 0.7 μg/μl for transient transformations. The physical structure of the DNA should be supercoiled for transient and linearized—outside of the gene of interest—for stable transformations. Addition of carrier DNA (e.g. fish-sperm DNA) to the transforming plasmid DNA usually gives better stable transformation frequencies. For stable transformations 10 μg of linearized plasmid DNA and 40 μg of sheared fish-sperm DNA are co-precipitated as indicated above, dried and dissolved in 30 μl of sterile double-distilled water.

Transformation Buffer 15 mM $MgCl_2$, 0.1% (w/v) morpholinoethanesulphonic acid (MES) and 0.5 M mannitol. After dissolving in distilled water, adjust pH 5.8 with KOH and autoclave. Store at 4° C.

PEG Solution

40% (w/v) PEG 4000 in 0.4 M mannitol and 0.1 M $Ca(NO_3)_2$. Dissolve PEG in 0.4 M mannitol and 0.1 M $Ca(NO_3)_2$ (the final concentration of these two components will be lower due to the volume of PEG). Adjust pH 8-9 and autoclave (the pH will take several hours, e.g. overnight, to stabilize in this solution and will drop to pH 6-7 after autoclaving).

Materials

- Sterile 1 ml pipettes
- Sterile 5 ml pipettes
- Sterile 10 ml pipettes
- Pipette boy
- Sterile 14 ml plastic round-bottomed centrifuge tubes
- Clements Orbital 500 bench centrifuge
- Waterbath
- 50×10 mm Petri dishes Media

- 14 ml round-bottomed centrifuge tubes containing isolated protoplast suspension, pelleted
- Solidified 1:1 mix of K3:H medium containing 0.6% Sea Plaque™ agarose Solutions

- Autoclaved W5 Solution
- Autoclaved K3 Solution
- Autoclaved H Solution
- 40% PEG Solution
- Transformation Buffer
- 10 μg Transforming DNA dissolved in 30 μl sterile double-distilled water.

Procedure

1. Pellet the protoplasts [spin 70 g (Clements Orbital 500 bench centrifuge, 400 rpm) for 5 min.] before removing all W5 solution, leaving pure protoplast suspension.
2. Using a 1 ml pipette, add (drop-wise) 300 μl (approximately 7 drops) of transformation buffer to each 14 ml round-bottomed centrifuge tube containing isolated protoplasts.
3. Carefully resuspend pellet by gently tapping base of tube.
4. To each protoplast suspension, add 10 μg (30 μl) of transforming DNA before adding 300 μl (approximately 7 drops when using a 1 ml pipette for dispensing) of pre-warmed PEG solution. Mix protoplast suspension by gently tapping tube base.
   Time interval between resuspending protoplasts in transformation buffer and the addition of transforming DNA and PEG should be kept at a minimum.
5. Incubate transformation mix for 15 minutes at room temperature with no agitation.
6. Using a 10 ml pipette, gradually add 10 ml W5 solution to each tube in intervals of:
   - 1 ml (approximately 12 drops) drop-wise to each tube. Gently invert all tubes to mix.
   - 1 ml (approximately 12 drops) drop-wise to each tube. Gently invert all tubes to mix.
   - 1 ml (approximately 12 drops) drop-wise to each tube. Gently invert all tubes to mix.
   - 2 ml as a gentle stream to each tube. Gently invert all tubes to mix.
   - 2 ml as a gentle stream to each tube. Gently invert all tubes to mix.
   - 3 ml as a gentle stream to each tube. Gently invert all tubes to mix.

To aid dispensing, in a 10 ml pipette collect the total volume required at each interval to fill each tube with the required volume of W5 solution, prior to dispensing. Repeat at each interval.
7. Pellet the protoplasts [spin 70 g (Clements Orbital 500 bench centrifuge, 400 rpm) for 10 min.] before removing all W5 solution, leaving pure protoplast suspension. Tap all tube bases once before proceeding.

For Transient Transformations

8. Resuspend protoplast pellet in equal volumes of K3 medium and H medium up to a total volume of 5 ml (2.5 ml of each solution).
9. Slowly transfer the liquid K3:H+protoplast-suspension-mix to the centre of a 50×10 mm Petri dish.
10. Seal all dishes with Parafilm® and culture protoplasts for 24-72 hours under dim light at 24° C., before proceeding with transient expression analysis.

For Stable Transformations

11. Continue with "Part III. Culture of Mesophyll-derived Protoplasts and Regeneration of Plants", below.

III. Culture of Mesophyll-Derived Protoplasts and Regeneration of Plants

For Steps 1 & 2, each protoplast-containing tube must be handled one tube at a time.

Materials

- Sterile 1 ml pipettes
- Sterile 5 ml pipettes
- Sterile 10 ml pipettes
- Pipette boy
- Clements Orbital 500 bench centrifuge
- Waterbath
- 50×10 mm Petri dishes
- Autoclaved stainless steel spatula Media

- 14 ml round-bottomed centrifuge tubes containing isolated protoplast suspension, pelleted
- Solidified 1:1 mix of K3:H medium containing 0.6% Sea Plaque™ agarose; 40° C.
- Autoclaved K3 Solution
- 250 ml culture vessel containing 20 ml A medium
- 12-well Costar® plates containing solidified MS Morpho medium
- 250 ml culture vessels containing solidified MS Morpho medium
- 250 ml culture vessels containing solidified MS medium Procedure 1. Add 0.5 ml K3 medium close to the protoplast pellet to resuspend the protoplasts.

2. Slowly transfer the K3+protoplast-suspension-mix to the centre of a 50×10 mm Petri dish.
3. Repeat Steps 1 and 2 for all protoplast-containing tubes before proceeding.
4. Add 5 ml pre-warmed 1:1 mix of K3:H medium containing 0.6% Sea Plaque™ agarose one plate at a time. In a gentle swirling motion, shake plate once only to evenly distribute protoplast suspension in medium. Repeat for all plates.
5. Leave plates to stand, untouched, until medium has solidified (10-30 minutes depending on ambient temperature).
6. Seal all dishes with Parafilm® and culture protoplasts for 24 h in complete darkness at 24° C., followed by 6 days under continuous dim light (5 μmol $m^{-2}$ $s^{1}$, Osram L36 W/21 Lumilux white tubes), where first and multiple cell divisions occur.
7. Using a sterile spatula, divide the protoplast-containing sea plaque agarose plugs into quadrants and place into 250 ml plastic culture vessels containing 20 ml of A medium supplemented with appropriate antibiotic (1 quadrant per 250 ml vessel). Incubate on a rotary shaker at 80 rpm and 1.25 cm throw at 24° C. in continuous dim light.
8. Replace liquid A medium+appropriate antibiotic every 2 weeks, monitoring growth of protoplast-derived colonies.
9. When protoplast-derived colonies are approximately 2-3 mm in diameter (5-6 weeks incubation in liquid A medium), transfer colonies into individual wells of a 24-well Costar® plate containing solidified MS Morpho medium.
10. Incubate plate/s for 1-2 weeks at 24° C. under continuous dim light (5 μmol $m^{-2}$ $s^{-1}$, Osram L36 W/21 Lumilux white tubes), where calli proliferate and reach a size of 8-10 mm in diameter.
11. When protoplast-derived calli are approximately 1-2 cm in diameter, transfer calli to individual 250 ml culture vessels containing solidified MS Morpho medium. Incubate vessels at 24° C. under 16 hour light/8 hour dark conditions (20 μmol $m^{-2}$ $s^{-1}$, Osram L36 W/21 Lumilux white tubes). Within 1-2 weeks, multiple shoots should be visible.
12. Transfer shoots of 3-4 cm lengths to 250 ml culture vessels containing solidified MS medium to encourage root formation. Incubate vessels at 24° C. under 16 hour light/8 hour dark conditions (20 μmol $m^{-2}$ $s^{-1}$, Osram L36 W/21 Lumilux white tubes). Within 3 weeks, signs of root formation should be visible.
13. Plantlets with an established root system should be maintained as in vitro plant cultures as sources for mesophyllprotoplasts of Tobacco.

Example 7

Evaluation of Tobacco Protoplast Viability Using Evans Blue Stain

See FIGS. 46 and 47.

BACKGROUND INFORMATION

Evans blue stain (EVB; 6,6'-[(3,3'-dimethyl1[1,1'-biphenyl]-4,4'-diyl)bis(azo)bis[4-amino-5-hydroxy-1,3-naphthalenedisulfonic acid] tetrasodium salt).

Non-fluorescent dye.

Method of action: Living cells retain the ability to exclude Evans blue at the plasma membrane and remain their natural colour. Cells damaged by salt or osmotic stress are unable to exclude Evans blue, are stained deep blue, and are readily distinguished upon microscopic examination.

Method of preparation: 400 mg/l stock solution (solvent: 0.65 M Mannitol)

Method of staining: Evans blue stock solution was added to an equal volume of protoplast suspension, gently mixed and incubated at room temperature for 10 minutes prior to microscopic visualisation.

Method of detection: Leica MZFL III Light Dissecting Microscope.

Example 8

Gene Expression Analysis in *Nicotiana Tabacum* Protoplasts

Aim of the experiment: The expression of the cloned genes AtRbcS::1-SST-SacB and AtRbcS::SPOR-SacB in transfected tobacco protoplasts was tested using RT-PCR Materials and methods: 3 plates of protoplasts named i) Transfected protoplasts (sample 9A): AtRbcS::1-SST-SacB ii) Transfected protoplasts (sample 12A): AtRbcS::SPOR-SacB iii) Untransfected protoplasts Steps involved in the expression analysis:

1. Primer design and optimisation of PCR
2. Total RNA isolation
3. RT reaction
4. qRT-PCR assay Primer design and PCR product identity: Primer pairs were designed to amplify the gene of interest using beacon design software (Premier Biosoft International) and the gene sequences available in gene bank. The gene specific primers were chosen so that the resulting PCR product size ranged from 200 to 250 bp. The PCR products were identified by melt curve analysis and size based on gel electrophoresis.

Total RNA isolation: Total RNA was isolated by SV Total RNA isolation system by PROMEGA from $1\times10^{6}$ protoplasts per treatment. www.promega.com/tbs/tm048/tm048.pdf Yield of Total RNA:

| Sample | Quantity |
|---|---|
| 9A | 3.4 ng/μl |
| 12A | 4.2 ng/μl |
| Control (untransfected protoplasts) | 10.2 ng/ul |

Reverse Transcriptase Reaction

RT reaction was performed by using QIAGEN RT kit. Four RT reactions were performed (9, 12, control and WT tobacco RNA) by using primer mix (QIAGEN). www1.qiagen.com/products/per/QuantiTectPcrSystems/QuantiTectRevTranscriptionKit.aspx#Tabs=t2

A replicate of each of the above samples was subjected to RT reaction using gene-specific primers. Specifically, samples 9A and 12A were transcribed using the reverse sacB primer, and the control (untransfected) sample with the reverse 18S primer.

PCR

Reactions were set up as follows:

| | |
|---|---|
| 2x GoTaq ® Green MasterMix (Promega) | 10 μL |
| cDNA template | 2.0 μL |
| Forward primer (10 μM) | 0.5 μL |

-continued

| | |
|---|---|
| Reverse primer (10 μM) | 0.5 μL |
| Nuclease free water | 7.0 μL |

Reactions were cycled:

| | | |
|---|---|---|
| Step 1: | 95° C. | 2 min |
| Step 2: | 95° C. | 30 sec |
| Step 3: | 55° C. | 30 sec |
| Step 4: | 72° C. | 60 sec |
| 25 cycles from Step 2 (18S) or 35 cycles from Step 2 (sacB) | | |
| Step 5: | 4° C. | hold |

Reaction products were visualised under UV light after electrophoresis through 1% (w/v) agarose in 1×TBE buffer, staining with SYBR (50 μL/L).

Detection of the sacB transcript was shown in both transfected protoplast cDNA samples (9 and 12), while the method used was validated by amplification of 18S from the untransfected protoplast cDNA sample (FIG. 50).

Expression of chimeric sacB genes under control of light regulated promoters was observed in transfected protoplasts. No products were observed for no-RT controls and no Template controls. sacB gene expression could be detected in protoplasts transfected with vectors used in samples 9A and 12A.

Example 9

*Agrobacterium tumefaciens*-Mediated Leaf Disc Transformation of Tobacco

This example describes stable transformation of tobacco leaf discs using *Agrobacterium* carrying binary vectors engineered with the expression cassettes hereinbefore described (see FIGS. 48 and 49).

Introduction

Utilising *Agrobacterium tumefaciens*-mediated leaf disc transformation is an efficient method of producing transgenic plants. *A. tumefaciens* is a natural dicot pathogen that contains the genetic machinery to infect the plant and incorporate the bacterial DNA into the plant genome. As a result of this capability, *A. tumefaciens* can be adopted as a cloning vehicle to incorporate DNA of specific interest into tobacco, for example.

The method can be used to generate a model system in tobacco, to assess the function of cDNA heterologous clones for the gene of interest.

Materials and Chemicals

Equipment and Instruments

Laminar flow hood with horizontal flow (series HWS180, CLYDE-APAC, a division of Evans Deakin Pty. Ltd., Woodville North, South Australia 5012, Australia), rotary shaker (Infors type RC-406, Infors AG, CH-4103 Bottmingen, Switzerland), bench centrifuge with swing-out rotor (Clements Orbital 500), forceps (bend, cat no. 2108/160, Crown Scientific, Rowville, Victoria 3178, Australia), scalpel handles (No 3, cat no. SHN3, Crown Scientific, Rowville Victoria 3178, Australia) with sterile surgical scalpel blades (size 11, cat no. 1838, Laboratory Supply Pty. Ltd., Milperra DC, New South Wales 1891, Australia) were used.

Stock Solutions

The macro-elements, micro-elements and vitamins required for all culture media must be prepared as concentrated stocks (macro-elements stock: 10-fold concentrated; micro-elements and vitamins stocks: 100-fold concentrated) to aid in their addition. All stocks, except that containing the micro-elements are prepared at room temperature. Preparation of the micro-elements stock requires the heating of components prior to mixing. $Na_2$-EDTA and $FeSO_4 \times 7H_2O$ must each be dissolved in 400 mL distilled water (for a total volume of 1000 mL) prior to mixing. Mix dissolved solutions and heat at ca. 60° C. until solution turns yellow in colour. Allow solution to cool before adding remaining components. Make solution up to 1000 mL with distilled water. Store all stocks at 4° C. Dissolve hormones [2,4-D (2,4-dichlorophenoxyacetic acid) and kinetin] in 1 M KOH and dilute with distilled water to prepare 100 mg/liter concentrated stocks.

Culture Media

The composition of the media used at the final concentrations of their individual ingredients is given in Appendix 1: MS micro, MS macro, B5 vitamins, Lauria Bertani media, Wash media, PC media, SEL media, RM media and SEM media.

Chemicals 2,4-D: 2,4-dichlorophenoxyacetic acid, Activated charcoal, Timentin (can be replaced by Cefotaxime at same concentrations), BAP (6-benzylaminopurine), Zeatin, $AgNO_3$, Rifampicin, Agar (Difco, Bacto-Agar, cat. no: 0140-01) is used as the gelling agent. Other chemicals (PEG 4000, Tween 80, KOH, $NH_4OH$, NaCl, KCl, $Ca(NO_3)_2$, $MgCl_2$ and $CaCl_2$) were purchased from BDH; MES (2-[N-morpholino]ethanesulfuric acid) from Sigma (Cat. No. N-8250), kanamycin sulphate were from Sigma; hygromycin B was purchased from Calbiochem; $Ca(OCl)_2$ (~65%) and phosphinotricin were from Roth and Riedel de Haen, respectively. Sucrose was purchased from Fluka (cat. no: 84100). Parafilm® "M" (American National Can™, Greenwich, Conn. 06836, USA) was used as sealing tape. Sterile disposable bottle-top filters (0.2 μm vacucap 90; cat. no 4622, Gelman Sciences® Pty. Ltd., Cheltenham, Victoria 3192, Australia) and disposable filter units (0.2 μm; cat. no. 16534, Sartorius AG, 37070 Gottingen, Germany) were used for filter-sterilisation. Sterile disposable pipettes: 1 mL_ (TRP®; cat. no. 94001) 5 mL_ (TRP®; cat. no. 94005) and 10 ml_ (TRP®; cat. no. 94010); all from Life Technologies Pty. Ltd., Mulgrave, 3170 Australia, sterile plastic centrifugal tubes with screw cap (14 mL, TRP®; cat. no. 91016, Life Technologies Pty. Ltd., Mulgrave, 3170 Australia); sterile plastic petri dishes (90×14 mm; cat. no. 82.9923.484, and 60×14 mm, cat. no. 83.1801.011, Sarstedt® Australia Pty. Ltd., Technology Park, South Australia 5095, Australia and 90×20 mm; cat. no. 664160, Greiner Labortechnik GmbH, 72636 Frickenhausen, Germany); and autoclavable culture vessels (250 mL, cat. no. 75.9922.519, Sarstedt Australia Pty. Ltd, Technology Park, South Australia 5095, Australia) were used.

Plant Material

A) Sterile shoot cultures of *N. tabacum* cv. Petit Havana SR1 can be utilised. They are established from corresponding seeds surface-sterilised in hypochlorite solution [1.4% (w/v) $Ca(OCl)_2$, 0.05% (v/v) Tween 80] for 15 min., and after 3-4 rinses in sterile distilled water, plated for germination on half-strength MS medium (Appendix 1) solidified with 0.8% (w/v) agar. Shoots with 2-3 leaves are cut and grown in 250 mL culture vessels on 0.8% (w/v) agar-solidified MS medium at 25° C. in 16 h/d light (20 μmol $m^{-2}$ $s^{-1}$, Osram L36 W/21 Lumilux white tubes). Rooted shoots are subcultured at 6 weeks intervals as stem cuttings, several times before use.

B) Glasshouse grown *N. tobacum* can also be utilised, but requires leaf surface sterilisation as described below [I. B)].

Plant seeds in sterile soil ensuring they are not planted too deeply and that they remain moist. Grow under 16 h/d light (20 umol m"2 s"[1], Osram L36 W/21 Lumilux white tubes) conditions 25° C., fertilising with Osmocote slow release fertiliser.

C) The strain of *Agrobacterium tumefaciens* utilised for leaf disc transformations is AGL1.

I. Preparation of *Agrobacterium tumefaciens* for Transforming Tobacco Leaf Discs with Vector pBinhph200

Commence pre-culture of transformed *Agrobacterium tumefaciens* strain AGL1 two days prior to tobacco transformation date ensuring sterile conditions are maintained, (see Appendix 2 for the ID card for pBinhph200)

1. Scratch the surface of −70° C. frozen glycerol bacterial stock with an innoculation loop and inoculate 2 mL of LB (containing 20 mg/mL rifampicin, plus 10 mg/L spectinomycin) in a sterile tube. Incubate for 24 hours at 28° C. at 150 rpm.
2. Inoculate 4 mL of LB plus antibiotics (in a 12 mL sterile tube) with 0.25 mL of the 24 hour pre-culture. Incubate for 6-7 hours at 28° C.
3. Inoculate 25 mL LB with no antibiotics (in a 150 mL sterile flask) with 0.025 ml of 6-7 hour pre-culture and incubate overnight at 28° C. and 150 rpm.
4. Add 25 ml of LB to the 25 ml overnight pre-culture and continue to grow at 28° C. for a further 90 minutes at 150 rpm.
5. Transfer 50 ml pre-culture to centrifuge tubes and spin for 12 minutes at 2,000 rpm at room temperature in a Clements bench centrifuge.
6. Remove supernatant and gently resuspend the pellet in 20 mL of WM. Measure $OD_{600}$. Add further WM to bacterial suspension to provide a final $OD_{600}$ of 0.45. This preparation is for use in step III) 1.

II. Preparation of Leaf Discs

A) Preparation of Leaf Discs Using Tobacco Shoot Cultures

1. In a laminar flow, harvest 4-6 leaves from tobacco plants grown on MS media. Place the leaves in 1.5×9 cm petri dishes containing WM. Using a scalpel, remove the mid-rib and cut the leaf tissue into squares ~1 $cm^2$. The tissue or leaf discs are now ready for transformation with *Agrobacterium tumefaciens* (AGL1). The discs should be transformed within an hour.

B) Preparation of Leaf Discs Using Non-Sterile Tobacco Tissue

1. Harvest 4 young leaves (~8 cm long) from a glasshouse grown tobacco plant.
2. Place leaves into a sterile beaker containing 70% ethanol, cover with aluminium foil and swirl gently on an orbital shaker (Bio-Line Orbital Shaker, Edwards Instrument Company) for 1 minute.
3. Remove 70% ethanol and replace with 1% $Ca(OCl)_2$. Swirl tissue for 8 minutes. Wash leaves in sterile water at least 3 times.
4. In a laminar flow, remove the mid-rib and cut the remaining leaf tissue into squares ~1 $cm^2$. Place the prepared discs in a 1.5×9 cm petri dish containing WM. The discs are now ready for transformation with *Agrobacterium tumefaciens* (AGL1).

III. Incubation and Co-Cultivation of Leaf Discs with *Agrobacterium tumefaciens*

1. Replace WM (from last step in leaf disc preparation) with *Agrobacterium* culture and incubate for 1-2 minutes.
2. Remove bacterial suspension and rinse explants briefly with WM. Blot explants on sterile napkins before plating onto PC media. Place in the growth room (16 h/d light (20 μmol $m^{-2}$ $s^{-1}$, Osram L36 W/21 Lumilux white tubes) conditions 25° C.) for 3 day co-cultivation.

IV. Pre-Regeneration of Leaf Discs Following *Agrobacterium*-Mediated Transformation 1. Transfer explants (5/plate) to SEL media and return to growth room for a further 7 days.

V. Regeneration

1. Transfer explants (5/plate) to RM and return to growth room. Shoot formation should occur within 3-6 weeks. Transfer explants to fresh RM after 4 weeks.
2. If calli becomes too large, and particularly if not all shoots are in contact with the media, divide calli using a scalpel. Expose as many of the shoots to selection as possible.

VI. Shoot Elongation and Root Development

1. After eight weeks on selection, or when the untransformed control explants on selection are dead, transfer green shoots (5/plate) to SEM media (include IBA (1 mg/L)) in 9×2 cm petri dishes. Roots should appear in 4-5 weeks.

VII. In Vitro Plantlet Development

1. When roots appear, transfer rooted plantlets to SEM media in tissue culture vessels.

REFERENCES

Stewart, C. N. Jr., Adang, M. J., All, J. N., Rayner, P. L., Ramachandran, S, and Parrott, W. A. (1996) Insect control and dosage effects in transgenic canola containing a synthetic *Bacillus thuringiensis* crylAc gene. *Plant Physiol* 112: 115-120.

APPENDICES

Appendix 1: Stock Solutions and Media

| MS Media | 1 Litre |
|---|---|
| MS powder | 4.74 g |
| 3% sucrose | 30 g |
| $dH_20$ | Up to 1 L |

Adjust pH to 5.8-6.0 with 1M NaOH
Autoclave

| MS Macro (10 x) | | |
|---|---|---|
| | 1 Litre | 2 Litre |
| $NH_4NO_3$ | 16.5 g | 33.0 g |
| $KNO_3$ | 19.0 g | 38.0 g |
| $CaCl_2 \times 2H_2O$ | 4.4 g | 8.8 g |
| $MgS0_4 \times 7H_2O$ | 3.7 g | 7.4 g |
| $KH_2PO_4$ | 1.7 g | 3.4 g |

| MS Micro (100 x) | | |
|---|---|---|
| | 1 Litre | 2 Litre |
| KI | 0.083 g | 0.166 g |
| $H_3BO_3$ | 0.62 g | 1.24 g |
| $MnS0_4 \times H_2O$ | 1.69 g | 3.38 g |
| $ZnS0_4 \times 7H_2O$ | 0.86 g | 1.72 g |
| $Na_2Mo0_4 \times 2H_2O$ | 0.025 g | 0.05 g |
| $CuS0_4 \times 5H_20$ | 0.0025 g | 0.005 g |

-continued

| MS Micro (100 x) | | |
|---|---|---|
| | 1 Litre | 2 Litre |
| $COCl_2 \times 6H_2O$ | 0.0025 g | 0.005 g |
| $Na_2$-EDTA | 3.73 g | 7.46 g |
| $FeSO_4 \times 7H_2O$ | 2.78 g | 5.56 g |

Dissolve $Na_2$-EDTA and $FeSO_4 \times 7H_2O$ in 400 ml dd$H_2O$, respectively, mix and heat (do not boil). Let cool down and add the other Micro salts in the remaining volume.

| MS Vitamins (100 x) | | |
|---|---|---|
| | 1 Litre | 2 Litre |
| Inositol | 10 g | 20 g |
| Nicotinic acid | 0.05 g | 0.1 g |
| Pyridoxine HCl | 0.05 g | 0.1 g |
| Thiamine | 0.01 g | 0.02 g |
| Glycine | 0.2 g | 0.4 g |

| B5 Vitamins (100 x) | | |
|---|---|---|
| | 1 Litre | 2 Litre |
| Inositol | 10 g | 20 g |
| Nicotinic acid | 0.1 g | 0.2 g |
| Pyridoxine HCl | 0.1 g | 0.2 g |
| Thiamine | 1.0 g | 2.0 g |

| RM Media: regeneration media | | |
|---|---|---|
| | stock | /1 litre |
| MS Macro | 10 x | 100 ml |
| MS Micro | 100 x | 10 m! |
| B5 Vitamins | 100 x | 10 ml |
| MES | | 500 mg |
| Sucrose | | 30 g |
| Adjust pH 5.80 with KOH (1M) | | |
| Agar | | 8.0 g |
| Autoclave | | |
| Once cool add: | | |
| BAP | 2 mg/ml | 2 ml |
| Zeatin | 1 mg/ml | 2 ml |
| $AgNO_3$ | 5 mg/ml | 1 ml |
| Timentin | 250 mg/ml | 1 ml |
| Hygromycin | 25 mg/ml | 0.4 mi |

To prepare BAP and Zeatin weigh powder into a small vessel and start dissolving with 0.5-1 ml of 1 M KOH. Transfer the solution to dd$H_2O$ and fill up to the final volume.

| SEL media: selection media | | |
|---|---|---|
| | stock | /litre |
| MS Macro | 10 x | 100 ml |
| MS Micro | 100 x | 10 ml |
| B5 Vitamins | 100 x | 10 ml |
| MES | | 500 mg |
| Sucrose | | 30 g |
| Adjust pH 5.80 with KOH (1M) | | |
| Agar | | 8.0 g |
| Autoclave | | |
| Once cool add: | | |
| 2,4-D | 1 mg/ml | 1 ml |
| Timentin | 250 mg/ml | 1 ml |
| Hygromycin | 25 mg/ml- | 0.4 ml |

To prepare 2,4-D weigh the powder into a small vessel and start dissolving with 0.5-1 ml of 1 M KOH. Transfer the solution to dd$H_2O$ and fill up to the final volume.

| SEM Media | | |
|---|---|---|
| | stock | /litre |
| MS Macro | 10 x | 50 ml |
| MS Micro | 100 x | 5 ml |
| B5 Vitamins | 100 x | 5 ml |
| MES | | 500 mg |
| Sucrose | | 10 g |
| Adjust pH 5.8 with KOH(1M) | | |
| Agar | | 8.0 g |
| Activated Charcoal | | 0.5 g |
| Autoclave | | |
| Once cool add: | | |
| Timentin | 250 mg/ml | 1 ml |

| WM medium: wash media | | |
|---|---|---|
| | stock | /litre |
| MS Macro | 10 x | 100 ml |
| MS Micro | 100X | 10 ml |
| B5 Vitamins | 100 x | 10 ml |
| MES | | 500 mg |
| Sucrose | | 3 0 g |
| Adjust pH 5.8 with KOH (1M) | | |
| Autoclave | | |

Example 10

Stable Transformation of *Arabidposis* Using *Agrobacterium tumefaciens* Carrying Binary Vectors Engineered with the Same Expression Cassettes Via the 'Floral Dip' Method.

Preparation of Electrocompetent *Agrobacterium tumefaciens* Cells

Experimental Procedure

1. Streak out *Agrobacterium tumefaciens* (AGL1 strain) from a frozen −80° C. glycerol stock onto MGL agar containing 20 mg/L rifampicin and 100 mg/L ampicillin, and incubate at 27° C. for two days.
2. Measure 5 ml MGL into a 50 ml Falcon tube and add rifampicin to a final concentration of 20 mg/L and ampicillin 100 mg/L. Inoculate with a single colony of *Agrobacterium tumefaciens* AGL1.
3. Incubate at 27° C. for 24 h on an orbital shaker at 150 rpm in a tilted rack (ca. 30 degrees).
4. In late afternoon inoculate 100 ml MGL containing 20 mg/L rifampicin and 100 mg/L amplicillin (in a 500 ml flask) with the 500 μl of an overnight culture.

5. Incubate at 27° C. overnight on an orbital shaker at 150 rpm until an $OD_{600}$ reading between 0.4-0.6 (max. 0.6) is obtained. See comments below if overgrown.
6. Transfer cells to an autoclaved JA10 centrifuge tube and chill on ice for 10 min.
7. Centrifuge for 10 min, 9000 rpm, at 4° C. using the JA10 rotor.
8. Carefully discard supernatant (pellet is not very stable) by pouring into the 500 ml flask used for culture.
9. Add 20 ml ice cold 10% glycerol to the pellet in the JA10 centrifuge tube and resuspend pellet by vortexing.
10. Pour the suspension into a JA20 centrifuge tube and spin for 10 min, 10000 rpm, at 4° C. using the JA20 rotor.
11. Discard supernatant by pouring into the 500 ml flask.
12. Add 15 ml ice cold 10% glycerol to the pellet and resuspend by pipetting. Centrifuge for 10 min, 10000 rpm, at 4° C. in the JA20 rotor.
13. Repeat steps 11 and 12 twice.
14. Resuspend the pellet in 1 ml ice cold 10% glycerol (pipette or vortex) and transfer to a sterile microfuge tube.
15. Spin for 3 min, 13000 rpm, at 4° C. in microfuge.
16. Finally resuspend pellet in 1 ml 10% ice cold glycerol.
17. Aliquot 50 µl batches into labelled 1.7 ml microtubes, snap freeze in liquid nitrogen.
18. Remove tubes from liquid nitrogen and store competent cells at −80° C.

Comments

Wear latex gloves while handling *A. tumefaciens* bacterial cultures. Collect all bacterial waste in 500 ml flask and autoclave. If the *A. tumefaciens* 100 ml culture overgrows, dilute ⅓-¼ with fresh MGL medium containing 20 mg/L rifampicin, and incubate for further 1-2 h.

Transformation of *Agrobacterium tumefaciens* Via Electroporation

Experimental Procedure

1. Pre-chill Gene pulser cuvette holder on ice.
2. Remove aliquots of competent *Agrobacterium* (AGL1) cells from −80° C. and thaw on ice.
3. Turn on main switch at the back of the Gene pulser. Adjust the voltage to 2.5 kV (use the 'raise' button until '2.5' registers on the display), capacitance 25 µFD and resistance 600Ω.
4. Add 0.1 µg of DNA in a volume not smaller than 50 µl of thawed cells.
5. Mix by pipetting and transfer the cell/DNA mix to a pre-chilled 0.2 cm gap Gene Pulser cuvette.
6. Carefully tap or shake the cells to the bottom of the cuvette so that the cells touch both electrodes.
7. Dry the outside of the cuvette with a tissue and place it into the cuvette holder. A notch on the cuvette ensures correct orientation. Slide the cuvette holder into the chamber until the cuvette is seated between the contacts at the base of the chamber.
8. Pulse the cells by depressing both red buttons until a beep sounds. The machine will display CHG whilst charging and will beep as it discharges. Place cells back on ice for 1 min to assist recovery.
9. Add 1 ml LB medium to the cells in the cuvette with a glass transfer pipette.
10. Mix the suspension up and down then transfer to a sterile 15 ml tube.
11. Incubate at 27° C. on an orbital shaker at 150 rpm for 1 to 2 hours using a tilted rack (ca. 30 degree).
12. Add 9 ml of LB to the cell suspension mix thoroughly and plate out 100 µl of this culture onto an LB plate containing 20 mg/L rifampicin and the appropriate antibiotic (e.g. 100 mg/L spectinomycin for pPZP series of vectors). Transfer 100 µl of this suspension into a 1.7 ml microtube containing 900 µl of LB broth, mix thoroughly and plate out 100 µl onto another LB plate containing the appropriate antibiotics. Remove 100 µl from the above suspension and place into a fresh 1.7 ml microtube and add 900 µl of LB broth. Mix thoroughly and plate out 100 µl onto another LB plate containing the appropriate antibiotics.
13. Seal plates with Parafilm and incubate at 27° C. for 2-3 days until single large colonies become visible.

Storage of Transformed *Agrobacterium*

Experimental Procedure

1. In a 50 ml sterile tube inoculate a single colony into 5 ml LB broth containing 20 mg/L rifampicin and appropriate selection antibiotic (i.e. 100 mg/L spectinomycin for pZP series and 50 mg/L kanamycin for pBin series). This is best done early morning so that you can closely monitor the degree of growth the following day.
2. Incubate tubes in the dark at 27° C. for 24-36 hours shaking at 250 rpm. Regularly observe culture growth after first 24 hours of incubation. Remove from incubation once cells are actively growing (highly visible). Rapid growth will occur soon after the first signs of turbidity. Growing time depends on individual strains and transformants.
3. Each culture should be checked to verify that AGL1 contains the desired binary vector. This is done using the protocol set out in section 5.2.
4. Aliquot 500 µl of culture into a cuvette. Measure $OD_{600}$ reading, blanking with 500 µl of LB broth, containing the appropriate antibiotics, between each reading.
5. Allow cultures to grow until the $OD_{600}$ reading ranges between 0.8 to 1.0.
6. In a sterile 15 ml tube add 5.0 ml of culture and 5.0 ml of conservation stock. Mix thoroughly before proceeding to step 7.
7. Aliquot 500 µl into fully labelled sterile cyrotubes. Invert all tubes before snap freezing in liquid nitrogen. Store at −80° C. until required. Discard any stock if shown to be PCR negative.

PCR Analysis of *Agrobacterium*

1. Add 1 µl of *Agrobacterium* culture to 9 µl of sterile MQ H2O in a sterile PCR tube.
2. Incubate cells at 98° C. for 5 mins. Transfer tubes to ice.
3. Add 10 µl of the prepared 2×PCR master mix. 10 µl of 2×PCR master mix contains the following:

| | |
|---|---|
| 10 × Dynazyme Buffer | 2 µl |
| 10 mM dNTPs | 1.0 µl |
| 10 µM forward primer (10 µM) | 1.0 µl |
| 10 µM reverse primer (10 µM) | 1.0 µl |
| Dynazyme II polymerise | 1 µl |
| MQ water | 3 µl |

4. Include a positive control (50 ng of the original plasmid DNA) and a negative control (no template DNA). Carry out a total of 35 cycles using standard PCR conditions
   1. 95'C for 3 mins
   2. 94° C. for 30 secs
   3. 55° C. for 30 secs 4. 72° C. for 1 mins
5. 72° C. 10 mins Repeat steps 2 to 4 a total of 35 times.

5. Analyse the PCR product on a 1% agarose gel.

Comments

Wear gloves while handling *Agrobacterium*. Collect and autoclave all bacterial and DNA waste. Gene pulser cuvettes are reusable: Soak lids in 70% EtOH and autoclave cuvettes in a closed container with water to remove *Agrobacterium*. Cuvettes can then be stored in 70% EtOH and be reused after drying.

In Planta Transformation of *Arabidopsis thailana*

Experimental Procedure

Preparation of Plant Material

1. Fill seedling punnets with seed raising mixture to form a mound. Cover with two layers of anti-bird netting and secure with rubber bands at each end. Saturate the soil by sitting punnets in a tray of water. Sow sufficient seed to obtain ~40 plants per punnet.
2. Vernalise the seed by placing the punnets at 4° C. for 2-3 days. Transfer punnets to a growth chamber at 22° C. under fluorescent light (constant illumination, 55 μmol $m^{-2}s^{-1}$) and feed with Miracle-Gro or Aquasol once per week.
3. Remove primary bolts when they appear and allow secondary bolts to grow until around 2-10 cm tall (this should take around 4-6 days, the plants should have numerous unopened floral buds and few siliques). Using forceps carefully remove any siliques or open flowers. Water plants well the day before infiltration so that the stomata will be open. Prior to infiltration saturate the soil with water to minimise absorption of bacterial solution into the soil.
4. Enter details into LWS to generate barcodes. Label punnets with LWS barcode details.

Preparation of *Agrobacterium tumefaciens*

1. In the morning inoculate 200 ml LB media containing the appropriate selection antibiotic (ie 100 mg/ml of spectinomycin for pPZP vector) with a single 500 μl starter culture of *Agrobacterium* conservation stock (section 5.1). Incubate for 24 hours at 27° C. in an orbital shaker at 250 rpm. A 200 ml culture is sufficient to infiltrate about 2 punnets of plants.
2. Centrifuge overnight cultures in 500 ml centrifuge bottles at 5500 g at room temperature for 15 mins to pellet cells. Discard the supernatant removing as much liquid as possible. Resuspend the pellet in infiltration media (see appendix 1) to an $OD_{600}$ reading of approximately 0.7 to 0.9

Agroinfiltration

1. Place half of the *Agrobacterium* solution into a 250 ml vessel.
2. Invert the punnet immersing the entire plant including rosette leaves in the bacterial solution and shake gently to dislodge air bubbles. Co-cultivate the plants for 2 mins.
3. Remove the punnet and briefly drain, however, the thin layer of film surrounding the plants should be retained. Cover the plants with plastic film to maintain humidity and return to the growth room away from direct light. Autoclave waste solution and dispose of in a chemical waste drum for correct disposal.
4. Repeat steps one to three for all punnets of *A. thaliana* to be transformed.
5. Enter details into LWS to generate barcodes. Label individual punnets with LWS barcode details.
6. The next day, uncover the pots and place back into direct light. Water the plants until plants have fully developed siliques.

Seed Collection

1. Once plants have dried out, remove the silique bearing stems and place them into a paper bag and leave to dry for one week at 37° C. Label bags with LWS barcode. Crush the dried siliques in the paper bag. This will shatter the siliques and release the seed.
2. Place a 200 micron sieve onto a fresh piece of A4 paper and tip the seed and crushed siliques into it. Tap the sieve gently allowing the seed to fall onto the paper underneath. Discard the plant material that remains in the sieve. Repeat this process until the majority of the plant material has been removed (note plant material can be a source of contamination in subsequent steps). Place seeds into a 1.7 ml microfuge tube and label with LWS barcode details. Place the tube into a small manila envelope and label with LWS barcode. Note that this barcode will relate back to the original transformation event.
3. Store seeds at −20° C. for 24 hours before transferring the seeds to 4° C. for storage.

Selection of Positive $T_1$ Transgenic *Arabidopsis thaliana* Plants

Surface Sterilisation of Seeds

1. Working in a laminar flow hood, place seed to be sterilised (40 mg =~2000 seeds per 150×15 mm plate) into a 2.0 ml microtube.
2. Add 1000 μl 70% ethanol and leave for two mins.
3. Remove the ethanol and add 1000 μl of seed sterilisation solution (4% chlorine:water:5% SDS at a ratio of 8:15:1 respectively) and mix thoroughly by vortexing.
4. Place the tubes on the Ratek 'ferris wheel' to ensure mixing of the seeds and solution, leave for ten mins.
5. In the laminar flow, remove the sterilisation solution and replace with sterile water. Vortex the tube(s) and spin for 30 seconds in a bench top centrifuge to sediment the seeds. Remove the water and replace with another 1 ml of sterile water. The seed washing steps should be repeated until no visible bubbles are apparent (at least 4 times). After the final wash, leave approximately 200 μl of water covering the seeds.

Selection of $T_1$ Transformants

1. Prepare 150×15 mm plates with selection germination medium (SGM) containing the appropriate selection antibiotic (eg. Hygromycin at 8 mg/L for PZP200 series). Include Timentin (250 mg/L) to inhibit growth of *Agrobacterium*. Approximately 125 ml of SGM is required for each plate.
2. Working in a laminar flow hood, run a sterile scalpel across the surface of the SGM agar plate in a parallel fashion (see FIG. 4). This will help to spread the seeds.
3. Using a sterile 1 ml tips, with its end removed, pipette the sterilised seeds onto a plate. Distribute the seeds with a sterile disposable spreader.
4. Cold treat the seeds at 4° C. for two days, and then grow under continuous fluorescent light (55 μmol $m^{-2}$ $s^{-1}$) at 22° C.
5. When putative transformants are at the 6-8 leaf stage they can be transferred to soil. With a pair of forceps carefully remove plants from the tissue culture media ensuring the roots remain intact. Transplant into moist in-vitro mix soil using the ARASYSTEM (see FIG. 5 in appendix 2) Cover with a plastic tube. Create new LWS barcode and label tubes. Cover top of tubes with plastic wrap for a few days to assist recovery.

Verification of Integration of Transgene: Alkali-Treated Leaf Tissue as a Source of Genomic DNA Three days after putative transformants have been transferred to soil, individual plants can be molecularly characterised for presence of the transgene using the following protocol.

1. Prepare a 1×PCR buffer mix for every alkali-treated leaf tissue to be tested (see below for details).
2. In a 1.7 ml microtube, add 200 μl of 0.25 M NaOH to a small young leaf (removed from a $T_1$ plant).
3. Immerse the tube in boiling water for 2 min. Note, to prevent lid popping during boiling, secure the lid with a microtube lid lock or pierce the lid with a fine needle.
4. After boiling, remove the tube from the water and add 200 μl of 0.25 M HCl and 100 μl of 0.25% (v/v) igepal [0.5 M Tris HCl pH 8.0]. Immerse the tube in boiling water for a further 4 mins.
5. Remove a small portion of the alkali-treated leaf (~2 $mm^2$) and place in the pre-prepared PCR mix:

| | |
|---|---|
| 10 × PCR reaction buffer (including Mg(SO4)•7H2O) | 5.0 ml |
| 10 mM dNTP's | 1.0 μl |
| 10 μM forward primer | 1.0 μl |
| 10 μM reverse primer | 1.0 μl |
| PWO DNA polymerase | 1.0 μl |
| MQ H2O | 41.5 μl |

6. Carry out 35 cycles using standard PCR conditions;
   1. 95° C. for 3 mins
   2. 94° C. for 30 secs
   3. 55° C. for 30 secs
   4. 72° C. for 1 mins
   5. 72° C. 10 mins Repeat steps 2 to 4 a total of 35 times.
7. Analyse the PCR Product on a 1% Agarose Gel.

Note if an insert is not amplified using alkali-treated leaf tissue the first time, re-boil the tissue for a further 2 mins and repeat the PCR amplification of the transgene. If this second PCR fails, extract a small quantity of genomic DNA from leaf tissue using Qiagen plant genomic DNA extraction kit. Update LWS.

Seed Collection

1. Once plants have dried out, remove the silique bearing stems and place them a paper bag and leave to dry for one week at room temperature. Label bags with LWS barcode. Crush the dried siliques in the paper bag. This will shatter the siliques and release the seed.
2. Place a 200 micron sieve onto a fresh piece of A4 paper and tip the seed and crushed siliques into it. Tap the sieve gently allowing the seed to fall onto the paper underneath. Discard the plant material that remains in the sieve. Repeat this process until the majority of the plant material has been removed (note plant material can be a source of contamination in subsequent steps). Place seeds into a 1.7 ml microfuge tube and label with LWS barcode details. Place the tube into a small manila envelope and label with LWS barcode. Note that this barcode will relate back to the original transformation event.
3. Store the $T_2$ seed at −20° C. for 24 hours (helps reduce chances of fungal contamination during selection for positive transgenic $T_2$ plants) before storing the seeds at 4° C.

Comments

All containers that come into contact with *Agrobacterium*, including the ARASYSTEM trays, holders, etc should be thoroughly cleaned using commercial bleach and 70% ethanol.

Depending on the experiment, $T_1$ plants can be used for phenotypic characterisation, i.e. reporter gene analysis, and it may not be necessary to continue these lines beyond the $T_1$ stage.

Generation of Homozygous $T_3$ Seeds

Introduction

The protocols detailed below describe the methods employed to select for homozygous plants carrying a single copy of a transgene. Integration of the transgene into *Arabidopsis thaliana* using the infiltration method occurs in the gynoecium prior to fertilisation of the ovary. Therefore any seeds produced by infiltration that carry the transgene are considered to be $T_1$. $T_1$ seeds germinate to produce $T_1$ plants, which in turn produce $T_2$ seeds. The aim is to obtain at least five independent transgenic plants per construct that have a single insert and are expressing the transgene. Each LWS barcode generated for $T_1$ seeds represents a distinct transformation event. As each $T_1$ plant is harvested for $T_2$ seeds they are given a new LWS barcode number. This LWS barcode will relate back to the original transformation event.

Selection of $T_2$ Transformants to Generate $T_3$ Seeds

1. Working in a laminar flow hood surface sterilise approximately 100 $T_2$ seeds (see section 7.1)
2. Plate out approximately 25 seeds per plate (4 in total) onto selection SGM media containing 250 mg/L timetin and 8 mg/L hygromycin (selection agent for pPZP200-35s-hph-35st).
3. Cold treat the seeds at 4° C. for two days then transfer to growth room with constant illumination (55 $\mu mol \cdot m^{-2} \cdot s^{-1}$) at 22° C.
4. After two weeks, segregation analysis of plants resistant or sensitive to hygromycin is performed.
5. When the putative transformants are at the 6 to 8-leaf stage, transfer at least 10 individual plants into soil using the Arasystem. Generate new LWS barcode (relates back to original transformation) and label each plant individually with the barcode. Cover tubes with plastic film for a few days to aid recovery.
6. To confirm that each individual plant has the transgene integrated, use the alkali treated leaf tissue method (section 7.3). Update LWS.
7. Once plants have dried out, remove the silique bearing stems and place them into a paper bag and leave to dry for one week at 37° C. Label bags with LWS barcode. Crush the dried siliques in the paper bag. This will shatter the siliques and release the seeds.
8. Place a 200 micron sieve onto a fresh piece of A4 paper and tip the seed and crushed siliques into it. Tap the sieve gently allowing the seed to fall onto the paper underneath. Discard the plant material that remains in the sieve. Repeat this process until the majority of the plant material has been removed (note plant material can be a source of contamination in subsequent steps). Place seeds into a 1.7 ml microfuge tube and label with LWS barcode details. Place the tube into a small manila envelope and label with LWS barcode. Note that this barcode will relate back to the original transformation event.
9. Store the seed at −20° C. for 24 hours (helps reduce chances of fungal contamination during selection for positive transgenic $T_3$ plants) before transferring the seeds to 4° C. for storage.

Segregation Analysis

1. Score the total number of $T_2$ plants from each line that is either resistant or sensitive to hygromycin.
2. If the T-DNA is inserted at one locus, the ratio of resistant to sensitive plants should be 3:1. If the T-DNA locus is inserted at two loci, the ratio of resistant to sensitive plants should be 15:1. If the T-DNA is inserted at more than two loci, the ratio of resistant to sensitive plants should be >15:1.

3. Use the Chi-square ($\chi 2$) statistical test to determine how well the segregation data fits a particular hypothesis.
4. Continue growing transgenic lines that Chi-square analysis indicated contained a single copy of the transgene.
5. Update LWS Verification of Integration of Transgene: Alkali-Treated Leaf Tissue as a Source of Genomic DNA 1. Harvest one small leaf for each $T_2$ plant.
2. Follow alkali-treated leaf protocol (section 7.3) to determine presence of a transgene.
3. Update LWS.

Selection for Homozygous $T_3$ Lines

1. Continue growing $T_2$ transgenic lines that indicate that they contain a single insertion of the transgene.
2. Collect $T_2$ seeds (section 8.2), and update LWS and generate new barcodes.
3. Germinate ~40 $T_3$ seeds on SGM
4. After 2 weeks score the total number of $T_3$ plants from each line that is either resistant or sensitive to hygromycin.
5. Homozygous $T_3$ lines will be indicated by the absence of sensitive plants.
6. When the putative transformants are at the 6 to 8-leaf stage, transfer at least 20 individual plants into soil using the Arasystem. Generate new LWS barcode and label each plant individually with the barcode. Cover tubes with plastic film for a few days to aid recovery.
7. To further validate that a line is homozygous for a single insertion use the alkali treated leaf tissue method (section 7.3) to confirm that all plants contain a transgene. Update LWS.
8. Harvest sufficient material from putative homozygous lines to perform a Southern Hybridisation to confirm transgene integrated number. Update LWS.
9. Harvest seeds from $T_3$ homozygous lines following the protocol set out in section 8.2.

REFERENCES

Caimi P G, McCole L M, Klein T M, Hershey H P. 1997. Cytosolic expression of the *Bacillus amyloliquefaciens* SacB protein inhibits tissue development in transgenic tobacco and potato. New Phytologist 136, 19-28

Caimi P G, McCole L M, Klein T M, Kerr P S. 1996. Fructan accumulation and sucrose metabolism in transgenic maize endosperm expressing a *Bacillus amyloliquefaciens* sacB gene. Plant Physiology 110, 355-363

Cairns A J. Fructan biosynthesis in transgenic plants. 2003. J Expt Biol 54: 549-67

Clough, S. J. and Bent, A. F., 1998. Floral dip: a simplified method for *Agrobacterium*-mediated transformation of *Arabidopsis thaliana*. The Plant Journal 16: 735-743.

Ebskamp M J M, van der Meer I M, Spronk B A, Weisbeek P J, Smeekens S C M. 1994. Accumulation of fructose polymers in transgenic tobacco. Bio/Technology 12, 272-275

Hattori T, Nakagawa T, Maeshima M, Nakamura K, Asahi T (1985) Molecular cloning and nucleotide sequence of cDNA for sporamin, the major soluble protein of sweet potato tuberous roots. Plant Mol Biol 5: 313-320

Klimyuk, V. I., Carroll, B. J. Thomas, C. M. and Jones, J. D. (1993) The Plant Journal 3(3):493-494

Sasanuma, T. (2001). Characterization of the rbcS multigene family in wheat: subfamily classification, determination of chromosomal location and evolutionary analysis. Mol Genetics Genomics 265(1): 161-171.

Ye X D, Wu X L, Zhao H, Frehner M, Noesberger J, Potrykus I, Spangenberg G. 2001. Altered fructan accumulation in transgenic *Lolium multiflorum* plants expressing a *Bacillus subtilis* sacB gene. Plant Cell Reports 20, 205-212

Zeng, W. K., et al. (1995). PCR Amplification and Sequencing of a Wheat rbcS Gene Promoter. Acta Bot Sinica 37, 496-500.

The invention claimed is:

1. A method for manipulating fructan biosynthesis in photosynthetic cells of a plant, said method comprising the step of introducing into said plant an effective amount of genetic construct encoding a fusion protein, wherein the genetic construct comprises:

(a) a first nucleic acid encoding (i) the catalytic core of a naturally occurring bacterial fructosyltransferase enzyme, or (ii) a variant of the catalytic core of a naturally occurring bacterial fructosyltransferase enzyme which differs from the naturally occurring enzyme as a consequence of one or more nucleic acid substitutions, additions or deletions, with the proviso that the variant retains the amino acids of the sucrose binding/hydrolysis domains of the naturally occurring bacterial fructosyltransferase enzyme and has at least 80% amino acid identity to the naturally occurring bacterial fructosyltransferase enzyme of which it is a variant;

(b) a second nucleic acid encoding a transmembrane domain of a fructosyltransferase enzyme, said second nucleic acid being positioned in the construct such that expression of the construct results in the fusion protein of the transmembrane domain and the catalytic core, with the transmembrane domain at the N-terminus of the catalytic core; and (c) a light regulated promoter operatively linked to the nucleic acids of (a) and (b) to control expression of the fusion protein.

2. The method of claim 1, wherein the transmembrane domain is a transmembrane domain of a sucrose:sucrose 1-fructosyltransferase (1-SST).

3. The method of claim 1, wherein said naturally occurring bacterial FT enzyme includes both sucrose:sucrose 1-fructosyltransferase (1-SST) and fructan:fructan 1-fructosyltransferase (1-FFT) enzymatic activities.

4. The method of claim 3, wherein said a naturally occurring bacterial FT enzyme is selected from the group consisting of SacB, Lsc and FTF.

5. The method of claim 1, wherein nucleic acid encoding a transmembrane domain encodes SEQ ID No. 24.

6. The method of claim 1, wherein the naturally occurring bacterial FT enzyme is SacB.

7. The method of claim 1, wherein the catalytic core of the bacterial FT enzyme comprises amino acids 65-468 of SEQ ID NO: 7.

8. The method of claim 7, wherein nucleic acid encoding a transmembrane domain encodes SEQ ID No. 24.

9. A genetic construct encoding a fusion protein, said construct comprising (a) a first nucleic acid encoding:

(i) the catalytic core of a naturally occurring bacterial fructosyltransferase enzyme, or (ii) a variant of the catalytic core of a naturally occurring bacterial fructosyltransferase enzyme which differs from the naturally occurring enzyme as a consequence of one or more nucleic acid substitutions, additions or deletions, with the proviso that the variant retains the amino acids of the sucrose binding/hydrolysis domains of the naturally occurring bacterial fructosyltransferase enzyme and has at least 80% amino acid identity to the naturally occurring bacterial fructosyltransferase enzyme of which it is a variant;

(b) a second nucleic acid encoding a transmembrane domain of a fructosyltransferase enzyme, said second nucleic acid being positioned in the construct such that expression of the construct results in the fusion protein of the transmembrane domain and the catalytic core, with the transmembrane domain at the N-terminus of the catalytic core; and (c) a light regulated promoter operatively linked to the nucleic acids of (a) and (b) to control expression of the fusion protein.

10. The genetic construct of claim 9, wherein the transmembrane domain is a transmembrane domain of a sucrose: sucrose 1-fructosyltransferase (1-SST).

11. The genetic construct of claim 9, wherein said naturally occurring bacterial FT enzyme includes both sucrose: sucrose 1-fructosyltransferase (1-SST) and fructan:fructan 1-fructosyltransferase (1-FFT) enzymatic activities.

12. The genetic construct of claim 9, wherein said a naturally occurring bacterial FT enzyme is selected from the group consisting of SacB, Lsc and FTF.

13. The genetic construct of claim 9, wherein the nucleic acid encoding a transmembrane domain encodes SEQ ID No. 24.

14. The genetic construct of claim 9, wherein the light regulated promoter is a Ribulose-1,5-biphosphate carboxylase/oxygenase Small subunit (RbcS) promoter.

15. The genetic construct of claim 14, wherein the catalytic core of the bacterial FT enzyme comprises amino acids 65-468 of SEQ ID NO: 7.

16. The genetic construct of claim 15, wherein the nucleic acid encoding a transmembrane domain encodes SEQ ID No. 24.

17. The genetic construct of claim 14, wherein the nucleic acid encoding a transmembrane domain encodes SEQ ID No. 24.

18. The genetic construct of claim 9, wherein the construct comprises SEQ ID NO: 25 as the nucleic acids encoding a catalytic core and a transmembrane domain.

19. The genetic construct of claim 9, wherein the construct comprises SEQ ID NO: 29 as the nucleic acids encoding a catalytic core and a transmembrane domain.

20. The genetic construct of claim 9, wherein the construct comprises SEQ ID NO: 32.

21. The genetic construct of claim 9, wherein the construct comprises SEQ ID NO: 33.

22. The genetic construct of claim 9, wherein the construct comprises SEQ ID NO: 38.

23. The genetic construct of claim 9, wherein the construct comprises SEQ ID NO: 39.

24. The genetic construct of claim 9, wherein the construct comprises SEQ ID NO: 40.

25. The genetic construct of claim 9, wherein the first nucleic acid encodes a variant of the catalytic core having only conservative amino acid substitutions.

26. A transgenic plant cell, plant, plant seed or other plant part with modified fructan biosynthetic characteristics or enhanced biomass relative to an untransformed control plant; said plant cell, plant, plant seed or other plant part including a genetic construct according to claim 9.

27. A method of selecting for transformed plants, said method comprising the steps of:

introducing into said plants an effective amount of a genetic construct encoding a fusion protein, wherein the genetic construct comprises:

(a) a first nucleic acid encoding:

(i) the catalytic core of a naturally occurring bacterial fructosyltransferase enzyme, or (ii) a variant of the catalytic core of a naturally occurring bacterial fructosyltransferase enzyme which differs from the naturally occurring enzyme as a consequence of one or more nucleic acid substitutions, additions or deletions, with the proviso that the variant retains the amino acids of the sucrose binding/hydrolysis domains of the naturally occurring bacterial fructosyltransferase enzyme and has at least 80% amino acid identity to the naturally occurring bacterial fructosyltransferase enzyme of which it is a variant;

(b) a second nucleic acid encoding a transmembrane domain of a fructosyltransferase enzyme, said second nucleic acid being positioned in the construct such that expression of the construct results in the fusion protein of the transmembrane domain and the catalytic core, with the transmembrane domain at the N-terminus of the catalytic core; and (c) a light regulated promoter operatively linked to the nucleic acids of (a) and (b) to control expression of the fusion protein;

thereby producing transformed plants with enhanced biomass as measured by an increase in one or more growth characteristics selected from the group consisting of total leaf area, cumulative leaf area, leaf growth dynamics, number of shoots, number of tillers, number of roots, root mass or weight, shoot mass or weight, root length, stolon length, number of tubers, tuber weight, number of flowers, number of fruits, number of seeds, seed weight, fruit weight, percentage of flowering plants and seed yield per flower or sown area in comparison to non-transformed plants, and selecting plants with enhanced biomass as indicated by an increase in one of more of the growth characteristics.

* * * * *

UNITED STATES PATENT AND TRADEMARK OFFICE

CERTIFICATE OF CORRECTION

PATENT NO. : 10,106,805 B2
APPLICATION NO. : 13/283813
DATED : October 23, 2018
INVENTOR(S) : Spangenberg et al.

It is certified that error appears in the above-identified patent and that said Letters Patent is hereby corrected as shown below:

In the Claims

Column 146, Lines 30-31, Claim 27 should read: -- selecting plants with enhanced biomass as indicated by an increase in one or more of the growth characteristics. --

Signed and Sealed this
Twenty-sixth Day of March, 2019

Andrei Iancu
*Director of the United States Patent and Trademark Office*

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: Conserved domain

<400> SEQUENCE: 1

Leu Asp Val Trp Asp Ser Trp Pro
1               5


<210> SEQ ID NO 2
<211> LENGTH: 7
<212> TYPE: PRT
<213> ORGANISM: Artificial Sequence
<220> FEATURE:
<223> OTHER INFORMATION: Conserved domain

<400> SEQUENCE: 2

Gln Glu Trp Ser Gly Ser Ala
1               5
```

<210> SEQ ID NO 3
<211> LENGTH: 5
<212> TYPE: PRT
<213> ORGANISM: Artificial Sequence
<220> FEATURE:
<223> OTHER INFORMATION: Conserved domain

<400> SEQUENCE: 3

Leu Arg Asp Pro His
1 5

<210> SEQ ID NO 4
<211> LENGTH: 5
<212> TYPE: PRT
<213> ORGANISM: Artificial Sequence
<220> FEATURE:
<223> OTHER INFORMATION: Conserved domain

<400> SEQUENCE: 4

Asp Glu Ile Glu Arg
1 5

<210> SEQ ID NO 5
<211> LENGTH: 1422
<212> TYPE: DNA
<213> ORGANISM: Bacillus subtilis

<400> SEQUENCE: 5
atgaacatca aaaagtttgc aaaacaagca acagtattaa cctttactac cgcactgctg 60
gcaggaggcg caactcaagc gtttgcgaaa gaaacgaacc aaaagccata taaggaaaca 120
tacggcattt cccatattac acgccatgat atgctgcaaa tccctgaaca gcaaaaaaat 180
gaaaaatatc aagttcctga attcgattcg tccacaatta aaaatatctc ttctgcaaaa 240
ggcctggacg tttgggacag ctggccatta caaaacgctg acggcactgt cgcaaactat 300
cacggctacc acatcgtctt tgcattagcc ggagatccta aaaatgcgga tgacacatcg 360
atttacatgt tctatcaaaa agtcggcgaa acttctattg acagctggaa aaacgctggc 420
cgcgtcttta aagacagcga caaattcgat gcaaatgatt ctatcctaaa agaccaaaca 480
caagaatggt caggttcagc cacatttaca tctgacggaa aaatccgttt attctacact 540
gatttctccg gtaaacatta cggcaaacaa acactgacaa ctgcacaagt taacgtatca 600
gcatcagaca gctctttgaa catcaacggt gtagaggatt ataaatcaat ctttgacggt 660
gacggaaaaa cgtatcaaaa tgtacagcag ttcatcgatg aaggcaacta cagctcaggc 720
gacaaccata cgctgagaga tcctcactac gtagaagata aaggccacaa atacttagta 780
tttgaagcaa acactggaac tgaagatggc taccaaggcg aagaatcttt atttaacaaa 840
gcatactatg gcaaaagcac atcattcttc cgtcaagaaa gtcaaaaact tctgcaaagc 900
gataaaaaac gcacggctga gttagcaaac ggcgctctcg gtatgattga gctaaacgat 960
gattacacac tgaaaaaagt gatgaaaccg ctgattgcat ctaacacagt aacagatgaa 1020
attgaacgcg cgaacgtctt taaaatgaac ggcaaatggt acctgttcac tgactcccgc 1080
ggatcaaaaa tgacgattga cggcattacg tctaacgata tttacatgct tggttatgtt 1140
tctaattctt taactggccc atacaagccg ctgaacaaaa ctggccttgt gttaaaaatg 1200
gatcttgatc ctaacgatgt aacctttact tactcacact tcgctgtacc tcaagcgaaa 1260
ggaaacaatg tcgtgattac aagctatatg acaaacagag gattctacgc agacaaacaa 1320
tcaacgtttg cgccaagctt cctgctgaac atcaaaggca agaaaacatc tgttgtcaaa 1380

```
gacagcatcc ttgaacaagg acaattaaca gttaacaaat aa                  1422


<210> SEQ ID NO 6
<211> LENGTH: 93
<212> TYPE: DNA
<213> ORGANISM: Bacillus subtilis

<400> SEQUENCE: 6

atgaacatca aaaagtttgc aaaacaagca acagtattaa cctttactac cgcactgctg     60

gcaggaggcg caactcaagc gtttgcgaaa gaa                                 93


<210> SEQ ID NO 7
<211> LENGTH: 473
<212> TYPE: PRT
<213> ORGANISM: Bacillus subtilis

<400> SEQUENCE: 7

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300
```

```
Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470


<210> SEQ ID NO 8
<211> LENGTH: 31
<212> TYPE: PRT
<213> ORGANISM: Bacillus subtilis

<400> SEQUENCE: 8

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu
            20                  25                  30


<210> SEQ ID NO 9
<211> LENGTH: 2394
<212> TYPE: DNA
<213> ORGANISM: Lactobacillus johnsonii

<400> SEQUENCE: 9

atgttggaaa ataaaaatca taaaaagata tctttaagcg gaaaatcttt gttaatggga     60

accttgtcaa cagcagcaat tgtattaagt gcatcaactg caaatgctgc gactattaat    120

gcagacaatg ttaatgaaaa tcaaactgta gaagtaactg ctagttcagt aaacaatgaa    180

aataataagc aagtaactga aaaagatagt gcagataaaa gtactagtga tgtggctgaa    240

gatgctaaca ccaagaaatc aaacgaaaat acagaaacta cagaaaagaa tactcaaaca    300

gttgttacta atgcgccagt aagtgatgtg aaaaatacaa acacagttac cgctgaaaca    360

cctgttgata aagtagtaaa taatagtgat caaaagacaa ctaatgctgc aactactgat    420

actaaaaaag atgatgtaaa acaagttgaa aagaaagact cagtagataa aacaaatgct    480

gaggaaaata aagatagttc agtaaagcca gctgaaaatg ctactaaggc tgaattaaag    540

ggccaagtta aagatatcgt tgaagaatct ggtgttgata ctagcaagtt aactaatgat    600

caaattaatg aattaaataa aattaatttc tccaaagaag caaaaagtgg tactcagtta    660

acttacaacg actttaaaaa aattgctaaa actttaattg aacaagatgc tcgttatgct    720
```

attccattct tcaatgcaag taaaattaaa aatatgcctg ctgctaaaac acttgatgct 780
caaagtggaa aagtagaaga tttggaaatt tgggattcat ggcctgttca agatgcaaaa 840
actggttacg tatctaactg gaatggctac caattagtga ttggtatgat gggagttcca 900
aacgtcaatg ataaccacat ttatcttctt tacaacaagt atggtgataa tgactttaat 960
cattggaaga atgccggtcc tattttcggt ctaggtactc cagttattca acaatggtct 1020
ggatcagcaa ctttaaataa agatggctca attcaacttt actacactaa ggttgatact 1080
agtgataata atactaacca ccaaaaactc gctagtgcaa ctgtttactt aaatcttgaa 1140
aaagatcaag ataagatttc tattgctcat gttgacaacg accatattgt ctttgaaggt 1200
gatggttacc actaccaaac ttatgaccaa tggaaagaaa ctaacaaggg tgctgacaat 1260
atcgcaatgc gtgatgcaca cgtgattgat gatgataatg gtaatcgtta ccttgtgttt 1320
gaagcaagta ctggaaccga aaattatcaa ggtgatgatc aaatttatca atggttaaat 1380
tacggcggta ctaacaagga taatttaggt gatttcttcc aaattttatc taactccgat 1440
attaaagata gagctaaatg gtcaaacgct gcaattggta tcattaaatt aaatgatgat 1500
gttaagaatc caagtgttgc aaaggtctac agcccactta ttagtgcacc aatggtaagt 1560
gatgaaattg aacgccctga tgttgttaaa ttaggtaata agtattactt atttgctgct 1620
actagattaa accgtggtag taacgatgat gcttggatgg caactaacaa agcagttggt 1680
gataacgtag ctatgattgg ttatgtttct gataacttaa ctcatggtta tgttccattg 1740
aatgaatctg gcgttgtttt aactgcatct gtaccggcta actggcgtac tgcaacttat 1800
tcatactatg cagttccagt agaaggaaga gatgatcaac ttttaattac ttcatacatc 1860
actaatcgtg gtgaggttgc tggaaagggt atgcatgcaa cttgggcacc aagtttcttg 1920
ttacaaatta atccagataa cactactact gttttagcta aaatgactaa ccaaggggat 1980
tggatttggg atgatagtag tgaaaatcca gatatgatgg gtgtacttga aaaagatgct 2040
ccaaatagtg ctgcccttcc tggagaatgg ggaaaaccag ttgattggga tttaattggt 2100
ggatacaact tgaagccaca ccaacctgta actcctattc caaatgtacc aactactcct 2160
gaaaccccaa ccacaccaga taagccagag gtaccaacta cccctgaagt tccaaccact 2220
ccagaaactc caactccaga agctccaaag aatccagtta agaaaactag tcagtctaaa 2280
cttccaaagg ctggagataa aaatagcttt gcagcagttg ttttaggtgc tgtaagttca 2340
atattaggtg ctgttggttt aacaggtgtt tcaaaacgta aacgtaataa ttaa 2394

<210> SEQ ID NO 10
<211> LENGTH: 112
<212> TYPE: DNA
<213> ORGANISM: Lactobacillus johnsonii

<400> SEQUENCE: 10
atgttggaaa ataaaaatca taaaaagata tctttaagcg gaaaatcttt gttaatggga 60
accttgtcaa cagcagcaat tgtattaagt gcatcaactg caaatgctgc ga 112

<210> SEQ ID NO 11
<211> LENGTH: 797
<212> TYPE: PRT
<213> ORGANISM: Lactobacillus johnsonii

<400> SEQUENCE: 11

Met Leu Glu Asn Lys Asn His Lys Lys Ile Ser Leu Ser Gly Lys Ser
1 5 10 15

-continued

```
Leu Leu Met Gly Thr Leu Ser Thr Ala Ala Ile Val Leu Ser Ala Ser
            20                  25                  30

Thr Ala Asn Ala Ala Thr Ile Asn Ala Asp Asn Val Asn Glu Asn Gln
        35                  40                  45

Thr Val Glu Val Thr Ala Ser Ser Val Asn Asn Glu Asn Asn Lys Gln
    50                  55                  60

Val Thr Glu Lys Asp Ser Ala Asp Lys Ser Thr Ser Asp Val Ala Glu
65                  70                  75                  80

Asp Ala Asn Thr Lys Lys Ser Asn Glu Asn Thr Glu Thr Thr Glu Lys
                85                  90                  95

Asn Thr Gln Thr Val Val Thr Asn Ala Pro Val Ser Asp Val Lys Asn
            100                 105                 110

Thr Asn Thr Val Thr Ala Glu Thr Pro Val Asp Lys Val Val Asn Asn
        115                 120                 125

Ser Asp Gln Lys Thr Thr Asn Ala Ala Thr Thr Asp Thr Lys Lys Asp
    130                 135                 140

Asp Val Lys Gln Val Glu Lys Lys Asp Ser Val Asp Lys Thr Asn Ala
145                 150                 155                 160

Glu Glu Asn Lys Asp Ser Ser Val Lys Pro Ala Glu Asn Ala Thr Lys
                165                 170                 175

Ala Glu Leu Lys Gly Gln Val Lys Asp Ile Val Glu Glu Ser Gly Val
            180                 185                 190

Asp Thr Ser Lys Leu Thr Asn Asp Gln Ile Asn Glu Leu Asn Lys Ile
        195                 200                 205

Asn Phe Ser Lys Glu Ala Lys Ser Gly Thr Gln Leu Thr Tyr Asn Asp
    210                 215                 220

Phe Lys Lys Ile Ala Lys Thr Leu Ile Glu Gln Asp Ala Arg Tyr Ala
225                 230                 235                 240

Ile Pro Phe Phe Asn Ala Ser Lys Ile Lys Asn Met Pro Ala Ala Lys
                245                 250                 255

Thr Leu Asp Ala Gln Ser Gly Lys Val Glu Asp Leu Glu Ile Trp Asp
            260                 265                 270

Ser Trp Pro Val Gln Asp Ala Lys Thr Gly Tyr Val Ser Asn Trp Asn
        275                 280                 285

Gly Tyr Gln Leu Val Ile Gly Met Met Gly Val Pro Asn Val Asn Asp
    290                 295                 300

Asn His Ile Tyr Leu Leu Tyr Asn Lys Tyr Gly Asp Asn Asp Phe Asn
305                 310                 315                 320

His Trp Lys Asn Ala Gly Pro Ile Phe Gly Leu Gly Thr Pro Val Ile
                325                 330                 335

Gln Gln Trp Ser Gly Ser Ala Thr Leu Asn Lys Asp Gly Ser Ile Gln
            340                 345                 350

Leu Tyr Tyr Thr Lys Val Asp Thr Ser Asp Asn Asn Thr Asn His Gln
        355                 360                 365

Lys Leu Ala Ser Ala Thr Val Tyr Leu Asn Leu Glu Lys Asp Gln Asp
    370                 375                 380

Lys Ile Ser Ile Ala His Val Asp Asn Asp His Ile Val Phe Glu Gly
385                 390                 395                 400

Asp Gly Tyr His Tyr Gln Thr Tyr Asp Gln Trp Lys Glu Thr Asn Lys
                405                 410                 415

Gly Ala Asp Asn Ile Ala Met Arg Asp Ala His Val Ile Asp Asp Asp
            420                 425                 430

Asn Gly Asn Arg Tyr Leu Val Phe Glu Ala Ser Thr Gly Thr Glu Asn
```

```
        435                 440                 445

Tyr Gln Gly Asp Asp Gln Ile Tyr Gln Trp Leu Asn Tyr Gly Gly Thr
    450                 455                 460

Asn Lys Asp Asn Leu Gly Asp Phe Phe Gln Ile Leu Ser Asn Ser Asp
465                 470                 475                 480

Ile Lys Asp Arg Ala Lys Trp Ser Asn Ala Ala Ile Gly Ile Ile Lys
                485                 490                 495

Leu Asn Asp Asp Val Lys Asn Pro Ser Val Ala Lys Val Tyr Ser Pro
            500                 505                 510

Leu Ile Ser Ala Pro Met Val Ser Asp Glu Ile Glu Arg Pro Asp Val
        515                 520                 525

Val Lys Leu Gly Asn Lys Tyr Tyr Leu Phe Ala Ala Thr Arg Leu Asn
    530                 535                 540

Arg Gly Ser Asn Asp Asp Ala Trp Met Ala Thr Asn Lys Ala Val Gly
545                 550                 555                 560

Asp Asn Val Ala Met Ile Gly Tyr Val Ser Asp Asn Leu Thr His Gly
                565                 570                 575

Tyr Val Pro Leu Asn Glu Ser Gly Val Val Leu Thr Ala Ser Val Pro
            580                 585                 590

Ala Asn Trp Arg Thr Ala Thr Tyr Ser Tyr Tyr Ala Val Pro Val Glu
        595                 600                 605

Gly Arg Asp Asp Gln Leu Leu Ile Thr Ser Tyr Ile Thr Asn Arg Gly
    610                 615                 620

Glu Val Ala Gly Lys Gly Met His Ala Thr Trp Ala Pro Ser Phe Leu
625                 630                 635                 640

Leu Gln Ile Asn Pro Asp Asn Thr Thr Thr Val Leu Ala Lys Met Thr
                645                 650                 655

Asn Gln Gly Asp Trp Ile Trp Asp Asp Ser Ser Glu Asn Pro Asp Met
            660                 665                 670

Met Gly Val Leu Glu Lys Asp Ala Pro Asn Ser Ala Ala Leu Pro Gly
        675                 680                 685

Glu Trp Gly Lys Pro Val Asp Trp Asp Leu Ile Gly Gly Tyr Asn Leu
    690                 695                 700

Lys Pro His Gln Pro Val Thr Pro Ile Pro Asn Val Pro Thr Thr Pro
705                 710                 715                 720

Glu Thr Pro Thr Thr Pro Asp Lys Pro Glu Val Pro Thr Thr Pro Glu
                725                 730                 735

Val Pro Thr Thr Pro Glu Thr Pro Thr Pro Glu Ala Pro Lys Asn Pro
            740                 745                 750

Val Lys Lys Thr Ser Gln Ser Lys Leu Pro Lys Ala Gly Asp Lys Asn
        755                 760                 765

Ser Phe Ala Ala Val Val Leu Gly Ala Val Ser Ser Ile Leu Gly Ala
    770                 775                 780

Val Gly Leu Thr Gly Val Ser Lys Arg Lys Arg Asn Asn
785                 790                 795


<210> SEQ ID NO 12
<211> LENGTH: 37
<212> TYPE: PRT
<213> ORGANISM: Lactobacillus johnsonii

<400> SEQUENCE: 12

Met Leu Glu Asn Lys Asn His Lys Lys Ile Ser Leu Ser Gly Lys Ser
1               5                   10                  15
```

```
Leu Leu Met Gly Thr Leu Ser Thr Ala Ala Ile Val Leu Ser Ala Ser
            20                  25                  30

Thr Ala Asn Ala Ala
        35


<210> SEQ ID NO 13
<211> LENGTH: 657
<212> TYPE: DNA
<213> ORGANISM: Ipomoea batatas

<400> SEQUENCE: 13

atgaaagcct tcacactcgc tctcttctta gctcttttcc tctatctcct gcccaatcca      60

gcccattcca ggttcaatcc catccgcctc cccaccacac acgaacccgc ctcctctgaa     120

actccagtac tcgacatcaa cggcgacgag gtccgcgccg gcgggaacta ctacatggtc     180

tccgccatat ggggagccgg cgggggaggg ctaagactcg cccacttgga cacgatgtcc     240

aaatgcgcca gcgacgtcat cgtatccccc aacgacttag acaacggcga ccccatcacc     300

atcacgccgg cgacggccga cccggaatcc accgtggtca tggcgtcgac ctaccagact     360

ttccggttca atatcgccaa caacaaactg tgcgtgaaga acgtgaactg gggaatccag     420

cacgacagcg cgtccgggca gtatttcctg aaagacggcg agtttgtctc cgacaatagc     480

aaccagttca agattgaggt ggtggatgcc aaccttaact tctacaaact cacttactgt     540

cagttcggct ccgacaaatg ctacaactgc ggcagattcc acgaccccat gttgaggacc     600

acgcgcttgg ctctctccaa ttctcccttc gtttttgtca tcaaacctac cgatgtg        657


<210> SEQ ID NO 14
<211> LENGTH: 69
<212> TYPE: DNA
<213> ORGANISM: Ipomoea batatas

<400> SEQUENCE: 14

atgaaagcct tcacactcgc tctcttctta gctcttttcc tctatctcct gcccaatcca      60

gcccattcc                                                              69


<210> SEQ ID NO 15
<211> LENGTH: 219
<212> TYPE: PRT
<213> ORGANISM: Ipomoea batatas

<400> SEQUENCE: 15

Met Lys Ala Phe Thr Leu Ala Leu Phe Leu Ala Leu Phe Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala Ser Ser Glu Thr Pro Val Leu Asp Ile Asn Gly
        35                  40                  45

Asp Glu Val Arg Ala Gly Gly Asn Tyr Tyr Met Val Ser Ala Ile Trp
    50                  55                  60

Gly Ala Gly Gly Gly Gly Leu Arg Leu Ala His Leu Asp Thr Met Ser
65                  70                  75                  80

Lys Cys Ala Ser Asp Val Ile Val Ser Pro Asn Asp Leu Asp Asn Gly
                85                  90                  95

Asp Pro Ile Thr Ile Thr Pro Ala Thr Ala Asp Pro Glu Ser Thr Val
            100                 105                 110

Val Met Ala Ser Thr Tyr Gln Thr Phe Arg Phe Asn Ile Ala Asn Asn
        115                 120                 125
```

```
Lys Leu Cys Val Lys Asn Val Asn Trp Gly Ile Gln His Asp Ser Ala
    130                 135                 140

Ser Gly Gln Tyr Phe Leu Lys Asp Gly Glu Phe Val Ser Asp Asn Ser
145                 150                 155                 160

Asn Gln Phe Lys Ile Glu Val Val Asp Ala Asn Leu Asn Phe Tyr Lys
                165                 170                 175

Leu Thr Tyr Cys Gln Phe Gly Ser Asp Lys Cys Tyr Asn Cys Gly Arg
            180                 185                 190

Phe His Asp Pro Met Leu Arg Thr Thr Arg Leu Ala Leu Ser Asn Ser
        195                 200                 205

Pro Phe Val Phe Val Ile Lys Pro Thr Asp Val
    210                 215


<210> SEQ ID NO 16
<211> LENGTH: 23
<212> TYPE: PRT
<213> ORGANISM: Ipomoea batatas

<400> SEQUENCE: 16

Met Lys Ala Phe Thr Leu Ala Leu Phe Leu Ala Leu Phe Leu Tyr Leu
1               5                   10                  15

Leu Pro Asn Pro Ala His Ser
            20


<210> SEQ ID NO 17
<211> LENGTH: 1398
<212> TYPE: DNA
<213> ORGANISM: Artificial Sequence
<220> FEATURE:
<223> OTHER INFORMATION: Chimeric sequence

<400> SEQUENCE: 17

atgaaagcct tcacactcgc tctcttctta gctcttttcc tctatctcct gcccaatcca     60

gcccattcca cgaaccaaaa gccatataag gaaacatacg gcatttccca tattacacgc    120

catgatatgc tgcaaatccc tgaacagcaa aaaaatgaaa aatatcaagt tcctgaattc    180

gattcgtcca caattaaaaa tatctcttct gcaaaaggcc tggacgtttg ggacagctgg    240

ccattacaaa acgctgacgg cactgtcgca aactatcacg gctaccacat cgtctttgca    300

ttagccggag atcctaaaaa tgcggatgac acatcgattt acatgttcta tcaaaaagtc    360

ggcgaaactt ctattgacag ctggaaaaac gctggccgcg tctttaaaga cagcgacaaa    420

ttcgatgcaa atgattctat cctaaaagac caaacacaag aatggtcagg ttcagccaca    480

tttacatctg acggaaaaat ccgtttattc tacactgatt tctccggtaa acattacggc    540

aaacaaacac tgacaactgc acaagttaac gtatcagcat cagacagctc tttgaacatc    600

aacggtgtag aggattataa atcaatcttt gacggtgacg gaaaaacgta tcaaaatgta    660

cagcagttca tcgatgaagg caactacagc tcaggcgaca accatacgct gagagatcct    720

cactacgtag aagataaagg ccacaaatac ttagtatttg aagcaaacac tggaactgaa    780

gatggctacc aaggcgaaga atctttattt aacaaagcat actatggcaa aagcacatca    840

ttcttccgtc aagaaagtca aaaacttctg caaagcgata aaaaacgcac ggctgagtta    900

gcaaacggcg ctctcggtat gattgagcta aacgatgatt acacactgaa aaaagtgatg    960

aaaccgctga ttgcatctaa cacagtaaca gatgaaattg aacgcgcgaa cgtctttaaa   1020

atgaacggca aatggtacct gttcactgac tcccgcggat caaaaatgac gattgacggc   1080
```

```
attacgtcta acgatattta catgcttggt tatgtttcta attctttaac tggcccatac   1140

aagccgctga acaaaactgg ccttgtgtta aaaatggatc ttgatcctaa cgatgtaacc   1200

tttacttact cacacttcgc tgtacctcaa gcgaaaggaa acaatgtcgt gattacaagc   1260

tatatgacaa acagaggatt ctacgcagac aaacaatcaa cgtttgcgcc aagcttcctg   1320

ctgaacatca aaggcaagaa aacatctgtt gtcaaagaca gcatccttga acaaggacaa   1380

ttaacagtta acaaataa                                                 1398


<210> SEQ ID NO 18
<211> LENGTH: 465
<212> TYPE: PRT
<213> ORGANISM: Artificial Sequence
<220> FEATURE:
<223> OTHER INFORMATION: Chimeric sequence

<400> SEQUENCE: 18

Met Lys Ala Phe Thr Leu Ala Leu Phe Leu Ala Leu Phe Leu Tyr Leu
1               5                   10                  15

Leu Pro Asn Pro Ala His Ser Thr Asn Gln Lys Pro Tyr Lys Glu Thr
            20                  25                  30

Tyr Gly Ile Ser His Ile Thr Arg His Asp Met Leu Gln Ile Pro Glu
        35                  40                  45

Gln Gln Lys Asn Glu Lys Tyr Gln Val Pro Glu Phe Asp Ser Ser Thr
    50                  55                  60

Ile Lys Asn Ile Ser Ser Ala Lys Gly Leu Asp Val Trp Asp Ser Trp
65                  70                  75                  80

Pro Leu Gln Asn Ala Asp Gly Thr Val Ala Asn Tyr His Gly Tyr His
                85                  90                  95

Ile Val Phe Ala Leu Ala Gly Asp Pro Lys Asn Ala Asp Asp Thr Ser
            100                 105                 110

Ile Tyr Met Phe Tyr Gln Lys Val Gly Glu Thr Ser Ile Asp Ser Trp
        115                 120                 125

Lys Asn Ala Gly Arg Val Phe Lys Asp Ser Asp Lys Phe Asp Ala Asn
    130                 135                 140

Asp Ser Ile Leu Lys Asp Gln Thr Gln Glu Trp Ser Gly Ser Ala Thr
145                 150                 155                 160

Phe Thr Ser Asp Gly Lys Ile Arg Leu Phe Tyr Thr Asp Phe Ser Gly
                165                 170                 175

Lys His Tyr Gly Lys Gln Thr Leu Thr Thr Ala Gln Val Asn Val Ser
            180                 185                 190

Ala Ser Asp Ser Ser Leu Asn Ile Asn Gly Val Glu Asp Tyr Lys Ser
        195                 200                 205

Ile Phe Asp Gly Asp Gly Lys Thr Tyr Gln Asn Val Gln Gln Phe Ile
    210                 215                 220

Asp Glu Gly Asn Tyr Ser Ser Gly Asp Asn His Thr Leu Arg Asp Pro
225                 230                 235                 240

His Tyr Val Glu Asp Lys Gly His Lys Tyr Leu Val Phe Glu Ala Asn
                245                 250                 255

Thr Gly Thr Glu Asp Gly Tyr Gln Gly Glu Glu Ser Leu Phe Asn Lys
            260                 265                 270

Ala Tyr Tyr Gly Lys Ser Thr Ser Phe Phe Arg Gln Glu Ser Gln Lys
        275                 280                 285

Leu Leu Gln Ser Asp Lys Lys Arg Thr Ala Glu Leu Ala Asn Gly Ala
    290                 295                 300
```

```
Leu Gly Met Ile Glu Leu Asn Asp Asp Tyr Thr Leu Lys Lys Val Met
305                 310                 315                 320

Lys Pro Leu Ile Ala Ser Asn Thr Val Thr Asp Glu Ile Glu Arg Ala
                325                 330                 335

Asn Val Phe Lys Met Asn Gly Lys Trp Tyr Leu Phe Thr Asp Ser Arg
            340                 345                 350

Gly Ser Lys Met Thr Ile Asp Gly Ile Thr Ser Asn Asp Ile Tyr Met
        355                 360                 365

Leu Gly Tyr Val Ser Asn Ser Leu Thr Gly Pro Tyr Lys Pro Leu Asn
    370                 375                 380

Lys Thr Gly Leu Val Leu Lys Met Asp Leu Asp Pro Asn Asp Val Thr
385                 390                 395                 400

Phe Thr Tyr Ser His Phe Ala Val Pro Gln Ala Lys Gly Asn Asn Val
                405                 410                 415

Val Ile Thr Ser Tyr Met Thr Asn Arg Gly Phe Tyr Ala Asp Lys Gln
            420                 425                 430

Ser Thr Phe Ala Pro Ser Phe Leu Leu Asn Ile Lys Gly Lys Lys Thr
        435                 440                 445

Ser Val Val Lys Asp Ser Ile Leu Glu Gln Gly Gln Leu Thr Val Asn
    450                 455                 460

Lys
465
```

<210> SEQ ID NO 19
<211> LENGTH: 2352
<212> TYPE: DNA
<213> ORGANISM: Artificial Sequence
<220> FEATURE:
<223> OTHER INFORMATION: Chimeric sequence

<400> SEQUENCE: 19

```
atgaaagcct tcacactcgc tctcttctta gctcttttcc tctatctcct gcccaatcca      60

gcccattcca ctattaatgc agacaatgtt aatgaaaatc aaactgtaga agtaactgct     120

agttcagtaa acaatgaaaa taataagcaa gtaactgaaa aagatagtgc agataaaagt     180

actagtgatg tggctgaaga tgctaacacc aagaaatcaa acgaaaatac agaaactaca     240

gaaaagaata ctcaaacagt tgttactaat gcgccagtaa gtgatgtgaa aaatacaaac     300

acagttaccg ctgaaacacc tgttgataaa gtagtaaata atagtgatca aaagacaact     360

aatgctgcaa ctactgatac taaaaaagat gatgtaaaac aagttgaaaa gaaagactca     420

gtagataaaa caaatgctga ggaaaataaa gatagttcag taaagccagc tgaaaatgct     480

actaaggctg aattaaaggg ccaagttaaa gatatcgttg aagaatctgg tgttgatact     540

agcaagttaa ctaatgatca aattaatgaa ttaaataaaa ttaatttctc caaagaagca     600

aaaagtggta ctcagttaac ttacaacgac tttaaaaaaa ttgctaaaac tttaattgaa     660

caagatgctc gttatgctat tccattcttc aatgcaagta aaattaaaaa tatgcctgct     720

gctaaaacac ttgatgctca aagtggaaaa gtagaagatt tggaaatttg ggattcatgg     780

cctgttcaag atgcaaaaac tggttacgta tctaactgga atggctacca attagtgatt     840

ggtatgatgg gagttccaaa cgtcaatgat aaccacattt atcttcttta caacaagtat     900

ggtgataatg actttaatca ttggaagaat gccggtccta ttttcggtct aggtactcca     960

gttattcaac aatggtctgg atcagcaact ttaaataaag atggctcaat tcaactttac    1020

tacactaagg ttgatactag tgataataat actaaccacc aaaaactcgc tagtgcaact    1080
```

```
gtttacttaa atcttgaaaa agatcaagat aagatttcta ttgctcatgt tgacaacgac   1140

catattgtct ttgaaggtga tggttaccac taccaaactt atgaccaatg gaaagaaact   1200

aacaagggtg ctgacaatat cgcaatgcgt gatgcacacg tgattgatga tgataatggt   1260

aatcgttacc ttgtgtttga agcaagtact ggaaccgaaa attatcaagg tgatgatcaa   1320

atttatcaat ggttaaatta cggcggtact aacaaggata atttaggtga tttcttccaa   1380

attttatcta actccgatat taaagataga gctaaatggt caaacgctgc aattggtatc   1440

attaaattaa atgatgatgt taagaatcca agtgttgcaa aggtctacag cccacttatt   1500

agtgcaccaa tggtaagtga tgaaattgaa cgccctgatg ttgttaaatt aggtaataag   1560

tattacttat ttgctgctac tagattaaac cgtggtagta acgatgatgc ttggatggca   1620

actaacaaag cagttggtga taacgtagct atgattggtt atgtttctga taacttaact   1680

catggttatg ttccattgaa tgaatctggc gttgttttaa ctgcatctgt accggctaac   1740

tggcgtactg caacttattc atactatgca gttccagtag aaggaagaga tgatcaactt   1800

ttaattactt catacatcac taatcgtggt gaggttgctg gaaagggtat gcatgcaact   1860

tgggcaccaa gtttcttgtt acaaattaat ccagataaca ctactactgt tttagctaaa   1920

atgactaacc aaggggattg gatttgggat gatagtagtg aaaatccaga tatgatgggt   1980

gtacttgaaa aagatgctcc aaatagtgct gcccttcctg gagaatgggg aaaaccagtt   2040

gattgggatt taattggtgg atacaacttg aagccacacc aacctgtaac tcctattcca   2100

aatgtaccaa ctactcctga aaccccaacc acaccagata agccagaggt accaactacc   2160

cctgaagttc caaccactcc agaaactcca actccagaag ctccaaagaa tccagttaag   2220

aaaactagtc agtctaaact tccaaaggct ggagataaaa atagctttgc agcagttgtt   2280

ttaggtgctg taagttcaat attaggtgct gttggtttaa caggtgtttc aaaacgtaaa   2340

cgtaataatt aa                                                       2352
```

<210> SEQ ID NO 20
<211> LENGTH: 783
<212> TYPE: PRT
<213> ORGANISM: Artificial Sequence
<220> FEATURE:
<223> OTHER INFORMATION: Chimeric sequence

<400> SEQUENCE: 20

```
Met Lys Ala Phe Thr Leu Ala Leu Phe Leu Ala Leu Phe Leu Tyr Leu
1               5                   10                  15

Leu Pro Asn Pro Ala His Ser Thr Ile Asn Ala Asp Asn Val Asn Glu
            20                  25                  30

Asn Gln Thr Val Glu Val Thr Ala Ser Ser Val Asn Asn Glu Asn Asn
        35                  40                  45

Lys Gln Val Thr Glu Lys Asp Ser Ala Asp Lys Ser Thr Ser Asp Val
    50                  55                  60

Ala Glu Asp Ala Asn Thr Lys Lys Ser Asn Glu Asn Thr Glu Thr Thr
65                  70                  75                  80

Glu Lys Asn Thr Gln Thr Val Val Thr Asn Ala Pro Val Ser Asp Val
                85                  90                  95

Lys Asn Thr Asn Thr Val Thr Ala Glu Thr Pro Val Asp Lys Val Val
            100                 105                 110

Asn Asn Ser Asp Gln Lys Thr Thr Asn Ala Ala Thr Thr Asp Thr Lys
        115                 120                 125

Lys Asp Asp Val Lys Gln Val Glu Lys Lys Asp Ser Val Asp Lys Thr
```

```
    130                 135                 140

Asn Ala Glu Glu Asn Lys Asp Ser Ser Val Lys Pro Ala Glu Asn Ala
145                 150                 155                 160

Thr Lys Ala Glu Leu Lys Gly Gln Val Lys Asp Ile Val Glu Glu Ser
                165                 170                 175

Gly Val Asp Thr Ser Lys Leu Thr Asn Asp Gln Ile Asn Glu Leu Asn
            180                 185                 190

Lys Ile Asn Phe Ser Lys Glu Ala Lys Ser Gly Thr Gln Leu Thr Tyr
        195                 200                 205

Asn Asp Phe Lys Lys Ile Ala Lys Thr Leu Ile Glu Gln Asp Ala Arg
    210                 215                 220

Tyr Ala Ile Pro Phe Phe Asn Ala Ser Lys Ile Lys Asn Met Pro Ala
225                 230                 235                 240

Ala Lys Thr Leu Asp Ala Gln Ser Gly Lys Val Glu Asp Leu Glu Ile
                245                 250                 255

Trp Asp Ser Trp Pro Val Gln Asp Ala Lys Thr Gly Tyr Val Ser Asn
            260                 265                 270

Trp Asn Gly Tyr Gln Leu Val Ile Gly Met Met Gly Val Pro Asn Val
        275                 280                 285

Asn Asp Asn His Ile Tyr Leu Leu Tyr Asn Lys Tyr Gly Asp Asn Asp
    290                 295                 300

Phe Asn His Trp Lys Asn Ala Gly Pro Ile Phe Gly Leu Gly Thr Pro
305                 310                 315                 320

Val Ile Gln Gln Trp Ser Gly Ser Ala Thr Leu Asn Lys Asp Gly Ser
                325                 330                 335

Ile Gln Leu Tyr Tyr Thr Lys Val Asp Thr Ser Asp Asn Asn Thr Asn
            340                 345                 350

His Gln Lys Leu Ala Ser Ala Thr Val Tyr Leu Asn Leu Glu Lys Asp
        355                 360                 365

Gln Asp Lys Ile Ser Ile Ala His Val Asp Asn Asp His Ile Val Phe
    370                 375                 380

Glu Gly Asp Gly Tyr His Tyr Gln Thr Tyr Asp Gln Trp Lys Glu Thr
385                 390                 395                 400

Asn Lys Gly Ala Asp Asn Ile Ala Met Arg Asp Ala His Val Ile Asp
                405                 410                 415

Asp Asp Asn Gly Asn Arg Tyr Leu Val Phe Glu Ala Ser Thr Gly Thr
            420                 425                 430

Glu Asn Tyr Gln Gly Asp Asp Gln Ile Tyr Gln Trp Leu Asn Tyr Gly
        435                 440                 445

Gly Thr Asn Lys Asp Asn Leu Gly Asp Phe Phe Gln Ile Leu Ser Asn
    450                 455                 460

Ser Asp Ile Lys Asp Arg Ala Lys Trp Ser Asn Ala Ala Ile Gly Ile
465                 470                 475                 480

Ile Lys Leu Asn Asp Asp Val Lys Asn Pro Ser Val Ala Lys Val Tyr
                485                 490                 495

Ser Pro Leu Ile Ser Ala Pro Met Val Ser Asp Glu Ile Glu Arg Pro
            500                 505                 510

Asp Val Val Lys Leu Gly Asn Lys Tyr Tyr Leu Phe Ala Ala Thr Arg
        515                 520                 525

Leu Asn Arg Gly Ser Asn Asp Asp Ala Trp Met Ala Thr Asn Lys Ala
    530                 535                 540

Val Gly Asp Asn Val Ala Met Ile Gly Tyr Val Ser Asp Asn Leu Thr
545                 550                 555                 560
```

```
His Gly Tyr Val Pro Leu Asn Glu Ser Gly Val Val Leu Thr Ala Ser
                565                 570                 575

Val Pro Ala Asn Trp Arg Thr Ala Thr Tyr Ser Tyr Tyr Ala Val Pro
            580                 585                 590

Val Glu Gly Arg Asp Asp Gln Leu Leu Ile Thr Ser Tyr Ile Thr Asn
        595                 600                 605

Arg Gly Glu Val Ala Gly Lys Gly Met His Ala Thr Trp Ala Pro Ser
    610                 615                 620

Phe Leu Leu Gln Ile Asn Pro Asp Asn Thr Thr Thr Val Leu Ala Lys
625                 630                 635                 640

Met Thr Asn Gln Gly Asp Trp Ile Trp Asp Asp Ser Ser Glu Asn Pro
                645                 650                 655

Asp Met Met Gly Val Leu Glu Lys Asp Ala Pro Asn Ser Ala Ala Leu
            660                 665                 670

Pro Gly Glu Trp Gly Lys Pro Val Asp Trp Asp Leu Ile Gly Gly Tyr
        675                 680                 685

Asn Leu Lys Pro His Gln Pro Val Thr Pro Ile Pro Asn Val Pro Thr
    690                 695                 700

Thr Pro Glu Thr Pro Thr Thr Pro Asp Lys Pro Glu Val Pro Thr Thr
705                 710                 715                 720

Pro Glu Val Pro Thr Thr Pro Glu Thr Pro Thr Pro Glu Ala Pro Lys
                725                 730                 735

Asn Pro Val Lys Lys Thr Ser Gln Ser Lys Leu Pro Lys Ala Gly Asp
            740                 745                 750

Lys Asn Ser Phe Ala Ala Val Val Leu Gly Ala Val Ser Ser Ile Leu
        755                 760                 765

Gly Ala Val Gly Leu Thr Gly Val Ser Lys Arg Lys Arg Asn Asn
    770                 775                 780
```

<210> SEQ ID NO 21
<211> LENGTH: 2148
<212> TYPE: DNA
<213> ORGANISM: Lolium perenne

<400> SEQUENCE: 21

```
atgcaaccag ggaacgtcgt ccaccccttc cacatcctgt atcaaattaa ggaacgggcg      60

ctgagcctat gccgagacat atataatgcg gcgactcgga catggagggg cctcaggcat     120

agcccagcta gttatctcat tctctcctta gcaataatac ttagcaccat ggcccccgcg     180

gtggaattca tggagtcccc aagcgccgtc gtccccggca ccacggcgcc gctgcttcct     240

tatgcgtacg cgccgctgcc gtcgtccgcc gacgacgccc gtcaaaaccg gagtggcggg     300

aggtggcgcg cgtgcgccgc cgtgctggcc gcatcggcgt tggcggtggt cgtcgtggtc     360

gggctcctcg cgggcggcag ggtggatcgg gtcccggccg gcggagacgt ggcgtcggcc     420

acggtgccgg ccgtgccgat ggagttcccg aggagccggg gcaaggactt cggcgtgtcg     480

gagaagtcct ccggtgccta ctccaccgac ggcgggttcc cgtggagcaa cgccatgctg     540

cagtggcagc gcaccgggtt ccatttccag ccggagcagc actacatgaa cgatcccaac     600

ggccccgtgt actacggcgg atggtaccac ctcttctacc agcacaaccc caagggcgac     660

agctggggca acatcgcgtg ggcccacgcc gtctccaagg acatggtcaa ctggcgccac     720

ctccctctcg ccatggttcc cgaccagtgg tacgacagca acggcgtcct caccggctcc     780

atcaccgtgc tccccgacgg ccaggtcatc ctgctctaca ccggcaacac cgacacccta     840
```

gcccaggtcc agtgcctcgc cacgcccgcc gacccgtccg acccgctcct ccgcgagtgg 900
gtcaagcacc ccgccaaccc catcctctac cctccccccg gcatcggcct caaggacttc 960
cgcgaccccc tcaccgcctg gttcgaccac tccgaccaca cctggcgcac cgtcatcggc 1020
tccaaggacg acgacggcca cgccggcatc atcctcagct acaagaccaa ggacttcgtc 1080
aactacgagc tcatgccggg gaacatgcac cgcgggcccg acggcaccgg aatgtacgag 1140
tgcatcgacc tctaccccgt cggcggcaac tcgtccgaga tgctcggcgg cgacgactcg 1200
cccggcgtgc tcttcgtgct caaggagagc agcgacgacg agcgccacga ctactacgcg 1260
ctcggaaggt tcgacgccgt cgccaacgtt tggacgccca tcgaccggga gctggacctt 1320
gggatcgggc tcagatacga ctggggaaag tactacgcct ccaagtcctt ctacgaccag 1380
aagaagaacc gccgcatcgt atgggcatac atcggcgaga ccgactccga gcaggccgac 1440
atcaccaagg gatgggccaa tctcatgacg attccaagaa cggtggagct tgacaggaag 1500
acccgcacaa acctcatcca atggccagtg gaggaggtcg acaccctccg caggaactcc 1560
acggacctcg gtcgcatcac cgtcaacgcc ggctccgtca ttcgcctccc cctccaccag 1620
ggcgctcaac tcgacatcga ggcctccttc caactcaact cttccgacgt ggatgctatc 1680
aacgaggccg acgtcggcta caactgcagc accagtggtg ccgccgtacg gggggcgctc 1740
ggcccctttg gcctcctcgt ccttgccaac ggccgcaccg aacagacggc tgtgtacttc 1800
tacgtgtcca agggcgtcga cggtgccctc cagacccact tctgccacga cgagtcacgg 1860
tcaacgcggg caaaggatgt cgtgaatagg atgattggca gcatcgtgcc ggtgcttgac 1920
ggtgagacct tttcggtgag ggtgctagtg gaccactcca tcgtgcagag cttcgcgatg 1980
ggcgggagga tcacggcgac gtcgcgggcg tacccgacgg aggccatcta cgcggccgcg 2040
ggggtctacc tcttcaacaa cgccacgggc gccaccgtca ccgccgagag gctcgtcgtg 2100
cacgagatgg cctcagctga caaccatatc ttcacgaacg acgacttg 2148

<210> SEQ ID NO 22
<211> LENGTH: 405
<212> TYPE: DNA
<213> ORGANISM: Lolium perenne

<400> SEQUENCE: 22
atgcaaccag ggaacgtcgt ccaccccttc cacatcctgt atcaaattaa ggaacgggcg 60
ctgagcctat gccgagacat atataatgcg gcgactcgga catggagggg cctcaggcat 120
agcccagcta gttatctcat tctctcctta gcaataatac ttagcaccat ggcccccgcg 180
gtggaattca tggagtcccc aagcgccgtc gtccccggca ccacggcgcc gctgcttcct 240
tatgcgtacg cgccgctgcc gtcgtccgcc gacgacgccc gtcaaaaccg gagtggcggg 300
aggtggcgcg cgtgcgccgc cgtgctggcc gcatcggcgt tggcggtggt cgtcgtggtc 360
gggctcctcg cgggcggcag ggtggatcgg gtcccggccg gcgga 405

<210> SEQ ID NO 23
<211> LENGTH: 653
<212> TYPE: PRT
<213> ORGANISM: Lolium perenne

<400> SEQUENCE: 23

Met Glu Ser Pro Ser Ala Val Val Pro Gly Thr Thr Ala Pro Leu Leu
1 5 10 15

Pro Tyr Ala Tyr Ala Pro Leu Pro Ser Ser Ala Asp Asp Ala Arg Gln
20 25 30

```
Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445
```

```
Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Asp Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Glu Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620

Ala Thr Gly Ala Thr Val Thr Ala Glu Arg Leu Val Val His Glu Met
625                 630                 635                 640

Ala Ser Ala Asp Asn His Ile Phe Thr Asn Asp Asp Leu
                645                 650


<210> SEQ ID NO 24
<211> LENGTH: 72
<212> TYPE: PRT
<213> ORGANISM: Lolium perenne

<400> SEQUENCE: 24

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly
65                  70


<210> SEQ ID NO 25
<211> LENGTH: 1545
<212> TYPE: DNA
<213> ORGANISM: Artificial Sequence
<220> FEATURE:
<223> OTHER INFORMATION: Chimeric sequence

<400> SEQUENCE: 25

atggagtccc caagcgccgt cgtccccggc accacggcgc cgctgcttcc ttatgcgtac      60

gcgccgctgc cgtcgtccgc cgacgacgcc cgtcaaaacc ggagtggcgg gaggtggcgc     120

gcgtgcgccg ccgtgctggc cgcatcggcg ttggcggtgg tcgtcgtggt cgggctcctc     180

gcgggcggca gggtggatcg ggtcccggcc ggcggaacga accaaaagcc atataaggaa     240
```

```
acatacggca tttcccatat tacacgccat gatatgctgc aaatccctga acagcaaaaa    300

aatgaaaaat atcaagttcc tgaattcgat tcgtccacaa ttaaaaatat ctcttctgca    360

aaaggcctgg acgtttggga cagctggcca ttacaaaacg ctgacggcac tgtcgcaaac    420

tatcacggct accacatcgt ctttgcatta gccggagatc ctaaaaatgc ggatgacaca    480

tcgatttaca tgttctatca aaaagtcggc gaaacttcta ttgacagctg gaaaaacgct    540

ggccgcgtct ttaaagacag cgacaaattc gatgcaaatg attctatcct aaaagaccaa    600

acacaagaat ggtcaggttc agccacattt acatctgacg gaaaaatccg tttattctac    660

actgatttct ccggtaaaca ttacggcaaa caaacactga caactgcaca agttaacgta    720

tcagcatcag acagctcttt gaacatcaac ggtgtagagg attataaatc aatctttgac    780

ggtgacggaa aaacgtatca aaatgtacag cagttcatcg atgaaggcaa ctacagctca    840

ggcgacaacc atacgctgag agatcctcac tacgtagaag ataaaggcca caaatactta    900

gtatttgaag caaacactgg aactgaagat ggctaccaag gcgaagaatc tttatttaac    960

aaagcatact atggcaaaag cacatcattc ttccgtcaag aaagtcaaaa acttctgcaa   1020

agcgataaaa aacgcacggc tgagttagca aacggcgctc tcggtatgat tgagctaaac   1080

gatgattaca cactgaaaaa agtgatgaaa ccgctgattg catctaacac agtaacagat   1140

gaaattgaac gcgcgaacgt ctttaaaatg aacggcaaat ggtacctgtt cactgactcc   1200

cgcggatcaa aaatgacgat tgacggcatt acgtctaacg atatttacat gcttggttat   1260

gtttctaatt ctttaactgg cccatacaag ccgctgaaca aaactggcct tgtgttaaaa   1320

atggatcttg atcctaacga tgtaaccttt acttactcac acttcgctgt acctcaagcg   1380

aaaggaaaca atgtcgtgat tacaagctat atgacaaaca gaggattcta cgcagacaaa   1440

caatcaacgt ttgcgccaag cttcctgctg aacatcaaag gcaagaaaac atctgttgtc   1500

aaagacagca tccttgaaca aggacaatta acagttaaca aataa                    1545
```

<210> SEQ ID NO 26
<211> LENGTH: 216
<212> TYPE: DNA
<213> ORGANISM: Lolium perenne

<400> SEQUENCE: 26

```
atggagtccc caagcgccgt cgtccccggc accacggcgc cgctgcttcc ttatgcgtac     60

gcgccgctgc cgtcgtccgc cgacgacgcc cgtcaaaacc ggagtggcgg gaggtggcgc    120

gcgtgcgccg ccgtgctggc cgcatcggcg ttggcggtgg tcgtcgtggt cgggctcctc    180

gcgggcggca gggtggatcg ggtcccggcc ggcgga                              216
```

<210> SEQ ID NO 27
<211> LENGTH: 514
<212> TYPE: PRT
<213> ORGANISM: Artificial Sequence
<220> FEATURE:
<223> OTHER INFORMATION: Chimeric sequence

<400> SEQUENCE: 27

```
Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45
```

```
Ser Ala Leu Ala Val Val Val Val Val Gly Leu Leu Ala Gly Gly Arg
    50                  55                  60

Val Asp Arg Val Pro Ala Gly Gly Thr Asn Gln Lys Pro Tyr Lys Glu
65                  70                  75                  80

Thr Tyr Gly Ile Ser His Ile Thr Arg His Asp Met Leu Gln Ile Pro
                85                  90                  95

Glu Gln Gln Lys Asn Glu Lys Tyr Gln Val Pro Glu Phe Asp Ser Ser
            100                 105                 110

Thr Ile Lys Asn Ile Ser Ser Ala Lys Gly Leu Asp Val Trp Asp Ser
        115                 120                 125

Trp Pro Leu Gln Asn Ala Asp Gly Thr Val Ala Asn Tyr His Gly Tyr
    130                 135                 140

His Ile Val Phe Ala Leu Ala Gly Asp Pro Lys Asn Ala Asp Asp Thr
145                 150                 155                 160

Ser Ile Tyr Met Phe Tyr Gln Lys Val Gly Glu Thr Ser Ile Asp Ser
                165                 170                 175

Trp Lys Asn Ala Gly Arg Val Phe Lys Asp Ser Asp Lys Phe Asp Ala
            180                 185                 190

Asn Asp Ser Ile Leu Lys Asp Gln Thr Gln Glu Trp Ser Gly Ser Ala
        195                 200                 205

Thr Phe Thr Ser Asp Gly Lys Ile Arg Leu Phe Tyr Thr Asp Phe Ser
    210                 215                 220

Gly Lys His Tyr Gly Lys Gln Thr Leu Thr Thr Ala Gln Val Asn Val
225                 230                 235                 240

Ser Ala Ser Asp Ser Ser Leu Asn Ile Asn Gly Val Glu Asp Tyr Lys
                245                 250                 255

Ser Ile Phe Asp Gly Asp Gly Lys Thr Tyr Gln Asn Val Gln Gln Phe
            260                 265                 270

Ile Asp Glu Gly Asn Tyr Ser Ser Gly Asp Asn His Thr Leu Arg Asp
        275                 280                 285

Pro His Tyr Val Glu Asp Lys Gly His Lys Tyr Leu Val Phe Glu Ala
    290                 295                 300

Asn Thr Gly Thr Glu Asp Gly Tyr Gln Gly Glu Glu Ser Leu Phe Asn
305                 310                 315                 320

Lys Ala Tyr Tyr Gly Lys Ser Thr Ser Phe Phe Arg Gln Glu Ser Gln
                325                 330                 335

Lys Leu Leu Gln Ser Asp Lys Lys Arg Thr Ala Glu Leu Ala Asn Gly
            340                 345                 350

Ala Leu Gly Met Ile Glu Leu Asn Asp Asp Tyr Thr Leu Lys Lys Val
        355                 360                 365

Met Lys Pro Leu Ile Ala Ser Asn Thr Val Thr Asp Glu Ile Glu Arg
    370                 375                 380

Ala Asn Val Phe Lys Met Asn Gly Lys Trp Tyr Leu Phe Thr Asp Ser
385                 390                 395                 400

Arg Gly Ser Lys Met Thr Ile Asp Gly Ile Thr Ser Asn Asp Ile Tyr
                405                 410                 415

Met Leu Gly Tyr Val Ser Asn Ser Leu Thr Gly Pro Tyr Lys Pro Leu
            420                 425                 430

Asn Lys Thr Gly Leu Val Leu Lys Met Asp Leu Asp Pro Asn Asp Val
        435                 440                 445

Thr Phe Thr Tyr Ser His Phe Ala Val Pro Gln Ala Lys Gly Asn Asn
    450                 455                 460
```

```
Val Val Ile Thr Ser Tyr Met Thr Asn Arg Gly Phe Tyr Ala Asp Lys
465                 470                 475                 480

Gln Ser Thr Phe Ala Pro Ser Phe Leu Leu Asn Ile Lys Gly Lys Lys
                485                 490                 495

Thr Ser Val Val Lys Asp Ser Ile Leu Glu Gln Gly Gln Leu Thr Val
            500                 505                 510

Asn Lys


<210> SEQ ID NO 28
<211> LENGTH: 2499
<212> TYPE: DNA
<213> ORGANISM: Artificial Sequence
<220> FEATURE:
<223> OTHER INFORMATION: Chimeric sequence

<400> SEQUENCE: 28

atggagtccc caagcgccgt cgtccccggc accacggcgc cgctgcttcc ttatgcgtac     60

gcgccgctgc cgtcgtccgc cgacgacgcc cgtcaaaacc ggagtggcgg gaggtggcgc    120

gcgtgcgccg ccgtgctggc cgcatcggcg ttggcggtgg tcgtcgtggt cgggctcctc    180

gcgggcggca gggtggatcg ggtcccggcc ggcggaacta ttaatgcaga caatgttaat    240

gaaaatcaaa ctgtagaagt aactgctagt tcagtaaaca atgaaaataa taagcaagta    300

actgaaaaag atagtgcaga taaaagtact agtgatgtgg ctgaagatgc taacaccaag    360

aaatcaaacg aaaatacaga aactacagaa aagaatactc aaacagttgt tactaatgcg    420

ccagtaagtg atgtgaaaaa tacaaacaca gttaccgctg aaacacctgt tgataaagta    480

gtaaataata gtgatcaaaa gacaactaat gctgcaacta ctgatactaa aaaagatgat    540

gtaaaacaag ttgaaaagaa agactcagta gataaaacaa atgctgagga aaataaagat    600

agttcagtaa agccagctga aaatgctact aaggctgaat taaagggcca agttaaagat    660

atcgttgaag aatctggtgt tgatactagc aagttaacta atgatcaaat taatgaatta    720

aataaaatta atttctccaa agaagcaaaa agtggtactc agttaactta caacgacttt    780

aaaaaaattg ctaaaacttt aattgaacaa gatgctcgtt atgctattcc attcttcaat    840

gcaagtaaaa ttaaaaatat gcctgctgct aaaacacttg atgctcaaag tggaaaagta    900

gaagatttgg aaatttggga ttcatggcct gttcaagatg caaaaactgg ttacgtatct    960

aactggaatg gctaccaatt agtgattggt atgatgggag ttccaaacgt caatgataac   1020

cacatttatc ttctttacaa caagtatggt gataatgact ttaatcattg gaagaatgcc   1080

ggtcctattt tcggtctagg tactccagtt attcaacaat ggtctggatc agcaacttta   1140

aataaagatg gctcaattca actttactac actaaggttg atactagtga taataatact   1200

aaccaccaaa aactcgctag tgcaactgtt tacttaaatc ttgaaaaaga tcaagataag   1260

atttctattg ctcatgttga caacgaccat attgtctttg aaggtgatgg ttaccactac   1320

caaacttatg accaatggaa agaaactaac aagggtgctg acaatatcgc aatgcgtgat   1380

gcacacgtga ttgatgatga taatggtaat cgttaccttg tgtttgaagc aagtactgga   1440

accgaaaatt atcaaggtga tgatcaaatt tatcaatggt taaattacgg cggtactaac   1500

aaggataatt taggtgattt cttccaaatt ttatctaact ccgatattaa agatagagct   1560

aaatggtcaa acgctgcaat tggtatcatt aaattaaatg atgatgttaa gaatccaagt   1620

gttgcaaagg tctacagccc acttattagt gcaccaatgg taagtgatga aattgaacgc   1680

cctgatgttg ttaaattagg taataagtat tacttatttg ctgctactag attaaaccgt   1740
```

```
ggtagtaacg atgatgcttg gatggcaact aacaaagcag ttggtgataa cgtagctatg   1800

attggttatg tttctgataa cttaactcat ggttatgttc cattgaatga atctggcgtt   1860

gttttaactg catctgtacc ggctaactgg cgtactgcaa cttattcata ctatgcagtt   1920

ccagtagaag gaagagatga tcaacttta attacttcat acatcactaa tcgtggtgag    1980

gttgctggaa agggtatgca tgcaacttgg gcaccaagtt tcttgttaca aattaatcca   2040

gataacacta ctactgtttt agctaaaatg actaaccaag ggattggat ttgggatgat    2100

agtagtgaaa atccagatat gatgggtgta cttgaaaaag atgctccaaa tagtgctgcc   2160

cttcctggag aatggggaaa accagttgat tgggatttaa ttggtggata caacttgaag   2220

ccacaccaac ctgtaactcc tattccaaat gtaccaacta ctcctgaaac cccaaccaca   2280

ccagataagc cagaggtacc aactacccct gaagttccaa ccactccaga aactccaact   2340

ccagaagctc caaagaatcc agttaagaaa actagtcagt ctaaacttcc aaaggctgga   2400

gataaaaata gctttgcagc agttgtttta ggtgctgtaa gttcaatatt aggtgctgtt   2460

ggtttaacag gtgtttcaaa acgtaaacgt aataattaa                          2499
```

```
<210> SEQ ID NO 29
<211> LENGTH: 832
<212> TYPE: PRT
<213> ORGANISM: Artificial Sequence
<220> FEATURE:
<223> OTHER INFORMATION: Chimeric sequence

<400> SEQUENCE: 29

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Thr Ile Asn Ala Asp Asn Val Asn
65                  70                  75                  80

Glu Asn Gln Thr Val Glu Val Thr Ala Ser Ser Val Asn Asn Glu Asn
                85                  90                  95

Asn Lys Gln Val Thr Glu Lys Asp Ser Ala Asp Lys Ser Thr Ser Asp
            100                 105                 110

Val Ala Glu Asp Ala Asn Thr Lys Lys Ser Asn Glu Asn Thr Glu Thr
        115                 120                 125

Thr Glu Lys Asn Thr Gln Thr Val Val Thr Asn Ala Pro Val Ser Asp
    130                 135                 140

Val Lys Asn Thr Asn Thr Val Thr Ala Glu Thr Pro Val Asp Lys Val
145                 150                 155                 160

Val Asn Asn Ser Asp Gln Lys Thr Thr Asn Ala Ala Thr Thr Asp Thr
                165                 170                 175

Lys Lys Asp Asp Val Lys Gln Val Glu Lys Lys Asp Ser Val Asp Lys
            180                 185                 190

Thr Asn Ala Glu Glu Asn Lys Asp Ser Ser Val Lys Pro Ala Glu Asn
        195                 200                 205

Ala Thr Lys Ala Glu Leu Lys Gly Gln Val Lys Asp Ile Val Glu Glu
    210                 215                 220

Ser Gly Val Asp Thr Ser Lys Leu Thr Asn Asp Gln Ile Asn Glu Leu
```

```
225                 230                 235                 240

Asn Lys Ile Asn Phe Ser Lys Glu Ala Lys Ser Gly Thr Gln Leu Thr
                245                 250                 255

Tyr Asn Asp Phe Lys Lys Ile Ala Lys Thr Leu Ile Glu Gln Asp Ala
            260                 265                 270

Arg Tyr Ala Ile Pro Phe Phe Asn Ala Ser Lys Ile Lys Asn Met Pro
        275                 280                 285

Ala Ala Lys Thr Leu Asp Ala Gln Ser Gly Lys Val Glu Asp Leu Glu
    290                 295                 300

Ile Trp Asp Ser Trp Pro Val Gln Asp Ala Lys Thr Gly Tyr Val Ser
305                 310                 315                 320

Asn Trp Asn Gly Tyr Gln Leu Val Ile Gly Met Met Gly Val Pro Asn
                325                 330                 335

Val Asn Asp Asn His Ile Tyr Leu Leu Tyr Asn Lys Tyr Gly Asp Asn
            340                 345                 350

Asp Phe Asn His Trp Lys Asn Ala Gly Pro Ile Phe Gly Leu Gly Thr
        355                 360                 365

Pro Val Ile Gln Gln Trp Ser Gly Ser Ala Thr Leu Asn Lys Asp Gly
    370                 375                 380

Ser Ile Gln Leu Tyr Tyr Thr Lys Val Asp Thr Ser Asp Asn Asn Thr
385                 390                 395                 400

Asn His Gln Lys Leu Ala Ser Ala Thr Val Tyr Leu Asn Leu Glu Lys
                405                 410                 415

Asp Gln Asp Lys Ile Ser Ile Ala His Val Asp Asn Asp His Ile Val
            420                 425                 430

Phe Glu Gly Asp Gly Tyr His Tyr Gln Thr Tyr Asp Gln Trp Lys Glu
        435                 440                 445

Thr Asn Lys Gly Ala Asp Asn Ile Ala Met Arg Asp Ala His Val Ile
    450                 455                 460

Asp Asp Asp Asn Gly Asn Arg Tyr Leu Val Phe Glu Ala Ser Thr Gly
465                 470                 475                 480

Thr Glu Asn Tyr Gln Gly Asp Asp Gln Ile Tyr Gln Trp Leu Asn Tyr
                485                 490                 495

Gly Gly Thr Asn Lys Asp Asn Leu Gly Asp Phe Phe Gln Ile Leu Ser
            500                 505                 510

Asn Ser Asp Ile Lys Asp Arg Ala Lys Trp Ser Asn Ala Ala Ile Gly
        515                 520                 525

Ile Ile Lys Leu Asn Asp Asp Val Lys Asn Pro Ser Val Ala Lys Val
    530                 535                 540

Tyr Ser Pro Leu Ile Ser Ala Pro Met Val Ser Asp Glu Ile Glu Arg
545                 550                 555                 560

Pro Asp Val Val Lys Leu Gly Asn Lys Tyr Tyr Leu Phe Ala Ala Thr
                565                 570                 575

Arg Leu Asn Arg Gly Ser Asn Asp Asp Ala Trp Met Ala Thr Asn Lys
            580                 585                 590

Ala Val Gly Asp Asn Val Ala Met Ile Gly Tyr Val Ser Asp Asn Leu
        595                 600                 605

Thr His Gly Tyr Val Pro Leu Asn Glu Ser Gly Val Val Leu Thr Ala
    610                 615                 620

Ser Val Pro Ala Asn Trp Arg Thr Ala Thr Tyr Ser Tyr Tyr Ala Val
625                 630                 635                 640

Pro Val Glu Gly Arg Asp Asp Gln Leu Leu Ile Thr Ser Tyr Ile Thr
                645                 650                 655
```

```
Asn Arg Gly Glu Val Ala Gly Lys Gly Met His Ala Thr Trp Ala Pro
            660                 665                 670

Ser Phe Leu Leu Gln Ile Asn Pro Asp Asn Thr Thr Thr Val Leu Ala
        675                 680                 685

Lys Met Thr Asn Gln Gly Asp Trp Ile Trp Asp Asp Ser Ser Glu Asn
    690                 695                 700

Pro Asp Met Met Gly Val Leu Glu Lys Asp Ala Pro Asn Ser Ala Ala
705                 710                 715                 720

Leu Pro Gly Glu Trp Gly Lys Pro Val Asp Trp Asp Leu Ile Gly Gly
            725                 730                 735

Tyr Asn Leu Lys Pro His Gln Pro Val Thr Pro Ile Pro Asn Val Pro
            740                 745                 750

Thr Thr Pro Glu Thr Pro Thr Thr Pro Asp Lys Pro Glu Val Pro Thr
        755                 760                 765

Thr Pro Glu Val Pro Thr Thr Pro Glu Thr Pro Thr Pro Glu Ala Pro
    770                 775                 780

Lys Asn Pro Val Lys Lys Thr Ser Gln Ser Lys Leu Pro Lys Ala Gly
785                 790                 795                 800

Asp Lys Asn Ser Phe Ala Ala Val Val Leu Gly Ala Val Ser Ser Ile
            805                 810                 815

Leu Gly Ala Val Gly Leu Thr Gly Val Ser Lys Arg Lys Arg Asn Asn
            820                 825                 830
```

<210> SEQ ID NO 30
<211> LENGTH: 3353
<212> TYPE: DNA
<213> ORGANISM: Artificial Sequence
<220> FEATURE:
<223> OTHER INFORMATION: Chimeric sequence

<400> SEQUENCE: 30

```
cgtggtcgag attgtgtatt attctttagt tattacaaga cttttagcta aaatttgaaa     60

gaatttactt taagaaaatc ttaacatctg agataatttc agcaatagat tatatttttc    120

attactctag cagtattttt gcagatcaat cgcaacatat atggttgtta gaaaaaatgc    180

actatatata tatatattat tttttcaatt aaaagtgcat gatatataat atatatatat    240

atatatatat gtgtgtgtgt atatggtcaa agaaattctt atacaaatat acacgaacac    300

atatatttga caaaatcaaa gtattacact aaacaatgag ttggtgcatg gccaaaacaa    360

atatgtagat taaaaattcc agcctccaaa aaaaaatcca agtgttgtaa agcattatat    420

atatatagta gatcccaaat ttttgtacaa ttccacactg atcgaatttt taaagttgaa    480

tatctgacgt aggatttttt taatgtctta cctgaccatt tactaataac attcatacgt    540

tttcatttga aatatcctct ataattatat tgaatttggc acataataag aaacctaatt    600

ggtgatttat tttactagta aatttctggt gatgggcttt ctactagaaa gctctcggaa    660

aatcttggac caaatccata ttccatgact tcgattgtta accctattag ttttcacaaa    720

catactatca atatcattgc aacggaaaag gtacaagtaa aacattcaat ccgataggga    780

agtgatgtag gaggttggga agacaggccc agaaagagat ttatctgact tgttttgtgt    840

atagttttca atgttcataa aggaagatgg agacttgaga agtttttttt ggactttgtt    900

tagctttgtt gggcgttttt tttttttgat caataacttt gttgggctta tgatttgtaa    960

tattttcgtg gactctttag tttatttaga cgtgctaact ttgttgggct tatgacttgt   1020

tgtaacatat tgtaacagat gacttgatgt gcgactaatc tttacacatt aaacatagtt   1080
```

```
ctgttttttg aaagttctta ttttcatttt tatttgaatg ttatatattt ttctatattt   1140
ataattctag taaaaggcaa attttgcttt taaatgaaaa aaatatatat tccacagttt   1200
cacctaatct tatgcattta gcagtacaaa ttcaaaaatt tcccattttt attcatgaat   1260
cataccatta tatattaact aaatccaagg taaaaaaaag gtatgaaagc tctatagtaa   1320
gtaaaatata aattccccat aaggaaaggg ccaagtccac caggcaagta aaatgagcaa   1380
gcaccactcc accatcacac aatttcactc atagataacg ataagattca tggaattatc   1440
ttccacgtgg cattattcca gcggttcaag ccgataaggg tctcaacacc tctccttagg   1500
cctttgtggc cgttaccaag taaaattaac ctcacacata tccacactca aaatccaacg   1560
gtgtagatcc tagtccactt gaatctcatg tatcctagac cctccgatca ctccaaagct   1620
tgttctcatt gttgttatca ttatatatag atgaccaaag cactagacca aacctcagtc   1680
acacaaagag taaagaagaa caatgaaagc cttcacactc gctctcttct tagctctttt   1740
cctctatctc ctgcccaatc cagcccattc cacgaaccaa aagccatata aggaaacata   1800
cggcatttcc catattacac gccatgatat gctgcaaatc cctgaacagc aaaaaaatga   1860
aaaatatcaa gttcctgaat tcgattcgtc cacaattaaa aatatctctt ctgcaaaagg   1920
cctggacgtt tgggacagct ggccattaca aaacgctgac ggcactgtcg caaactatca   1980
cggctaccac atcgtctttg cattagccgg agatcctaaa aatgcggatg acacatcgat   2040
ttacatgttc tatcaaaaag tcggcgaaac ttctattgac agctggaaaa acgctggccg   2100
cgtctttaaa gacagcgaca aattcgatgc aaatgattct atcctaaaag accaaacaca   2160
agaatggtca ggttcagcca catttacatc tgacggaaaa atccgtttat tctacactga   2220
tttctccggt aaacattacg gcaaacaaac actgacaact gcacaagtta acgtatcagc   2280
atcagacagc tctttgaaca tcaacggtgt agaggattat aaatcaatct ttgacggtga   2340
cggaaaaacg tatcaaaatg tacagcagtt catcgatgaa ggcaactaca gctcaggcga   2400
caaccatacg ctgagagatc ctcactacgt agaagataaa ggccacaaat acttagtatt   2460
tgaagcaaac actggaactg aagatggcta ccaaggcgaa gaatctttat ttaacaaagc   2520
atactatggc aaaagcacat cattcttccg tcaagaaagt caaaaacttc tgcaaagcga   2580
taaaaaacgc acggctgagt tagcaaacgg cgctctcggt atgattgagc taaacgatga   2640
ttacacactg aaaaaagtga tgaaaccgct gattgcatct aacacagtaa cagatgaaat   2700
tgaacgcgcg aacgtcttta aaatgaacgg caaatggtac ctgttcactg actcccgcgg   2760
atcaaaaatg acgattgacg gcattacgtc taacgatatt tacatgcttg gttatgtttc   2820
taattcttta actggcccat acaagccgct gaacaaaact ggccttgtgt taaaaatgga   2880
tcttgatcct aacgatgtaa cctttactta ctcacacttc gctgtacctc aagcgaaagg   2940
aaacaatgtc gtgattacaa gctatatgac aaacagagga ttctacgcag acaaacaatc   3000
aacgtttgcg ccaagcttcc tgctgaacat caaaggcaag aaaacatctg ttgtcaaaga   3060
cagcatcctt gaacaaggac aattaacagt taacaaataa gatcgttcaa acatttggca   3120
ataaagtttc ttaagaatga atcctgttgc cggtcttgcg atgattatca tataatttct   3180
gttgaattac gttaagcatg aaataattaa catgtaatgc atgacgtaat ttatgagatg   3240
ggtttttatg attagagtcc cgcaattata catttaatac gcgatagaaa acaaaatata   3300
gcgcgcaaac taggataaat tatcgcgcgc ggtgtcatca atgttactag atc          3353
```

<210> SEQ ID NO 31

<211> LENGTH: 4307
<212> TYPE: DNA
<213> ORGANISM: Artificial Sequence
<220> FEATURE:
<223> OTHER INFORMATION: Chimeric sequence

<400> SEQUENCE: 31
cgtggtcgag attgtgtatt attctttagt tattacaaga cttttagcta aaatttgaaa 60
gaatttactt taagaaaatc ttaacatctg agataatttc agcaatagat tatatttttc 120
attactctag cagtattttt gcagatcaat cgcaacatat atggttgtta gaaaaaatgc 180
actatatata tatatattat tttttcaatt aaaagtgcat gatatataat atatatatat 240
atatatatat gtgtgtgtgt atatggtcaa agaaattctt atacaaatat acacgaacac 300
atatatttga caaaatcaaa gtattacact aaacaatgag ttggtgcatg gccaaaacaa 360
atatgtagat taaaaattcc agcctccaaa aaaaaatcca agtgttgtaa agcattatat 420
atatatagta gatcccaaat ttttgtacaa ttccacactg atcgaatttt taaagttgaa 480
tatctgacgt aggatttttt taatgtctta cctgaccatt tactaataac attcatacgt 540
tttcatttga aatatcctct ataattatat tgaatttggc acataataag aaacctaatt 600
ggtgatttat tttactagta aatttctggt gatgggcttt ctactagaaa gctctcggaa 660
aatcttggac caaatccata ttccatgact tcgattgtta accctattag ttttcacaaa 720
catactatca atatcattgc aacggaaaag gtacaagtaa aacattcaat ccgataggga 780
agtgatgtag gaggttggga agacaggccc agaaagagat ttatctgact tgttttgtgt 840
atagttttca atgttcataa aggaagatgg agacttgaga agtttttttt ggactttgtt 900
tagctttgtt gggcgttttt ttttttgat caataacttt gttgggctta tgatttgtaa 960
tattttcgtg gactctttag tttatttaga cgtgctaact ttgttgggct tatgacttgt 1020
tgtaacatat tgtaacagat gacttgatgt gcgactaatc tttacacatt aaacatagtt 1080 ctgtttttttg aaagttctta ttttcatttt tatttgaatg ttatatattt ttctatattt 1140
ataattctag taaaaggcaa attttgcttt taaatgaaaa aaatatatat tccacagttt 1200
cacctaatct tatgcattta gcagtacaaa ttcaaaaatt tcccattttt attcatgaat 1260
cataccatta tatattaact aaatccaagg taaaaaaaag gtatgaaagc tctatagtaa 1320
gtaaaatata aattccccat aaggaaaggg ccaagtccac caggcaagta aaatgagcaa 1380
gcaccactcc accatcacac aatttcactc atagataacg ataagattca tggaattatc 1440
ttccacgtgg cattattcca gcggttcaag ccgataaggg tctcaacacc tctccttagg 1500
cctttgtggc cgttaccaag taaaattaac ctcacacata tccacactca aaatccaacg 1560
gtgtagatcc tagtccactt gaatctcatg tatcctagac cctccgatca ctccaaagct 1620
tgttctcatt gttgttatca ttatatatag atgaccaaag cactagacca aacctcagtc 1680
acacaaagag taaagaagaa caatgaaagc cttcacactc gctctcttct tagctctttt 1740
cctctatctc ctgcccaatc cagcccattc cactattaat gcagacaatg ttaatgaaaa 1800
tcaaactgta gaagtaactg ctagttcagt aaacaatgaa aataataagc aagtaactga 1860
aaaagatagt gcagataaaa gtactagtga tgtggctgaa gatgctaaca ccaagaaatc 1920
aaacgaaaat acagaaacta cagaaaagaa tactcaaaca gttgttacta atgcgccagt 1980
aagtgatgtg aaaaatacaa acacagttac cgctgaaaca cctgttgata aagtagtaaa 2040
taatagtgat caaaagacaa ctaatgctgc aactactgat actaaaaaag atgatgtaaa 2100
acaagttgaa aagaaagact cagtagataa aacaaatgct gaggaaaata aagatagttc 2160

```
agtaaagcca gctgaaaatg ctactaaggc tgaattaaag ggccaagtta aagatatcgt   2220
tgaagaatct ggtgttgata ctagcaagtt aactaatgat caaattaatg aattaaataa   2280
aattaatttc tccaaagaag caaaaagtgg tactcagtta acttacaacg actttaaaaa   2340
aattgctaaa actttaattg aacaagatgc tcgttatgct attccattct tcaatgcaag   2400
taaaattaaa aatatgcctg ctgctaaaac acttgatgct caaagtggaa aagtagaaga   2460
tttggaaatt tgggattcat ggcctgttca agatgcaaaa actggttacg tatctaactg   2520
gaatggctac caattagtga ttggtatgat gggagttcca aacgtcaatg ataaccacat   2580
ttatcttctt tacaacaagt atggtgataa tgactttaat cattggaaga atgccggtcc   2640
tattttcggt ctaggtactc cagttattca acaatggtct ggatcagcaa ctttaaataa   2700
agatggctca attcaacttt actacactaa ggttgatact agtgataata atactaacca   2760
ccaaaaactc gctagtgcaa ctgtttactt aaatcttgaa aaagatcaag ataagatttc   2820
tattgctcat gttgacaacg accatattgt ctttgaaggt gatggttacc actaccaaac   2880
ttatgaccaa tggaaagaaa ctaacaaggg tgctgacaat atcgcaatgc gtgatgcaca   2940
cgtgattgat gatgataatg gtaatcgtta ccttgtgttt gaagcaagta ctggaaccga   3000
aaattatcaa ggtgatgatc aaatttatca atggttaaat tacggcggta ctaacaagga   3060
taatttaggt gatttcttcc aaattttatc taactccgat attaaagata gagctaaatg   3120
gtcaaacgct gcaattggta tcattaaatt aaatgatgat gttaagaatc caagtgttgc   3180
aaaggtctac agcccactta ttagtgcacc aatggtaagt gatgaaattg aacgccctga   3240
tgttgttaaa ttaggtaata agtattactt atttgctgct actagattaa accgtggtag   3300
taacgatgat gcttggatgg caactaacaa agcagttggt gataacgtag ctatgattgg   3360
ttatgtttct gataacttaa ctcatggtta tgttccattg aatgaatctg gcgttgtttt   3420
aactgcatct gtaccggcta actggcgtac tgcaacttat tcatactatg cagttccagt   3480
agaaggaaga gatgatcaac ttttaattac ttcatacatc actaatcgtg gtgaggttgc   3540
tggaaagggt atgcatgcaa cttgggcacc aagtttcttg ttacaaatta atccagataa   3600
cactactact gttttagcta aaatgactaa ccaaggggat tggatttggg atgatagtag   3660
tgaaaatcca gatatgatgg gtgtacttga aaaagatgct ccaaatagtg ctgcccttcc   3720
tggagaatgg ggaaaaccag ttgattggga tttaattggt ggatacaact tgaagccaca   3780
ccaacctgta actcctattc caaatgtacc aactactcct gaaaccccaa ccacaccaga   3840
taagccagag gtaccaacta cccctgaagt tccaaccact ccagaaactc caactccaga   3900
agctccaaag aatccagtta agaaaactag tcagtctaaa cttccaaagg ctggagataa   3960
aaatagcttt gcagcagttg ttttaggtgc tgtaagttca atattaggtg ctgttggttt   4020
aacaggtgtt tcaaaacgta aacgtaataa ttaagatcgt tcaaacattt ggcaataaag   4080
tttcttaaga atgaatcctg ttgccggtct tgcgatgatt atcatataat ttctgttgaa   4140
ttacgttaag catgaaataa ttaacatgta atgcatgacg taatttatga gatgggtttt   4200
tatgattaga gtcccgcaat tatacattta atacgcgata gaaaacaaaa tatagcgcgc   4260
aaactaggat aaattatcgc gcgcggtgtc atcaatgtta ctagatc                 4307
```

<210> SEQ ID NO 32
<211> LENGTH: 3500
<212> TYPE: DNA
<213> ORGANISM: Artificial Sequence
<220> FEATURE:

<223> OTHER INFORMATION: Chimeric sequence

<400> SEQUENCE: 32

```
cgtggtcgag attgtgtatt attctttagt tattacaaga cttttagcta aaatttgaaa      60
gaatttactt taagaaaatc ttaacatctg agataatttc agcaatagat tatatttttc     120
attactctag cagtattttt gcagatcaat cgcaacatat atggttgtta gaaaaaatgc     180
actatatata tatatattat tttttcaatt aaaagtgcat gatatataat atatatatat     240
atatatatat gtgtgtgtgt atatggtcaa agaaattctt atacaaatat acacgaacac     300
atatatttga caaaatcaaa gtattacact aaacaatgag ttggtgcatg gccaaaacaa     360
atatgtagat taaaaattcc agcctccaaa aaaaaatcca agtgttgtaa agcattatat     420
atatatagta gatcccaaat ttttgtacaa ttccacactg atcgaatttt taaagttgaa     480
tatctgacgt aggatttttt taatgtctta cctgaccatt tactaataac attcatacgt     540
tttcatttga aatatcctct ataattatat tgaatttggc acataataag aaacctaatt     600
ggtgatttat tttactagta aatttctggt gatgggcttt ctactagaaa gctctcggaa     660
aatcttggac caaatccata ttccatgact tcgattgtta accctattag ttttcacaaa     720
catactatca atatcattgc aacggaaaag gtacaagtaa aacattcaat ccgataggga     780
agtgatgtag gaggttggga agacaggccc agaaagagat ttatctgact tgttttgtgt     840
atagttttca atgttcataa aggaagatgg agacttgaga agtttttttt ggactttgtt     900
tagctttgtt gggcgttttt ttttttgat caataacttt gttgggctta tgatttgtaa     960
tattttcgtg gactctttag tttatttaga cgtgctaact ttgttgggct tatgacttgt    1020
tgtaacatat tgtaacagat gacttgatgt gcgactaatc tttacacatt aaacatagtt    1080
ctgtttttttg aaagttctta ttttcatttt tatttgaatg ttatatattt ttctatattt   1140
ataattctag taaaaggcaa attttgcttt taaatgaaaa aaatatatat tccacagttt    1200
cacctaatct tatgcattta gcagtacaaa ttcaaaaatt tcccattttt attcatgaat    1260
cataccatta tatattaact aaatccaagg taaaaaaaag gtatgaaagc tctatagtaa    1320
gtaaaatata aattccccat aaggaaaggg ccaagtccac caggcaagta aaatgagcaa    1380
gcaccactcc accatcacac aatttcactc atagataacg ataagattca tggaattatc    1440
ttccacgtgg cattattcca gcggttcaag ccgataaggg tctcaacacc tctccttagg    1500
cctttgtggc cgttaccaag taaaattaac ctcacacata tccacactca aaatccaacg    1560
gtgtagatcc tagtccactt gaatctcatg tatcctagac cctccgatca ctccaaagct    1620
tgttctcatt gttgttatca ttatatatag atgaccaaag cactagacca aacctcagtc    1680
acacaaagag taaagaagaa caatggagtc cccaagcgcc gtcgtccccg gcaccacggc    1740
gccgctgctt ccttatgcgt acgcgccgct gccgtcgtcc gccgacgacg cccgtcaaaa    1800
ccggagtggc gggaggtggc gcgcgtgcgc cgccgtgctg gccgcatcgg cgttggcggt    1860
ggtcgtcgtg gtcgggctcc tcgcgggcgg cagggtggat cgggtcccgg ccggcggaac    1920
gaaccaaaag ccatataagg aaacatacgg catttcccat attacacgcc atgatatgct    1980
gcaaatccct gaacagcaaa aaaatgaaaa atatcaagtt cctgaattcg attcgtccac    2040
aattaaaaat atctcttctg caaaaggcct ggacgtttgg gacagctggc cattacaaaa    2100
cgctgacggc actgtcgcaa actatcacgg ctaccacatc gtctttgcat tagccggaga    2160
tcctaaaaat gcggatgaca catcgattta catgttctat caaaaagtcg gcgaaacttc    2220
tattgacagc tggaaaaacg ctggccgcgt ctttaaagac agcgacaaat tcgatgcaaa    2280
```

```
tgattctatc ctaaaagacc aaacacaaga atggtcaggt tcagccacat ttacatctga   2340

cggaaaaatc cgtttattct acactgattt ctccggtaaa cattacggca aacaaacact   2400

gacaactgca caagttaacg tatcagcatc agacagctct ttgaacatca acggtgtaga   2460

ggattataaa tcaatctttg acggtgacgg aaaaacgtat caaaatgtac agcagttcat   2520

cgatgaaggc aactacagct caggcgacaa ccatacgctg agagatcctc actacgtaga   2580

agataaaggc cacaaatact tagtatttga agcaaacact ggaactgaag atggctacca   2640

aggcgaagaa tctttattta acaaagcata ctatggcaaa agcacatcat tcttccgtca   2700

agaaagtcaa aaacttctgc aaagcgataa aaaacgcacg gctgagttag caaacggcgc   2760

tctcggtatg attgagctaa acgatgatta cacactgaaa aaagtgatga aaccgctgat   2820

tgcatctaac acagtaacag atgaaattga acgcgcgaac gtctttaaaa tgaacggcaa   2880

atggtacctg ttcactgact cccgcggatc aaaaatgacg attgacggca ttacgtctaa   2940

cgatatttac atgcttggtt atgtttctaa ttctttaact ggcccataca agccgctgaa   3000

caaaactggc cttgtgttaa aaatggatct tgatcctaac gatgtaacct ttacttactc   3060

acacttcgct gtacctcaag cgaaaggaaa caatgtcgtg attacaagct atatgacaaa   3120

cagaggattc tacgcagaca aacaatcaac gtttgcgcca agcttcctgc tgaacatcaa   3180

aggcaagaaa acatctgttg tcaaagacag catccttgaa caaggacaat taacagttaa   3240

caaataagat cgttcaaaca tttggcaata aagtttctta agaatgaatc ctgttgccgg   3300

tcttgcgatg attatcatat aatttctgtt gaattacgtt aagcatgaaa taattaacat   3360

gtaatgcatg acgtaattta tgagatgggt ttttatgatt agagtcccgc aattatacat   3420

ttaatacgcg atagaaaaca aaatatagcg cgcaaactag gataaattat cgcgcgcggt   3480

gtcatcaatg ttactagatc                                                3500
```

<210> SEQ ID NO 33
<211> LENGTH: 5234
<212> TYPE: DNA
<213> ORGANISM: Artificial Sequence
<220> FEATURE:
<223> OTHER INFORMATION: Chimeric sequence

<400> SEQUENCE: 33

```
cgtggtcgag attgtgtatt attctttagt tattacaaga cttttagcta aaatttgaaa     60

gaatttactt taagaaaatc ttaacatctg agataatttc agcaatagat tatatttttc    120

attactctag cagtattttt gcagatcaat cgcaacatat atggttgtta gaaaaaatgc    180

actatatata tatatattat tttttcaatt aaaagtgcat gatatataat atatatatat    240

atatatatat gtgtgtgtgt atatggtcaa agaaattctt atacaaatat acacgaacac    300

atatatttga caaaatcaaa gtattacact aaacaatgag ttggtgcatg gccaaaacaa    360

atatgtagat taaaaattcc agcctccaaa aaaaaatcca agtgttgtaa agcattatat    420

atatatagta gatcccaaat ttttgtacaa ttccacactg atcgaatttt taaagttgaa    480

tatctgacgt aggatttttt taatgtctta cctgaccatt tactaataac attcatacgt    540

tttcatttga aatatcctct ataattatat tgaatttggc acataataag aaacctaatt    600

ggtgatttat tttactagta aatttctggt gatgggcttt ctactagaaa gctctcggaa    660

aatcttggac caaatccata ttccatgact tcgattgtta accctattag ttttcacaaa    720

catactatca atatcattgc aacggaaaag gtacaagtaa aacattcaat ccgataggga    780
```

```
cgtggtcgag attgtgtatt attctttagt tattacaaga cttttagcta aaatttgaaa    840
gaatttactt taagaaaatc ttaacatctg agataatttc agcaatagat tatatttttc    900
attactctag cagtattttt gcagatcaat cgcaacatat atggttgtta gaaaaaatgc    960
actatatata tatatattat tttttcaatt aaaagtgcat gatatataat atatatatat   1020
atatatatat gtgtgtgtgt atatggtcaa agaaattctt atacaaatat acacgaacac   1080
atatatttga caaaatcaaa gtattacact aaacaatgag ttggtgcatg gccaaaacaa   1140
atatgtagat taaaaattcc agcctccaaa aaaaaatcca agtgttgtaa agcattatat   1200
atatatagta gatcccaaat ttttgtacaa ttccacactg atcgaatttt taaagttgaa   1260
tatctgacgt aggatttttt taatgtctta cctgaccatt tactaataac attcatacgt   1320
tttcatttga aatatcctct ataattatat tgaatttggc acataataag aaacctaatt   1380
ggtgatttat tttactagta aatttctggt gatgggcttt ctactagaaa gctctcggaa   1440
aatcttggac caaatccata ttccatgact tcgattgtta accctattag ttttcacaaa   1500
catactatca atatcattgc aacggaaaag gtacaagtaa aacattcaat ccgataggga   1560
agtgatgtag gaggttggga agacaggccc agaaagagat ttatctgact tgttttgtgt   1620
atagttttca atgttcataa aggaagatgg agacttgaga agtttttttt ggactttgtt   1680
tagctttgtt gggcgttttt tttttttgat caataacttt gttgggctta tgatttgtaa   1740
tattttcgtg gactctttag tttatttaga cgtgctaact ttgttgggct tatgacttgt   1800
tgtaacatat tgtaacagat gacttgatgt gcgactaatc tttacacatt aaacatagtt   1860
ctgttttttg aaagttctta ttttcatttt tatttgaatg ttatatattt ttctatattt   1920
ataattctag taaaaggcaa attttgcttt taaatgaaaa aaatatatat tccacagttt   1980
cacctaatct tatgcattta gcagtacaaa ttcaaaaatt tcccattttt attcatgaat   2040
cataccatta tatattaact aaatccaagg taaaaaaaag gtatgaaagc tctatagtaa   2100
gtaaaatata aattccccat aaggaaaggg ccaagtccac caggcaagta aaatgagcaa   2160
gcaccactcc accatcacac aatttcactc atagataacg ataagattca tggaattatc   2220
ttccacgtgg cattattcca gcggttcaag ccgataaggg tctcaacacc tctccttagg   2280
cctttgtggc cgttaccaag taaaattaac ctcacacata tccacactca aaatccaacg   2340
gtgtagatcc tagtccactt gaatctcatg tatcctagac cctccgatca ctccaaagct   2400
tgttctcatt gttgttatca ttatatatag atgaccaaag cactagacca aacctcagtc   2460
acacaaagag taaagaagaa caatggagtc cccaagcgcc gtcgtccccg gcaccacggc   2520
gccgctgctt ccttatgcgt acgcgccgct gccgtcgtcc gccgacgacg cccgtcaaaa   2580
ccggagtggc gggaggtggc gcgcgtgcgc cgccgtgctg gccgcatcgg cgttggcggt   2640
ggtcgtcgtg gtcgggctcc tcgcgggcgg cagggtggat cgggtcccgg ccggcggaac   2700
tattaatgca gacaatgtta atgaaaatca aactgtagaa gtaactgcta gttcagtaaa   2760
caatgaaaat aataagcaag taactgaaaa agatagtgca gataaaagta ctagtgatgt   2820
ggctgaagat gctaacacca agaaatcaaa cgaaaataca gaaactacag aaaagaatac   2880
tcaaacagtt gttactaatg cgccagtaag tgatgtgaaa aatacaaaca cagttaccgc   2940
tgaaacacct gttgataaag tagtaaataa tagtgatcaa aagacaacta atgctgcaac   3000
tactgatact aaaaaagatg atgtaaaaca agttgaaaag aaagactcag tagataaaac   3060
aaatgctgag gaaaataaag atagttcagt aaagccagct gaaaatgcta ctaaggctga   3120
attaaagggc caagttaaag atatcgttga agaatctggt gttgatacta gcaagttaac   3180
```

```
taatgatcaa attaatgaat taaataaaat taatttctcc aaagaagcaa aaagtggtac   3240

tcagttaact tacaacgact ttaaaaaaat tgctaaaact ttaattgaac aagatgctcg   3300

ttatgctatt ccattcttca atgcaagtaa aattaaaaat atgcctgctg ctaaaacact   3360

tgatgctcaa agtggaaaag tagaagattt ggaaatttgg gattcatggc ctgttcaaga   3420

tgcaaaaact ggttacgtat ctaactggaa tggctaccaa ttagtgattg gtatgatggg   3480

agttccaaac gtcaatgata accacattta tcttctttac aacaagtatg gtgataatga   3540

ctttaatcat tggaagaatg ccggtcctat tttcggtcta ggtactccag ttattcaaca   3600

atggtctgga tcagcaactt taaataaaga tggctcaatt caactttact acactaaggt   3660

tgatactagt gataataata ctaaccacca aaaactcgct agtgcaactg tttacttaaa   3720

tcttgaaaaa gatcaagata agatttctat tgctcatgtt gacaacgacc atattgtctt   3780

tgaaggtgat ggttaccact accaaactta tgaccaatgg aaagaaacta acaagggtgc   3840

tgacaatatc gcaatgcgtg atgcacacgt gattgatgat gataatggta atcgttacct   3900

tgtgtttgaa gcaagtactg gaaccgaaaa ttatcaaggt gatgatcaaa tttatcaatg   3960

gttaaattac ggcggtacta acaaggataa tttaggtgat ttcttccaaa ttttatctaa   4020

ctccgatatt aaagatagag ctaaatggtc aaacgctgca attggtatca ttaaattaaa   4080

tgatgatgtt aagaatccaa gtgttgcaaa ggtctacagc ccacttatta gtgcaccaat   4140

ggtaagtgat gaaattgaac gccctgatgt tgttaaatta ggtaataagt attacttatt   4200

tgctgctact agattaaacc gtggtagtaa cgatgatgct tggatggcaa ctaacaaagc   4260

agttggtgat aacgtagcta tgattggtta tgtttctgat aacttaactc atggttatgt   4320

tccattgaat gaatctggcg ttgttttaac tgcatctgta ccggctaact ggcgtactgc   4380

aacttattca tactatgcag ttccagtaga aggaagagat gatcaacttt taattacttc   4440

atacatcact aatcgtggtg aggttgctgg aaagggtatg catgcaactt gggcaccaag   4500

tttcttgtta caaattaatc cagataacac tactactgtt ttagctaaaa tgactaacca   4560

aggggattgg atttgggatg atagtagtga aaatccagat atgatgggtg tacttgaaaa   4620

agatgctcca aatagtgctg cccttcctgg agaatgggga aaaccagttg attgggattt   4680

aattggtgga tacaacttga agccacacca acctgtaact cctattccaa atgtaccaac   4740

tactcctgaa accccaacca caccagataa gccagaggta ccaactaccc ctgaagttcc   4800

aaccactcca gaaactccaa ctccagaagc tccaaagaat ccagttaaga aaactagtca   4860

gtctaaactt ccaaaggctg gagataaaaa tagctttgca gcagttgttt taggtgctgt   4920

aagttcaata ttaggtgctg ttggtttaac aggtgtttca aaacgtaaac gtaataatta   4980

agatcgttca aacatttggc aataaagttt cttaagaatg aatcctgttg ccggtcttgc   5040

gatgattatc atataatttc tgttgaatta cgttaagcat gaaataatta acatgtaatg   5100

catgacgtaa tttatgagat gggtttttat gattagagtc ccgcaattat acatttaata   5160

cgcgatagaa aacaaaatat agcgcgcaaa ctaggataaa ttatcgcgcg cggtgtcatc   5220

aatgttacta gatc                                                      5234
```

<210> SEQ ID NO 34
<211> LENGTH: 2790
<212> TYPE: DNA
<213> ORGANISM: Artificial Sequence
<220> FEATURE:
<223> OTHER INFORMATION: Chimeric sequence

<400> SEQUENCE: 34

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgaa agccttcaca ctcgctctct    720
tcttagctct tttcctctat ctcctgccca atccagccca ttccacgaac caaaagccat    780
ataaggaaac atacggcatt tcccatatta cacgccatga tatgctgcaa atccctgaac    840
agcaaaaaaa tgaaaaatat caagttcctg aattcgattc gtccacaatt aaaaatatct    900
cttctgcaaa aggcctggac gtttgggaca gctggccatt acaaaacgct gacggcactg    960
tcgcaaacta tcacggctac cacatcgtct ttgcattagc cggagatcct aaaaatgcgg   1020
atgacacatc gatttacatg ttctatcaaa aagtcggcga aacttctatt gacagctgga   1080
aaaacgctgg ccgcgtcttt aaagacagcg acaaattcga tgcaaatgat tctatcctaa   1140
aagaccaaac acaagaatgg tcaggttcag ccacatttac atctgacgga aaaatccgtt   1200
tattctacac tgatttctcc ggtaaacatt acggcaaaca aacactgaca actgcacaag   1260
ttaacgtatc agcatcagac agctctttga acatcaacgg tgtagaggat tataaatcaa   1320
tctttgacgg tgacggaaaa acgtatcaaa atgtacagca gttcatcgat gaaggcaact   1380
acagctcagg cgacaaccat acgctgagag atcctcacta cgtagaagat aaaggccaca   1440
aatacttagt atttgaagca aacactggaa ctgaagatgg ctaccaaggc gaagaatctt   1500
tatttaacaa agcatactat ggcaaaagca catcattctt ccgtcaagaa agtcaaaaac   1560
ttctgcaaag cgataaaaaa cgcacggctg agttagcaaa cggcgctctc ggtatgattg   1620
agctaaacga tgattacaca ctgaaaaaag tgatgaaacc gctgattgca tctaacacag   1680
taacagatga aattgaacgc gcgaacgtct ttaaaatgaa cggcaaatgg tacctgttca   1740
ctgactcccg cggatcaaaa atgacgattg acggcattac gtctaacgat atttacatgc   1800
ttggttatgt ttctaattct ttaactggcc catacaagcc gctgaacaaa actggccttg   1860
tgttaaaaat ggatcttgat cctaacgatg taacctttac ttactcacac ttcgctgtac   1920
ctcaagcgaa aggaaacaat gtcgtgatta caagctatat gacaaacaga ggattctacg   1980
cagacaaaca atcaacgttt gcgccaagct tcctgctgaa catcaaaggc aagaaaacat   2040
ctgttgtcaa agacagcatc cttgaacaag gacaattaac agttaacaaa taaactatga   2100
gttgaaacaa tggcctatct catatgaaga tcttttgtga atttcacttt tgtccacgac   2160
ctctgttgca cgactctgct ttccgaccgg agcatacctt ttgttctata tgatttgtgt   2220
atgtatgtag gaacctatgt tctcgagcat gcatacataa ttcctcatag gtctatatac   2280
accggctatc catatgcaaa acctgtgtaa tatttgttat atacaacacg cggaccattg   2340
```

```
tcttgctgtt attaattctt ttttcccgca aaaaaggaaa agtttcttta tttggcactg   2400

caatggatat gcctcacagc tagtgggtgg agaattcagt atttgacatt aagattccct   2460

gatttgcaat tgcaaatttc agtttcttta cttatatcac tacaaaagtc ttattgtttc   2520

ttttccacgt cattaccatc tgctccattg gtttttgcta gtagaatagg atgaagcatg   2580

gacacagatt aactgagctc gagctcatat gagctcgggt gaacaataaa atctgaaaat   2640

acttagaaag aattcaaaat tttctgtttt ttgtggcaaa atttgacaaa tgttataaat   2700

gcttgcaaag tttcatcata gaacgacatt cgtggatgtc atggcaaaaa acaaattcag   2760

cactctgaaa ataacttttt tgaagtatcg                                    2790
```

<210> SEQ ID NO 35
<211> LENGTH: 4683
<212> TYPE: DNA
<213> ORGANISM: Artificial Sequence
<220> FEATURE:
<223> OTHER INFORMATION: Chimeric sequence

<400> SEQUENCE: 35

```
gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa ataccatgaa agccttcaca ctcgctctct    720

tcttagctct tttcctctat ctcctgccca atccagccca ttccacgaac caaaagccat    780

ataaggaaac atacggcatt tcccatatta cacgccatga tatgctgcaa atccctgaac    840

agcaaaaaaa tgaaaaatat caagttcctg aattcgattc gtccacaatt aaaaatatct    900

cttctgcaaa aggcctggac gtttgggaca gctggccatt acaaaacgct gacggcactg    960

tcgcaaacta tcacggctac cacatcgtct ttgcattagc cggagatcct aaaaatgcgg   1020

atgacacatc gatttacatg ttctatcaaa aagtcggcga aacttctatt gacagctgga   1080

aaaacgctgg ccgcgtcttt aaagacagcg acaaattcga tgcaaatgat tctatcctaa   1140

aagaccaaac acaagaatgg tcaggttcag ccacatttac atctgacgga aaaatccgtt   1200

tattctacac tgatttctcc ggtaaacatt acggcaaaca aacactgaca actgcacaag   1260

ttaacgtatc agcatcagac agctctttga acatcaacgg tgtagaggat tataaatcaa   1320

tctttgacgg tgacggaaaa acgtatcaaa atgtacagca gttcatcgat gaaggcaact   1380

acagctcagg cgacaaccat acgctgagag atcctcacta cgtagaagat aaaggccaca   1440

aatacttagt atttgaagca aacactggaa ctgaagatgg ctaccaaggc gaagaatctt   1500

tatttaacaa agcatactat ggcaaaagca catcattctt ccgtcaagaa agtcaaaaac   1560
```

-continued

```
ttctgcaaag cgataaaaaa cgcacggctg agttagcaaa cggcgctctc ggtatgattg   1620
agctaaacga tgattacaca ctgaaaaaag tgatgaaacc gctgattgca tctaacacag   1680
taacagatga aattgaacgc gcgaacgtct ttaaaatgaa cggcaaatgg tacctgttca   1740
ctgactcccg cggatcaaaa atgacgattg acggcattac gtctaacgat atttacatgc   1800
ttggttatgt ttctaattct ttaactggcc catacaagcc gctgaacaaa actggccttg   1860
tgttaaaaat ggatcttgat cctaacgatg taacctttac ttactcacac ttcgctgtac   1920
ctcaagcgaa aggaaacaat gtcgtgatta caagctatat gacaaacaga ggattctacg   1980
cagacaaaca atcaacgttt gcgccaagct tcctgctgaa catcaaaggc aagaaaacat   2040
ctgttgtcaa agacagcatc cttgaacaag gacaattaac agttaacaaa taaactatga   2100
gttgaaacaa tggcctatct catatgaaga tcttttgtga atttcacttt tgtccacgac   2160
ctctgttgca cgactctgct ttccgaccgg agcatacctt ttgttctata tgatttgtgt   2220
atgtatgtag gaacctatgt tctcgagcat gcatacataa ttcctcatag gtctatatac   2280
accggctatc catatgcaaa acctgtgtaa tatttgttat atacaacacg cggaccattg   2340
tcttgctgtt attaattctt ttttcccgca aaaaaggaaa agtttcttta tttggcactg   2400
caatggatat gcctcacagc tagtgggtgg agaattcagt atttgacatt aagattccct   2460
gatttgcaat tgcaaatttc agtttcttta cttatatcac tacaaaagtc ttattgtttc   2520
ttttccacgt cattaccatc tgctccattg gtttttgcta gtagaatagg atgaagcatg   2580
gacacagatt aactgagctc gagctcatat gagctcgggt gaacaataaa atctgaaaat   2640
acttagaaag aattcaaaat tttctgtttt ttgtggcaaa atttgacaaa tgttataaat   2700
gcttgcaaag tttcatcata gaacgacatt cgtggatgtc atggcaaaaa acaaattcag   2760
cactctgaaa ataacttttt tgaagtatcg gtttgtgtct tctagattaa tcctccaaac   2820
ttttgattaa ccaaaaaaat tatcaaacta acatgttctc ctttttttctt tagaaattct   2880
aacgaattta tctttatact gatttgaata tacttaattt ggtcatttgg atgcccttta   2940
caacctcctt accaaactca ctatggcaaa tatatactat tttccattgt aacataaatg   3000
tccataattt gaattaaatt cgttgcagta cgaaaccatc caactttgtc caaaaacaaa   3060
atccttataa ctatttactt taatgtaaat atatcctcta cttttgtttt tacaacccta   3120
gctcaaacaa atttattatt tgcgataaaa aatcatatcg aacaaactcg atgatttttt   3180
ttttcttacg ttattaatga aactaaaata tagaaaaaaa caagatgaac caaattttca   3240
cctatctaac tacttaaata taatatgatt aaatttggta aagtttgaaa agtttcttta   3300
ggaaatgtga aatattgatc acagtttcta ttgctaaaat caccaacaaa acgcatgtcg   3360
ccattcataa ttatggtttc acacctacaa ctaggctaat aagtaaataa gtagacaact   3420
agactcaggt ttgaaaaaac cataaaagcc atatagcgtt ttctcattga aactgcgaac   3480
acgatcgtgt gaatgttgca gtttctagtt ttgatacaaa caaacaaaaa cacaatttaa   3540
tcttagatta aaaagaaaaa agagaacgga gcccactagc cactccttca aacgtgtctt   3600
accaactctc ttctagaaac aaattaggct tcaccttcct cttccaacct ctctctctct   3660
ctctctctct ctttctcaaa ccatctctcc ataaagccct aatttcttca tcacaagaat   3720
cagaagaata ctgcaaaaaa cttatggacc tgcatctaat tttcggtcca acttgcacag   3780
gaaagacgac gaccgcgata gctcttgccc agcagacagg gcttccagtc ctttcgcttg   3840
atcgggtcca atgctgtcct caactatcaa ccggaagcgg acgaccaaca gtggaagaac   3900
tgaaaggaac gacgcgtctc taccttgatg atcggcctct ggtggagggt atcatcgcag   3960
```

```
ccaagcaagc tcatcatagg ctgatcgagg aggtgtataa tcatgaggcc aacggcgggc   4020

ttattcttga gggaggatcc acctcgttgc tcaactgcat ggcgcgaaac agctattgga   4080

gtgcagattt tcgttggcat attattcgcc acaagttacc cgaccaagag accttcatga   4140

aagcggccaa ggccagagtt aagcagatgt tgcaccccgc tgcaggccat tctattattc   4200

aagagttggt ttatctttgg aatgaacctc ggctgaggcc cattctgaaa gagatcgatg   4260

gatatcgata tgccatgttg tttgctagcc agaaccagat cacggcagat atgctattgc   4320

agcttgacgc aaatatggaa ggtaagttga ttaatgggat cgctcaggag tatttcatcc   4380

atgcgcgcca acaggaacag aaattccccc aagttaacgc agccgctttc gacggattcg   4440

aaggtcatcc gttcggaatg tattaggtaa gtccgcaaaa atcaccagtc tctctctaca   4500

aatctatctc tctctatttt tctccagaat aatgtgtgag tagttcccag ataagggaat   4560

tagggttctt atagggtttc gctcatgtgt tgagcatata agaaaccctt agtatgtatt   4620

tgtatttgta aaatacttct atcaataaaa tttctaattc ctaaaaccaa aatccagtga   4680

cct                                                                 4683
```

<210> SEQ ID NO 36
<211> LENGTH: 3744
<212> TYPE: DNA
<213> ORGANISM: Artificial Sequence
<220> FEATURE:
<223> OTHER INFORMATION: Chimeric sequence

<400> SEQUENCE: 36

```
gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa ataccatgaa agccttcaca ctcgctctct    720

tcttagctct tttcctctat ctcctgccca atccagccca ttccactatt aatgcagaca    780

atgttaatga aaatcaaact gtagaagtaa ctgctagttc agtaaacaat gaaaataata    840

agcaagtaac tgaaaaagat agtgcagata aaagtactag tgatgtggct gaagatgcta    900

acaccaagaa atcaaacgaa aatacagaaa ctacagaaaa gaatactcaa acagttgtta    960

ctaatgcgcc agtaagtgat gtgaaaaata caaacacagt taccgctgaa acacctgttg   1020

ataaagtagt aaataatagt gatcaaaaga caactaatgc tgcaactact gatactaaaa   1080

aagatgatgt aaaacaagtt gaaaagaaag actcagtaga taaaacaaat gctgaggaaa   1140

ataaagatag ttcagtaaag ccagctgaaa atgctactaa ggctgaatta aagggccaag   1200

ttaaagatat cgttgaagaa tctggtgttg atactagcaa gttaactaat gatcaaatta   1260
```

```
atgaattaaa taaaattaat ttctccaaag aagcaaaaag tggtactcag ttaacttaca   1320

acgactttaa aaaaattgct aaaactttaa ttgaacaaga tgctcgttat gctattccat   1380

tcttcaatgc aagtaaaatt aaaaatatgc ctgctgctaa aacacttgat gctcaaagtg   1440

gaaaagtaga agatttggaa atttgggatt catggcctgt tcaagatgca aaaactggtt   1500

acgtatctaa ctggaatggc taccaattag tgattggtat gatgggagtt ccaaacgtca   1560

atgataacca catttatctt ctttacaaca agtatggtga taatgacttt aatcattgga   1620

agaatgccgg tcctattttc ggtctaggta ctccagttat tcaacaatgg tctggatcag   1680

caactttaaa taaagatggc tcaattcaac tttactacac taaggttgat actagtgata   1740

ataatactaa ccaccaaaaa ctcgctagtg caactgttta cttaaatctt gaaaaagatc   1800

aagataagat ttctattgct catgttgaca acgaccatat tgtctttgaa ggtgatggtt   1860

accactacca aacttatgac caatggaaag aaactaacaa gggtgctgac aatatcgcaa   1920

tgcgtgatgc acacgtgatt gatgatgata atggtaatcg ttaccttgtg tttgaagcaa   1980

gtactggaac cgaaaattat caaggtgatg atcaaattta tcaatggtta aattacggcg   2040

gtactaacaa ggataattta ggtgatttct tccaaatttt atctaactcc gatattaaag   2100

atagagctaa atggtcaaac gctgcaattg gtatcattaa attaaatgat gatgttaaga   2160

atccaagtgt tgcaaaggtc tacagcccac ttattagtgc accaatggta agtgatgaaa   2220

ttgaacgccc tgatgttgtt aaattaggta ataagtatta cttatttgct gctactagat   2280

taaaccgtgg tagtaacgat gatgcttgga tggcaactaa caaagcagtt ggtgataacg   2340

tagctatgat tggttatgtt tctgataact taactcatgg ttatgttcca ttgaatgaat   2400

ctggcgttgt tttaactgca tctgtaccgg ctaactggcg tactgcaact tattcatact   2460

atgcagttcc agtagaagga agagatgatc aacttttaat tacttcatac atcactaatc   2520

gtggtgaggt tgctggaaag ggtatgcatg caacttgggc accaagtttc ttgttacaaa   2580

ttaatccaga taacactact actgttttag ctaaaatgac taaccaaggg gattggattt   2640

gggatgatag tagtgaaaat ccagatatga tgggtgtact tgaaaaagat gctccaaata   2700

gtgctgccct tcctggagaa tggggaaaac cagttgattg ggatttaatt ggtggataca   2760

acttgaagcc acaccaacct gtaactccta ttccaaatgt accaactact cctgaaaccc   2820

caaccacacc agataagcca gaggtaccaa ctacccctga agttccaacc actccagaaa   2880

ctccaactcc agaagctcca aagaatccag ttaagaaaac tagtcagtct aaacttccaa   2940

aggctggaga taaaaatagc tttgcagcag ttgttttagg tgctgtaagt tcaatattag   3000

gtgctgttgg tttaacaggt gtttcaaaac gtaaacgtaa taattaaact atgagttgaa   3060

acaatggcct atctcatatg aagatctttt gtgaatttca cttttgtcca cgacctctgt   3120

tgcacgactc tgctttccga ccggagcata ccttttgttc tatatgattt gtgtatgtat   3180

gtaggaacct atgttctcga gcatgcatac ataattcctc ataggtctat atacaccggc   3240

tatccatatg caaaacctgt gtaatatttg ttatatacaa cacgcggacc attgtcttgc   3300

tgttattaat tctttttttcc cgcaaaaaag gaaaagtttc tttatttggc actgcaatgg   3360

atatgcctca cagctagtgg gtggagaatt cagtatttga cattaagatt ccctgatttg   3420

caattgcaaa tttcagtttc tttacttata tcactacaaa agtcttattg tttcttttcc   3480

acgtcattac catctgctcc attggttttt gctagtagaa taggatgaag catggacaca   3540

gattaactga gctcgagctc atatgagctc gggtgaacaa taaaatctga aaatacttag   3600

aaagaattca aaattttctg tttttgtgg caaaatttga caaatgttat aaatgcttgc   3660
```

```
aaagtttcat catagaacga cattcgtgga tgtcatggca aaaaacaaat tcagcactct   3720

gaaaataact tttttgaagt atcg                                          3744


<210> SEQ ID NO 37
<211> LENGTH: 5637
<212> TYPE: DNA
<213> ORGANISM: Artificial Sequence
<220> FEATURE:
<223> OTHER INFORMATION: Chimeric sequence

<400> SEQUENCE: 37

gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa ataccatgaa agccttcaca ctcgctctct    720

tcttagctct tttcctctat ctcctgccca atccagccca ttccactatt aatgcagaca    780

atgttaatga aaatcaaact gtagaagtaa ctgctagttc agtaaacaat gaaaataata    840

agcaagtaac tgaaaaagat agtgcagata aaagtactag tgatgtggct gaagatgcta    900

acaccaagaa atcaaacgaa aatacagaaa ctacagaaaa gaatactcaa acagttgtta    960

ctaatgcgcc agtaagtgat gtgaaaaata caaacacagt taccgctgaa acacctgttg   1020

ataaagtagt aaataatagt gatcaaaaga caactaatgc tgcaactact gatactaaaa   1080

aagatgatgt aaaacaagtt gaaaagaaag actcagtaga taaaacaaat gctgaggaaa   1140

ataaagatag ttcagtaaag ccagctgaaa atgctactaa ggctgaatta aagggccaag   1200

ttaaagatat cgttgaagaa tctggtgttg atactagcaa gttaactaat gatcaaatta   1260

atgaattaaa taaaattaat ttctccaaag aagcaaaaag tggtactcag ttaacttaca   1320

acgactttaa aaaaattgct aaaactttaa ttgaacaaga tgctcgttat gctattccat   1380

tcttcaatgc aagtaaaatt aaaaatatgc ctgctgctaa aacacttgat gctcaaagtg   1440

gaaaagtaga agatttggaa atttgggatt catggcctgt tcaagatgca aaaactggtt   1500

acgtatctaa ctggaatggc taccaattag tgattggtat gatgggagtt ccaaacgtca   1560

atgataacca catttatctt ctttacaaca agtatggtga taatgacttt aatcattgga   1620

agaatgccgg tcctattttc ggtctaggta ctccagttat tcaacaatgg tctggatcag   1680

caactttaaa taaagatggc tcaattcaac tttactacac taaggttgat actagtgata   1740

ataatactaa ccaccaaaaa ctcgctagtg caactgttta cttaaatctt gaaaaagatc   1800

aagataagat ttctattgct catgttgaca acgaccatat tgtctttgaa ggtgatggtt   1860

accactacca aacttatgac caatggaaag aaactaacaa gggtgctgac aatatcgcaa   1920
```

```
tgcgtgatgc acacgtgatt gatgatgata atggtaatcg ttaccttgtg tttgaagcaa   1980

gtactggaac cgaaaattat caaggtgatg atcaaattta tcaatggtta aattacggcg   2040

gtactaacaa ggataattta ggtgatttct tccaaatttt atctaactcc gatattaaag   2100

atagagctaa atggtcaaac gctgcaattg gtatcattaa attaaatgat gatgttaaga   2160

atccaagtgt tgcaaaggtc tacagcccac ttattagtgc accaatggta agtgatgaaa   2220

ttgaacgccc tgatgttgtt aaattaggta ataagtatta cttatttgct gctactagat   2280

taaaccgtgg tagtaacgat gatgcttgga tggcaactaa caaagcagtt ggtgataacg   2340

tagctatgat tggttatgtt tctgataact taactcatgg ttatgttcca ttgaatgaat   2400

ctggcgttgt tttaactgca tctgtaccgg ctaactggcg tactgcaact tattcatact   2460

atgcagttcc agtagaagga agagatgatc aacttttaat tacttcatac atcactaatc   2520

gtggtgaggt tgctggaaag ggtatgcatg caacttgggc accaagtttc ttgttacaaa   2580

ttaatccaga taacactact actgttttag ctaaaatgac taaccaaggg gattggattt   2640

gggatgatag tagtgaaaat ccagatatga tgggtgtact tgaaaaagat gctccaaata   2700

gtgctgccct tcctggagaa tggggaaaac cagttgattg ggatttaatt ggtggataca   2760

acttgaagcc acaccaacct gtaactccta ttccaaatgt accaactact cctgaaaccc   2820

caaccacacc agataagcca gaggtaccaa ctacccctga agttccaacc actccagaaa   2880

ctccaactcc agaagctcca aagaatccag ttaagaaaac tagtcagtct aaacttccaa   2940

aggctggaga taaaaatagc tttgcagcag ttgttttagg tgctgtaagt tcaatattag   3000

gtgctgttgg tttaacaggt gtttcaaaac gtaaacgtaa taattaaact atgagttgaa   3060

acaatggcct atctcatatg aagatctttt gtgaatttca cttttgtcca cgacctctgt   3120

tgcacgactc tgctttccga ccggagcata ccttttgttc tatatgattt gtgtatgtat   3180

gtaggaacct atgttctcga gcatgcatac ataattcctc ataggtctat atacaccggc   3240

tatccatatg caaaacctgt gtaatatttg ttatatacaa cacgcggacc attgtcttgc   3300

tgttattaat tcttttttcc cgcaaaaaag gaaaagtttc tttatttggc actgcaatgg   3360

atatgcctca cagctagtgg gtggagaatt cagtatttga cattaagatt ccctgatttg   3420

caattgcaaa tttcagtttc tttacttata tcactacaaa agtcttattg tttcttttcc   3480

acgtcattac catctgctcc attggttttt gctagtagaa taggatgaag catggacaca   3540

gattaactga gctcgagctc atatgagctc gggtgaacaa taaaatctga aaatacttag   3600

aaagaattca aaattttctg tttttgtgg caaaatttga caaatgttat aaatgcttgc   3660

aaagtttcat catagaacga cattcgtgga tgtcatggca aaaaacaaat tcagcactct   3720

gaaaataact tttttgaagt atcggtttgt gtcttctaga ttaatcctcc aaacttttga   3780

ttaaccaaaa aaattatcaa actaacatgt tctccttttt tctttagaaa ttctaacgaa   3840

tttatcttta tactgatttg aatatactta atttggtcat ttggatgccc tttacaacct   3900

ccttaccaaa ctcactatgg caaatatata ctattttcca ttgtaacata aatgtccata   3960

atttgaatta aattcgttgc agtacgaaac catccaactt tgtccaaaaa caaaatcctt   4020

ataactattt actttaatgt aaatatatcc tctacttttg tttttacaac cctagctcaa   4080

acaaatttat tatttgcgat aaaaaatcat atcgaacaaa ctcgatgatt ttttttttct   4140

tacgttatta atgaaactaa aatatagaaa aaaacaagat gaaccaaatt ttcacctatc   4200

taactactta aatataatat gattaaattt ggtaaagttt gaaaagtttc tttaggaaat   4260

gtgaaatatt gatcacagtt tctattgcta aaatcaccaa caaaacgcat gtcgccattc   4320
```

```
ataattatgg tttcacacct acaactaggc taataagtaa ataagtagac aactagactc   4380

aggtttgaaa aaaccataaa agccatatag cgttttctca ttgaaactgc gaacacgatc   4440

gtgtgaatgt tgcagtttct agttttgata caaacaaaca aaaacacaat ttaatcttag   4500

attaaaaaga aaaaagagaa cggagcccac tagccactcc ttcaaacgtg tcttaccaac   4560

tctcttctag aaacaaatta ggcttcacct tcctcttcca acctctctct ctctctctct   4620

ctctctttct caaaccatct ctccataaag ccctaatttc ttcatcacaa gaatcagaag   4680

aatactgcaa aaaacttatg gacctgcatc taattttcgg tccaacttgc acaggaaaga   4740

cgacgaccgc gatagctctt gcccagcaga cagggcttcc agtcctttcg cttgatcggg   4800

tccaatgctg tcctcaacta tcaaccggaa gcggacgacc aacagtggaa gaactgaaag   4860

gaacgacgcg tctctacctt gatgatcggc ctctggtgga gggtatcatc gcagccaagc   4920

aagctcatca taggctgatc gaggaggtgt ataatcatga ggccaacggc gggcttattc   4980

ttgagggagg atccacctcg ttgctcaact gcatggcgcg aaacagctat tggagtgcag   5040

attttcgttg gcatattatt cgccacaagt tacccgacca agagaccttc atgaaagcgg   5100

ccaaggccag agttaagcag atgttgcacc ccgctgcagg ccattctatt attcaagagt   5160

tggtttatct ttggaatgaa cctcggctga ggcccattct gaaagagatc gatggatatc   5220

gatatgccat gttgtttgct agccagaacc agatcacggc agatatgcta ttgcagcttg   5280

acgcaaatat ggaaggtaag ttgattaatg ggatcgctca ggagtatttc atccatgcgc   5340

gccaacagga acagaaattc cccaagttta acgcagccgc tttcgacgga ttcgaaggtc   5400

atccgttcgg aatgtattag gtaagtccgc aaaaatcacc agtctctctc tacaaatcta   5460

tctctctcta tttttctcca gaataatgtg tgagtagttc ccagataagg gaattagggt   5520

tcttataggg tttcgctcat gtgttgagca tataagaaac ccttagtatg tatttgtatt   5580

tgtaaaatac ttctatcaat aaaatttcta attcctaaaa ccaaaatcca gtgacct      5637
```

<210> SEQ ID NO 38
<211> LENGTH: 2937
<212> TYPE: DNA
<213> ORGANISM: Artificial Sequence
<220> FEATURE:
<223> OTHER INFORMATION: Chimeric sequence

<400> SEQUENCE: 38

```
gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa ataccatgga gtccccaagc gccgtcgtcc    720
```

```
ccggcaccac ggcgccgctg cttccttatg cgtacgcgcc gctgccgtcg tccgccgacg    780

acgcccgtca aaaccggagt ggcgggaggt ggcgcgcgtg cgccgccgtg ctggccgcat    840

cggcgttggc ggtggtcgtc gtggtcgggc tcctcgcggg cggcagggtg gatcgggtcc    900

cggccggcgg aacgaaccaa aagccatata aggaaacata cggcatttcc catattacac    960

gccatgatat gctgcaaatc cctgaacagc aaaaaaatga aaaatatcaa gttcctgaat   1020

tcgattcgtc cacaattaaa aatatctctt ctgcaaaagg cctggacgtt tgggacagct   1080

ggccattaca aaacgctgac ggcactgtcg caaactatca cggctaccac atcgtctttg   1140

cattagccgg agatcctaaa aatgcggatg acacatcgat ttacatgttc tatcaaaaag   1200

tcggcgaaac ttctattgac agctggaaaa acgctggccg cgtctttaaa gacagcgaca   1260

aattcgatgc aaatgattct atcctaaaag accaaacaca agaatggtca ggttcagcca   1320

catttacatc tgacggaaaa atccgtttat tctacactga tttctccggt aaacattacg   1380

gcaaacaaac actgacaact gcacaagtta acgtatcagc atcagacagc tctttgaaca   1440

tcaacggtgt agaggattat aaatcaatct ttgacggtga cggaaaaacg tatcaaaatg   1500

tacagcagtt catcgatgaa ggcaactaca gctcaggcga caaccatacg ctgagagatc   1560

ctcactacgt agaagataaa ggccacaaat acttagtatt tgaagcaaac actggaactg   1620

aagatggcta ccaaggcgaa gaatctttat ttaacaaagc atactatggc aaaagcacat   1680

cattcttccg tcaagaaagt caaaaacttc tgcaaagcga taaaaaacgc acggctgagt   1740

tagcaaacgg cgctctcggt atgattgagc taaacgatga ttacacactg aaaaaagtga   1800

tgaaaccgct gattgcatct aacacagtaa cagatgaaat tgaacgcgcg aacgtcttta   1860

aaatgaacgg caaatggtac ctgttcactg actcccgcgg atcaaaaatg acgattgacg   1920

gcattacgtc taacgatatt tacatgcttg gttatgtttc taattcttta actggcccat   1980

acaagccgct gaacaaaact ggccttgtgt taaaaatgga tcttgatcct aacgatgtaa   2040

cctttactta ctcacacttc gctgtacctc aagcgaaagg aaacaatgtc gtgattacaa   2100

gctatatgac aaacagagga ttctacgcag acaaacaatc aacgtttgcg ccaagcttcc   2160

tgctgaacat caaaggcaag aaaacatctg ttgtcaaaga cagcatcctt gaacaaggac   2220

aattaacagt taacaaataa actatgagtt gaaacaatgg cctatctcat atgaagatct   2280

tttgtgaatt tcacttttgt ccacgacctc tgttgcacga ctctgctttc cgaccggagc   2340

ataccttttg ttctatatga tttgtgtatg tatgtaggaa cctatgttct cgagcatgca   2400

tacataattc ctcataggtc tatatacacc ggctatccat atgcaaaacc tgtgtaatat   2460

ttgttatata caacacgcgg accattgtct tgctgttatt aattcttttt tcccgcaaaa   2520

aaggaaaagt ttctttattt ggcactgcaa tggatatgcc tcacagctag tgggtggaga   2580

attcagtatt tgacattaag attccctgat ttgcaattgc aaatttcagt ttctttactt   2640

atatcactac aaaagtctta ttgtttcttt tccacgtcat taccatctgc tccattggtt   2700

tttgctagta gaataggatg aagcatggac acagattaac tgagctcgag ctcatatgag   2760

ctcgggtgaa caataaaatc tgaaaatact tagaaagaat tcaaaatttt ctgtttttttg   2820

tggcaaaatt tgacaaatgt tataaatgct tgcaaagttt catcatagaa cgacattcgt   2880

ggatgtcatg gcaaaaaaca aattcagcac tctgaaaata actttttttga agtatcg      2937
```

<210> SEQ ID NO 39
<211> LENGTH: 4830
<212> TYPE: DNA
<213> ORGANISM: Artificial Sequence
<220> FEATURE:
<223> OTHER INFORMATION: Chimeric sequence

<400> SEQUENCE: 39

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaaccggagt ggcgggaggt ggcgcgcgtg cgccgccgtg ctggccgcat    840
cggcgttggc ggtggtcgtc gtggtcgggc tcctcgcggg cggcagggtg gatcgggtcc    900
cggccggcgg aacgaaccaa aagccatata aggaaacata cggcatttcc catattacac    960
gccatgatat gctgcaaatc cctgaacagc aaaaaaatga aaaatatcaa gttcctgaat   1020
tcgattcgtc cacaattaaa aatatctctt ctgcaaaagg cctggacgtt tgggacagct   1080
ggccattaca aaacgctgac ggcactgtcg caaactatca cggctaccac atcgtctttg   1140
cattagccgg agatcctaaa aatgcggatg acacatcgat ttacatgttc tatcaaaaag   1200
tcggcgaaac ttctattgac agctggaaaa acgctggccg cgtctttaaa gacagcgaca   1260
aattcgatgc aaatgattct atcctaaaag accaaacaca agaatggtca ggttcagcca   1320
catttacatc tgacggaaaa atccgtttat tctacactga tttctccggt aaacattacg   1380
gcaaacaaac actgacaact gcacaagtta acgtatcagc atcagacagc tctttgaaca   1440
tcaacggtgt agaggattat aaatcaatct ttgacggtga cggaaaaacg tatcaaaatg   1500
tacagcagtt catcgatgaa ggcaactaca gctcaggcga caaccatacg ctgagagatc   1560
ctcactacgt agaagataaa ggccacaaat acttagtatt tgaagcaaac actggaactg   1620
aagatggcta ccaaggcgaa gaatctttat ttaacaaagc atactatggc aaaagcacat   1680
cattcttccg tcaagaaagt caaaaacttc tgcaaagcga taaaaaacgc acggctgagt   1740
tagcaaacgg cgctctcggt atgattgagc taaacgatga ttacacactg aaaaaagtga   1800
tgaaaccgct gattgcatct aacacagtaa cagatgaaat tgaacgcgcg aacgtcttta   1860
aaatgaacgg caaatggtac ctgttcactg actcccgcgg atcaaaaatg acgattgacg   1920
gcattacgtc taacgatatt tacatgcttg gttatgtttc taattcttta actggcccat   1980
acaagccgct gaacaaaact ggccttgtgt taaaaatgga tcttgatcct aacgatgtaa   2040
cctttactta ctcacacttc gctgtacctc aagcgaaagg aaacaatgtc gtgattacaa   2100
gctatatgac aaacagagga ttctacgcag acaaacaatc aacgtttgcg ccaagcttcc   2160
tgctgaacat caaaggcaag aaaacatctg ttgtcaaaga cagcatcctt gaacaaggac   2220
```

-continued

```
aattaacagt taacaaataa actatgagtt gaaacaatgg cctatctcat atgaagatct   2280

tttgtgaatt tcacttttgt ccacgacctc tgttgcacga ctctgctttc cgaccggagc   2340

ataccttttg ttctatatga tttgtgtatg tatgtaggaa cctatgttct cgagcatgca   2400

tacataattc ctcataggtc tatatacacc ggctatccat atgcaaaacc tgtgtaatat   2460

ttgttatata caacacgcgg accattgtct tgctgttatt aattcttttt tcccgcaaaa   2520

aaggaaaagt ttctttattt ggcactgcaa tggatatgcc tcacagctag tgggtggaga   2580

attcagtatt tgacattaag attccctgat ttgcaattgc aaatttcagt ttctttactt   2640

atatcactac aaaagtctta ttgtttcttt tccacgtcat taccatctgc tccattggtt   2700

tttgctagta gaataggatg aagcatggac acagattaac tgagctcgag ctcatatgag   2760

ctcgggtgaa caataaaatc tgaaaatact tagaaagaat tcaaaatttt ctgttttttg   2820

tggcaaaatt tgacaaatgt tataaatgct tgcaaagttt catcatagaa cgacattcgt   2880

ggatgtcatg gcaaaaaaca aattcagcac tctgaaaata actttttga agtatcggtt    2940

tgtgtcttct agattaatcc tccaaacttt tgattaacca aaaaaattat caaactaaca   3000

tgttctcctt ttttctttag aaattctaac gaatttatct ttatactgat ttgaatatac   3060

ttaatttggt catttggatg ccctttacaa cctccttacc aaactcacta tggcaaatat   3120

atactatttt ccattgtaac ataaatgtcc ataatttgaa ttaaattcgt tgcagtacga   3180

aaccatccaa ctttgtccaa aaacaaaatc cttataacta tttactttaa tgtaaatata   3240

tcctctactt ttgtttttac aaccctagct caaacaaatt tattatttgc gataaaaaat   3300

catatcgaac aaactcgatg attttttttt tcttacgtta ttaatgaaac taaaatatag   3360

aaaaaaacaa gatgaaccaa attttcacct atctaactac ttaaatataa tatgattaaa   3420

tttggtaaag tttgaaaagt ttctttagga aatgtgaaat attgatcaca gtttctattg   3480

ctaaaatcac caacaaaacg catgtcgcca ttcataatta tggtttcaca cctacaacta   3540

ggctaataag taaataagta gacaactaga ctcaggtttg aaaaaaccat aaaagccata   3600

tagcgttttc tcattgaaac tgcgaacacg atcgtgtgaa tgttgcagtt tctagttttg   3660

atacaaacaa acaaaaacac aatttaatct tagattaaaa agaaaaaaga gaacggagcc   3720

cactagccac tccttcaaac gtgtcttacc aactctcttc tagaaacaaa ttaggcttca   3780

ccttcctctt ccaacctctc tctctctctc tctctctctt tctcaaacca tctctccata   3840

aagccctaat ttcttcatca caagaatcag aagaatactg caaaaaactt atggacctgc   3900

atctaatttt cggtccaact tgcacaggaa agacgacgac cgcgatagct cttgcccagc   3960

agacagggct tccagtcctt tcgcttgatc gggtccaatg ctgtcctcaa ctatcaaccg   4020

gaagcggacg accaacagtg gaagaactga aaggaacgac gcgtctctac cttgatgatc   4080

ggcctctggt ggagggtatc atcgcagcca agcaagctca tcataggctg atcgaggagg   4140

tgtataatca tgaggccaac ggcgggctta ttcttgaggg aggatccacc tcgttgctca   4200

actgcatggc gcgaaacagc tattggagtg cagattttcg ttggcatatt attcgccaca   4260

agttacccga ccaagagacc ttcatgaaag cggccaaggc cagagttaag cagatgttgc   4320

accccgctgc aggccattct attattcaag agttggttta tctttggaat gaacctcggc   4380

tgaggcccat tctgaaagag atcgatggat atcgatatgc catgttgttt gctagccaga   4440

accagatcac ggcagatatg ctattgcagc ttgacgcaaa tatggaaggt aagttgatta   4500

atgggatcgc tcaggagtat ttcatccatg cgcgccaaca ggaacagaaa ttcccccaag   4560

ttaacgcagc cgctttcgac ggattcgaag gtcatccgtt cggaatgtat taggtaagtc   4620
```

```
cgcaaaaatc accagtctct ctctacaaat ctatctctct ctatttttct ccagaataat   4680
gtgtgagtag ttcccagata agggaattag ggttcttata gggtttcgct catgtgttga   4740
gcatataaga aacccttagt atgtatttgt atttgtaaaa tacttctatc aataaaattt   4800
ctaattccta aaaccaaaat ccagtgacct                                    4830
```

<210> SEQ ID NO 40
<211> LENGTH: 3891
<212> TYPE: DNA
<213> ORGANISM: Artificial Sequence
<220> FEATURE:
<223> OTHER INFORMATION: Chimeric sequence

<400> SEQUENCE: 40

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaaccggagt ggcgggaggt ggcgcgcgtg cgccgccgtg ctggccgcat    840
cggcgttggc ggtggtcgtc gtggtcgggc tcctcgcggg cggcagggtg gatcgggtcc    900
cggccggcgg aactattaat gcagacaatg ttaatgaaaa tcaaactgta gaagtaactg    960
ctagttcagt aaacaatgaa aataataagc aagtaactga aaaagatagt gcagataaaa   1020
gtactagtga tgtggctgaa gatgctaaca ccaagaaatc aaacgaaaat acagaaacta   1080
cagaaaagaa tactcaaaca gttgttacta atgcgccagt aagtgatgtg aaaaatacaa   1140
acacagttac cgctgaaaca cctgttgata aagtagtaaa taatagtgat caaaagacaa   1200
ctaatgctgc aactactgat actaaaaaag atgatgtaaa acaagttgaa aagaaagact   1260
cagtagataa aacaaatgct gaggaaaata aagatagttc agtaaagcca gctgaaaatg   1320
ctactaaggc tgaattaaag ggccaagtta aagatatcgt tgaagaatct ggtgttgata   1380
ctagcaagtt aactaatgat caaattaatg aattaaataa aattaatttc tccaaagaag   1440
caaaaagtgg tactcagtta acttacaacg actttaaaaa aattgctaaa actttaattg   1500
aacaagatgc tcgttatgct attccattct tcaatgcaag taaaattaaa aatatgcctg   1560
ctgctaaaac acttgatgct caaagtggaa aagtagaaga tttggaaatt tgggattcat   1620
ggcctgttca agatgcaaaa actggttacg tatctaactg gaatggctac caattagtga   1680
ttggtatgat gggagttcca aacgtcaatg ataaccacat ttatcttctt tacaacaagt   1740
atggtgataa tgactttaat cattggaaga atgccggtcc tattttcggt ctaggtactc   1800
```

```
cagttattca acaatggtct ggatcagcaa ctttaaataa agatggctca attcaacttt   1860

actacactaa ggttgatact agtgataata atactaacca ccaaaaactc gctagtgcaa   1920

ctgtttactt aaatcttgaa aaagatcaag ataagatttc tattgctcat gttgacaacg   1980

accatattgt ctttgaaggt gatggttacc actaccaaac ttatgaccaa tggaaagaaa   2040

ctaacaaggg tgctgacaat atcgcaatgc gtgatgcaca cgtgattgat gatgataatg   2100

gtaatcgtta ccttgtgttt gaagcaagta ctggaaccga aaattatcaa ggtgatgatc   2160

aaatttatca atggttaaat tacggcggta ctaacaagga taatttaggt gatttcttcc   2220

aaattttatc taactccgat attaaagata gagctaaatg gtcaaacgct gcaattggta   2280

tcattaaatt aaatgatgat gttaagaatc caagtgttgc aaaggtctac agcccactta   2340

ttagtgcacc aatggtaagt gatgaaattg aacgccctga tgttgttaaa ttaggtaata   2400

agtattactt atttgctgct actagattaa accgtggtag taacgatgat gcttggatgg   2460

caactaacaa agcagttggt gataacgtag ctatgattgg ttatgtttct gataacttaa   2520

ctcatggtta tgttccattg aatgaatctg gcgttgtttt aactgcatct gtaccggcta   2580

actggcgtac tgcaacttat tcatactatg cagttccagt agaaggaaga gatgatcaac   2640

ttttaattac ttcatacatc actaatcgtg gtgaggttgc tggaaagggt atgcatgcaa   2700

cttgggcacc aagtttcttg ttacaaatta atccagataa cactactact gttttagcta   2760

aaatgactaa ccaaggggat tggatttggg atgatagtag tgaaaatcca gatatgatgg   2820

gtgtacttga aaaagatgct ccaaatagtg ctgcccttcc tggagaatgg ggaaaaccag   2880

ttgattggga tttaattggt ggatacaact tgaagccaca ccaacctgta actcctattc   2940

caaatgtacc aactactcct gaaaccccaa ccacaccaga taagccagag gtaccaacta   3000

cccctgaagt tccaaccact ccagaaactc caactccaga agctccaaag aatccagtta   3060

agaaaactag tcagtctaaa cttccaaagg ctggagataa aaatagcttt gcagcagttg   3120

ttttaggtgc tgtaagttca atattaggtg ctgttggttt aacaggtgtt tcaaaacgta   3180

aacgtaataa ttaaactatg agttgaaaca atggcctatc tcatatgaag atcttttgtg   3240

aatttcactt ttgtccacga cctctgttgc acgactctgc tttccgaccg gagcatacct   3300

tttgttctat atgatttgtg tatgtatgta ggaacctatg ttctcgagca tgcatacata   3360

attcctcata ggtctatata caccggctat ccatatgcaa aacctgtgta atatttgtta   3420

tatacaacac gcggaccatt gtcttgctgt tattaattct tttttcccgc aaaaaaggaa   3480

aagtttcttt atttggcact gcaatggata tgcctcacag ctagtgggtg gagaattcag   3540

tatttgacat taagattccc tgatttgcaa ttgcaaattt cagtttcttt acttatatca   3600

ctacaaaagt cttattgttt cttttccacg tcattaccat ctgctccatt ggtttttgct   3660

agtagaatag gatgaagcat ggacacagat taactgagct cgagctcata tgagctcggg   3720

tgaacaataa aatctgaaaa tacttagaaa gaattcaaaa ttttctgttt tttgtggcaa   3780

aatttgacaa atgttataaa tgcttgcaaa gtttcatcat agaacgacat tcgtggatgt   3840

catggcaaaa aacaaattca gcactctgaa aataactttt ttgaagtatc g            3891
```

<210> SEQ ID NO 41
<211> LENGTH: 5784
<212> TYPE: DNA
<213> ORGANISM: Artificial Sequence
<220> FEATURE:
<223> OTHER INFORMATION: Chimeric sequence

<400> SEQUENCE: 41

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaaccggagt ggcgggaggt ggcgcgcgtg cgccgccgtg ctggccgcat    840
cggcgttggc ggtggtcgtc gtggtcgggc tcctcgcggg cggcagggtg gatcgggtcc    900
cggccggcgg aactattaat gcagacaatg ttaatgaaaa tcaaactgta gaagtaactg    960
ctagttcagt aaacaatgaa aataataagc aagtaactga aaaagatagt gcagataaaa   1020
gtactagtga tgtggctgaa gatgctaaca ccaagaaatc aaacgaaaat acagaaacta   1080
cagaaaagaa tactcaaaca gttgttacta atgcgccagt aagtgatgtg aaaaatacaa   1140
acacagttac cgctgaaaca cctgttgata aagtagtaaa taatagtgat caaaagacaa   1200
ctaatgctgc aactactgat actaaaaaag atgatgtaaa acaagttgaa aagaaagact   1260
cagtagataa aacaaatgct gaggaaaata aagatagttc agtaaagcca gctgaaaatg   1320
ctactaaggc tgaattaaag ggccaagtta aagatatcgt tgaagaatct ggtgttgata   1380
ctagcaagtt aactaatgat caaattaatg aattaaataa aattaatttc tccaaagaag   1440
caaaaagtgg tactcagtta acttacaacg actttaaaaa aattgctaaa actttaattg   1500
aacaagatgc tcgttatgct attccattct tcaatgcaag taaaattaaa aatatgcctg   1560
ctgctaaaac acttgatgct caaagtggaa aagtagaaga tttggaaatt tgggattcat   1620
ggcctgttca agatgcaaaa actggttacg tatctaactg gaatggctac caattagtga   1680
ttggtatgat gggagttcca aacgtcaatg ataaccacat ttatcttctt tacaacaagt   1740
atggtgataa tgactttaat cattggaaga atgccggtcc tattttcggt ctaggtactc   1800
cagttattca acaatggtct ggatcagcaa ctttaaataa agatggctca attcaacttt   1860
actacactaa ggttgatact agtgataata atactaacca ccaaaaactc gctagtgcaa   1920
ctgtttactt aaatcttgaa aaagatcaag ataagatttc tattgctcat gttgacaacg   1980
accatattgt ctttgaaggt gatggttacc actaccaaac ttatgaccaa tggaaagaaa   2040
ctaacaaggg tgctgacaat atcgcaatgc gtgatgcaca cgtgattgat gatgataatg   2100
gtaatcgtta ccttgtgttt gaagcaagta ctggaaccga aaattatcaa ggtgatgatc   2160
aaatttatca atggttaaat tacggcggta ctaacaagga taatttaggt gatttcttcc   2220
aaattttatc taactccgat attaaagata gagctaaatg gtcaaacgct gcaattggta   2280
tcattaaatt aaatgatgat gttaagaatc caagtgttgc aaaggtctac agcccactta   2340
```

```
ttagtgcacc aatggtaagt gatgaaattg aacgccctga tgttgttaaa ttaggtaata   2400
agtattactt atttgctgct actagattaa accgtggtag taacgatgat gcttggatgg   2460
caactaacaa agcagttggt gataacgtag ctatgattgg ttatgtttct gataacttaa   2520
ctcatggtta tgttccattg aatgaatctg gcgttgtttt aactgcatct gtaccggcta   2580
actggcgtac tgcaacttat tcatactatg cagttccagt agaaggaaga gatgatcaac   2640
ttttaattac ttcatacatc actaatcgtg gtgaggttgc tggaaagggt atgcatgcaa   2700
cttgggcacc aagtttcttg ttacaaatta atccagataa cactactact gttttagcta   2760
aaatgactaa ccaaggggat tggatttggg atgatagtag tgaaaatcca gatatgatgg   2820
gtgtacttga aaaagatgct ccaaatagtg ctgcccttcc tggagaatgg ggaaaaccag   2880
ttgattggga tttaattggt ggatacaact tgaagccaca ccaacctgta actcctattc   2940
caaatgtacc aactactcct gaaaccccaa ccacaccaga taagccagag gtaccaacta   3000
cccctgaagt tccaaccact ccagaaactc caactccaga agctccaaag aatccagtta   3060
agaaaactag tcagtctaaa cttccaaagg ctggagataa aaatagcttt gcagcagttg   3120
ttttaggtgc tgtaagttca atattaggtg ctgttggttt aacaggtgtt tcaaaacgta   3180
aacgtaataa ttaaactatg agttgaaaca atggcctatc tcatatgaag atcttttgtg   3240
aatttcactt ttgtccacga cctctgttgc acgactctgc tttccgaccg gagcatacct   3300
tttgttctat atgatttgtg tatgtatgta ggaacctatg ttctcgagca tgcatacata   3360
attcctcata ggtctatata caccggctat ccatatgcaa aacctgtgta atatttgtta   3420
tatacaacac gcggaccatt gtcttgctgt tattaattct tttttcccgc aaaaaaggaa   3480
aagtttcttt atttggcact gcaatggata tgcctcacag ctagtgggtg gagaattcag   3540
tatttgacat taagattccc tgatttgcaa ttgcaaattt cagtttcttt acttatatca   3600
ctacaaaagt cttattgttt cttttccacg tcattaccat ctgctccatt ggtttttgct   3660
agtagaatag gatgaagcat ggacacagat taactgagct cgagctcata tgagctcggg   3720
tgaacaataa aatctgaaaa tacttagaaa gaattcaaaa ttttctgttt tttgtggcaa   3780
aatttgacaa atgttataaa tgcttgcaaa gtttcatcat agaacgacat tcgtggatgt   3840
catggcaaaa aacaaattca gcactctgaa aataactttt ttgaagtatc ggtttgtgtc   3900
ttctagatta atcctccaaa cttttgatta accaaaaaaa ttatcaaact aacatgttct   3960
cctttttttct ttagaaattc taacgaattt atctttatac tgatttgaat atacttaatt   4020
tggtcatttg gatgcccttt acaacctcct taccaaactc actatggcaa atatatacta   4080
ttttccattg taacataaat gtccataatt tgaattaaat tcgttgcagt acgaaaccat   4140
ccaactttgt ccaaaaacaa aatccttata actatttact ttaatgtaaa tatatcctct   4200
acttttgttt ttacaaccct agctcaaaca aatttattat ttgcgataaa aaatcatatc   4260
gaacaaactc gatgattttt tttttcttac gttattaatg aaactaaaat atagaaaaaa   4320
acaagatgaa ccaaattttc acctatctaa ctacttaaat ataatatgat taaatttggt   4380
aaagtttgaa aagtttcttt aggaaatgtg aaatattgat cacagtttct attgctaaaa   4440
tcaccaacaa aacgcatgtc gccattcata attatggttt cacacctaca actaggctaa   4500
taagtaaata agtagacaac tagactcagg tttgaaaaaa ccataaaagc catatagcgt   4560
tttctcattg aaactgcgaa cacgatcgtg tgaatgttgc agtttctagt tttgatacaa   4620
acaaacaaaa acacaattta atcttagatt aaaaagaaaa aagagaacgg agcccactag   4680
ccactccttc aaacgtgtct taccaactct cttctagaaa caaattaggc ttcaccttcc   4740
```

```
tcttccaacc tctctctctc tctctctctc tctttctcaa accatctctc cataaagccc   4800
taatttcttc atcacaagaa tcagaagaat actgcaaaaa acttatggac ctgcatctaa   4860
ttttcggtcc aacttgcaca ggaaagacga cgaccgcgat agctcttgcc cagcagacag   4920
ggcttccagt cctttcgctt gatcgggtcc aatgctgtcc tcaactatca accggaagcg   4980
gacgaccaac agtggaagaa ctgaaaggaa cgacgcgtct ctaccttgat gatcggcctc   5040
tggtggaggg tatcatcgca gccaagcaag ctcatcatag gctgatcgag gaggtgtata   5100
atcatgaggc caacggcggg cttattcttg agggaggatc cacctcgttg ctcaactgca   5160
tggcgcgaaa cagctattgg agtgcagatt ttcgttggca tattattcgc cacaagttac   5220
ccgaccaaga gaccttcatg aaagcggcca aggccagagt taagcagatg ttgcaccccg   5280
ctgcaggcca ttctattatt caagagttgg tttatctttg gaatgaacct cggctgaggc   5340
ccattctgaa agagatcgat ggatatcgat atgccatgtt gtttgctagc cagaaccaga   5400
tcacggcaga tatgctattg cagcttgacg caaatatgga aggtaagttg attaatggga   5460
tcgctcagga gtatttcatc catgcgcgcc aacaggaaca gaaattcccc caagttaacg   5520
cagccgcttt cgacggattc gaaggtcatc cgttcggaat gtattaggta agtccgcaaa   5580
aatcaccagt ctctctctac aaatctatct ctctctattt ttctccagaa taatgtgtga   5640
gtagttccca gataagggaa ttagggttct tatagggttt cgctcatgtg ttgagcatat   5700
aagaaaccct tagtatgtat ttgtatttgt aaaatacttc tatcaataaa atttctaatt   5760
cctaaaacca aaatccagtg acct                                          5784
```

<210> SEQ ID NO 42
<211> LENGTH: 1702
<212> TYPE: DNA
<213> ORGANISM: Arabidopsis thaliana

<400> SEQUENCE: 42

```
cgtggtcgag attgtgtatt attctttagt tattacaaga cttttagcta aaatttgaaa     60
gaatttactt taagaaaatc ttaacatctg agataatttc agcaatagat tatatttttc    120
attactctag cagtattttt gcagatcaat cgcaacatat atggttgtta gaaaaaatgc    180
actatatata tatatattat tttttcaatt aaaagtgcat gatatataat atatatatat    240
atatatatat gtgtgtgtgt atatggtcaa agaaattctt atacaaatat acacgaacac    300
atatatttga caaaatcaaa gtattacact aaacaatgag ttggtgcatg gccaaaacaa    360
atatgtagat taaaaattcc agcctccaaa aaaaaatcca agtgttgtaa agcattatat    420
atatatagta gatcccaaat ttttgtacaa ttccacactg atcgaatttt taaagttgaa    480
tatctgacgt aggatttttt taatgtctta cctgaccatt tactaataac attcatacgt    540
tttcatttga aatatcctct ataattatat tgaatttggc acataataag aaacctaatt    600
ggtgatttat tttactagta aatttctggt gatgggcttt ctactagaaa gctctcggaa    660
aatcttggac caaatccata ttccatgact tcgattgtta accctattag ttttcacaaa    720
catactatca atatcattgc aacggaaaag gtacaagtaa aacattcaat ccgataggga    780
agtgatgtag gaggttggga agacaggccc agaaagagat ttatctgact tgttttgtgt    840
atagttttca atgttcataa aggaagatgg agacttgaga agtttttttt ggactttgtt    900
tagctttgtt gggcgttttt tttttttgat caataacttt gttgggctta tgatttgtaa    960
tattttcgtg gactctttag tttatttaga cgtgctaact ttgttgggct tatgacttgt   1020
```

```
tgtaacatat tgtaacagat gacttgatgt gcgactaatc tttacacatt aaacatagtt   1080

ctgtttttg aaagttctta ttttcatttt tatttgaatg ttatatattt ttctatattt   1140

ataattctag taaaaggcaa attttgcttt taaatgaaaa aaatatatat tccacagttt   1200

cacctaatct tatgcattta gcagtacaaa ttcaaaaatt tcccattttt attcatgaat   1260

cataccatta tatattaact aaatccaagg taaaaaaaag gtatgaaagc tctatagtaa   1320

gtaaaatata aattccccat aaggaaaggg ccaagtccac caggcaagta aaatgagcaa   1380

gcaccactcc accatcacac aatttcactc atagataacg ataagattca tggaattatc   1440

ttccacgtgg cattattcca gcggttcaag ccgataaggg tctcaacacc tctccttagg   1500

cctttgtggc cgttaccaag taaaattaac ctcacacata tccacactca aaatccaacg   1560

gtgtagatcc tagtccactt gaatctcatg tatcctagac cctccgatca ctccaaagct   1620

tgttctcatt gttgttatca ttatatatag atgaccaaag cactagacca aacctcagtc   1680

acacaaagag taaagaagaa ca                                              1702
```

<210> SEQ ID NO 43
<211> LENGTH: 695
<212> TYPE: DNA
<213> ORGANISM: Triticum aestivum

<400> SEQUENCE: 43

```
gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa atacc                                695
```

<210> SEQ ID NO 44
<211> LENGTH: 941
<212> TYPE: DNA
<213> ORGANISM: Arabidopsis thaliana

<400> SEQUENCE: 44

```
gtttgtgtct tctagattaa tcctccaaac ttttgattaa ccaaaaaaat tatcaaacta     60

acatgttctc cttttttctt tagaaattct aacgaattta tctttatact gatttgaata    120

tacttaattt ggtcatttgg atgcccttta caacctcctt accaaactca ctatggcaaa    180

tatatactat tttccattgt aacataaatg tccataattt gaattaaatt cgttgcagta    240

cgaaaccatc caactttgtc caaaaacaaa atccttataa ctatttactt taatgtaaat    300

atatcctcta cttttgtttt tacaacccta gctcaaacaa atttattatt tgcgataaaa    360

aatcatatcg aacaaactcg atgatttttt ttttcttacg ttattaatga aactaaaata    420

tagaaaaaaa caagatgaac caaattttca cctatctaac tacttaaata taatatgatt    480
```

```
aaatttggta aagtttgaaa agtttcttta gaaatgtgaa atattgatca cagtttctat    540

tgctaaaatc accaacaaaa cgcatgtcgc cattcataat tatggtttca cacctacaac    600

taggctaata agtaaataag tagacaacta gactcaggtt tgaaaaaacc ataaaagcca    660

tatagcgttt tctcattgaa actgcgaaca cgatcgtgtg aatgttgcag tttctagttt    720

tgatacaaac aaacaaaaac acaatttaat cttagattaa aaagaaaaaa gagaacggag    780

cccactagcc actccttcaa acgtgtctta ccaactctct tctagaaaca aattaggctt    840

caccttcctc ttccaacctc tctctctctc tctctctctt tttctcaaac catctctcca    900

taaagcccta atttcttcat cacaagaatc agaagaagaa a                         941
```

```
<210> SEQ ID NO 45
<211> LENGTH: 588
<212> TYPE: DNA
<213> ORGANISM: Arabidopsis thaliana

<400> SEQUENCE: 45

gtttgtgtct tctagattaa tcctccaaac ttttgattaa ccaaaaaaat tatcaaacta     60

acatgttctc ctttttttctt tagaaattct aacgaattta tctttatact gatttgaata    120

tacttaattt ggtcatttgg atgcccttta caacctcctt accaaactca ttgatcacag    180

tttctattgc taaaatcacc aacaaaacgc atgtcgccat tcataattat ggtttcacac    240

ctacaactag gctaataagt aaataagtag acaactagac tcaggtttga aaaaaccata    300

aaagccatat agcgttttct cattgaaact gcgaacacga tcgtgtgaat gttgcagttt    360

ctagttttga tacaaacaaa caaaaacaca atttaatctt agattaaaaa gaaaaaagag    420

aacggagccc actagccact ccttcaaacg tgtcttacca actctcttct agaaacaaat    480

taggcttcac cttcctcttc caacctctct ctctctctct ctctcttttt ctcaaaccat    540

ctctccataa agccctaatt tcttcatcac aagaatcaga agaagaaa                  588
```

```
<210> SEQ ID NO 46
<211> LENGTH: 468
<212> TYPE: DNA
<213> ORGANISM: Arabidopsis thaliana

<400> SEQUENCE: 46

tacttaattt ggtcatttgg atgcccttta caacctcctt accaaactca ttgatcacag     60

tttctattgc taaaatcacc aacaaaacgc atgtcgccat tcataattat ggtttcacac    120

ctacaactag gctaataagt aaataagtag acaactagac tcaggtttga aaaaaccata    180

aaagccatat agcgttttct cattgaaact gcgaacacga tcgtgtgaat gttgcagttt    240

ctagttttga tacaaacaaa caaaaacaca atttaatctt agattaaaaa gaaaaaagag    300

aacggagccc actagccact ccttcaaacg tgtcttacca actctcttct agaaacaaat    360

taggcttcac cttcctcttc caacctctct ctctctctct ctctcttttt ctcaaaccat    420

ctctccataa agccctaatt tcttcatcac aagaatcaga agaagaaa                  468
```

```
<210> SEQ ID NO 47
<211> LENGTH: 419
<212> TYPE: DNA
<213> ORGANISM: Arabidopsis thaliana

<400> SEQUENCE: 47

attgatcaca gtttctattg ctaaaatcac caacaaaacg catgtcgcca ttcataatta     60
```

```
tggtttcaca cctacaacta ggctaataag taaataagta gacaactaga ctcaggtttg    120

aaaaaaccat aaaagccata tagcgttttc tcattgaaac tgcgaacacg atcgtgtgaa    180

tgttgcagtt tctagttttg atacaaacaa acaaaaacac aatttaatct tagattaaaa    240

agaaaaaaga gaacggagcc cactagccac tccttcaaac gtgtcttacc aactctcttc    300

tagaaacaaa ttaggcttca ccttcctctt ccaacctctc tctctctctc tctctctttt    360

tctcaaacca tctctccata aagccctaat ttcttcatca caagaatcag aagaagaaa     419


<210> SEQ ID NO 48
<211> LENGTH: 723
<212> TYPE: DNA
<213> ORGANISM: Agrobacterium tumefaciens

<400> SEQUENCE: 48

atggacctgc atctaatttt cggtccaact tgcacaggaa agacgacgac cgcgatagct     60

cttgcccagc agacagggct tccagtcctt tcgcttgatc gggtccaatg ctgtcctcaa    120

ctatcaaccg gaagcggacg accaacagtg gaagaactga aaggaacgac gcgtctctac    180

cttgatgatc ggcctctggt ggagggtatc atcgcagcca agcaagctca tcataggctg    240

atcgaggagg tgtataatca tgaggccaac ggcgggctta ttcttgaggg aggatccacc    300

tcgttgctca actgcatggc gcgaaacagc tattggagtg cagattttcg ttggcatatt    360

attcgccaca agttacccga ccaagagacc ttcatgaaag cggccaaggc cagagttaag    420

cagatgttgc accccgctgc aggccattct attattcaag agttggttta tctttggaat    480

gaacctcggc tgaggcccat tctgaaagag atcgatggat atcgatatgc catgttgttt    540

gctagccaga accagatcac ggcagatatg ctattgcagc ttgacgcaaa tatggaaggt    600

aagttgatta atgggatcgc tcaggagtat ttcatccatg cgcgccaaca ggaacagaaa    660

ttcccccaag ttaacgcagc cgctttcgac ggattcgaag gtcatccgtt cggaatgtat    720

tag                                                                  723


<210> SEQ ID NO 49
<211> LENGTH: 975
<212> TYPE: DNA
<213> ORGANISM: Lotus japonicus

<400> SEQUENCE: 49

atgtccatct caatgctaat gtgcagacta agacaaccct taataaacgt tccctgcagt     60

ggcaaaaaac tgagcatgag gcagattcaa aaggagaagg tagtgttggt gatgggagct    120

acagggacag gaaagtcaaa gctctccatt gacctcgcca cctgtttccc ctcagaaatc    180

atcaactccg acaagattca aatctacgac ggcctcgaca tcgtcaccaa caaaatctcc    240

aaggaagaac aacgtggaat cccccaccac ctcctcggaa ctcaaaaccc taacacagac    300

ttcaccgccg gcgatttcag tgactgttcc accgccgcca ttgacgcaat cacaagccgc    360

gaccaccttc cgatcatcgc cggaggttcg aactcctacc tggaggcgtt aatcgacgac    420

gacgactaca aattccgatc gaggtacgac ttctgctgcc tctgggtcga cgtggcaatg    480

ccggtgctgg actcatacgt ggcggcgcgt gtggatcaga tgctccggag cggaatggtg    540

gaggagctga gaccgttttt caacgcgaac ggcgactact cgagaggaat cagaagagcg    600

attggggttc ctgaattcga cgagtatttc cggcgggaag ggttcgccga tgaggaaacg    660

aggaaattgt tactggagcg agcggtgagg gagatgaagg tgaacacgtg caagctcgcg    720

aggaggcaat tggggaagat tcagaggctg aggaatgtga agaggtggga gattcaccgt    780
```

gttgatgcga cgccggtgtt ttggaagcgt ggggaggagg ctgatgaggc gtggcggaag 840
gtggtggcag agcctagtgc tatgatcgta gcgcagtttc tgtataaggc aaagagtgat 900
gtgaatgttg tttctggcgg tttcagagtg ccggcgggtt caacggagag tgttatggcg 960
gcggcgacgt gttag 975

<210> SEQ ID NO 50
<211> LENGTH: 1053
<212> TYPE: DNA
<213> ORGANISM: Petunia x hybrida

<400> SEQUENCE: 50
atgttaattg tagtacatat tattagcatc acacgcatca tattcatcac cttaacccat 60
aatcatctcc atttccttat gtttagatca ttatcataca atcacaagca cctcaaattc 120
cttacaaacc cgaccacacg ggtactccga agaaacatgt cgtcatccac tgtagtaaca 180
atacccggcc ccacacaaaa aaacaaaaac aaaatcatag taataatggg tgcaacaggt 240
tcaggaaaat caaaactctc aatagacctc gtcacacgtc actatccttt ttccgaaatc 300
attaactccg acaaaatcca aattaccaaa ggtttaaaca taaccacaaa caaaatcact 360
gtacccgacc gacgtggcgt agttcatcat ttactcggcg agattgaccc cgactttaac 420
ttttctcctt ctcatttccg gtcaattgct ggtcaacgca ttaactccat tattaatcgc 480
cataaactcc cattcctcgt tggtgggtcc aactcatata tctacgcttt attaacaaac 540
cggttcgacc cggattttaa ccctgattca aacccggttc attttatatc caacgagtta 600
cgctacaact gttgttttat ttgggtcgat gtattaaacc cggttttgaa tgagtatttg 660
gataaacggg tcgatgagat gatgaactcg ggtatgtatg aagaactgga acagtttttt 720
aaagaaaaca ggttttcgga tccgggtttg gaaccgggtc gggccaccgg gttgaggaaa 780
gcgatagggg taccggaaat ggagaggtat tttaagaaga gctgtacgta tgaggaagca 840
gtgagggaaa taaaagaaaa cacgtggcgg ttagcgaaga agcagatgtg gaagatccaa 900
cggttgagag aagcagggtg ggacctacaa agagtagatg ccacggaggc atttgtggag 960
gcgatgagta ataagaagga aaagggaatt atttgggaaa aacaagtagt ggaaccaagt 1020
gtcaagattg tgaaccgttt tttgttggac tga 1053

<210> SEQ ID NO 51
<211> LENGTH: 240
<212> TYPE: PRT
<213> ORGANISM: Agrobacterium tumefaciens

<400> SEQUENCE: 51

Met Asp Leu His Leu Ile Phe Gly Pro Thr Cys Thr Gly Lys Thr Thr
1 5 10 15

Thr Ala Ile Ala Leu Ala Gln Gln Thr Gly Leu Pro Val Leu Ser Leu
20 25 30

Asp Arg Val Gln Cys Cys Pro Gln Leu Ser Thr Gly Ser Gly Arg Pro
35 40 45

Thr Val Glu Glu Leu Lys Gly Thr Thr Arg Leu Tyr Leu Asp Asp Arg
50 55 60

Pro Leu Val Glu Gly Ile Ile Ala Ala Lys Gln Ala His His Arg Leu
65 70 75 80

Ile Glu Glu Val Tyr Asn His Glu Ala Asn Gly Gly Leu Ile Leu Glu
85 90 95

```
Gly Gly Ser Thr Ser Leu Leu Asn Cys Met Ala Arg Asn Ser Tyr Trp
            100                 105                 110

Ser Ala Asp Phe Arg Trp His Ile Ile Arg His Lys Leu Pro Asp Gln
        115                 120                 125

Glu Thr Phe Met Lys Ala Ala Lys Ala Arg Val Lys Gln Met Leu His
    130                 135                 140

Pro Ala Ala Gly His Ser Ile Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ala Asp Met Leu Leu
            180                 185                 190

Gln Leu Asp Ala Asn Met Glu Gly Lys Leu Ile Asn Gly Ile Ala Gln
        195                 200                 205

Glu Tyr Phe Ile His Ala Arg Gln Gln Glu Gln Lys Phe Pro Gln Val
    210                 215                 220

Asn Ala Ala Ala Phe Asp Gly Phe Glu Gly His Pro Phe Gly Met Tyr
225                 230                 235                 240


<210> SEQ ID NO 52
<211> LENGTH: 324
<212> TYPE: PRT
<213> ORGANISM: Lotus japonicus

<400> SEQUENCE: 52

Met Ser Ile Ser Met Leu Met Cys Arg Leu Arg Gln Pro Leu Ile Asn
1               5                   10                  15

Val Pro Cys Ser Gly Lys Lys Leu Ser Met Arg Gln Ile Gln Lys Glu
            20                  25                  30

Lys Val Val Leu Val Met Gly Ala Thr Gly Thr Gly Lys Ser Lys Leu
        35                  40                  45

Ser Ile Asp Leu Ala Thr Cys Phe Pro Ser Glu Ile Ile Asn Ser Asp
    50                  55                  60

Lys Ile Gln Ile Tyr Asp Gly Leu Asp Ile Val Thr Asn Lys Ile Ser
65                  70                  75                  80

Lys Glu Glu Gln Arg Gly Ile Pro His His Leu Leu Gly Thr Gln Asn
                85                  90                  95

Pro Asn Thr Asp Phe Thr Ala Gly Asp Phe Ser Asp Cys Ser Thr Ala
            100                 105                 110

Ala Ile Asp Ala Ile Thr Ser Arg Asp His Leu Pro Ile Ile Ala Gly
        115                 120                 125

Gly Ser Asn Ser Tyr Leu Glu Ala Leu Ile Asp Asp Asp Asp Tyr Lys
    130                 135                 140

Phe Arg Ser Arg Tyr Asp Phe Cys Cys Leu Trp Val Asp Val Ala Met
145                 150                 155                 160

Pro Val Leu Asp Ser Tyr Val Ala Ala Arg Val Asp Gln Met Leu Arg
                165                 170                 175

Ser Gly Met Val Glu Glu Leu Arg Pro Phe Phe Asn Ala Asn Gly Asp
            180                 185                 190

Tyr Ser Arg Gly Ile Arg Arg Ala Ile Gly Val Pro Glu Phe Asp Glu
        195                 200                 205

Tyr Phe Arg Arg Glu Gly Phe Ala Asp Glu Glu Thr Arg Lys Leu Leu
    210                 215                 220

Leu Glu Arg Ala Val Arg Glu Met Lys Val Asn Thr Cys Lys Leu Ala
225                 230                 235                 240
```

```
Arg Arg Gln Leu Gly Lys Ile Gln Arg Leu Arg Asn Val Lys Arg Trp
            245                 250                 255

Glu Ile His Arg Val Asp Ala Thr Pro Val Phe Trp Lys Arg Gly Glu
            260                 265                 270

Glu Ala Asp Glu Ala Trp Arg Lys Val Val Ala Glu Pro Ser Ala Met
        275                 280                 285

Ile Val Ala Gln Phe Leu Tyr Lys Ala Lys Ser Asp Val Asn Val Val
    290                 295                 300

Ser Gly Gly Phe Arg Val Pro Ala Gly Ser Thr Glu Ser Val Met Ala
305                 310                 315                 320

Ala Ala Thr Cys


<210> SEQ ID NO 53
<211> LENGTH: 350
<212> TYPE: PRT
<213> ORGANISM: Petunia x hybrida

<400> SEQUENCE: 53

Met Leu Ile Val Val His Ile Ile Ser Ile Thr Arg Ile Ile Phe Ile
1               5                   10                  15

Thr Leu Thr His Asn His Leu His Phe Leu Met Phe Arg Ser Leu Ser
            20                  25                  30

Tyr Asn His Lys His Leu Lys Phe Leu Thr Asn Pro Thr Thr Arg Val
        35                  40                  45

Leu Arg Arg Asn Met Ser Ser Ser Thr Val Val Thr Ile Pro Gly Pro
    50                  55                  60

Thr Gln Lys Asn Lys Asn Lys Ile Ile Val Ile Met Gly Ala Thr Gly
65                  70                  75                  80

Ser Gly Lys Ser Lys Leu Ser Ile Asp Leu Val Thr Arg His Tyr Pro
                85                  90                  95

Phe Ser Glu Ile Ile Asn Ser Asp Lys Ile Gln Ile Thr Lys Gly Leu
            100                 105                 110

Asn Ile Thr Thr Asn Lys Ile Thr Val Pro Asp Arg Arg Gly Val Val
        115                 120                 125

His His Leu Leu Gly Glu Ile Asp Pro Asp Phe Asn Phe Ser Pro Ser
    130                 135                 140

His Phe Arg Ser Ile Ala Gly Gln Arg Ile Asn Ser Ile Ile Asn Arg
145                 150                 155                 160

His Lys Leu Pro Phe Leu Val Gly Gly Ser Asn Ser Tyr Ile Tyr Ala
                165                 170                 175

Leu Leu Thr Asn Arg Phe Asp Pro Asp Phe Asn Pro Asp Ser Asn Pro
            180                 185                 190

Val His Phe Ile Ser Asn Glu Leu Arg Tyr Asn Cys Cys Phe Ile Trp
        195                 200                 205

Val Asp Val Leu Asn Pro Val Leu Asn Glu Tyr Leu Asp Lys Arg Val
    210                 215                 220

Asp Glu Met Met Asn Ser Gly Met Tyr Glu Glu Leu Glu Gln Phe Phe
225                 230                 235                 240

Lys Glu Asn Arg Phe Ser Asp Pro Gly Leu Glu Pro Gly Arg Ala Thr
                245                 250                 255

Gly Leu Arg Lys Ala Ile Gly Val Pro Glu Met Glu Arg Tyr Phe Lys
            260                 265                 270

Lys Ser Cys Thr Tyr Glu Glu Ala Val Arg Glu Ile Lys Glu Asn Thr
        275                 280                 285
```

-continued

```
Trp Arg Leu Ala Lys Lys Gln Met Trp Lys Ile Gln Arg Leu Arg Glu
    290                 295                 300

Ala Gly Trp Asp Leu Gln Arg Val Asp Ala Thr Glu Ala Phe Val Glu
305                 310                 315                 320

Ala Met Ser Asn Lys Lys Glu Lys Gly Ile Ile Trp Glu Lys Gln Val
                325                 330                 335

Val Glu Pro Ser Val Lys Ile Val Asn Arg Phe Leu Leu Asp
            340                 345                 350
```